US008367892B2

(12) United States Patent
Davies et al.

(10) Patent No.: US 8,367,892 B2
(45) Date of Patent: Feb. 5, 2013

(54) GENERATION OF PLANTS WITH ALTERED PROTEIN, FIBER, OR OIL CONTENT

(75) Inventors: John P. Davies, Portland, OR (US); Hein Tsoeng (Medard) Ng, Charlottesville, VA (US); D. Ry Wagner, Pleasant Hill, OR (US)

(73) Assignee: Agrigenetics, Inc., Indianapolis, IN (US)

( * ) Notice: Subject to any disclaimer, the term of this patent is extended or adjusted under 35 U.S.C. 154(b) by 0 days.

(21) Appl. No.: 13/401,682

(22) Filed: Feb. 21, 2012

(65) Prior Publication Data
US 2012/0151628 A1    Jun. 14, 2012

Related U.S. Application Data

(62) Division of application No. 13/078,843, filed on Apr. 1, 2011, now Pat. No. 8,163,978, which is a division of application No. 12/814,412, filed on Jun. 11, 2010, now Pat. No. 7,943,817, which is a division of application No. 11/940,284, filed on Nov. 14, 2007, now Pat. No. 7,763,771.

(60) Provisional application No. 60/866,060, filed on Nov. 15, 2006.

(51) Int. Cl.
A01H 1/00    (2006.01)
A01H 5/00    (2006.01)
A01H 5/10    (2006.01)
C12N 5/04    (2006.01)
C12N 15/82   (2006.01)

(52) U.S. Cl. ........ 800/278; 800/295; 800/298; 800/306; 800/312; 800/314; 800/320; 800/320.1; 800/320.2; 800/320.3; 800/322; 435/419; 435/468

(58) Field of Classification Search .................. None
See application file for complete search history.

(56) References Cited

U.S. PATENT DOCUMENTS

| | | | |
|---|---|---|---|
| 5,322,783 A | 6/1994 | Tomes et al. | |
| 5,538,880 A | 7/1996 | Lundquist et al. | |
| 5,550,318 A | 8/1996 | Adams et al. | |
| 5,563,055 A | 10/1996 | Townsend et al. | |
| 5,610,042 A | 3/1997 | Chang et al. | |
| 5,639,790 A | 6/1997 | Voelker et al. | |
| 5,704,160 A | 1/1998 | Bergquist et al. | |
| 5,952,544 A | 9/1999 | Browse et al. | |
| 5,977,445 A * | 11/1999 | Soper et al. ................... | 800/312 |
| 6,229,033 B1 | 5/2001 | Knowlton | |
| 6,248,939 B1 | 6/2001 | Leto et al. | |
| 2003/0046723 A1 | 3/2003 | Heard et al. | |
| 2004/0019927 A1 | 1/2004 | Sherman et al. | |
| 2004/0025202 A1 | 2/2004 | Laurie et al. | |
| 2006/0048240 A1 | 3/2006 | Alexandrov et al. | |
| 2006/0150283 A1 | 7/2006 | Alexandrov et al. | |
| 2006/0277630 A1 | 12/2006 | Lightner et al. | |

FOREIGN PATENT DOCUMENTS

| | | |
|---|---|---|
| EP | 1033405 | 9/2000 |
| WO | WO 94/11516 | 5/1994 |
| WO | WO 95/06128 | 3/1995 |
| WO | WO 2004/035798 | 4/2004 |
| WO | WO 2004/093528 | 11/2004 |
| WO | WO 2004/093532 | 11/2004 |
| WO | WO 2005/047516 | 5/2005 |
| WO | WO 2005/107437 | 11/2005 |
| WO | WO 2007/053482 | 5/2007 |

OTHER PUBLICATIONS

Blast Results, May 5, 2012.*
Corbin et al, 2006, Gene, vol. 367, pp. 17-37.*
Vashisht et al, 2006, Journal of Photochemistry and Photobiology B: Biology, vol. 84, pp. 150-160.*
Rocak and Linder, Mar. 2004, Nature Reviews, Molecular Cell Biology, vol. 5, pp. 232-241.*
Bevan et al, Accession No. T49915, Database PIR__80, Jun. 2, 2000.*
Accession No. NP__198848, Aug. 21, 2009.
Anoop et al., "Modulation of citrate metabolism alters aluminum tolerance in yeast and transgenic canola overexpressing a mitochondrial citrate synthase," *Plant Physiol.*, 132:2205-2217 (2003).
Bateman et al., "Pfam 3.1: 1313 multiple alignments and profile HMMs match the majority of proteins," *Nucleic Acids Res.*, 27:260-262 (1999).
Beisson et al., "Arabidopsis genes involved in acyl lipid metabolism. A 2003 census of the candidates, a study of the distribution of expressed sequence tags in organs, and a web-based database," *Plant Physiol.*, 132:681-697 (2003).
Bert et al., "Comparative genetic analysis of quantitative traits in sunflower (*Helianthus annuus* L.). 2. Characterisation of QTL involved in developmental and agronomic traits," *Theor. Appl. Genet.*, 107:181-9, (2003).
Browse et al., "Fluxes through the prokaryotic and eukaryotic pathways of lipid synthesis in the '16:3' plant *Arabidopsis thaliana*," *Biochem J.* 235:25-31 (1986).
Chapple and Carpita, "Plant cell walls as targets for biotechnology," *Current Opinion in Plant Biology*, 1:179-185 (1998).
Christensen et al., $9^{th}$ *International Conference on* Arabidopsis Research, Univ. of Wisconsin-Madison, Jun. 24-28, Abstract 165 (1998).
Christou et al., "Inheritance and expression of foreign genes in transgenic soybean plants," *Proc. Natl. Acad. Sci. USA*, 86:7500-7504 (1989).
Colbert et al., "High-throughput screening for induced point mutations," *Plant Physiol*. 126:480-484 (2001).
Comai et al., "Efficient discovery of DNA polymorphisms in natural populations by Ecotilling," *The Plant Journal*, 37:778-786 (2004).
Database EMBL, "Arabidopsis thaliana putative serine carboxypeptidase II (At4g30810) mRNA, complete cds." Database Accession No. AY050958, Aug. 27, 2001.
Database Geneseq, "Thale cress cDNA repressed in E2Fa/Dpa expressing plants SeqID 2241," Database Accession No. ADN74346; Jul. 15, 2004.

(Continued)

*Primary Examiner* — Eileen B O'Hara
(74) *Attorney, Agent, or Firm* — Marcia I. Rosenfeld; Klarquist Sparkman, LLP

(57) ABSTRACT

The present invention is directed to plants that display an improved oil quantity phenotype or an improved meal quality phenotype due to altered expression of an IMQ nucleic acid. The invention is further directed to methods of generating plants with an improved oil quantity phenotype or improved meal quality phenotype.

31 Claims, No Drawings

OTHER PUBLICATIONS

Database Geneseq, "Thale cress protein repressed in E2Fa/Dpa expressing plants SeqID 2242," Database Accession No. ADN74347; Jul. 15, 2004.
Database UniProt_201110, Accession No. F4K567, Gene ID: 836897, Jul. 30, 2003.
De Block et al., "Transformation of *Brassica napus* and *Brassica oleracea* Using Agrobacterium tumefaciens and the Expression of the bar and neo Genes in the Transgenic Plants," *Plant Physiol.*, 91:694-701 (1989).
Dehesh et al., "Overexpression of 3-ketoacyl-acyl-carrier protein synthase IIIs in plants reduces the rate of lipid synthesis," *Plant Physiol.*, 125:1103-1114 (2001).
Douglas et al., "Nutritional evaluation of low phytate and high protein corns," *Poultry Sci.* 79:1586-1591 (2000).
Eastmond and Graham, "Re-examining the role of glyoxylate cycle in oilseeds," *Trends Plant Sci.*, 6(2):72-77 (2001).
Eccleston and Ohlrogge, "Expression of lauroyl-acyl carrier protein thioesterase in *Brassica napus* seeds induces pathways for both fatty acid oxidation and biosynthesis and implies a set point for triacylglycerol accumulation," *Plant Cell.* 10:613-621 (1998).
Edwards et al., "Protein and energy evaluation of soybean meals processed from genetically modified high-protein soybeans," *Poultry Sci.* 79:525-527 (1999).
Everett et al., "Genetic engineering of sunflower (*Helianthus annuus* L.)," *Bio/Technology*, 5:1201 (1987).
Falco et al., "Transgenic canola and soybean seeds with increased lysine," *Bio/Technology*, 13:577-582 (1995).
Fatland et al., "Molecular biology of cytosolic acetyl-CoA generation," *Biochem. Soc. Trans.*, 28(6):593-595 (2000).
Fatland et al., "Reverse genetic characterization of cytosolic acetyl-CoA generation by ATP-citrate lyase in *Arabidopsis*," *Plant Cell*, 17:182-203 (2005).
Feldmann et al., "A Dwarf Mutant of *Arabidopsis* Generated by T-DNA Insertion Mutagenesis," *Science*, 243:1351-1354 (1989).
Focks and Benning, "wrinkled1: A novel, low-seed-oil mutant of *Arabidopsis* with a deficiency in the seed-specific regulation of carbohydrate metabolism," *Plant Physiol.*, 118:91-101 (1998).
Fridborg et al., "The *Arabidopsis* dwarf mutant *shi* exhibits reduced gibberellin responses conferred by overexpression of a new putative zinc finger protein," *Plant Cell*, 11:1019-1032 (1999).
Girke et al., "Microarray analysis of developing Arabidopsis seeds," *Plant Physiol.*, 124:1570-1581 (2000).
Hayashi et al., "Activation of a plant gene by T-DNA tagging: auxin-independent growth in vitro," *Science*, 258:1350-1353 (1992).
Honig and Rackis, "Determination of the total pepsin-pancreatin indigestible content (dietary fiber) of soybean products, wheat bran, and corn bran," *J. Agri. Food Chem.*, 27:1262-1266 (1979).
Jako et al., "Seed-specific over-expression of an *Arabidopsis* cDNA encoding a diacylglycerol acyltransferase enhances seed oil content and seed weight," *Plant Physiol.*, 126(2):861-74 (2001).
James and Dooner, "Isolation of EMS-induced mutants in Arabidopsis altered in seed fatty acid composition," *Theor. Appl. Genet.*, 80:241-245 (1990).
Kardailsky et al., "Activation tagging of the floral inducer FT," *Science*, 286:1962-1965 (1999).
Katavic et al., "Alteration of seed fatty acid composition by an ethyl methanesulfonate-induced mutation in *Arabidopsis thaliana* affecting diacylglycerol acyltransferase activity," *Plant Physiol.*, 108:399-409 (1995).
Katavic et al., "Utility of the *Arabidopsis FAE1* and yeast *SLC1-1* genes for improvements in erucic acid and oil content in rapeseed," *Biochem Soc. Trans.*, 28(6):935-937 (2000).
Klein et al., "High velocity microprojectiles for delivering nucleic acids into living cells," *Nature*, 327:70-73 (1987).
Larson et al., "Acyl CoA profiles of transgenic plants that accumulate medium-chain fatty acids indicate inefficient storage lipid synthesis in developing oilseeds," *Plant J.*, 32:519-527 (2002).
Lemieux et al., "Mutants of *Arabidopsis* with alterations in seed lipid fatty acid composition," *Theor. Appl. Genet.*, 80:234-240 (1990).
Lin et al., "The Pex16p Homolog SSE1 and Storage Organelle Formation in *Arabidopsis* Seeds," *Science*, 284:328-330 (1999).
Lionneton et al., "Development of an AFLP-based linkage map and localization of QTLs for seed fatty acid content in condiment mustard (*Brassica juncea*)," *Genome*, 45:1203-15 (2002).

Liu and Butow, "A transcriptional switch in the expression of yeast tricarboxylic acid cycle genes in response to a reduction or loss of respiratory function," *Mol. Cell. Biol.*, 19:6720-6728 (1999).
McCallum et al., "Targeted screening for induced mutations," *Nature Biotechnology*, 18:455-457 (2000).
Mekhedov et al., "Toward a Functional Catalog of the Plant Genome. A Survey of Genes for Lipid Biosynthesis," *Plant Physiology*, 122:389-401 (2000).
Moire et al., "Impact of Unusual Fatty Acid Synthesis on Futile Cycling through β-Oxidation and on Gene Expression in Transgenic Plants," *Plant Physiology*, 134:432-442 (2004).
Moore et al., "Chromatography of Amino Acids on Sulfonated Polystyrene Resins," *Anal. Chem.*, 30:1185-1190 (1958).
Mulder et al., "The InterPro Database, 2003 brings increased coverage and new features," *Nucleic Acids Res.*, 31:315-318 (2003).
Neuhaus et al., "Nonphotosynthetic Metabolism in Plastids," *Annu. Rev. Plant Physiol. Plant Mol.*, 51:111-140 (2000).
O'Hara et al., "Fatty Acid and Lipid Biosynthetic Genes Are Expressed at Constant Molar Ratios But Different Absolute Levels during Embryogenesis," *Plant Physiology*, 129:310-320 (2002).
Okuley et al., "*Arabidopsis FAD2* gene encodes the enzyme that is essential for polyunsaturated lipid synthesis," *Plant Cell*, 6:147-158 (1994).
Parsons et al., "Nutritional evaluation of soybean meals varying in oligosaccharide content," *Poultry Sci.*, 79:1127-1131 (2000).
Pritchard et al., "Germination and storage reserve mobilization are regulated independently in *Arabidopsis*," *The Plant Journal*, 31(5):639-647 (2002).
Rangasamy and Ratledge, "Genetic enhancement of fatty acid synthesis by targeting rat liver ATP:citrate lyase into plastids of tobacco," *Plant Physiol.*, 122:1231-1238 (2000).
Rangasamy et al., "Compartmentation of ATP:Citrate Lyase in Plants," *Plant Physiology*, 122:1225-1230 (2000).
Ratledge et al., "Correlation of ATP/Citrate Lyase Activity with Lipid Accumulation in Developing Seeds of *Brassica napus* L.," *Lipids*, 32(1):7-12 (1997).
Rawsthorne, Stephen, "Carbon flux and fatty acid synthesis in plants," *Progress in Lipid Research*, 41:182-196 (2002).
Ruuska et al., "Contrapuntal Networks of Gene Expression during *Arabidopsis* Seed Filling," *The Plant Cell*, 14:1191-1206 (2002).
Rylott et al., "Co-ordinate regulation of genes involved in storage lipid mobilization in *Arabidopsis thaliana*," *Biochem Soc. Trans.*, 29:283-287 (2001).
Schaffer et al., "The late elongated hypocotyl mutation of *Arabidopsis* disrupts circadian rhythms and the photoperiodic control of flowering," *Cell*, 93:1219-1229 (1998).
Schnarrenberger and Martin, "Evolution of the enzymes of the citric acid cycle and the glyoxylate cycle of higher plants, A case study of endosymbiotic gene transfer," *Eur. J. Biochem.*, 269:868-883 (2002).
Schnurr et al., "Characterization of an acyl-CoA synthetase from *Arabidopsis thaliana*," *Biochem Soc. Trans.*, 28(6):957-958 (2000).
Shewry, "Seed storage proteins: structures and biosynthesis," *Plant Cell*, 7:945-956 (1995).
Shockey et al., "Characterization of the AMP-binding protein gene family in *Arabidopsis thaliana*: will the real acyl-CoA synthetases please stand up?" *Biochem Soc. Trans.*, 28(6):955-957 (2000).
Tabata et al., Database UniProt_201011, Accession No. Q9FNE7 (Q9FNE7_ARATH), Mar. 1, 2001.
Thelen et al., "Biotin carboxyl carrier protein isoforms in Brassicaceae oilseeds," *Biochem. Soc. Trans.*, 28(6):595-598 (2000).
Weigel et al., "Activation tagging in *Arabidopsis*," *Plant Physiology*, 122:1003-1013 (2000).
White et al., "A new set of *Arabidopsis* expressed sequence tags from developing seeds. The metabolic pathway from carbohydrates to seed oil," *Plant Physiol.*, 124:1582-1594 (2000).
Wilson et al., "A Dissociation insertion causes a semidominant mutation that increases expression of TINY, an *Arabidopsis* gene related to APETALA2," *Plant Cell*, 8:659-671 (1996).
Yadav et al., "Cloning of higher plant omega-3 fatty acid desaturases," *Plant Physiol.*, 103:467-476 (1993).
Zou et al., "Modification of Seed Oil Content and Acyl Composition in the Brassicaceae by Expression of a Yeast *sn*-2 Acyltransferase Gene," *The Plant Cell*, 9:909-923 (1997).

\* cited by examiner

GENERATION OF PLANTS WITH ALTERED PROTEIN, FIBER, OR OIL CONTENT

CROSS REFERENCE TO RELATED APPLICATIONS

The present application is a divisional of U.S. patent application Ser. No. 13/078,843, filed Apr. 1, 2011, now U.S. Pat. No. 8,163,978, issued Apr. 24, 2012, which is a divisional of U.S. patent application Ser. No. 12/814,412, filed Jun. 11, 2010, now U.S. Pat. No. 7,943,817, issued May 17, 2011, which is a divisional of U.S. patent application Ser. No. 11/940,284, filed Nov. 14, 2007, now U.S. Pat. No. 7,763,771, issued Jul. 27, 2010, which claims the benefit of U.S. Provisional Application No. 60/866,060, filed Nov. 15, 2006, all of which are incorporated herein by reference in their entirety.

FIELD OF THE DISCLOSURE

The present disclosure is related to transgenic plants with altered oil, protein, and/or fiber content, as well as methods of making plants having altered oil, protein, and/or fiber content and producing oil from such plants.

BACKGROUND

The ability to manipulate the composition of crop seeds, particularly the content and composition of seed oil and protein, as well as the available metabolizable energy ("AME") in the seed meal in livestock, has important applications in the agricultural industries, relating both to processed food oils and to animal feeds. Seeds of agricultural crops contain a variety of valuable constituents, including oil, protein and starch. Industrial processing can separate some or all of these constituents for individual sale in specific applications. For instance, nearly 60% of the U.S. soybean crop is crushed by the soy processing industry. Soy processing yields purified oil, which is sold at high value, while the remaining seed meal is sold for livestock feed (U.S. Soybean Board, 2001 Soy Stats). Canola seed is also crushed to produce oil and the co-product canola meal (Canola Council of Canada). Canola meal contains a high percentage of protein and a good balance of amino acids but because it has a high fiber and phytate content, it is not readily digested by livestock (Slominski et al., 1999 Proceedings of the 10$^{th}$ International Rapeseed Congress, Canberra, Australia) and has a lower value than soybean meal.

Over 55% of the corn produced in the U.S. is used as animal feed (Iowa Corn Growers Association). The value of the corn is directly related to its ability to be digested by livestock. Thus, it is desirable to maximize both oil content of seeds and the AME of meal. For processed oilseeds such as soy and canola, increasing the absolute oil content of the seed will increase the value of such grains, while increasing the AME of meal will increase its value. For processed corn, either an increase or a decrease in oil content may be desired, depending on how the other major constituents are to be used. Decreasing oil may improve the quality of isolated starch by reducing undesired flavors associated with oil oxidation. Alternatively, when the starch is used for ethanol production, where flavor is unimportant, increasing oil content may increase overall value.

In many feed grains, such as corn and wheat, it is desirable to increase seed oil content, because oil has higher energy content than other seed constituents such as carbohydrate. Oilseed processing, like most grain processing businesses, is a capital-intensive business; thus small shifts in the distribution of products from the low valued components to the high value oil component can have substantial economic impacts for grain processors. In addition, increasing the AME of meal by adjusting seed protein and fiber content and composition, without decreasing seed oil content, can increase the value of animal feed.

Biotechnological manipulation of oils has been shown to provide compositional alteration and improvement of oil yield. Compositional alterations include high oleic acid soybean and corn oil (U.S. Pat. Nos. 6,229,033 and 6,248,939), and laurate-containing seeds (U.S. Pat. No. 5,639,790), among others. Work in compositional alteration has predominantly focused on processed oilseeds, but has been readily extendable to non-oilseed crops, including corn. While there is considerable interest in increasing oil content, the only currently practiced biotechnology in this area is High-Oil Corn (HOC) technology (DuPont, U.S. Pat. No. 5,704,160). HOC employs high oil pollinators developed by classical selection breeding along with elite (male-sterile) hybrid females in a production system referred to as TopCross. The TopCross High Oil system raises harvested grain oil content in maize from about 3.5% to about 7%, improving the energy content of the grain.

While it has been fruitful, the HOC production system has inherent limitations. First, the system of having a low percentage of pollinators responsible for an entire field's seed set contains inherent risks, particularly in drought years. Second, oil content in current HOC fields has plateaued at about 9% oil. Finally, high-oil corn is not primarily a biochemical change, but rather an anatomical mutant (increased embryo size) that has the indirect result of increasing oil content. For these reasons, an alternative high oil strategy, particularly one that derives from an altered biochemical output, would be especially valuable.

Manipulation of seed composition has identified several components that improve the nutritive quality, digestibility, and AME in seed meal. Increasing the lysine content in canola and soybean (Falco et al., 1995 *Bio/Technology* 13:577-582) increases the availability of this essential amino acid and decreases the need for nutritional supplements. Soybean varieties with increased seed protein were shown to contain considerably more metabolizable energy than conventional varieties (Edwards et al., 1999, *Poultry Sci.* 79:525-527). Decreasing the phytate content of corn seed has been shown to increase the bioavailability of amino acids in animal feeds (Douglas et al., 2000, *Poultry Sci.* 79:1586-1591) and decreasing oligosaccharide content in soybean meal increases the metabolizable energy in the meal (Parsons et al., 2000, *Poultry Sci.* 79:1127-1131).

Soybean and canola are the most obvious target crops for the processed oil and seed meal markets since both crops are crushed for oil and the remaining meal sold for animal feed. A large body of commercial work (e.g., U.S. Pat. No. 5,952,544; PCT Application No. WO9411516) demonstrates that *Arabidopsis* is an excellent model for oil metabolism in these crops. Biochemical screens of seed oil composition have identified *Arabidopsis* genes for many critical biosynthetic enzymes and have led to identification of agrinomically important gene orthologs. For instance, screens using chemically mutagenized populations have identified lipid mutants whose seeds display altered fatty acid composition (Lemieux et al., 1990, *Theor. Appl. Genet.* 80, 234-240; James and Dooner, 1990, *Theor. Appl. Genet.* 80, 241-245). T-DNA mutagenesis screens (Feldmann et al., 1989, *Science* 243: 1351-1354) that detected altered fatty acid composition identified the omega 3 desaturase (FADS) and delta-12 desaturase (FAD2) genes (U.S. Pat. No. 5,952,544; Yadav et al., 1993, *Plant Physiol.* 103, 467-476; Okuley et al., 1994, *Plant Cell* 6(1):147-158). A screen which focused on oil content rather than oil quality, analyzed chemically-induced mutants for wrinkled seeds or altered seed density, from which altered seed oil content was inferred (Focks and Benning, 1998, *Plant Physiol.* 118:91-101).

Another screen, designed to identify enzymes involved in production of very long chain fatty acids, identified a mutation in the gene encoding a diacylglycerol acyltransferase (DGAT) as being responsible for reduced triacyl glycerol accumulation in seeds (Katavic V et al., 1995, *Plant Physiol.* 108(1):399-409). It was further shown that seed-specific over-expression of the DGAT cDNA was associated with increased seed oil content (Jako et al., 2001, *Plant Physiol.* 126(2):861-74). *Arabidopsis* is also a model for understanding the accumulation of seed components that affect meal quality. For example, *Arabidopsis* contains albumin and globulin seed storage proteins found in many dicotyledonous plants including canola and soybean (Shewry 1995, *Plant Cell* 7:945-956). The biochemical pathways for synthesizing components of fiber, such as cellulose and lignin, are conserved within the vascular plants, and mutants of *Arabidopsis* affecting these components have been isolated (reviewed in Chapel and Carpita 1998, *Current Opinion in Plant Biology* 1:179-185).

Activation tagging in plants refers to a method of generating random mutations by insertion of a heterologous nucleic acid construct comprising regulatory sequences (e.g., an enhancer) into a plant genome. The regulatory sequences can act to enhance transcription of one or more native plant genes; accordingly, activation tagging is a fruitful method for generating gain-of-function, generally dominant mutants (see, e.g., Hayashi et al., 1992, *Science* 258: 1350-1353; Weigel D et al., 2000, *Plant Physiology*, 122:1003-1013). The inserted construct provides a molecular tag for rapid identification of the native plant whose mis-expression causes the mutant phenotype. Activation tagging may also cause loss-of-function phenotypes. The insertion may result in disruption of a native plant gene, in which case the phenotype is generally recessive.

Activation tagging has been used in various species, including tobacco and *Arabidopsis*, to identify many different kinds of mutant phenotypes and the genes associated with these phenotypes (Wilson et al., 1996, *Plant Cell* 8: 659-671; Schaffer et al., 1998, *Cell* 93: 1219-1229; Fridborg et al., 1999, *Plant Cell* 11: 1019-1032; Kardailsky et al., 1999, *Science* 286: 1962-1965; and Christensen S et al., 1998, 9$^{th}$ *International Conference on Arabidopsis Research*, Univ. of Wisconsin-Madison, June 24-28, Abstract 165).

SUMMARY

Provided herein are transgenic plants having an Improved Seed Quality phenotype. Transgenic plants with an Improved Seed Quality phenotype may include an improved oil quantity and/or an improved meal quality. Transgenic plants with improved meal quality have an Improved Meal Quality (IMQ) phenotype and transgenic plants with improved oil quantity have an Improved Oil Quantity (IOQ) phenotype. The IMQ phenotype in a transgenic plant may include altered protein and/or fiber content in any part of the transgenic plant, for example in the seeds. The IOQ phenotype in a transgenic plant may include altered oil content in any part of the transgenic plant, for example in the seeds. In particular embodiments, a transgenic plant may include an IOQ phenotype and/or an IMQ phenotype. In some embodiments of a transgenic plant, the IMQ phenotype may be an increase in protein content in the seed and/or a decrease in the fiber content of the seed. In other embodiments of a transgenic plant, the IOQ phenotype is an increase in the oil content of the seed (a high oil phenotype). Also provided is seed meal derived from the seeds of transgenic plants, wherein the seeds have altered protein content and/or altered fiber content. Further provided is oil derived from the seeds of transgenic plants, wherein the seeds have altered oil content. Any of these changes can lead to an increase in the AME from the seed or seed meal from transgenic plants, relative to control, non-transgenic, or wild-type plants. Also provided herein is meal, feed, or food produced from any part of the transgenic plant with an IMQ phenotype and/or IOQ phenotype.

In certain embodiments, the disclosed transgenic plants comprise a transformation vector comprising an IMQ nucleotide sequence that encodes or is complementary to a sequence that encodes an "IMQ" polypeptide. In particular embodiments, expression of an IMQ polypeptide in a transgenic plant causes an altered oil content, an altered protein content, and/or an altered fiber content in the transgenic plant. In preferred embodiments, the transgenic plant is selected from the group consisting of plants of the *Brassica* species, including canola and rapeseed, soy, corn, sunflower, cotton, cocoa, safflower, oil palm, coconut palm, flax, castor, peanut, wheat, oat and rice. Also provided is a method of producing oil or seed meal, comprising growing the transgenic plant and recovering oil and/or seed meal from said plant. The disclosure further provides feed, meal, grain, or seed comprising a nucleic acid sequence that encodes an IMQ polypeptide. The disclosure also provides feed, meal, grain, or seed comprising the IMQ polypeptide, or an ortholog thereof.

Examples of the disclosed transgenic plant are produced by a method that comprises introducing into progenitor cells of the plant a plant transformation vector comprising an IMQ nucleotide sequence that encodes, or is complementary to a sequence that encodes, an IMQ polypeptide, and growing the transformed progenitor cells to produce a transgenic plant, wherein the IMQ polynucleotide sequence is expressed, causing an IOQ phenotype and/or and IMQ phenotype in the transgenic plant. In some specific, non-limiting examples, the method produces transgenic plants wherein expression of the IMQ polypeptide causes a high (increased) oil, high (increased) protein, and/or low (decreased) fiber phenotype in the transgenic plant, relative to control, non-transgenic, or wild-type plants.

Additional methods are disclosed herein of generating a plant having an IMQ and/or an IOQ phenotype, wherein a plant is identified that has an allele in its IMQ nucleic acid sequence that results in an IMQ phenotype and/or an IOQ phenotype, compared to plants lacking the allele. The plant can generate progeny, wherein the progeny inherit the allele and have an IMQ phenotype and/or an IOQ phenotype. In some embodiments of the method, the method employs candidate gene/QTL methodology or TILLING methodology.

Also provided herein is a transgenic plant cell having an IMQ phenotype and/or an IOQ phenotype. The transgenic plant cell comprises a transformation vector comprising an IMQ nucleotide sequence that encodes or is complementary to a sequence that encodes an IMQ polypeptide. In preferred embodiments, the transgenic plant cell is selected from the group consisting of plants of the *Brassica* species, including canola and rapeseed, soy, corn, sunflower, cotton, cocoa, safflower, oil palm, coconut palm, flax, castor, peanut, wheat, oat and rice. In other embodiments, the plant cell is a seed, pollen, propagule, or embryo cell. The disclosure also provides plant cells from a plant that is the direct progeny or the indirect progeny of a plant grown from said progenitor cells.

Incorporation-By-Reference Of Material Submitted as an ASCII Text File

A Sequence Listing is submitted herewith as an ASCII compliant text file named "Sequence_Listing.txt", created on Feb. 14, 2012, and having a size of 397 kilobytes, as permitted under 37 CFR 1.821(c). The material in the aforementioned file is hereby incorporated by reference in its entirety.

DETAILED DESCRIPTION

Terms

Unless otherwise indicated, all technical and scientific terms used herein have the same meaning as they would to one skilled in the art of the present disclosure. Practitioners are particularly directed to Sambrook et al. (*Molecular Cloning: A Laboratory Manual* (Second Edition), Cold Spring Harbor Press, Plainview, N.Y., 1989) and Ausubel F M et al. (*Current Protocols in Molecular Biology*, John Wiley & Sons, New York, N.Y., 1993) for definitions and terms of the art. It is to be understood that this disclosure is not limited to the particular methodology, protocols, and reagents described, as these may vary.

As used herein, the term "IMQ phenotype" refers to plants, or any part of a plant (for example, seeds, or meal produced from seeds), with an altered protein and/or fiber content (phenotype). As provided herein, altered protein and/or fiber content includes either an increased or decreased level of protein and/or fiber content in plants, seeds or seed meal. Any combination of these changes can lead to an IMQ phenotype. For example, in one specific non-limiting example, an IMQ phenotype can refer to increased protein and decreased fiber content. In another specific non-limiting example, an IMQ phenotype can refer to unchanged protein and decreased fiber content. In yet another specific non-limiting example, an IMQ phenotype can refer to increased protein and unchanged fiber content. It is also provided that any combination of these changes can lead to an increase in the AME (available metabolizable energy) from the seed or meal generated from the seed. An IMQ phenotype also includes an improved seed quality (ISQ) phenotype or an improved seed meal quality phenotype.

As used herein, the term "IOQ phenotype" refers to plants, or any part of a plant (for example, seeds), with an altered oil content (phenotype). As provided herein, altered oil content includes an increased, for example a high, oil content in plants or seeds. In some embodiments, a transgenic plant can express both an IOQ phenotype and an IMQ phenotype. In specific, non-limiting examples, a transgenic plant having a combination of an IOQ phenotype and an IMQ phenotype can lead to an increase in the AME (available metabolizable energy) from the seed or meal generated from the seed. An IOQ phenotype also includes an improved seed quality (ISQ) phenotype.

As used herein, the term "available metabolizable energy" (AME) refers to the amount of energy in the feed that is able to be extracted by digestion in an animal and is correlated with the amount of digestible protein and oil available in animal meal. AME is determined by estimating the amount of energy in the feed prior to feeding and measuring the amount of energy in the excreta of the animal following consumption of the feed. In one specific, non-limiting example, a transgenic plant with an increase in AME includes transgenic plants with altered seed protein and/or fiber content and without a decrease in seed oil content (seed oil content remains unchanged or is increased), resulting in an increase in the value of animal feed derived from the seed.

As used herein, the term "content" refers to the type and relative amount of, for instance, a seed or seed meal component.

As used herein, the term "fiber" refers to non-digestible components of the plant seed including cellular components such as cellulose, hemicellulose, pectin, lignin, and phenolics.

As used herein, the term "meal" refers to seed components remaining following the extraction of oil from the seed. Examples of components of meal include protein and fiber.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell by infection, transfection, microinjection, electroporation, or the like. A "heterologous" nucleic acid construct may contain a control sequence/DNA coding sequence combination that is the same as, or different from, a control sequence/DNA coding sequence combination found in the native plant. Specific, non-limiting examples of a heterologous nucleic acid sequence include an IMQ nucleic acid sequence, or a fragment, derivative (variant), or ortholog thereof.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequences.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed, or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-altered or wild-type plant. "Under-expression" refers to decreased expression of a polynucleotide and/or polypeptide sequence, generally of an endogenous gene, relative to its expression in a wild-type plant. The terms "mis-expression" and "altered expression" encompass over-expression, under-expression, and ectopic expression.

The term "introduced" in the context of inserting a nucleic acid sequence into a cell, includes "transfection," "transformation," and "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus), as well as from plant seeds, pollen, propagules, and embryos.

As used herein, the terms "native" and "wild-type" relative to a given plant trait or phenotype refers to the form in which that trait or phenotype is found in the same variety of plant in nature. In one embodiment, a wild-type plant is also a control plant. In another embodiment, a wild-type plant is a non-transgenic plant.

As used herein, the term "modified" regarding a plant trait, refers to a change in the phenotype of a transgenic plant (for example, a transgenic plant with any combination of an altered oil content, an altered protein content, and/or an altered fiber content) in any part of the transgenic plant, for example the seeds, relative to a similar non-transgenic plant. As used herein, the term "altered" refers to either an increase or a decrease of a plant trait or phenotype (for example, oil content, protein content, and/or fiber content) in a transgenic plant, relative to a similar non-transgenic plant. In one specific, non-limiting example, a transgenic plant with a modified trait includes a plant with an increased oil content, increased protein content, and/or decreased fiber content relative to a similar non-transgenic plant. In another specific, non-limiting example, a transgenic plant with a modified trait includes unchanged oil content, increased protein content, and/or decreased fiber content relative to a similar non-transgenic plant. In yet another specific, non-limiting example, a transgenic plant with a modified trait includes an increased oil content, increased protein content, and/or unchanged fiber content relative to a similar non-transgenic plant. Specific, non-limiting examples of a change in phenotype include an IMQ phenotype or an IOQ phenotype.

An "interesting phenotype (trait)" with reference to a transgenic plant refers to an observable or measurable phenotype demonstrated by a T1 and/or subsequent generation plant, which is not displayed by the corresponding non-transgenic plant (i.e., a genotypically similar plant that has been raised or assayed under similar conditions). An interesting phenotype may represent an improvement in the plant (for example, increased oil content, increased protein content, and/or decreased fiber content in seeds of the plant) or may provide a means to produce improvements in other plants. An "improvement" is a feature that may enhance the utility of a plant species or variety by providing the plant with a unique and/or novel phenotype or quality. Such transgenic plants may have an improved phenotype, such as an IMQ phenotype or an IOQ phenotype.

The phrase "altered oil content phenotype" refers to a measurable phenotype of a genetically modified (transgenic) plant, where the plant displays a statistically significant increase or decrease in overall oil content (i.e., the percentage of seed mass that is oil), as compared to the similar, but non-modified (non-transgenic) plant. A high oil phenotype refers to an increase in overall oil content. The phrase "altered protein content phenotype" refers to measurable phenotype of a genetically modified plant, where the plant displays a statistically significant increase or decrease in overall protein content (i.e., the percentage of seed mass that is protein), as compared to the similar, but non-modified plant. A high protein phenotype refers to an increase in overall protein content. The phrase "altered fiber content phenotype" refers to measurable phenotype of a genetically modified plant, where the plant displays a statistically significant increase or decrease in overall fiber content (i.e., the percentage of seed mass that is fiber), as compared to the similar, but non-modified plant. A low fiber phenotype refers to decrease in overall fiber content.

As used herein, a "mutant" polynucleotide sequence or gene differs from the corresponding wild-type polynucleotide sequence or gene either in terms of sequence or expression, where the difference contributes to a modified or altered plant phenotype or trait. Relative to a plant or plant line, the term "mutant" refers to a plant or plant line which has a modified or altered plant phenotype or trait, where the modified or altered phenotype or trait is associated with the modified or altered expression of a wild-type polynucleotide sequence or gene.

As used herein, the term "T1" refers to the generation of plants from the seed of T0 plants. The T1 generation is the first set of transformed plants that can be selected by application of a selection agent, e.g., an antibiotic or herbicide, for which the transgenic plant contains the corresponding resistance gene. The term "T2" refers to the generation of plants by self-fertilization of the flowers of T1 plants, previously selected as being transgenic. T3 plants are generated from T2 plants, etc. As used herein, the "direct progeny" of a given plant derives from the seed (or, sometimes, other tissue) of that plant and is in the immediately subsequent generation; for instance, for a given lineage, a T2 plant is the direct progeny of a T1 plant. The "indirect progeny" of a given plant derives from the seed (or other tissue) of the direct progeny of that plant, or from the seed (or other tissue) of subsequent generations in that lineage; for instance, a T3 plant is the indirect progeny of a T1 plant.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. Provided herein is a transgenic plant cell having an IMQ phenotype and/or an IOQ phenotype. The transgenic plant cell comprises a transformation vector comprising an IMQ nucleotide sequence that encodes or is complementary to a sequence that encodes an IMQ polypeptide. In preferred embodiments, the transgenic plant cell is selected from the group consisting of plants of the *Brassica* species, including canola and rapeseed, soy, corn, sunflower, cotton, cocoa, safflower, oil palm, coconut palm, flax, castor, peanut, wheat, oat and rice. In other embodiments, the plant cell is a seed, pollen, propagule, or embryo cell. The disclosure also provides plant cells from a plant that is the direct progeny or the indirect progeny of a plant grown from said progenitor cells. The class of plants which can be used in the methods of the present invention is generally as broad as the class of higher plants amenable to transformation techniques, including both monocotyledonous and dicotyledonous plants.

As used herein, "transgenic plant" includes a plant that comprises within its genome a heterologous polynucleotide.

The heterologous polynucleotide can be either stably integrated into the genome, or can be extra-chromosomal. Preferably, the polynucleotide of the present invention is stably integrated into the genome such that the polynucleotide is passed on to successive generations. A plant cell, tissue, organ, or plant into which the heterologous polynucleotides have been introduced is considered "transformed," "transfected," or "transgenic." Direct and indirect progeny of transformed plants or plant cells that also contain the heterologous polynucleotide are also considered transgenic.

Disclosed herein are transgenic plants having an Improved Seed Quality phenotype. Transgenic plants with an Improved Seed Quality phenotype may include an improved oil quantity and/or an improved meal quality. Transgenic plants with improved meal quality have an IMQ phenotype and transgenic plants with improved oil quantity have an IOQ phenotype. The IMQ phenotype in a transgenic plant may include altered protein and/or fiber content in any part of the transgenic plant, for example in the seeds. The IOQ phenotype in a transgenic plant may include altered oil content in any part of the transgenic plant, for example in the seeds. In particular embodiments, a transgenic plant may include an IOQ phenotype and/or an IMQ phenotype. In some embodiments of a transgenic plant, the IMQ phenotype may be an increase in protein content in the seed and/or a decrease in the fiber content of the seed. In other embodiments of a transgenic plant, the IOQ phenotype is an increase in the oil content of the seed (a high oil phenotype). Also provided is seed meal derived from the seeds of transgenic plants, wherein the seeds have altered protein content and/or altered fiber content. Further provided is oil derived from the seeds of transgenic plants, wherein the seeds have altered oil content. Any of these changes can lead to an increase in the AME from the seed or seed meal from transgenic plants, relative to control, non-transgenic, or wild-type plants. Also provided herein is meal, feed, or food produced from any part of the transgenic plant with an IMQ phenotype and/or IOQ phenotype.

In certain embodiments, the disclosed transgenic plants comprise a transformation vector comprising an IMQ nucleotide sequence that encodes or is complementary to a sequence that encodes an "IMQ" polypeptide. In particular embodiments, expression of an IMQ polypeptide in a transgenic plant causes an altered oil content, an altered protein content, and/or an altered fiber content in the transgenic plant. In preferred embodiments, the transgenic plant is selected from the group consisting of plants of the Brassica species, including canola and rapeseed, soy, corn, sunflower, cotton, cocoa, safflower, oil palm, coconut palm, flax, castor, peanut, wheat, oat and rice. Also provided is a method of producing oil or seed meal, comprising growing the transgenic plant and recovering oil and/or seed meal from said plant. The disclosure further provides feed, meal, grain, or seed comprising a nucleic acid sequence that encodes an IMQ polypeptide. The disclosure also provides feed, meal, grain, or seed comprising the IMQ polypeptide, or an ortholog thereof.

Various methods for the introduction of a desired polynucleotide sequence encoding the desired protein into plant cells are available and known to those of skill in the art and include, but are not limited to: (1) physical methods such as microinjection, electroporation, and microprojectile mediated delivery (biolistics or gene gun technology); (2) virus mediated delivery methods; and (3) Agrobacterium-mediated transformation methods (see, for example, WO 2007/053482 and WO 2005/107437, which are incorporated herein by reference in their entirety).

The most commonly used methods for transformation of plant cells are the Agrobacterium-mediated DNA transfer process and the biolistics or microprojectile bombardment mediated process (i.e., the gene gun). Typically, nuclear transformation is desired but where it is desirable to specifically transform plastids, such as chloroplasts or amyloplasts, plant plastids may be transformed utilizing a microprojectile-mediated delivery of the desired polynucleotide.

Agrobacterium-mediated transformation is achieved through the use of a genetically engineered soil bacterium belonging to the genus Agrobacterium. A number of wild-type and disarmed strains of Agrobacterium tumefaciens and Agrobacterium rhizogenes harboring Ti or Ri plasmids can be used for gene transfer into plants. Gene transfer is done via the transfer of a specific DNA known as "T-DNA" that can be genetically engineered to carry any desired piece of DNA into many plant species.

Agrobacterium-mediated genetic transformation of plants involves several steps. The first step, in which the virulent Agrobacterium and plant cells are first brought into contact with each other, is generally called "inoculation." Following the inoculation, the Agrobacterium and plant cells/tissues are permitted to be grown together for a period of several hours to several days or more under conditions suitable for growth and T-DNA transfer. This step is termed "co-culture." Following co-culture and T-DNA delivery, the plant cells are treated with bactericidal or bacteriostatic agents to kill the Agrobacterium remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps.

With respect to microprojectile bombardment (U.S. Pat. Nos. 5,550,318; 5,538,880, 5,610,042; and PCT Publication WO 95/06128; each of which is specifically incorporated herein by reference in its entirety), particles are coated with nucleic acids and delivered into cells by a propelling force. Exemplary particles include those comprised of tungsten, platinum, and preferably, gold.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension.

Microprojectile bombardment techniques are widely applicable, and may be used to transform virtually any plant species. Examples of species that have been transformed by microprojectile bombardment include monocot species such as maize (PCT Publication No. WO 95/06128), barley, wheat (U.S. Pat. No. 5,563,055, incorporated herein by reference in its entirety), rice, oat, rye, sugarcane, and sorghum, as well as a number of dicots including tobacco, soybean (U.S. Pat. No. 5,322,783, incorporated herein by reference in its entirety), sunflower, peanut, cotton, tomato, and legumes in general (U.S. Pat. No. 5,563,055, incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to GUS, green fluorescent protein (GFP), luciferase (LUX), antibiotic or herbicide tolerance genes. Examples of antibiotic resistance genes include the penicillins, kanamycin (and neomycin, G418, bleomycin), methotrexate (and trimethoprim), chloramphenicol, and tetracycline. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. Nos. 5,627,061, 5,633,435, and 6,040,497 and aroA described in U.S. Pat. No. 5,094,945 for glyphosate tolerance; a polynucleotide molecule encoding bromoxynil nitrilase (Bxn) described in U.S. Pat. No. 4,810,648 for Bromoxynil tolerance; a polynucleotide molecule encoding phytoene desaturase (crtI) described in Misawa et al., (*Plant J.* 4:833-840, 1993) and Misawa et al., (*Plant J.* 6:481-489, 1994) for norflurazon tolerance; a polynucleotide molecule encoding acetohydroxyacid synthase (AHAS, also known as ALS) described in Sathasiivan et al. (*Nucl. Acids Res.* 18:2188-2193, 1990) for tolerance to sulfonylurea herbicides; and the bar gene described in DeBlock, et al., (*EMBO J.* 6:2513-2519, 1987) for glufosinate and bialaphos tolerance.

The regeneration, development, and cultivation of plants from various transformed explants are well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil less plant growth mix, and hardened off, prior to transfer to a greenhouse or growth chamber for maturation.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

Any suitable plant culture medium can be used. Examples of suitable media would include but are not limited to MS-based media (Murashige and Skoog, *Physiol. Plant,* 15:473-497, 1962) or $N^6$-based media (Chu et al., *Scientia Sinica* 18:659, 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

One of ordinary skill will appreciate that, after an expression cassette is stably incorporated in transgenic plants and confirmed to be operable, it can be introduced into other plants by sexual crossing. Any of a number of standard breeding techniques can be used, depending upon the species to be crossed.

Identification of Plants with an Improved Oil Quantity Phenotype and/or Improved Meal Quality Phenotype An *Arabidopsis* activation tagging screen (ACTTAG) was used to identify the association between 1) ACTTAG plant lines with an altered protein, fiber and/or oil content (phenotype, for example, see columns 4, 5 and 6, respectively, of Table 1, below) and 2) the nucleic acid sequences identified in column 3 of Tables 2 and 3, wherein each nucleic acid sequence is provided with a gene alias or an IMQ designation (IMQ#; see column 1 in Tables 1, 2, and 3). Briefly, and as further described in the Examples, a large number of *Arabidopsis* plants were mutated with the pSKI015 vector, which comprises a T-DNA from the Ti plasmid of *Agrobacterium tumefaciens*, a viral enhancer element, and a selectable marker gene (Weigel et al., 2000, *Plant Physiology,* 122: 1003-1013). When the T-DNA inserts into the genome of transformed plants, the enhancer element can cause up-regulation of genes in the vicinity, generally within about nine kilobases (kb) of the enhancers. T1 plants were exposed to the selective agent in order to specifically recover transformed plants that expressed the selectable marker and therefore harbored T-DNA insertions. T1 plants were allowed to grow to maturity, self-fertilize and produce seed. T2 seed was harvested, labeled and stored. To amplify the seed stocks, about eighteen T2 were sown in soil and, after germination, exposed to the selective agent to recover transformed T2 plants. T3 seed from these plants was harvested and pooled. Oil, protein and fiber content of the seed were estimated using Near Infrared Spectroscopy (NIR) as described in the Examples.

Quantitative determination of fatty acid (FA) content (column 7, Table 1) in T2 seeds was performed using the following methods. A sample of 15 to 20 T2 seeds from each line tested. This sample generally contained plants with homozygous insertions, no insertions, and hemizygous insertions in a standard 1:1:2 ratios. The seed sample was massed on UMT-2 ultra-microbalance (Mettler-Toledo Co., Ohio, USA) and then transferred to a glass extraction vial. Lipids were extracted from the seeds and trans-esterified in 500 µl 2.5% $H_2SO_4$ in MeOH for 3 hours at 80° C., following the method of Browse et al. (Biochem J 235:25-31, 1986) with modifications. A known amount of heptadecanoic acid was included in the reaction as an internal standard. 750 µl of water and 400 µl of hexane were added to each vial, which was then shaken vigorously and allowed to phase separate. Reaction vials were loaded directly onto gas chromatography (GC) for analysis and the upper hexane phase was sampled by the autosampler. Gas chromatography with Flame Ionization detection was used to separate and quantify the fatty acid methyl esters. Agilent 6890 Plus GC's were used for separation with Agilent Innowax columns (30 m×0.25 mm ID, 250 um film thickness). The carrier gas was Hydrogen at a constant flow of 2.5 ml/minute. 1 ul of sample was injected in splitless mode (inlet temperature 220° C., Purge flow 15 ml/min at 1 minute). The oven was programmed for an initial temperature of 105° C., initial time 0.5 minutes, followed by a ramp of 60° C. per minute to 175° C., a 40° C./minute ramp to 260° C. with a final hold time of 2 minutes. Detection was by Flame Ionization (Temperature 275° C., Fuel flow 30.0 ml/min, Oxidizer 400.0 ml/min). Instrument control and data collection and analysis were monitored using the Millennium Chromatography Management System (Version 3.2, Waters Corporation, Milford, Mass.). Peaks were initially identified by comparison with standards. Integration and quantification were performed automatically, but all analyses were subsequently examined manually to verify correct peak identification and acceptable signal to noise ratio before inclusion of the derived results in the study.

The association of an IMQ nucleic acid sequence with an IMQ phenotype or an IOQ phenotype was discovered by analysis of the genomic DNA sequence flanking the T-DNA insertion in the ACTTAG line identified in column 3 of Table 1. An ACTTAG line is a family of plants derived from a single plant that was transformed with a T-DNA element containing four tandem copies of the CaMV 35S enhancers. Accordingly, the disclosed IMQ nucleic acid sequences and/or polypeptides may be employed in the development of transgenic plants having an improved seed quality phenotype, including an IMQ phenotype and/or an IOQ phenotype. IMQ nucleic acid sequences may be used in the generation of transgenic plants, such as oilseed crops, that provide improved oil yield from oilseed processing and result in an increase in the quantity of oil recovered from seeds of the transgenic plant. IMQ nucleic acid sequences may also be used in the generation of transgenic plants, such as feed grain crops, that provide an IMQ phenotype resulting in increased energy for animal feeding, for example, seeds or seed meal with an altered protein and/or fiber content, resulting in an increase in AME. IMQ nucleic acid sequences may further be used to increase the oil content of specialty oil crops, in order to augment yield and/or recovery of desired unusual fatty acids. Transgenic plants that have been genetically modified to express IMQ polypeptides can be used in the production of seeds, wherein the transgenic plants are grown, and oil and seed meal are *obtained* from plant parts (e.g. seed) using standard methods.

IMQ Nucleic Acids and Polypeptides

The IMQ designation for each of the IMQ nucleic acid sequences discovered in the activation tagging screen described herein are listed in column 1 of Tables 1-3, below. The disclosed IMQ polypeptides are listed in column 5 of Table 2 and column 4 of Table 3. As used herein, the term "IMQ polypeptide" refers to any polypeptide that when expressed in a plant causes an IMQ phenotype and/or an IOQ phenotype in any part of the plant, for example the seeds. In one embodiment, an IMQ polypeptide refers to a full-length IMQ protein, or a fragment, derivative (variant), or ortholog thereof that is "functionally active," such that the protein fragment, derivative, or ortholog exhibits one or more or the functional activities associated with one or more of the disclosed full-length IMQ polypeptides, for example, the amino acid sequences provided in the GenBank entry referenced in column 5 of Table 2, which correspond to the amino acid sequences set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, or SEQ ID NO: 122, or an ortholog thereof. In one preferred embodiment, a functionally active IMQ polypeptide causes an IMQ phenotype and/or an IOQ phenotype in a transgenic plant. In another embodiment, a functionally active IMQ polypeptide causes an altered oil, protein, and/or fiber content phenotype (for example, an altered seed meal content phenotype) when mis-expressed in a plant. In other preferred embodiments, mis-expression of the IMQ polypeptide causes a high oil (such as, increased oil), high protein (such as, increased protein), and/or low fiber (such as, decreased fiber) phenotype in a plant. In another embodiment, mis-expression of the IMQ polypeptide causes an improved AME of meal. In yet another embodiment, a functionally active IMQ polypeptide can rescue defective (including deficient) endogenous IMQ activity when expressed in a plant or in plant cells; the rescuing polypeptide may be from the same or from a different species as the species with the defective polypeptide activity. The disclosure also provides feed, meal, grain, food, or seed comprising the IMQ polypeptide, or a fragment, derivative (variant), or ortholog thereof.

In another embodiment, a functionally active fragment of a full length IMQ polypeptide (for example, a functionally active fragment of a native polypeptide having the amino acid sequence set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, or SEQ ID NO: 122, or a naturally occurring ortholog thereof) retains one or more of the biological properties associated with the full-length IMQ polypeptide, such as signaling activity, binding activity, catalytic activity, or cellular or extra-cellular localizing activity. An IMQ fragment preferably comprises an IMQ domain, such as a C- or N-terminal or catalytic domain, among others, and preferably comprises at least 10, preferably at least 20, more preferably at least 25, and most preferably at least 50 contiguous amino acids of an IMQ protein. Functional domains of IMQ genes are listed in column 8 of Table 2 and can be identified using the PFAM program (Bateman A et al., 1999, *Nucleic Acids Res.* 27:260-262) or INTERPRO (Mulder et al., 2003, *Nucleic Acids Res.* 31, 315-318) program. Functionally active variants of full-length IMQ polypeptides, or fragments thereof, include polypeptides with amino acid insertions, deletions, or substitutions that retain one of more of the biological properties associated with the full-length IMQ polypeptide. In some cases, variants are generated that change the post-translational processing of an IMQ polypeptide. For instance, variants may have altered protein transport or protein localization characteristics, or altered protein half-life, compared to the native polypeptide.

As used herein, the term "IMQ nucleic acid" refers to any polynucleotide that when expressed in a plant causes an IMQ phenotype and/or an IOQ phenotype in any part of the plant, for example the seeds. In one embodiment, an IMQ polynucleotide encompasses nucleic acids with the sequence provided in or complementary to the GenBank entry referenced in column 3 of Table 2, which correspond to nucleic acid sequences set forth as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, or SEQ ID NO: 121, as well as functionally active fragments, derivatives, or orthologs thereof. An IMQ nucleic acid of this disclosure may be DNA, derived from genomic DNA or cDNA, or RNA. Genomic sequences of the genes listed in Table 2 are known and available in public databases such as GenBank.

In one embodiment, a functionally active IMQ nucleic acid encodes or is complementary to a nucleic acid that encodes a functionally active IMQ polypeptide. A functionally active IMQ nucleic acid also includes genomic DNA that serves as a template for a primary RNA transcript (i.e., an mRNA precursor) that requires processing, such as splicing, before encoding the functionally active IMQ polypeptide. An IMQ nucleic acid can include other non-coding sequences, which may or may not be transcribed; such sequences include 5' and 3' UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed IMQ polypeptide, or an intermediate form. An IMQ polynucleotide can also include heterologous coding sequences, for example, sequences that encode a marker included to facilitate the purification of the fused polypeptide, or a transformation marker. In another embodiment, a functionally active IMQ nucleic acid is capable of being used in the generation of loss-of-function IMQ phenotypes, for instance, via antisense suppression, co-suppression, etc. The disclosure also provides feed, meal, grain, food, or seed comprising a nucleic acid sequence that encodes an IMQ polypeptide.

In one preferred embodiment, an IMQ nucleic acid used in the disclosed methods comprises a nucleic acid sequence that encodes, or is complementary to a sequence that encodes, an IMQ polypeptide having at least 50%, 60%, 70%, 75%, 80%, 85%, 90%, 95%, 97%, 98%, or 99% sequence identity to a disclosed IMQ polypeptide sequence, for example the amino acid sequence set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, or SEQ ID NO: 122.

In another embodiment, an IMQ polypeptide comprises a polypeptide sequence with at least 50% or 60% identity to a disclosed IMQ polypeptide sequence (for example, the amino acid sequence set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, or SEQ ID NO: 122) and may have at least 70%, 80%, 85%, 90%, 95%, 97%, 98%, or 99% sequence identity to a disclosed IMQ polypeptide sequence. In a further embodiment, an IMQ polypeptide comprises 50%, 60%, 70%, 80%, 85%, 90%, 95%, 97%, 98%, or 99% sequence identity to a disclosed IMQ polypeptide sequence, and may include a conserved protein domain of the IMQ polypeptide (such as the protein domain(s) listed in column 8 of Table 2). In another embodiment, an IMQ polypeptide comprises a polypeptide sequence with at least 50%, 60%, 70%, 80%, 85%, 90%, 95%, 97%, 98%, or 99% sequence identity to a functionally active fragment of the polypeptide referenced in column 5 of Table 2. In yet another embodiment, an IMQ polypeptide comprises a polypeptide sequence with at least 50%, 60%, 70%, 80%, 90%, 95%, 97%, 98%, or 99% identity to the polypeptide sequence of the GenBank entry referenced in column 5 of Table 2 over its entire length and comprises a conserved protein domain(s) listed in column 8 of Table 2.

In another aspect, an IMQ polynucleotide sequence is at least 50% to 60% identical over its entire length to a disclosed IMQ nucleic acid sequence, such as the nucleic acid sequence set forth as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, or SEQ ID NO: 121, or nucleic acid sequences that are complementary to such an IMQ sequence, and may comprise at least 70%, 80%, 85%, 90%, 95%, 97%, 98%, or 99% sequence identity to the disclosed IMQ sequence, or a functionally active fragment thereof, or complementary sequences. In another embodiment, a disclosed IMQ nucleic acid comprises a nucleic acid sequence as shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, or SEQ ID NO: 121, or nucleic acid sequences that are complementary to such an IMQ sequence, and nucleic acid sequences that have substantial sequence homology to a such IMQ sequences. As used herein, the phrase "substantial sequence homology" refers to those nucleic acid sequences that have slight or inconsequential sequence variations from such IMQ sequences, i.e., the sequences function in substantially the same manner and encode an IMQ polypeptide.

As used herein, "percent (%) sequence identity" with respect to a specified subject sequence, or a specified portion thereof, is defined as the percentage of nucleotides or amino acids in an identified sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., *J. Mol. Biol.*, 1990, 215:403-410) with search parameters set to default values. The HSP S and HSP S2 parameters are dynamic values and are established by the program itself depending upon the composition of the particular sequence and composition of the particular database against which the sequence of interest is being searched. A "percent (%) identity value" is determined by the number of matching identical nucleotides or amino acids divided by the sequence length for which the percent identity is being reported. "Percent (%) amino acid sequence similarity" is determined by performing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that selectively hybridize to the disclosed IMQ nucleic acid sequences (for example, the nucleic acid sequence set forth as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, or SEQ ID NO: 121). The stringency of hybridization can be controlled by temperature, ionic strength, pH, and the presence of denaturing agents such as formamide during hybridization and washing. Conditions routinely used are well known (see, e.g., *Current Protocol in Molecular Biology*, Vol. 1, Chap. 2.10, John Wiley & Sons, Publishers (1994); Sambrook et al., 1989, Molecular Cloning: A Laboratory Manual (Second Edition), Cold Spring Harbor Press, Plainview, N.Y.).

In some embodiments, a nucleic acid molecule of the disclosure is capable of hybridizing to a nucleic acid molecule containing the disclosed nucleotide sequence under stringent hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate). In other embodiments, moderately stringent hybridization conditions are used that are: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding an IMQ polypeptide can be produced. For example, codons may be selected to increase the rate at which expression of the polypeptide occurs in a particular host species, in accordance with the optimum codon usage dictated by the particular host organism (see, e.g., Nakamura et al., 1999, *Nucleic Acids Res.* 27:292). Such sequence variants may be used in the methods disclosed herein.

The disclosed methods may use orthologs of a disclosed *Arabidopsis* IMQ nucleic acid sequence. Representative putative orthologs of each of the disclosed *Arabidopsis* IMQ genes are identified in column 3 of Table 3, below. Methods of identifying the orthologs in other plant species are known in the art. In general, orthologs in different species retain the same function, due to presence of one or more protein motifs and/or 3-dimensional structures. In evolution, when a gene duplication event follows speciation, a single gene in one species, such as *Arabidopsis*, may correspond to multiple genes (paralogs) in another. As used herein, the term "orthologs" encompasses paralogs. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, 1998, *Proc. Natl. Acad. Sci.*, 95:5849-5856; Huynen M A et al., 2000, *Genome Research,* 10:1204-1210). Programs for multiple sequence alignment, such as CLUSTAL (Thompson J D et al., 1994, *Nucleic Acids Res.* 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, 1989, *Molecular Cloning: A Laboratory Manual* (Second Edition), Cold Spring Harbor Press, Plainview, N.Y.; Dieffenbach and Dveksler, 1995, *PCR Primer: A Laboratory Manual*, Cold Spring Harbor Laboratory Press, NY). For instance, methods for generating a cDNA library from the plant species of interest and probing the library with partially homologous gene probes are described in Sambrook et al. A highly conserved portion of the *Arabidopsis* IMQ coding sequence may be used as a probe. IMQ ortholog nucleic acids may hybridize to the nucleic acid of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, or SEQ ID NO: 121 under high, moderate, or low stringency conditions. After amplification or isolation of a segment of a putative ortholog, that segment may be cloned and sequenced by standard techniques and utilized as a probe to isolate a complete cDNA or genomic DNA clone.

Alternatively, it is possible to initiate an EST project to generate a database of sequence information for the plant species of interest. In another approach, antibodies that specifically bind known IMQ polypeptides are used for ortholog isolation (see, e.g., Harlow and Lane, 1988, 1999, *Antibodies: A Laboratory Manual,* Cold Spring Harbor Laboratory Press, New York). Western blot analysis can determine that an IMQ ortholog (i.e., a protein orthologous to a disclosed IMQ polypeptide) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., 1989. Once the candidate ortholog(s) are identified by any of these means, candidate orthologous sequence are used as bait (the "query") for the reverse BLAST against sequences from *Arabidopsis* or other species in which IMQ nucleic acid and/or polypeptide sequences have been identified.

IMQ nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel T A et al., 1991, *Methods Enzymol.* 204:125-39), may be used to introduce desired changes into a cloned nucleic acid.

In general, the methods disclosed herein involve incorporating the desired form of the IMQ nucleic acid into a plant expression vector for transformation of plant cells, and the IMQ polypeptide is expressed in the host plant. Transformed plants and plant cells expressing an IMQ polypeptide express an IMQ phenotype and/or an IOQ phenotype and, in one specific, non-limiting example, may have high (increased) oil, high (increased) protein, and/or low (decreased) fiber content.

An "isolated" IMQ nucleic acid molecule is other than in the form or setting in which it is found in nature, and is identified and separated from least one contaminant nucleic acid molecule with which it is ordinarily associated in the natural source of the IMQ nucleic acid. However, an isolated IMQ nucleic acid molecule includes IMQ nucleic acid molecules contained in cells that ordinarily express IMQ where, for example, the nucleic acid molecule is in a chromosomal location different from that of natural cells.

Generation of Genetically Modified Plants with an Improved Oil Quantity Phenotype and/or an Improved Meal Quality Phenotype The disclosed IMQ nucleic acids and polypeptides may be used in the generation of transgenic plants having a modified or altered oil, protein, and/or fiber content phenotype. As used herein, an "altered oil content (phenotype)" may refer to altered oil content in any part of the plant. In a preferred embodiment, altered expression of the IMQ gene in a plant is used to generate plants with a high oil content (phenotype). As used herein, an "altered protein content (phenotype)" may refer to altered protein content in any part of the plant. In a preferred embodiment, altered expression of the IMQ gene in a plant is used to generate plants with a high (or increased)

protein content (phenotype). As used herein, an "altered fiber content (phenotype)" may refer to altered fiber content in any part of the plant. In a preferred embodiment, altered expression of the IMQ gene in a plant is used to generate plants with a low (or decreased) fiber content (phenotype). The altered oil, protein, and/or fiber content is often observed in seeds. Examples of a transgenic plant include plants comprising a plant transformation vector with a nucleotide sequence that encodes or is complementary to a sequence that encodes an IMQ polypeptide having the amino acid sequence as set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, or SEQ ID NO: 122, or an ortholog thereof.

Transgenic plants, such as corn, soybean and canola containing the disclosed nucleic acid sequences, can be used in the production of vegetable oil and meal. Vegetable oil is used in a variety of food products, while meal from seed is used as an animal feed. After harvesting seed from transgenic plants, the seed is cleaned to remove plant stalks and other material and then flaked in roller mills to break the hulls. The crushed seed is heated to 75-100° C. to denature hydrolytic enzymes, lyse the unbroken oil containing cells, and allow small oil droplets to coalesce. Most of the oil is then removed (and can be recovered) by pressing the seed material in a screw press. The remaining oil is removed from the presscake by extraction with and organic solvents, such as hexane. The solvent is removed from the meal by heating it to approximately 100° C. After drying, the meal is then granulated to a consistent form. The meal, containing the protein, digestible carbohydrate, and fiber of the seed, may be mixed with other materials prior to being used as an animal feed.

The methods described herein for generating transgenic plants are generally applicable to all plants. Although activation tagging and gene identification is carried out in *Arabidopsis*, the IMQ nucleic acid sequence (or an ortholog, variant or fragment thereof) may be expressed in any type of plant. In a preferred embodiment, oil-producing plants produce and store triacylglycerol in specific organs, primarily in seeds. Such species include soybean (*Glycine max*), rapeseed and canola (including *Brassica napus, B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*), and peanut (*Arachis hypogaea*), as well as wheat, rice and oat. Fruit- and vegetable-bearing plants, grain-producing plants, nut-producing plants, rapid cycling *Brassica* species, alfalfa (*Medicago sativa*), tobacco (*Nicotiana*), turfgrass (Poaceae family), other forage crops, and wild species may also be a source of unique fatty acids. In other embodiments, any plant expressing the IMQ nucleic acid sequence can also express increased protein and/or decreased fiber content in a specific plant part or organ, such as in seeds.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to, as a strand of DNA, in a plasmid, or in an artificial chromosome. The introduction of the constructs into the target plant cells can be accomplished by a variety of techniques, including, but not limited to, *Agrobacterium*-mediated transformation, electroporation, microinjection, microprojectile bombardment, calcium-phosphate-DNA co-precipitation, or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising an IMQ polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.). A construct or vector may include a plant promoter to express the nucleic acid molecule of choice. In a preferred embodiment, the promoter is a plant promoter.

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature. Of particular relevance are methods to transform commercially important crops, such as plants of the *Brassica* species, including canola and rapeseed, (De Block et al., 1989, *Plant Physiol.*, 91:694-701), sunflower (Everett et al., 1987, *Bio/Technology*, 5:1201), soybean (Christou et al., 1989, *Proc. Natl. Acad. Sci. USA*, 86:7500-7504; Kline et al., 1987, *Nature*, 327:70), wheat, rice and oat.

Expression (including transcription and translation) of an IMQ nucleic acid sequence may be regulated with respect to the level of expression, the tissue type(s) where expression takes place and/or developmental stage of expression. A number of heterologous regulatory sequences (e.g., promoters and enhancers) are available for controlling the expression of an IMQ nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the nopaline synthase (NOS) promoter (Ebert et al., *Proc. Natl. Acad. Sci. (U.S.A.)* 84:5745-5749, 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324, 1987) and the CaMV 35S promoter (Odell et al., *Nature* 313:810-812, 1985 and Jones J D et al, 1992, *Transgenic Res.*, 1:285-297), the figwort mosaic virus $^{35}$S-promoter (U.S. Pat. No. 5,378,619), the light-inducible promoter from the small subunit of ribulose-1,5-bis-phosphate carboxylase (ss-RUBISCO), the Adh promoter (Walker et al., *Proc. Natl. Acad. Sci. (U.S.A.)* 84:6624-6628, 1987), the sucrose synthase promoter (Yang et al., *Proc. Natl. Acad. Sci. (U.S.A.)* 87:4144-4148, 1990), the R gene complex promoter (Chandler et al., *The Plant Cell* 1:1175-1183, 1989), the chlorophyll a/b binding protein gene promoter, the CsVMV promoter (Verdaguer et al., 1998, *Plant Mol Biol.*, 37:1055-1067), and the melon actin promoter (published PCT application WO0056863). Exemplary tissue-specific promoters include the tomato E4 and E8 promoters (U.S. Pat. No. 5,859,330) and the tomato 2AII gene promoter (Van Haaren et al., 1993, *Plant Mol. Bio.*, 21:625-640).

In one preferred embodiment, expression of the IMQ nucleic acid sequence is under control of regulatory sequences from genes whose expression is associated with early seed and/or embryo development. Indeed, in a preferred embodiment, the promoter used is a seed-enhanced promoter. Examples of such promoters include the 5' regulatory regions from such genes as napin (Kridl et al., *Seed Sci. Res.* 1:209-219, 1991), globulin (Belanger and Kriz, *Genet.*, 129: 863-872, 1991, GenBank Accession No. L22295), gamma zein Z 27 (Lopes et al., *Mol Gen Genet.*, 247:603-613, 1995), L3 oleosin promoter (U.S. Pat. No. 6,433,252), phaseolin (Bustos et al., Plant Cell, 1(9):839-853, 1989), arcelin5 (U.S. Application No. 2003/0046727), a soybean 7S promoter, a 7S α' promoter (U.S. Application No. 2003/0093828), the soybean 7S α' beta conglycinin promoter, a 7S α' promoter (Beachy et al., *EMBO J.*, 4:3047, 1985; Schuler et al., *Nucleic Acid Res.*, 10(24):8225-8244, 1982), soybean trypsin inhibitor (Riggs et al., *Plant Cell* 1(6):609-621, 1989), ACP (Baerson et al., *Plant Mol. Biol.*, 22(2):255-267, 1993), stearoyl-ACP desaturase (Slocombe et al., *Plant Physiol.* 104(4):167-176, 1994), soybean a' subunit of β-conglycinin (Chen et al., *Proc. Natl. Acad. Sci.* 83:8560-8564, 1986), *Vicia faba* USP (P-Vf.Usp, SEQ ID NO: 1, 2, and 3 in (U.S. Application No. 2003/229918) and *Zea mays* L3 oleosin promoter (Hong et al., *Plant Mol. Biol.*, 34(3):549-555, 1997). Also included are the zeins, which are a group of storage proteins found in corn endosperm. Genomic clones for zein genes have been isolated (Pedersen et al., *Cell*, 29:1015-1026, 1982; and Russell et al., Transgenic Res. 6(2):157-168) and the promoters from these clones, including the 15 kD, 16 kD, 19 kD, 22 kD, 27 kD and genes, could also be used. Other promoters known to function, for example, in corn include the promoters for the following genes: waxy, Brittle, Shrunken 2, Branching enzymes I and II, starch synthases, debranching enzymes, oleosins, glutelins and sucrose synthases. Legume genes whose promoters are associated with early seed and embryo development include *V. faba* legumin (Baumlein et al., 1991, *Mol. Gen. Genet.* 225:121-8; Baumlein et al., 1992, *Plant J.* 2:233-9), *V. faba* usp (Fiedler et al., 1993, *Plant Mol. Biol.* 22:669-79), pea convicilin (Bown et al., 1988, *Biochem. J.* 251:717-26), pea lectin (dePater et al., 1993, *Plant Cell* 5:877-86), *P. vulgaris* beta phaseolin (Bustos et al., 1991, *EMBO J.* 10:1469-79), *P. vulgaris* DLEC2 and PHS [beta] (Bobb et al., 1997, *Nucleic Acids Res.* 25:641-7), and soybean beta-Conglycinin, 7S storage protein (Chamberland et al., 1992, *Plant Mol. Biol.* 19:937-49).

Cereal genes whose promoters are associated with early seed and embryo development include rice glutelin ("GluA-3,"Yoshihara and Takaiwa, 1996, *Plant Cell Physiol.* 37:107-11; "GluB-1," Takaiwa et al., 1996, *Plant Mol. Biol.* 30:1207-21; Washida et al., 1999, *Plant Mol. Biol.* 40:1-12; "Gt3," Leisy et al., 1990, *Plant Mol. Biol.* 14:41-50), rice prolamin (Zhou & Fan, 1993, *Transgenic Res.* 2:141-6), wheat prolamin (Hammond-Kosack et al., 1993, *EMBO J.* 12:545-54), maize zein (Z4, Matzke et al., 1990, *Plant Mol. Biol.* 14:323-32), and barley B-hordeins (Entwistle et al., 1991, *Plant Mol. Biol.* 17:1217-31).

Other genes whose promoters are associated with early seed and embryo development include oil palm GLO7A (7S globulin, Morcillo et al., 2001, *Physiol. Plant* 112:233-243), *Brassica napus* napin, 2S storage protein, and napA gene (Josefsson et al., 1987, *J. Biol. Chem.* 262:12196-201; Stalberg et al., 1993, *Plant Mol. Biol.* 1993 23:671-83; Ellerstrom et al., 1996, *Plant Mol. Biol.* 32:1019-27), *Brassica napus* oleosin (Keddie et al., 1994, *Plant Mol. Biol.* 24:327-40), *Arabidopsis* oleosin (Plant et al., 1994, *Plant Mol. Biol.* 25:193-205), *Arabidopsis* FAE1 (Rossak et al., 2001, *Plant Mol. Biol.* 46:717-25), *Canavalia gladiata* conA (Yamamoto et al., 1995, *Plant Mol. Biol.* 27:729-41), and *Catharanthus roseus* strictosidine synthase (Str, Ouwerkerk and Memelink, 1999, *Mol. Gen. Genet.* 261:635-43). In another preferred embodiment, regulatory sequences from genes expressed during oil biosynthesis are used (see, e.g., U.S. Pat. No. 5,952,544). Alternative promoters are from plant storage protein genes (Bevan et al., 1993, *Philos. Trans. R. Soc. Lond. B. Biol. Sci.* 342:209-15). Additional promoters that may be utilized are described, for example, in U.S. Pat. Nos. 5,378, 619; 5,391,725; 5,428,147; 5,447,858; 5,608,144; 5,608,144; 5,614,399; 5,633,441; 5,633,435; and 4,633,436.

In yet another aspect, in some cases it may be desirable to inhibit the expression of the endogenous IMQ nucleic acid sequence in a host cell. Exemplary methods for practicing this aspect of the invention include, but are not limited to antisense suppression (Smith, et al., 1988, *Nature*, 334:724-726; van der Krol et al., 1988, BioTechniques, 6:958-976); co-suppression (Napoli, et al., 1990, *Plant Cell*, 2:279-289); ribozymes (PCT Publication WO 97/10328); and combinations of sense and antisense (Waterhouse, et al., 1998, *Proc. Natl. Acad. Sci. USA*, 95:13959-13964). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., 1988, *Proc. Natl. Acad. Sci. USA*, 85:8805-8809), a partial cDNA sequence including fragments of 5' coding sequence, (Cannon et al., 1990, *Plant Mol. Biol.*, 15:39-47), or 3' non-coding sequences (Ch'ng et al., 1989, *Proc. Natl. Acad. Sci. USA*, 86:10006-10010). Cosuppression techniques may use the entire cDNA sequence (Napoli et al., 1990, *Plant Cell*, 2:279-289; van der Krol et al., 1990, *Plant Cell*, 2:291-299), or a partial cDNA sequence (Smith et al., 1990, *Mol. Gen. Genetics*, 224:477-481).

Standard molecular and genetic tests may be performed to further analyze the association between a nucleic acid sequence and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include over-expression, ectopic expression, expression in other plant species and gene knock-out (reverse genetics, targeted knock-out, viral induced gene silencing (VIGS; see, Baulcombe D, 1999, *Arch. Virol. Suppl.* 15:189-201).

In a preferred application expression profiling, generally by microarray analysis, is used to simultaneously measure differences or induced changes in the expression of many different genes. Techniques for microarray analysis are well known in the art (Schena M et al., *Science* 1995 270:467-470; Baldwin D et al., 1999, *Cur. Opin. Plant Biol.* 2(2):96-103; Dangond F, *Physiol Genomics* (2000) 2:53-58; van Hal N L et al., *J Biotechnol.* (2000) 78:271-280; Richmond T and Somerville S, *Curr. Opin. Plant Biol.* 2000 3:108-116). Expression profiling of individual tagged lines may be performed. Such analysis can identify other genes that are coordinately regulated as a consequence of the over-expression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

Generation of Mutated Plants with an Improved Oil Quantity Phenotype and/or Improved Meal Quality Phenotype Additional methods are disclosed herein of generating a plant having an IMQ and/or an IOQ phenotype, wherein a plant is identified that has an allele in its IMQ nucleic acid sequence that results in an IMQ phenotype and/or an IOQ phenotype, compared to plants lacking the allele. The plant can generate progeny, wherein the progeny inherit the allele and have an IMQ phenotype and/or an IOQ phenotype. For example, provided herein is a method of identifying plants that have mutations in the endogenous IMQ nucleic acid sequence that confer an IMQ phenotype and/or an IOQ phenotype and generating progeny of these plants with an IMQ and/or IOQ phenotype that are not genetically modified. In some embodiments, the plants have an IMQ phenotype with an altered protein and/or fiber content or seed meal content, or an IOQ phenotype, with an altered oil content.

In one method, called "TILLING" (for targeting induced local lesions in genomes), mutations are induced in the seed of a plant of interest, for example, using EMS (ethylmethane sulfonate) treatment. The resulting plants are grown and self-fertilized, and the progeny are used to prepare DNA samples. PCR amplification and sequencing of the IMQ nucleic acid sequence is used to identify whether a mutated plant has a mutation in the IMQ nucleic acid sequence. Plants having IMQ mutations may then be tested for altered oil, protein, and/or fiber content, or alternatively, plants may be tested for altered oil, protein, and/or fiber content, and then PCR amplification and sequencing of the IMQ nucleic acid sequence is used to determine whether a plant having altered oil, protein, and/or fiber content has a mutated IMQ nucleic acid sequence. TILLING can identify mutations that may alter the expression of specific genes or the activity of proteins encoded by these genes (see Colbert et al., 2001, *Plant Physiol.* 126:480-484; McCallum et al., 2000, *Nature Biotechnology* 18:455-457).

In another method, a candidate gene/Quantitative Trait Locus (QTLs) approach can be used in a marker-assisted breeding program to identify alleles of or mutations in the IMQ nucleic acid sequence or orthologs of the IMQ nucleic acid sequence that may confer altered oil, protein, and/or fiber content (see Bert et al., *Theor Appl Genet.*, 2003 June; 107 (1):181-9; and Lionneton et al., Genome, 2002 December; 45(6):1203-15). Thus, in a further aspect of the disclosure, an IMQ nucleic acid is used to identify whether a plant having altered oil, protein, and/or fiber content has a mutation an endogenous IMQ nucleic acid sequence or has a particular allele that causes altered oil, protein, and/or fiber content.

While the disclosure has been described with reference to specific methods and embodiments, it will be appreciated that various modifications and changes may be made without departing from the disclosure. All publications cited herein are expressly incorporated herein by reference for the purpose of describing and disclosing compositions and methodologies that might be used in connection with the disclosure. All cited patents, patent applications, and sequence information in referenced public databases are also incorporated by reference.

EXAMPLES

Example 1

Generation of Plants with an IMQ Phenotype and/or an IOQ Phenotype by Transformation with an Activation Tagging Construct This Example describes the generation of transgenic plants with altered oil, protein, and/or fiber content.

Mutants were generated using the activation tagging "ACTTAG" vector, pSKI015 (GI#6537289; Weigel D et al., 2000, *Plant Physiology*, 122:1003-1013). Standard methods were used for the generation of *Arabidopsis* transgenic plants, and were essentially as described in published application PCT WO0183697. Briefly, T0 *Arabidopsis* (Col-0) plants were transformed with *Agrobacterium* carrying the pSKI015 vector, which comprises T-DNA derived from the *Agrobacterium* Ti plasmid, an herbicide resistance selectable marker gene, and the 4× CaMV 35S enhancer element. Transgenic plants were selected at the T1 generation based on herbicide resistance. T2 seed (from T1 plants) was harvested and sown in soil. T2 plants were exposed to the herbicide to kill plants lacking the ACTTAG vector. T2 plants were grown to maturity, allowed to self-fertilize and set seed. T3 seed (from the T2 plants) was harvested in bulk for each line.

T3 seed was analyzed by Near Infrared Spectroscopy (NIR) at the time of harvest. NIR spectra were captured using a Bruker 22 near infrared spectrometer. Bruker Software was used to estimate total seed oil, total seed protein and total seed fiber content using data from NIR analysis and reference methods according to the manufacturer's instructions. Oil content predicting calibrations were developed following the general method of AOCS Procedure Am1-92, Official Methods and Recommended Practices of the American Oil Chemists Society, 5th Ed., AOCS, Champaign, Ill. A NIR protein content predicting calibration was developed using total nitrogen content data of seed samples following the general method of Dumas Procedure AOAC 968.06 (Official Methods of Analysis of AOAC International $17^{th}$ Edition AOAC, Gaithersburg, Md.). A fiber content predicting calibration was developed by measuring crude fiber content in a set of seed samples. Fiber content of in a known mass of seed was determined using the method of Honig and Rackis, (1979, *J. Agri. Food Chem.*, 27: 1262-1266). Digestible protein content of in a known mass of seed was determined by quantifying the individual amino acids liberated by an acid hydrolysis Steine and Moore (1958, *Anal. Chem.*, 30:1185-1190). The quantification was performed by the Amino Quant (Agilent). The undigested protein remaining associated with the non digestible fraction is measured by the same method described for the whole seed homogenate. Digestible protein content is determined by subtracting the amount of undigested protein associated with the non digestible fraction from the total amount of protein in the seed sample.

Seed oil, protein, digestible protein and fiber values in 82,274 lines were determined by NIR spectroscopy and normalized to allow comparison of seed component values in plants grown at different times. Oil, protein and fiber values were normalized by calculating the average oil, protein and fiber values in seed from all plants planted on the same day (including a large number of other ACTTAG plants, including control, wild-type, or non-transgenic plants). The seed components for each line was expressed as a "percent relative value" which was calculated by dividing the component value for each line with the average component value for all lines planted on the same day (which should approximate the value in control, wild-type, or non-transgenic plants). The "percent relative protein" and "percent relative fiber" were calculated similarly.

Inverse PCR was used to recover genomic DNA flanking the T-DNA insertion. The PCR product was subjected to sequence analysis and placed on the genome using a basic BLASTN search and/or a search of the *Arabidopsis* Information Resource (TAIR) database (available at the publicly available website). Promoters within 9 kb of the enhancers in the ACTTAG element are considered to be within "activation space." Genes with T-DNA inserts within coding sequences were not considered to be within "activation space." The ACTTAG lines with the above average oil and protein values, and below average fiber values were identified and are listed in column 3 of Table 1.

TABLE 1

| 1. Gene alias | 2. Tair | 3. ACTTAG Line | 4. Relative Seed Protein Content | 5. Relative Seed Fiber Content | 6. Relative Seed Oil Content | 7. GC FA |
|---|---|---|---|---|---|---|
| IMQ66.4 | At4g30810 | W000092135 | 105.82% | 89.32% | 100.61% | |
| IMQ67.1 | At4g32230 | W000148824 | 126.48% | 88.73% | 86.88% | |
| IMQ67.2 | At4g32240 | W000148824 | 126.48% | 88.73% | 86.88% | 93.73% |
| IMQ67.3 | At4g32250 | W000148824 | 126.48% | 88.73% | 86.88% | |
| IMQ67.3 | At4g32250 | W000148824 | 126.48% | 88.73% | 86.88% | |
| IMQ67.3 | At4g32250 | W000148824 | 126.48% | 88.73% | 86.88% | |
| IMQ67.4 | At4g32260 | W000148824 | 126.48% | 88.73% | 86.88% | |
| IMQ68.1 | At4g36560 | W000203116 | 74.59% | 97.16% | 124.22% | |
| IMQ68.2 | At4g36570 | W000203116 | 74.59% | 97.16% | 124.22% | |
| IMQ68.3 | At4g36580 | W000203116 | 74.59% | 97.16% | 124.22% | |
| IMQ68.4 | At4g36590 | W000203116 | 74.59% | 97.16% | 124.22% | |
| IMQ68.5 | At4g36600 | W000203116 | 74.59% | 97.16% | 124.22% | |
| IMQ69.1 | At4g38510 | W000050668 | 106.15% | 91.34% | 95.23% | |
| IMQ69.1 | At4g38510 | W000050668 | 106.15% | 91.34% | 95.23% | |
| IMQ69.1 | At4g38510 | W000050668 | 106.15% | 91.34% | 95.23% | |
| IMQ69.1 | At4g38510 | W000050668 | 106.15% | 91.34% | 95.23% | |
| IMQ69.2 | At4g38520 | W000050668 | 106.15% | 91.34% | 95.23% | |
| IMQ69.2 | At4g38520 | W000050668 | 106.15% | 91.34% | 95.23% | |
| IMQ69.2 | At4g38520 | W000050668 | 106.15% | 91.34% | 95.23% | |
| IMQ69.3 | At4g38530 | W000050668 | 106.15% | 91.34% | 95.23% | 104.43% |
| IMQ69.4 | At4g38540 | W000050668 | 106.15% | 91.34% | 95.23% | 104.43% |
| IMQ69.5 | At4g38550 | W000050668 | 106.15% | 91.34% | 95.23% | |
| IMQ69.6 | At4g38560 | W000050668 | 106.15% | 91.34% | 95.23% | |
| IMQ69.7 | At4g38570 | W000050668 | 106.15% | 91.34% | 95.23% | |
| IMQ70.1 | At5g11820 | W000088626 | 111.40% | 91.87% | 89.89% | |
| IMQ70.2 | At5g11830 | W000088626 | 111.40% | 91.87% | 89.89% | |
| IMQ70.3 | At5g11840 | W000088626 | 111.40% | 91.87% | 89.89% | |
| IMQ70.4 | At5g11850 | W000088626 | 111.40% | 91.87% | 89.89% | |
| IMQ70.5 | At5g11860 | W000088626 | 111.40% | 91.87% | 89.89% | |
| IMQ70.5 | At5g11860 | W000088626 | 111.40% | 91.87% | 89.89% | |
| IMQ70.5 | At5g11860 | W000088626 | 111.40% | 91.87% | 89.89% | |
| IMQ70.6 | At5g11870 | W000088626 | 111.40% | 91.87% | 89.89% | |
| IMQ70.7 | At5g11880 | W000088626 | 111.40% | 91.87% | 89.89% | |
| IMQ71.1 | At5g12990 | W000085787 | 140.67% | 97.38% | 76.10% | |
| IMQ71.2 | At5g13000 | W000085787 | 140.67% | 97.38% | 76.10% | 89.87% |
| IMQ71.3 | At5g13010 | W000085787 | 140.67% | 97.38% | 76.10% | 89.87% |
| IMQ72.1 | At5g15700 | W000114932 | 113.33% | 94.87% | 96.37% | |
| IMQ72.2 | At5g15710 | W000114932 | 113.33% | 94.87% | 96.37% | |
| IMQ72.3 | At5g15720 | W000114932 | 113.33% | 94.87% | 96.37% | |
| IMQ72.4 | At5g15725 | W000114932 | 113.33% | 94.87% | 96.37% | |
| IMQ72.5 | At5g15730 | W000114932 | 113.33% | 94.87% | 96.37% | |
| IMQ73.1 | At5g35960 | W000154027 | 105.39% | 92.83% | 100.07% | |
| IMQ73.1 | At5g35960 | W000192343 | 102.55% | 87.48% | 105.14% | |
| IMQ73.2 | At5g35970 | W000154027 | 105.39% | 92.83% | 100.07% | |
| IMQ73.2 | At5g35970 | W000192343 | 102.55% | 87.48% | 105.14% | |
| IMQ73.3 | At5g35980 | W000154027 | 105.39% | 92.83% | 100.07% | 103.52% |
| IMQ73.3 | At5g35980 | W000192343 | 102.55% | 87.48% | 105.14% | |
| IMQ73.3 | At5g35980 | W000154027 | 105.39% | 92.83% | 100.07% | |
| IMQ73.3 | At5g35980 | W000192343 | 102.55% | 87.48% | 105.14% | |
| IMQ74.1 | At5g38530 | W000095258 | 119.82% | 93.87% | 88.43% | |
| IMQ74.2 | At5g38540 | W000095258 | 119.82% | 93.87% | 88.43% | 98.68% |
| IMQ74.3 | At5g38550 | W000095258 | 119.82% | 93.87% | 88.43% | |
| IMQ74.4 | At5g38560 | W000095258 | 119.82% | 93.87% | 88.43% | |
| IMQ75.1 | At5g40300 | W000209623 | 88.58% | 86.86% | 117.55% | 121.36% |

TABLE 1-continued

| 1. Gene alias | 2. Tair | 3. ACTTAG Line | 4. Relative Seed Protein Content | 5. Relative Seed Fiber Content | 6. Relative Seed Oil Content | 7. GC FA |
|---|---|---|---|---|---|---|
| IMQ75.2 | At5g40310 | W000209623 | 88.58% | 86.86% | 117.55% | |
| IMQ75.3 | At5g40320 | W000209623 | 88.58% | 86.86% | 117.55% | 121.36% |
| IMQ76.1 | At5g44180 | W000064064 | 118.55% | 96.22% | 85.55% | |
| IMQ77.1 | At5g62600 | W000156072 | 119.26% | 92.93% | 90.48% | |
| IMQ77.2 | At5g62610 | W000156072 | 119.26% | 92.93% | 90.48% | |
| IMQ78.1 | At5g67580 | W000156087 | 111.66% | 92.09% | 96.86% | |
| IMQ78.1 | At5g67580 | W000156087 | 111.66% | 92.09% | 96.86% | |
| IMQ78.2 | At5g67590 | W000156087 | 111.66% | 92.09% | 96.86% | |
| IMQ78.3 | At5g67600 | W000156087 | 111.66% | 92.09% | 96.86% | |
| IMQ78.4 | At5g67610 | W000156087 | 111.66% | 92.09% | 96.86% | 101.88% |
| IMQ78.4 | At5g67610 | W000156087 | 111.66% | 92.09% | 96.86% | |

TABLE 2

| 1. Gene alias | 2. Tair | 3. Nucleic Acid seq. GI# | 4. SEQ ID NO | 5. Polypeptide seq. GI# | 6. SEQ ID NO | 7. Putative biochemical function/protein name | 8. Conserved protein domain |
|---|---|---|---|---|---|---|---|
| IMQ66.4 | At4g30810 | gi\|30688809 | SEQ ID NO: 1 | gi\|18417667 | SEQ ID NO: 2 | SCPL29; catalytic/ serine carboxypeptidase | IPR000379 Esterase/lipase/thioesterase; IPR001563 Peptidase S10, serine carboxypeptidase |
| IMQ67.1 | At4g32230 | gi\|18417967 | SEQ ID NO: 3 | gi\|15236713 | SEQ ID NO: 4 | unknown protein | IPR000719 Protein kinase |
| IMQ67.2 | At4g32240 | gi\|42567326 | SEQ ID NO: 5 | gi\|18417969 | SEQ ID NO: 6 | unknown protein | |
| IMQ67.3 | At4g32250 | gi\|79326107 | SEQ ID NO: 7 | gi\|79326108 | SEQ ID NO: 8 | ATP binding/kinase/ protein kinase/ protein serine/threonine kinase/protein-tyrosine kinase | IPR000719 Protein kinase; IPR008271 Serine/threonine protein kinase, active site |
| IMQ67.3 | At4g32250 | gi\|30689315 | SEQ ID NO: 9 | gi\|30689316 | SEQ ID NO: 10 | ATP binding/kinase/ protein kinase/ protein serine/threonine kinase/protein-tyrosine kinase | IPR000719 Protein kinase; IPR008271 Serine/threonine protein kinase, active site |
| IMQ67.3 | At4g32250 | gi\|30689320 | SEQ ID NO: 11 | gi\|22329080 | SEQ ID NO: 12 | ATP binding/kinase/ protein kinase/ protein serine/threonine kinase/protein-tyrosine kinase | IPR000719 Protein kinase; IPR008271 Serine/threonine protein kinase, active site |
| IMQ67.4 | At4g32260 | gi\|30689323 | SEQ ID NO: 13 | gi\|15236722 | SEQ ID NO: 14 | hydrolase, acting on acid anhydrides, catalyzing transmembrane movement of substances | IPR002146 H+-transporting two-sector ATPase, B/B' subunit; IPR005864 ATP synthase F0, subunit B |
| IMQ68.1 | At4g36560 | gi\|18419861 | SEQ ID NO: 15 | gi\|15234443 | SEQ ID NO: 16 | unknown protein | |
| IMQ68.2 | At4g36570 | gi\|18419863 | SEQ ID NO: 17 | gi\|15234454 | SEQ ID NO: 18 | DNA binding/ transcription factor | IPR001005 Myb, DNA-binding |
| IMQ68.3 | At4g36580 | gi\|18419864 | SEQ ID NO: 19 | gi\|15234455 | SEQ ID NO: 20 | ATP binding/ ATPase/nucleoside-triphosphatase/ nucleotide binding | IPR000641 CbxX/CfqX; IPR003593 AAA ATPase; IPR003959 AAA ATPase, central region; IPR003960 AAA-protein subdomain |
| IMQ68.4 | At4g36590 | gi\|18419866 | SEQ ID NO: 21 | gi\|15234456 | SEQ ID NO: 22 | DNA binding/ transcription factor | IPR002100 Transcription factor, MADS-box |
| IMQ68.5 | At4g36600 | gi\|30690703 | SEQ ID NO: 23 | gi\|30690704 | SEQ ID NO: 24 | unknown protein | IPR004238 Late embryogenesis abundant protein |
| IMQ69.1 | At4g38510 | gi\|79326467 | SEQ ID NO: 25 | gi\|79326468 | SEQ ID NO: 26 | ATP binding/ hydrogen-exporting ATPase, phosphorylative mechanism/hydrogen-transporting ATP synthase, rotational | IPR000194 H+-transporting two-sector ATPase, alpha/beta subunit, central region; IPR000793 H+-transporting two-sector ATPase, alpha/beta subunit, C-terminal; IPR004100 H+-transporting |

TABLE 2-continued

| 1. Gene alias | 2. Tair | 3. Nucleic Acid seq. GI# | 4. SEQ ID NO | 5. Polypeptide seq. GI# | 6. SEQ ID NO | 7. Putative biochemical function/protein name | 8. Conserved protein domain |
|---|---|---|---|---|---|---|---|
| | | | | | | mechanism/hydrogen-transporting ATPase, rotational mechanism | two-sector ATPase, alpha/beta subunit, N-terminal; IPR005723 ATP synthase V-type, B subunit |
| IMQ69.1 | At4g38510 | gi\|79326459 | SEQ ID NO: 27 | gi\|79326460 | SEQ ID NO: 28 | ATP binding/hydrogen-exporting ATPase, phosphorylative mechanism/hydrogen-transporting ATP synthase, rotational mechanism/hydrogen-transporting ATPase, rotational mechanism | IPR000194 H+-transporting two-sector ATPase, alpha/beta subunit, central region; IPR000793 H+-transporting two-sector ATPase, alpha/beta subunit, C-terminal; IPR004100 H+-transporting two-sector ATPase, alpha/beta subunit, N-terminal; IPR005723 ATP synthase V-type, B subunit |
| IMQ69.1 | At4g38510 | gi\|42573220 | SEQ ID NO: 29 | gi\|42573221 | SEQ ID NO: 30 | ATP binding/hydrogen-exporting ATPase, phosphorylative mechanism/hydrogen-transporting ATP synthase, rotational mechanism/hydrogen-transporting ATPase, rotational mechanism | IPR000194 H+-transporting two-sector ATPase, alpha/beta subunit, central region; IPR000793 H+-transporting two-sector ATPase, alpha/beta subunit, C-terminal; IPR004100 H+-transporting two-sector ATPase, alpha/beta subunit, N-terminal; IPR005723 ATP synthase V-type, B subunit |
| IMQ69.1 | At4g38510 | gi\|30691994 | SEQ ID NO: 31 | gi\|15233891 | SEQ ID NO: 32 | ATP binding/hydrogen-exporting ATPase, phosphorylative mechanism/hydrogen-transporting ATP synthase, rotational mechanism/hydrogen-transporting ATPase, rotational mechanism | IPR000194 H+-transporting two-sector ATPase, alpha/beta subunit, central region; IPR000793 H+-transporting two-sector ATPase, alpha/beta subunit, C-terminal; IPR004100 H+-transporting two-sector ATPase, alpha/beta subunit, N-terminal; IPR005723 ATP synthase V-type, B subunit |
| IMQ69.2 | At4g38520 | gi\|42573222 | SEQ ID NO: 33 | gi\|42573223 | SEQ ID NO: 34 | protein phosphatase 2C family protein/PP2C family protein | IPR000222 Protein phosphatase 2C; IPR001932 Protein phosphatase 2C-like |
| IMQ69.2 | At4g38520 | gi\|42567510 | SEQ ID NO: 35 | gi\|22329238 | SEQ ID NO: 36 | catalytic/protein phosphatase type 2C | IPR000222 Protein phosphatase 2C; IPR001932 Protein phosphatase 2C-like |
| IMQ69.2 | At4g38520 | gi\|79313268 | SEQ ID NO: 37 | gi\|79313269 | SEQ ID NO: 38 | catalytic/protein phosphatase type 2C | IPR000222 Protein phosphatase 2C; IPR001932 Protein phosphatase 2C-like |
| IMQ69.3 | At4g38530 | gi\|79499921 | SEQ ID NO: 39 | gi\|79499922 | SEQ ID NO: 40 | ATPLC1; phospholipase C | IPR000008 C2; IPR000909 Phosphatidylinositol-specific phospholipase C, X region; IPR001192 Phosphoinositide-specific phospholipase C (PLC); IPR008973 C2 calcium/lipid-binding region, CaLB; IPR001711 Phosphatidylinositol-specific phospholipase C, Y domain; |
| IMQ69.4 | At4g38540 | gi\|30692001 | SEQ ID NO: 41 | gi\|15233923 | SEQ ID NO: 42 | monooxygenase | IPR001327 FAD-dependent pyridine nucleotide-disulphide oxidoreductase; IPR003042 Aromatic-ring hydroxylase; IPR006076 FAD dependent oxidoreductase |
| IMQ69.5 | At4g38550 | gi\|42567511 | SEQ ID NO: 43 | gi\|22329240 | SEQ ID NO: 44 | unknown protein | IPR007942 *Arabidopsis* phospholipase-like; IPR006706 Extensin-like region |
| IMQ69.6 | At4g38560 | gi\|18420262 | SEQ ID NO: 45 | gi\|15233931 | SEQ ID NO: 46 | unknown protein | IPR007942 *Arabidopsis* phospholipase-like |

TABLE 2-continued

| 1. Gene alias | 2. Tair | 3. Nucleic Acid seq. GI# | 4. SEQ ID NO | 5. Polypeptide seq. GI# | 6. SEQ ID NO | 7. Putative biochemical function/protein name | 8. Conserved protein domain |
|---|---|---|---|---|---|---|---|
| IMQ69.7 | At4g38570 | gi\|30692008 | SEQ ID NO: 47 | gi\|15233934 | SEQ ID NO: 48 | unknown protein | IPR000462 CDP-alcohol phosphatidyltransferase |
| IMQ70.1 | At5g11820 | gi\|18416683 | SEQ ID NO: 49 | gi\|15239789 | SEQ ID NO: 50 | unknown protein | IPR010264 Plant self-incompatibility S1 |
| IMQ70.2 | At5g11830 | gi\|18416686 | SEQ ID NO: 51 | gi\|15239794 | SEQ ID NO: 52 | unknown protein | IPR010264 Plant self-incompatibility S1 |
| IMQ70.3 | At5g11840 | gi\|18416688 | SEQ ID NO: 53 | gi\|15239796 | SEQ ID NO: 54 | unknown protein | IPR009631 Protein of unknown function DUF1230 |
| IMQ70.4 | At5g11850 | gi\|30683823 | SEQ ID NO: 55 | gi\|22326737 | SEQ ID NO: 56 | ATP binding/kinase/ protein kinase/protein serine/threonine kinase/protein-tyrosine kinase | IPR011009 Protein kinase-like; IPR000719 Protein kinase; IPR008271 Serine/threonine protein kinase, active site |
| IMQ70.5 | At5g11860 | gi\|42573340 | SEQ ID NO: 57 | gi\|42573341 | SEQ ID NO: 58 | unknown protein | IPR004274 NLI interacting factor |
| IMQ70.5 | At5g11860 | gi\|30683827 | SEQ ID NO: 59 | gi\|30683828 | SEQ ID NO: 60 | unknown protein | IPR004274 NLI interacting factor |
| IMQ70.5 | At5g11860 | gi\|30683826 | SEQ ID NO: 61 | gi\|15239800 | SEQ ID NO: 62 | unknown protein | IPR004274 NLI interacting factor |
| IMQ70.6 | At5g11870 | gi\|30683836 | SEQ ID NO: 63 | gi\|15239801 | SEQ ID NO: 64 | unknown protein | |
| IMQ70.7 | At5g11880 | gi\|42567795 | SEQ ID NO: 65 | gi\|18416698 | SEQ ID NO: 66 | diaminopimelate decarboxylase | IPR000183 Orn/DAP/Arg decarboxylase 2; IPR002986 Diaminopimelate decarboxylase; IPR009006 Alanine racemase/group IV decarboxylase, C-terminal |
| IMQ71.1 | At5g12990 | gi\|18416924 | SEQ ID NO: 67 | gi\|15239964 | SEQ ID NO: 68 | CLE40 (CLAVATA3/ESR-RELATED 40); receptor binding | |
| IMQ71.2 | At5g13000 | gi\|42567812 | SEQ ID NO: 69 | gi\|30684210 | SEQ ID NO: 70 | ATGSL12 (GLUCAN SYNTHASE-LIKE 12); 1,3-beta-glucan synthase/transferase, transferring glycosyl groups | IPR001093 IMP dehydrogenase/GMP reductase; IPR003440 Glycosyl transferase, family 48; IPR008207 Hpt |
| IMQ71.3 | At5g13010 | gi\|30684214 | SEQ ID NO: 71 | gi\|15239967 | SEQ ID NO: 72 | EMB3011; ATP binding/ATP-dependent helicase/ RNA helicase/helicase/ nucleic acid binding | IPR001410 DEAD/DEAH box helicase; IPR001650 Helicase, C-terminal; IPR007502 Helicase-associated region; IPR011545 DEAD/DEAH box helicase, N-terminal; IPR011709 Protein of unknown function DUF1605 |
| IMQ72.1 | At5g15700 | gi\|30685486 | SEQ ID NO: 73 | gi\|15242369 | SEQ ID NO: 74 | DNA binding/DNA-directed RNA polymerase | IPR002092 DNA-directed RNA polymerase, bacteriophage type |
| IMQ72.2 | At5g15710 | gi\|30685493 | SEQ ID NO: 75 | gi\|15242370 | SEQ ID NO: 76 | unknown protein | IPR001810 Cyclin-like F-box |
| IMQ72.3 | At5g15720 | gi\|18417759 | SEQ ID NO: 77 | gi\|18417760 | SEQ ID NO: 78 | carboxylic ester hydrolase/hydrolase, acting on ester bonds | IPR001087 Lipolytic enzyme, G-D-S-L |
| IMQ72.4 | At5g15725 | gi\|30685500 | SEQ ID NO: 79 | gi\|18417762 | SEQ ID NO: 80 | unknown protein | |
| IMQ72.5 | At5g15730 | gi\|30685503 | SEQ ID NO: 81 | gi\|18417765 | SEQ ID NO: 82 | ATP binding/kinase/ protein kinase/protein serine/threonine kinase/protein-tyrosine kinase | IPR011009 Protein kinase-like; IPR000719 Protein kinase; IPR008271 Serine/threonine protein kinase, active site |
| IMQ73.1 | At5g35960 | gi\|18421515 | SEQ ID NO: 83 | gi\|15239245 | SEQ ID NO: 84 | ATP binding/kinase/ protein kinase/protein serine/threonine kinase/protein-tyrosine kinase | IPR011009 Protein kinase-like; IPR000719 Protein kinase; IPR008271 Serine/threonine protein kinase, active site |
| IMQ73.2 | At5g35970 | gi\|30692867 | SEQ ID NO: 85 | gi\|30692868 | SEQ ID NO: 86 | ATP binding/ATP-dependent helicase/ DNA binding | IPR001093 IMP dehydrogenase/GMP reductase; IPR003593 AAA ATPase; IPR011545 DEAD/DEAH box helicase, N-terminal |

TABLE 2-continued

| 1. Gene alias | 2. Tair | 3. Nucleic Acid seq. GI# | 4. SEQ ID NO | 5. Polypeptide seq. GI# | 6. SEQ ID NO | 7. Putative biochemical function/protein name | 8. Conserved protein domain |
|---|---|---|---|---|---|---|---|
| IMQ73.3 | At5g35980 | gi\|42568144 | SEQ ID NO: 87 | gi\|42568145 | SEQ ID NO: 88 | ATP binding/kinase/protein kinase/protein serine/threonine kinase/protein-tyrosine kinase | IPR011009 Protein kinase-like; IPR000719 Protein kinase; IPR008271 Serine/threonine protein kinase, active site |
| IMQ73.3 | At5g35980 | gi\|79329053 | SEQ ID NO: 89 | gi\|79329054 | SEQ ID NO: 90 | ATP binding/kinase/protein kinase/protein serine/threonine kinase/protein-tyrosine kinase | IPR011009 Protein kinase-like; IPR000719 Protein kinase; IPR008271 Serine/threonine protein kinase, active site |
| IMQ74.1 | At5g38530 | gi\|30693265 | SEQ ID NO: 91 | gi\|15240941 | SEQ ID NO: 92 | catalytic/pyridoxal phosphate binding/tryptophan synthase | IPR001926 Pyridoxal-5'-phosphate-dependent enzyme, beta subunit; IPR006316 Tryptophan synthase, beta chain-like |
| IMQ74.2 | At5g38540 | gi\|18421768 | SEQ ID NO: 93 | gi\|15240944 | SEQ ID NO: 94 | unknown protein | IPR001229 Jacalin-related lectin |
| IMQ74.3 | At5g38550 | gi\|42568183 | SEQ ID NO: 95 | gi\|15240945 | SEQ ID NO: 96 | unknown protein | IPR001229 Jacalin-related lectin |
| IMQ74.4 | At5g38560 | gi\|30693271 | SEQ ID NO: 97 | gi\|15240947 | SEQ ID NO: 98 | ATP binding/kinase/protein kinase/protein serine/threonine kinase/protein-tyrosine kinase/structural constituent of cell wall | IPR011009 Protein kinase-like; IPR000719 Protein kinase; IPR008271 Serine/threonine protein kinase, active site; IPR003882 Pistil-specific extensin-like protein |
| IMQ75.1 | At5g40300 | gi\|30693576 | SEQ ID NO: 99 | gi\|15242642 | SEQ ID NO: 100 | unknown protein | IPR006702 Protein of unknown function DUF588 |
| IMQ75.2 | At5g40310 | gi\|18421971 | SEQ ID NO: 101 | gi\|15242645 | SEQ ID NO: 102 | exonuclease/nucleic acid binding/zinc ion binding | IPR006055 Exonuclease; IPR007087 Zinc finger, C2H2-type; IPR012337 Polynucleotidyl transferase, Ribonuclease H fold |
| IMQ75.3 | At5g40320 | gi\|18421972 | SEQ ID NO: 103 | gi\|15242647 | SEQ ID NO: 104 | protein binding/zinc ion binding | IPR001965 Zinc finger, PHD-type; IPR002219 Protein kinase C, phorbol ester/diacylglycerol binding; IPR004146 DC1; IPR011424 C1-like |
| IMQ76.1 | At5g44180 | gi\|18422414 | SEQ ID NO: 105 | gi\|15241428 | SEQ ID NO: 106 | transcription factor | IPR001356 Homeobox; IPR004022 DDT; IPR009057 Homeodomain-like |
| IMQ77.1 | At5g62600 | gi\|42568711 | SEQ ID NO: 107 | gi\|42568712 | SEQ ID NO: 108 | protein transporter | IPR001494 Importin-beta, N-terminal |
| IMQ77.2 | At5g62610 | gi\|30697712 | SEQ ID NO: 109 | gi\|15241896 | SEQ ID NO: 110 | DNA binding/transcription factor | IPR001092 Basic helix-loop-helix dimerisation region bHLH; IPR011598 Helix-loop-helix DNA-binding |
| IMQ78.1 | At5g67580 | gi\|30698319 | SEQ ID NO: 111 | gi\|30698320 | SEQ ID NO: 112 | DNA binding/transcription factor | IPR001005 Myb, DNA-binding; IPR003216 Linker histone, N-terminal; IPR005818 Histone H1/H5; IPR009057 Homeodomain-like |
| IMQ78.1 | At5g67580 | gi\|30698321 | SEQ ID NO: 113 | gi\|15240783 | SEQ ID NO: 114 | DNA binding/transcription factor | IPR001005 Myb, DNA-binding; IPR003216 Linker histone, N-terminal; IPR005818 Histone H1/H5; IPR009057 Homeodomain-like |
| IMQ78.2 | At5g67590 | gi\|30698322 | SEQ ID NO: 115 | gi\|15240784 | SEQ ID NO: 116 | FRO1 (FROSTBITE1) | IPR006885 ETC complex I subunit conserved region |
| IMQ78.3 | At5g67600 | gi\|30698323 | SEQ ID NO: 117 | gi\|18425209 | SEQ ID NO: 118 | rhodopsin-like receptor | |
| IMQ78.4 | At5g67610 | gi\|79332806 | SEQ ID NO: 119 | gi\|79332807 | SEQ ID NO: 120 | unknown protein | IPR001093 IMP dehydrogenase/GMP reductase |
| IMQ78.4 | At5g67610 | gi\|30698324 | SEQ ID NO: 121 | gi\|15240786 | SEQ ID NO: 122 | unknown protein | IPR001093 IMP dehydrogenase/GMP reductase |

TABLE 3

| 1. Gene alias | 2. Tair | 3. Nucleic Acid seq. GI# | 4. Polypeptide seq. GI# | 5. Orthologous Genes: Nucleic Acid/Polypeptide seq. GI# | | |
|---|---|---|---|---|---|---|
| | | | | Nucleic Acid GI# | Polypeptide GI# | Species |
| IMQ66.4 | At4g30810 | gi|30688809 | gi|18417667 | gi|55773860 | gi|55773861 | *Oryza sativa* (*japonica* cultivar-group) |
| | | | | gi|474390 | gi|6102957 | *Hordeum vulgare* subsp. *vulgare* |
| | | | | gi|42569653 | gi|15227493 | *Arabidopsis thaliana* |
| IMQ67.1 | At4g32230 | gi|18417967 | gi|15236713 | gi|30689315 | gi|30689316 | *Arabidopsis thaliana* |
| | | | | gi|30689320 | gi|22329080 | *Arabidopsis thaliana* |
| | | | | gi|79326107 | gi|79326108 | *Arabidopsis thaliana* |
| | | | | gi|533631 | gi|1235831 | *Streptococcus pyogenes* |
| | | | | gi|687746 | gi|687747 | *Streptococcus pyogenes* |
| IMQ67.2 | At4g32240 | gi|42567326 | gi|18417969 | | | |
| IMQ67.3 | At4g32250 | gi|79326107 | gi|79326108 | gi|30689315 | gi|30689316 | *Arabidopsis thaliana* |
| | | | | gi|30689320 | gi|22329080 | *Arabidopsis thaliana* |
| | | | | gi|51535562 | gi|51535592 | *Oryza sativa* (*japonica* cultivar-group) |
| | | | | gi|22417471 | gi|39588025 | *Caenorhabditis briggsae* |
| | | | | gi|18420243 | gi|18420244 | *Arabidopsis thaliana* |
| IMQ67.3 | At4g32250 | gi|30689315 | gi|30689316 | gi|30689320 | gi|22329080 | *Arabidopsis thaliana* |
| | | | | gi|51535562 | gi|51535592 | *Oryza sativa* (*japonica* cultivar-group) |
| | | | | gi|22417471 | gi|39588025 | *Caenorhabditis briggsae* |
| | | | | gi|18420243 | gi|18420244 | *Arabidopsis thaliana* |
| IMQ67.3 | At4g32250 | gi|30689320 | gi|22329080 | gi|30689315 | gi|30689316 | *Arabidopsis thaliana* |
| | | | | gi|51535562 | gi|51535592 | *Oryza sativa* (*japonica* cultivar-group) |
| | | | | gi|22417471 | gi|39588025 | *Caenorhabditis briggsae* |
| | | | | gi|18420243 | gi|18420244 | *Arabidopsis thaliana* |
| IMQ67.4 | At4g32260 | gi|30689323 | gi|15236722 | gi|394754 | gi|394755 | *Spinacia oleracea* |
| | | | | gi|29367412 | gi|29367413 | *Oryza sativa* (*japonica* cultivar-group) |
| | | | | gi|31980476 | gi|31980477 | *Drosera tokaiensis* |
| IMQ68.1 | At4g36560 | gi|18419861 | gi|15234443 | | | |
| IMQ68.2 | At4g36570 | gi|18419863 | gi|15234454 | gi|42569222 | gi|15226604 | *Arabidopsis thaliana* |
| | | | | gi|30686408 | gi|30686409 | *Arabidopsis thaliana* |
| | | | | gi|18410812 | gi|15222161 | *Arabidopsis thaliana* |
| IMQ68.3 | At4g36580 | gi|18419864 | gi|15234455 | gi|30680342 | gi|18398708 | *Arabidopsis thaliana* |
| | | | | gi|30686107 | gi|22326858 | *Arabidopsis thaliana* |
| | | | | gi|50911948 | gi|50911949 | *Oryza sativa* (*japonica* cultivar-group) |
| IMQ68.4 | At4g36590 | gi|18419866 | gi|15234456 | gi|18424355 | gi|15239333 | *Arabidopsis thaliana* |
| | | | | gi|18378850 | gi|15223420 | *Arabidopsis thaliana* |
| | | | | gi|18408263 | gi|15218647 | *Arabidopsis thaliana* |
| IMQ68.5 | At4g36600 | gi|30690703 | gi|30690704 | | | |
| IMQ69.1 | At4g38510 | gi|79326467 | gi|79326468 | gi|79326459 | gi|79326460 | *Arabidopsis thaliana* |
| | | | | gi|42573220 | gi|42573221 | *Arabidopsis thaliana* |
| | | | | gi|30691994 | gi|15233891 | *Arabidopsis thaliana* |
| | | | | gi|26986105 | gi|26986106 | *Mesembryanthemum crystallinum* |
| | | | | gi|34910487 | gi|34910488 | *Oryza sativa* (*japonica* cultivar-group) |
| | | | | gi|459197 | gi|459198 | *Gossypium hirsutum* |
| IMQ69.1 | At4g38510 | gi|79326459 | gi|79326460 | gi|79326467 | gi|79326468 | *Arabidopsis thaliana* |
| | | | | gi|42573220 | gi|42573221 | *Arabidopsis thaliana* |
| | | | | gi|30691994 | gi|15233891 | *Arabidopsis thaliana* |
| | | | | gi|26986105 | gi|26986106 | *Mesembryanthemum crystallinum* |
| | | | | gi|34910487 | gi|34910488 | *Oryza sativa* (*japonica* cultivar-group) |
| | | | | gi|459197 | gi|459198 | *Gossypium hirsutum* |
| IMQ69.1 | At4g38510 | gi|42573220 | gi|42573221 | gi|79326467 | gi|79326468 | *Arabidopsis thaliana* |
| | | | | gi|79326459 | gi|79326460 | *Arabidopsis thaliana* |
| | | | | gi|30691994 | gi|15233891 | *Arabidopsis thaliana* |
| | | | | gi|26986105 | gi|26986106 | *Mesembryanthemum crystallinum* |
| | | | | gi|34910487 | gi|34910488 | *Oryza sativa* (*japonica* cultivar-group) |
| | | | | gi|459197 | gi|459198 | *Gossypium hirsutum* |
| IMQ69.1 | At4g38510 | gi|30691994 | gi|15233891 | gi|79326467 | gi|79326468 | *Arabidopsis thaliana* |
| | | | | gi|79326459 | gi|79326460 | *Arabidopsis thaliana* |
| | | | | gi|42573220 | gi|42573221 | *Arabidopsis thaliana* |
| | | | | gi|26986105 | gi|26986106 | *Mesembryanthemum crystallinum* |
| | | | | gi|34910487 | gi|34910488 | *Oryza sativa* (*japonica* cultivar-group) |
| | | | | gi|459197 | gi|459198 | *Gossypium hirsutum* |
| IMQ69.2 | At4g38520 | gi|42573222 | gi|42573223 | gi|42567510 | gi|22329238 | *Arabidopsis thaliana* |
| | | | | gi|4206121 | gi|4206122 | *Mesembryanthemum crystallinum* |
| | | | | gi|7768152 | gi|7768153 | *Fagus sylvatica* |
| | | | | gi|30698190 | gi|15239244 | *Arabidopsis thaliana* |
| IMQ69.2 | At4g38520 | gi|42567510 | gi|22329238 | gi|42573222 | gi|42573223 | *Arabidopsis thaliana* |
| | | | | gi|4206121 | gi|4206122 | *Mesembryanthemum crystallinum* |
| | | | | gi|7768152 | gi|7768153 | *Fagus sylvatica* |
| | | | | gi|30698190 | gi|15239244 | *Arabidopsis thaliana* |
| IMQ69.2 | At4g38520 | gi|79313268 | gi|79313269 | gi|30684366 | gi|18401370 | *Arabidopsis thaliana* |
| | | | | gi|50919604 | gi|50919605 | *Oryza sativa* (*japonica* cultivar-group) |
| | | | | gi|42567510 | gi|22329238 | *Arabidopsis thaliana* |
| | | | | gi|42573222 | gi|42573223 | *Arabidopsis thaliana* |
| IMQ69.3 | At4g38530 | gi|79499921 | gi|79499922 | gi|30691998 | gi|15233918 | *Arabidopsis thaliana* |
| | | | | gi|18424131 | gi|18424132 | *Arabidopsis thaliana* |
| | | | | gi|1399304 | gi|1399305 | *Glycine max* |

TABLE 3-continued

| 1. Gene alias | 2. Tair | 3. Nucleic Acid seq. GI# | 4. Polypeptide seq. GI# | 5. Orthologous Genes: Nucleic Acid/Polypeptide seq. GI# | | |
|---|---|---|---|---|---|---|
| | | | | Nucleic Acid GI# | Polypeptide GI# | Species |
| IMQ69.4 | At4g38540 | gi|30692001 | gi|15233923 | gi|30680885 | gi|15239070 | Arabidopsis thaliana |
| | | | | gi|24745926 | gi|24745927 | Solanum tuberosum |
| | | | | gi|30686498 | gi|18403916 | Arabidopsis thaliana |
| IMQ69.5 | At4g38550 | gi|42567511 | gi|22329240 | gi|42570854 | gi|42570855 | Arabidopsis thaliana |
| | | | | gi|42570292 | gi|42570293 | Arabidopsis thaliana |
| | | | | gi|42570850 | gi|42570851 | Arabidopsis thaliana |
| IMQ69.6 | At4g38560 | gi|18420262 | gi|15233931 | gi|30681216 | gi|15226430 | Arabidopsis thaliana |
| | | | | gi|18416479 | gi|15238969 | Arabidopsis thaliana |
| | | | | gi|42567511 | gi|22329240 | Arabidopsis thaliana |
| IMQ69.7 | At4g38570 | gi|30692008 | gi|15233934 | gi|21745397 | gi|21745398 | Brassica napus |
| | | | | gi|18408916 | gi|15220618 | Arabidopsis thaliana |
| | | | | gi|50402823 | gi|50402824 | Solanum tuberosum |
| IMQ70.1 | At5g11820 | gi|18416683 | gi|15239789 | gi|18420982 | gi|15239570 | Arabidopsis thaliana |
| | | | | gi|18420983 | gi|18420984 | Arabidopsis thaliana |
| | | | | gi|3097261 | gi|3097262 | Papaver nudicaule |
| IMQ70.2 | At5g11830 | gi|18416686 | gi|15239794 | gi|18420987 | gi|15239591 | Arabidopsis thaliana |
| | | | | gi|18400929 | gi|15233219 | Arabidopsis thaliana |
| | | | | gi|18420988 | gi|15239593 | Arabidopsis thaliana |
| IMQ70.3 | At5g11840 | gi|18416688 | gi|15239796 | gi|50932538 | gi|50932539 | Oryza sativa (japonica cultivar-group) |
| | | | | gi|30698299 | gi|15240715 | Arabidopsis thaliana |
| | | | | gi|3184553 | gi|3184557 | Synechococcus sp. PCC 7002 |
| IMQ70.4 | At5g11850 | gi|30683823 | gi|22326737 | gi|50906404 | gi|50906405 | Oryza sativa (japonica cultivar-group) |
| | | | | gi|30698956 | gi|15219517 | Arabidopsis thaliana |
| | | | | gi|30685720 | gi|22329643 | Arabidopsis thaliana |
| IMQ70.5 | At5g11860 | gi|42573340 | gi|42573341 | gi|30683827 | gi|30683828 | Arabidopsis thaliana |
| | | | | gi|30683826 | gi|15239800 | Arabidopsis thaliana |
| | | | | gi|34897435 | gi|34897436 | Oryza sativa (japonica cultivar-group) |
| | | | | gi|66803904 | gi|66803905 | Dictyostelium discoideum |
| | | | | gi|19612100 | gi|55239669 | Anopheles gambiae str. PEST |
| IMQ70.5 | At5g11860 | gi|30683827 | gi|30683828 | gi|42573340 | gi|42573341 | Arabidopsis thaliana |
| | | | | gi|30683826 | gi|15239800 | Arabidopsis thaliana |
| | | | | gi|34897435 | gi|34897436 | Oryza sativa (japonica cultivar-group) |
| | | | | gi|66803904 | gi|66803905 | Dictyostelium discoideum |
| | | | | gi|19612100 | gi|55239669 | Anopheles gambiae str. PEST |
| IMQ70.5 | At5g11860 | gi|30683826 | gi|15239800 | gi|42573340 | gi|42573341 | Arabidopsis thaliana |
| | | | | gi|30683827 | gi|30683828 | Arabidopsis thaliana |
| | | | | gi|34897435 | gi|34897436 | Oryza sativa (japonica cultivar-group) |
| | | | | gi|66803904 | gi|66803905 | Dictyostelium discoideum |
| | | | | gi|19612100 | gi|55239669 | Anopheles gambiae str. PEST |
| IMQ70.6 | At5g11870 | gi|30683836 | gi|15239801 | gi|18409783 | gi|15223970 | Arabidopsis thaliana |
| | | | | gi|14276070 | gi|57899179 | Oryza sativa (japonica cultivar-group) |
| | | | | gi|34905817 | gi|34905818 | Oryza sativa (japonica cultivar-group) |
| IMQ70.7 | At5g11880 | gi|42567795 | gi|18416698 | gi|30683117 | gi|15231844 | Arabidopsis thaliana |
| | | | | gi|50907772 | gi|50907773 | Oryza sativa (japonica cultivar-group) |
| | | | | gi|77917618 | gi|77920014 | Pelobacter carbinolicus DSM 2380 |
| IMQ71.1 | At5g12990 | gi|18416924 | gi|15239964 | gi|18424867 | gi|15238257 | Arabidopsis thaliana |
| | | | | gi|76791618 | gi|76791764 | Pseudoalteromonas atlantica T6c |
| | | | | gi|40841719 | gi|50428681 | Oryza sativa (japonica cultivar-group) |
| IMQ71.2 | At5g13000 | gi|42567812 | gi|30684210 | gi|18390541 | gi|18390542 | Arabidopsis thaliana |
| | | | | gi|30685130 | gi|30685131 | Arabidopsis thaliana |
| | | | | gi|50916184 | gi|50916185 | Oryza sativa (japonica cultivar-group) |
| IMQ71.3 | At5g13010 | gi|30684214 | gi|15239967 | gi|50937582 | gi|50937583 | Oryza sativa (japonica cultivar-group) |
| | | | | gi|12044831 | gi|12044832 | Chlamydomonas reinhardtii |
| | | | | gi|41053697 | gi|41053698 | Danio rerio |
| IMQ72.1 | At5g15700 | gi|30685486 | gi|15242369 | gi|21425638 | gi|21425639 | Nicotiana sylvestris |
| | | | | gi|21425664 | gi|21425665 | Nicotiana tabacum |
| | | | | gi|17221594 | gi|17221595 | Nicotiana sylvestris |
| IMQ72.2 | At5g15710 | gi|30685493 | gi|15242370 | gi|50929496 | gi|50929497 | Oryza sativa (japonica cultivar-group) |
| | | | | gi|42795314 | gi|42795315 | Mimulus lewisii |
| | | | | gi|50904332 | gi|50904333 | Oryza sativa (japonica cultivar-group) |
| IMQ72.3 | At5g15720 | gi|18417759 | gi|18417760 | gi|30684589 | gi|18415211 | Arabidopsis thaliana |
| | | | | gi|30690834 | gi|15220514 | Arabidopsis thaliana |
| | | | | gi|18397193 | gi|15220512 | Arabidopsis thaliana |
| IMQ72.4 | At5g15725 | gi|30685500 | gi|18417762 | gi|30678513 | gi|30678514 | Arabidopsis thaliana |
| IMQ72.5 | At5g15730 | gi|30685503 | gi|18417765 | gi|505145 | gi|505146 | Nicotiana tabacum |
| | | | | gi|55297390 | gi|55297406 | Oryza sativa (japonica cultivar-group) |
| | | | | gi|50940950 | gi|50940951 | Oryza sativa (japonica cultivar-group) |
| IMQ73.1 | At5g35960 | gi|18421515 | gi|15239245 | gi|30687060 | gi|30687061 | Arabidopsis thaliana |
| | | | | gi|22330851 | gi|22330852 | Arabidopsis thaliana |
| | | | | gi|47169781 | gi|52075932 | Oryza sativa (japonica cultivar-group) |
| IMQ73.2 | At5g35970 | gi|30692867 | gi|30692868 | gi|50911900 | gi|50911901 | Oryza sativa (japonica cultivar-group) |
| | | | | gi|50252625 | gi|50252651 | Oryza sativa (japonica cultivar-group) |
| | | | | gi|290918 | gi|290919 | Mesocricetus auratus |

TABLE 3-continued

| 1. Gene alias | 2. Tair | 3. Nucleic Acid seq. GI# | 4. Polypeptide seq. GI# | 5. Orthologous Genes: Nucleic Acid/Polypeptide seq. GI# | | |
|---|---|---|---|---|---|---|
| | | | | Nucleic Acid GI# | Polypeptide GI# | Species |
| IMQ73.3 | At5g35980 | gi\|42568144 | gi\|42568145 | gi\|50911864 | gi\|50911865 | *Oryza sativa* (*japonica* cultivar-group) |
| | | | | gi\|50928502 | gi\|50928503 | *Oryza sativa* (*japonica* cultivar-group) |
| | | | | gi\|60467544 | gi\|60467548 | *Dictyostelium discoideum* |
| IMQ73.3 | At5g35980 | gi\|79329053 | gi\|79329054 | gi\|42568144 | gi\|42568145 | *Arabidopsis thaliana* |
| | | | | gi\|50911864 | gi\|50911865 | *Oryza sativa* (*japonica* cultivar-group) |
| | | | | gi\|50928502 | gi\|50928503 | *Oryza sativa* (*japonica* cultivar-group) |
| | | | | gi\|66810394 | gi\|66810395 | *Dictyostelium discoideum* |
| IMQ74.1 | At5g38530 | gi\|30693265 | gi\|15240941 | gi\|51535750 | gi\|51535758 | *Oryza sativa* (*japonica* cultivar-group) |
| | | | | gi\|51535750 | gi\|51535759 | *Oryza sativa* (*japonica* cultivar-group) |
| | | | | gi\|76258946 | gi\|76258962 | *Chloroflexus aurantiacus* J-10-fl |
| IMQ74.2 | At5g38540 | gi\|18421768 | gi\|15240944 | gi\|42568183 | gi\|15240945 | *Arabidopsis thaliana* |
| | | | | gi\|18406629 | gi\|15218997 | *Arabidopsis thaliana* |
| | | | | gi\|30696152 | gi\|30696153 | *Arabidopsis thaliana* |
| IMQ74.3 | At5g38550 | gi\|42568183 | gi\|15240945 | gi\|18421768 | gi\|15240944 | *Arabidopsis thaliana* |
| | | | | gi\|30696152 | gi\|30696153 | *Arabidopsis thaliana* |
| | | | | gi\|18406632 | gi\|15219000 | *Arabidopsis thaliana* |
| IMQ74.4 | At5g38560 | gi\|30693271 | gi\|15240947 | gi\|30689350 | gi\|15222649 | *Arabidopsis thaliana* |
| | | | | gi\|55765765 | gi\|34894174 | *Oryza sativa* (*japonica* cultivar-group) |
| | | | | gi\|57900560 | gi\|57900576 | *Oryza sativa* (*japonica* cultivar-group) |
| IMQ75.1 | At5g40300 | gi\|30693576 | gi\|15242642 | gi\|42568716 | gi\|15241975 | *Arabidopsis thaliana* |
| | | | | gi\|2598568 | gi\|2598569 | *Medicago truncatula* |
| | | | | gi\|18404104 | gi\|15227628 | *Arabidopsis thaliana* |
| IMQ75.2 | At5g40310 | gi\|18421971 | gi\|15242645 | gi\|18405598 | gi\|15232874 | *Arabidopsis thaliana* |
| | | | | gi\|50911998 | gi\|50911999 | *Oryza sativa* (*japonica* cultivar-group) |
| | | | | gi\|34894119 | gi\|34894120 | *Oryza sativa* (*japonica* cultivar-group) |
| IMQ75.3 | At5g40320 | gi\|18421972 | gi\|15242647 | gi\|30688433 | gi\|22326989 | *Arabidopsis thaliana* |
| | | | | gi\|18405393 | gi\|15229491 | *Arabidopsis thaliana* |
| | | | | gi\|18413571 | gi\|15234233 | *Arabidopsis thaliana* |
| IMQ76.1 | At5g44180 | gi\|18422414 | gi\|15241428 | gi\|30690429 | gi\|15218656 | *Arabidopsis thaliana* |
| | | | | gi\|34911025 | gi\|34911026 | *Oryza sativa* (*japonica* cultivar-group) |
| | | | | gi\|46879193 | gi\|51854271 | *Oryza sativa* (*japonica* cultivar-group) |
| IMQ77.1 | At5g62600 | gi\|42568711 | gi\|42568712 | gi\|62733638 | gi\|62733653 | *Lycopersicon esculentum* |
| | | | | gi\|68358861 | gi\|68358862 | *Danio rerio* |
| | | | | gi\|32135050 | gi\|55962517 | *Danio rerio* |
| IMQ77.2 | At5g62610 | gi\|30697712 | gi\|15241896 | gi\|55419645 | gi\|55419646 | *Gossypium hirsutum* |
| | | | | gi\|33339702 | gi\|33339703 | *Catharanthus roseus* |
| | | | | gi\|42562809 | gi\|18406408 | *Arabidopsis thaliana* |
| IMQ78.1 | At5g67580 | gi\|30698319 | gi\|30698320 | gi\|30698321 | gi\|15240783 | *Arabidopsis thaliana* |
| | | | | gi\|30693241 | gi\|15229625 | *Arabidopsis thaliana* |
| | | | | gi\|30694681 | gi\|18402853 | *Arabidopsis thaliana* |
| | | | | gi\|42571814 | gi\|42571815 | *Arabidopsis thaliana* |
| | | | | gi\|30694687 | gi\|30694688 | *Arabidopsis thaliana* |
| | | | | gi\|34105722 | gi\|34105723 | *Zea mays* subsp. *mays* |
| IMQ78.1 | At5g67580 | gi\|30698321 | gi\|15240783 | gi\|30698319 | gi\|30698320 | *Arabidopsis thaliana* |
| | | | | gi\|30693241 | gi\|15229625 | *Arabidopsis thaliana* |
| | | | | gi\|30694681 | gi\|18402853 | *Arabidopsis thaliana* |
| | | | | gi\|42571814 | gi\|42571815 | *Arabidopsis thaliana* |
| | | | | gi\|30694687 | gi\|30694688 | *Arabidopsis thaliana* |
| | | | | gi\|34105722 | gi\|34105723 | *Zea mays* subsp. *mays* |
| IMQ78.2 | At5g67590 | gi\|30698322 | gi\|15240784 | gi\|50509944 | gi\|50509945 | *Oryza sativa* (*japonica* cultivar-group) |
| | | | | gi\|50938780 | gi\|50938781 | *Oryza sativa* (*japonica* cultivar-group) |
| | | | | gi\|51593212 | gi\|51593213 | *Xenopus laevis* |
| IMQ78.3 | At5g67600 | gi\|30698323 | gi\|18425209 | | | |
| IMQ78.4 | At5g67610 | gi\|79332806 | gi\|79332807 | gi\|30698324 | gi\|15240786 | *Arabidopsis thaliana* |
| | | | | gi\|42565787 | gi\|42565788 | *Arabidopsis thaliana* |
| | | | | gi\|41393266 | gi\|50838976 | *Oryza sativa* (*japonica* cultivar-group) |
| | | | | gi\|50917330 | gi\|50917331 | *Oryza sativa* (*japonica* cultivar-group) |
| IMQ78.4 | At5g67610 | gi\|30698324 | gi\|15240786 | gi\|42565787 | gi\|42565788 | *Arabidopsis thaliana* |
| | | | | gi\|41393266 | gi\|50838976 | *Oryza sativa* (*japonica* cultivar-group) |
| | | | | gi\|50917330 | gi\|50917331 | *Oryza sativa* (*japonica* cultivar-group) |

Example 2

Analysis of the *Arabidopsis* IMQ Sequence

Sequence analyses were performed with BLAST (Altschul et al., 1990, *J. Mol. Biol.* 215:403-410), PFAM (Bateman et al., 1999, *Nucleic Acids Res.* 27:260-262), INTERPRO (Mulder et al. 2003 *Nucleic Acids Res.* 31, 315-318.), PSORT (Nakai K, and Horton P, 1999, *Trends Biochem. Sci.* 24:34-6), and/or CLUSTAL (Thompson J D et al., 1994, *Nucleic Acids Res.* 22:4673-4680). Conserved domains for each protein are listed in column 8 of Table 2.

Example 3

To test whether over-expression of the genes in Tables 1 and 2 alter the seed composition phenotype, protein, digestible protein, oil and fiber content in seeds from transgenic plants expressing these genes was compared with protein, digestible protein, oil and fiber content in seeds from non-transgenic control plants. To do this, the genes were cloned into plant transformation vectors behind the strong constitutive CsVMV promoter and the seed specific PRU promoter. These constructs were transformed into *Arabidopsis* plants using the floral dip method. The plant transformation vector contains a gene, which provides resistance to a toxic compound, and serves as a selectable marker. Seed from the transformed plants were plated on agar medium containing the toxic compound. After 7 days, transgenic plants were identified as healthy green plants and transplanted to soil. Non-transgenic control plants were germinated on agar medium, allowed to grow for 7 days and then transplanted to soil. Transgenic seedlings and non-transgenic control plants were transplanted to two inch pots that were placed in random positions in a 10 inch by 20 inch tray. The plants were grown to maturity, allowed to self-fertilize and set seed. Seed was harvested from each plant and its oil content estimated by Near Infrared (NIR) Spectroscopy using methods previously described. The effect of each construct on seed composition was examined in at least two experiments.

Table 4 lists constructs tested for causing a significant increase in oil, protein, digestible protein or a significant decrease in fiber were identified by a two-way Analysis of Variance (ANOVA) test at a p-value≦0.05. The ANOVA p-values for Protein, Oil, Digestible Protein and Fiber are listed in columns 4-7, respectively. Those with a significant p-value are listed in bold. The Average values for Protein, Oil, Digestible Protein and Fiber are listed in columns 8-11, respectively and were calculated by averaging the average values determined for the transgenic plants in each experiment.

Tables 1-4 is used to transform *Brassica napus* (canola). To do this, the genes are cloned into plant transformation vectors behind the strong constitutive CsVMV promoter and the seed specific phaseolin promoter. These constructs (which include a gene encoding a selection agent) are transformed into canola plants.

Transformation of canola is accomplished via *Agrobacterium*-mediated transformation. Seeds are surface-sterilized with 10% commercial bleach for 10 minutes and rinsed 3 times with sterile distilled water. The seeds are then placed on one half concentration of MS basal medium (Murashige and Skoog, *Physiol. Plant.* 15:473-497, 1962) and maintained under growth regime set at 25° C., and a photoperiod of 16 hrs light/8 hrs dark.

Hypocotyl segments (3-5 mm) are excised from 5-7 day old seedlings and placed on callus induction medium K1D1 (MS medium with 1 mg/l kinetin and 1 mg/l 2,4-D) for 3 days as pre-treatment. The segments are then transferred into a petri plate, treated with *Agrobacterium* Z7075 or LBA4404 strain containing pDAB721. The *Agrobacterium* is grown overnight at 28° C. in the dark on a shaker at 150 rpm and subsequently re-suspended in the culture medium.

After 30 minute treatment of the hypocotyl segments with *Agrobacterium*, these are placed back on the callus induction medium for 3 days. Following co-cultivation, the segments are placed on K1D1TC (callus induction medium containing 250 mg/l Carbenicillin and 300 mg/l Timentin) for one week of recovery. Alternately, the segments are placed directly on selection medium K1D1H1 (above medium with 1 mg/l selection agent, for example an herbicide). Carbenicillin and

TABLE 4

| 1. Gene | 2. TAIR | 3. Construct | 4. ANOVA Protein | 5. ANOVA Oil | 6. ANOVA Digestible Protein | 7. ANOVA Fiber | 8. Protein | 9. Oil | 10. Digestible Protein | 11. Fiber |
|---|---|---|---|---|---|---|---|---|---|---|
| IMQ67.1 | At4g32230 | Pru::At4g32230 | 0.066 | 0.175 | 0.015 | 0.135 | 102.5% | 97.9% | 101.4% | 98.6% |
| IMQ67.2 | At4g32240 | CsVMV::At4g32240 | 0.368 | 0.260 | 0.355 | 0.277 | 98.1% | 102.0% | 99.3% | 99.2% |
| IMQ67.2 | At4g32240 | Pru::At4g32240 | 0.013 | 0.027 | 0.084 | 0.426 | 104.2% | 95.8% | 101.0% | 99.3% |
| IMQ67.3 | At4g32250 | CsVMV::At4g32250 | 0.392 | 0.134 | 0.037 | 0.630 | 102.1% | 97.3% | 101.6% | 99.6% |
| IMQ67.4 | At4g32260 | Pru::At4g32260 | 0.024 | 0.146 | 0.068 | 0.181 | 103.5% | 96.8% | 101.2% | 98.5% |
| IMQ69.3 | At4g38530 | CsVMV::At4g38530 | 0.115 | 0.040 | 0.507 | 0.487 | 102.2% | 97.0% | 100.5% | 99.3% |
| IMQ69.3 | At4g38530 | Pru::At4g38530 | 0.043 | 0.004 | 0.211 | 0.114 | 103.0% | 93.7% | 98.8% | 102.7% |
| IMQ69.4 | At4g38540 | CsVMV::At4g38540 | 0.156 | 0.077 | 0.127 | 0.201 | 102.5% | 97.4% | 101.2% | 99.0% |
| IMQ69.4 | At4g38540 | Pru::At4g38540 | 0.015 | 0.002 | 0.459 | 0.044 | 106.0% | 91.2% | 99.3% | 103.8% |
| IMQ69.5 | At4g38550 | CsVMV::At4g38550 | 0.028 | 0.003 | 0.862 | 0.293 | 102.4% | 96.0% | 100.1% | 101.0% |
| IMQ71.2 | At5g13000 | CsVMV::At5g13000 | 0.455 | 0.564 | 0.006 | 0.004 | 100.8% | 99.3% | 102.6% | 96.3% |
| IMQ71.2 | At5g13000 | Pru::At5g13000 | 0.232 | 0.155 | 0.443 | 0.564 | 101.7% | 98.0% | 100.5% | 99.5% |
| IMQ71.3 | At5g13010 | CsVMV::At5g13010 | 0.000 | 0.002 | 0.000 | 0.019 | 110.8% | 91.3% | 103.5% | 98.1% |
| IMQ71.3 | At5g13010 | Pru::At5g13010 | 0.025 | 0.502 | 0.224 | 0.617 | 96.4% | 101.7% | 99.2% | 100.6% |
| IMQ73.3 | At5g35980 | CsVMV::At5g35980 | 0.450 | 0.721 | 0.064 | 0.007 | 99.7% | 100.3% | 102.0% | 96.4% |
| IMQ73.3 | At5g35980 | Pru::At5g35980 | 0.461 | 0.718 | 0.075 | 0.017 | 99.2% | 100.7% | 101.4% | 96.8% |
| IMQ74.1 | At5g38530 | Pru::At5g38530 | 0.310 | 0.475 | 0.002 | 0.066 | 101.7% | 98.4% | 101.9% | 98.1% |
| IMQ74.2 | At5g38540 | CsVMV::At5g38540 | 0.020 | 0.004 | 0.801 | 0.353 | 103.4% | 92.9% | 99.7% | 101.8% |
| IMQ74.2 | At5g38540 | Pru::At5g38540 | 0.956 | 0.853 | 0.460 | 0.514 | 100.0% | 99.6% | 100.5% | 99.3% |
| IMQ75.1 | At5g40300 | CsVMV::At5g40300 | 0.025 | 0.153 | 0.537 | 0.362 | 97.6% | 102.6% | 100.7% | 98.8% |
| IMQ75.1 | At5g40300 | Pru::At5g40300 | 0.431 | 0.881 | 0.050 | 0.044 | 101.4% | 100.1% | 101.2% | 98.0% |
| IMQ75.2 | At5g40310 | Pru::At5g40310 | 0.349 | 0.096 | 0.015 | 0.005 | 99.0% | 102.9% | 101.9% | 97.0% |
| IMQ75.3 | At5g40320 | CsVMV::At5g40320 | 1.238 | 0.106 | 0.800 | 0.188 | 98.55% | 102.95% | 100.20% | 98.50% |
| IMQ75.3 | At5g40320 | Pru::At5g40320 | 0.048 | 0.444 | 0.000 | 0.000 | 102.5% | 99.0% | 103.0% | 96.5% |
| IMQ78.4 | At5g67610 | CsVMV::At5g67610 | 0.777 | 0.586 | 0.325 | 0.158 | 100.4% | 101.2% | 100.8% | 98.1% |
| IMQ78.4 | At5g67610 | Pru::At5g67610 | 0.009 | 0.045 | 0.730 | 0.026 | 95.0% | 105.2% | 100.3% | 98.0% |

Example 4

To test whether over-expression of the genes identified in Tables 1-4 alter the seed composition phenotype, protein, digestible protein, oil, and fiber content in seeds from transgenic plants expressing these genes is compared with protein, digestible protein, oil and fiber content in seeds from non-transgenic control plants. Any one of the genes identified in Timentin are antibiotics used to kill the *Agrobacterium*. The selection agent is used to allow the growth of the transformed cells.

Callus samples from independent events are tested by PCR. All the samples tested are positive for the presence of the transformed gene, whereas the non-transformed controls are negative. Callus samples are confirmed to express the appropriate protein as determined by ELISA.

Callused hypocotyl segments are then placed on B3Z1H1 (MS medium, 3 mg/l benzylamino purine, 1 mg/l Zeatin, 0.5 gm/l MES [2-(N-morpholino) ethane sulfonic acid], 5 mg/l silver nitrate, 1 mg/l selection agent, Carbenicillin and Timentin) shoot regeneration medium. After shoots start to regenerate (approximately 3 weeks), hypocotyl segments along with the shoots are transferred to B3Z1H3 medium (MS medium, 3 mg/l benzylamino purine, 1 mg/l Zeatin, 0.5 gm/l MES [2-(N-morpholino) ethane sulfonic acid], 5 mg/l silver nitrate, 3 mg/l selection agent, Carbenicillin and Timentin) for 3 weeks.

Shoots are excised from the hypocotyl segments and transferred to shoot elongation medium MESH10 (MS, 0.5 gm/l MES, 10 mg/l selection agent, Carbenicillin, Timentin) for 2-4 weeks. The elongated shoots are cultured for root induction on MSI.1 (MS with 0.1 mg/l Indolebutyric acid). Once the plants have a well established root system, these are transplanted into soil. The plants are acclimated under controlled environmental conditions in the Conviron for 1-2 weeks before transfer to the greenhouse. The transformed T0 plants self-pollinate in the greenhouse to obtain T1 seed. Transgenic plants are selected at the T1 generation based on resistance to a selection agent. T2 seed (from T1 plants) is harvested and sown in soil. T2 plants are grown to maturity, allowed to self-fertilize and set seed. T3 seed (from the T2 plants) is harvested in bulk for each line. Seed oil, protein, digestible protein, and fiber values are measured as discussed in Example 1.

It is claimed:

1. A transgenic plant, comprising a plant transformation vector comprising a nucleic acid molecule that encodes an IMQ (Improved Meal Quality) polypeptide comprising the amino acid sequence as set forth in SEQ ID NO: 72, or an IMQ polypeptide comprising an amino acid sequence at least 95% identical to the amino acid sequence as set forth in SEQ ID NO: 72, whereby the transgenic plant has an improved meal quality phenotype, relative to control plants.

2. The transgenic plant of claim 1, wherein the IMQ polypeptide comprises the amino acid sequence as set forth in SEQ ID NO: 72.

3. The transgenic plant of claim 1, which is selected from the group consisting of plants of the *Brassica* species, including canola and rapeseed, soy, corn, sunflower, cotton, cocoa, safflower, oil palm, coconut palm, flax, castor, peanut, wheat, oat, and rice.

4. The transgenic plant of claim 3, wherein the plant is canola.

5. The transgenic plant of claim 1, wherein an improved meal quality phenotype comprises an increase in available metabolizable energy in meal produced from seeds of the transgenic plant, relative to control plants.

6. The transgenic plant of claim 5, wherein an increase in available metabolizable energy comprises an altered protein and/or fiber content in the seeds of the transgenic plant.

7. The transgenic plant of claim 6, wherein the protein content is increased and/or the fiber content is decreased.

8. The transgenic plant of claim 5, wherein an increase in available metabolizable energy comprises a decreased fiber content in the seeds of the transgenic plant.

9. A plant part obtained from the plant according to claim 1, wherein the plant part comprises said nucleic acid molecule.

10. The plant part of claim 9, which is a seed.

11. Meal, feed, or food produced from the seed of claim 10, whereby the meal, feed or food from the transgenic plant has improved meal quality, relative to meal, feed or food from a control plant that does not comprise the nucleic acid molecule, and wherein the meal, feed, or food comprises the nucleic acid molecule or the polypeptide encoded by the nucleic acid molecule or both.

12. A method of producing meal, comprising growing the transgenic plant of claim 1, and recovering meal from the plant,
thereby producing meal.

13. The method of claim 12, wherein the meal is produced from seeds of the plant.

14. The feed, meal, grain, food, or seed from the transgenic plant of claim 1, wherein the feed, meal, grain, food, or seed comprises a nucleic acid molecule comprising a nucleotide sequence encoding a polypeptide comprising an amino acid sequence at least 95% identical to the amino acid sequence as set forth in SEQ ID NO: 72, whereby the feed, meal, grain, food, or seed from the transgenic plant has an improved meal quality phenotype, relative to a control plant that does not comprise the nucleic acid.

15. The feed, meal, grain, food, or seed of claim 14, wherein the polypeptide is encoded by the nucleotide sequence as set forth in SEQ ID NO: 71.

16. The feed, meal, grain, food, or seed of claim 14, wherein the polypeptide comprises an amino acid sequence at least 97% identical to the amino acid sequence as set forth in SEQ ID NO: 72.

17. The feed, meal, grain, food, or seed of claim 16, wherein the polypeptide comprises an amino acid sequence at least 99% identical to the amino acid sequence as set forth in SEQ ID NO: 72.

18. The feed, meal, grain, food, or seed from the transgenic plant of claim 1, wherein the feed, meal, grain, food, or seed comprises a polypeptide comprising the amino acid sequence as set forth in SEQ ID NO: 72, or a polypeptide comprising an amino acid sequence at least 95% identical to the amino acid sequence as set forth in SEQ ID NO: 72, whereby the feed, meal, grain, food, or seed from the transgenic plant has an improved meal quality phenotype, relative to a control plant.

19. The feed, meal, grain, food, or seed of claim 18, wherein the polypeptide comprises the amino acid sequence as set forth in SEQ ID NO: 72.

20. The feed, meal, grain, food, or seed of claim 18, wherein the polypeptide comprises an amino acid sequence at least 97% identical to the amino acid sequence as set forth in SEQ ID NO: 72.

21. The feed, meal, grain, food, or seed of claim 20, wherein the polypeptide comprises an amino acid sequence at least 99% identical to the amino acid sequence as set forth in SEQ ID NO: 72.

22. The transgenic plant of claim 1, wherein the IMQ polypeptide comprises an amino acid sequence at least 97% identical to the amino acid sequence as set forth in SEQ ID NO: 72.

23. The transgenic plant of claim 22, wherein the IMQ polypeptide comprises an amino acid sequence at least 99% identical to the amino acid sequence as set forth in SEQ ID NO: 72.

24. A method of producing an improved meal quality phenotype in a plant, said method comprising:
   a) introducing into progenitor cells of the plant a plant transformation vector comprising a nucleic acid molecule that encodes an IMQ polypeptide comprising the amino acid sequence set forth in SEQ ID NO: 72, or an IMQ polypeptide comprising an amino acid sequence at least 95% identical to the amino acid sequence as set forth in SEQ ID NO: 72, and
   b) growing the transformed progenitor cells to produce a transgenic plant, wherein the nucleic acid molecule is expressed, and the transgenic plant exhibits an improved meal quality phenotype relative to control plants,
   thereby producing the improved meal quality phenotype in the plant.

25. The method of claim 24, wherein the IMQ polypeptide comprises the amino acid sequence as set forth in SEQ ID NO: 72.

26. A plant obtained by the method of claim 24.

27. The plant of claim 26, which is selected from the group consisting of plants of the *Brassica* species, including canola and rapeseed, soy, corn, sunflower, cotton, cocoa, safflower, oil palm, coconut palm, flax, castor, peanut, wheat, oat, and rice.

28. The plant of claim 27, wherein the plant is canola.

29. The plant of claim 26, wherein the plant is selected from the group consisting of a plant grown from said progenitor cells, a plant that is the direct progeny of a plant grown from said progenitor cells, and a plant that is the indirect progeny of a plant grown from said progenitor cells, wherein said progeny comprise the vector comprising the nucleic acid molecule that encodes the IMQ polypeptide.

30. The method of claim 24, wherein the IMQ polypeptide comprises an amino acid sequence at least 97% identical to the amino acid sequence as set forth in SEQ ID NO: 72.

31. The method of claim 30, wherein the IMQ polypeptide comprises an amino acid sequence at least 99% identical to the amino acid sequence as set forth in SEQ ID NO: 72.

* * * * *

UNITED STATES PATENT AND TRADEMARK OFFICE
CERTIFICATE OF CORRECTION

PATENT NO. : 8,367,892 B2  Page 1 of 1
APPLICATION NO. : 13/401682
DATED : February 5, 2013
INVENTOR(S) : Davies et al.

It is certified that error appears in the above-identified patent and that said Letters Patent is hereby corrected as shown below:

In the Specification:

Column 2, line 67, "(FADS)" should read --(FAD3)--.

Column 11, line 14, "(crtl)" should read --(crtI)--.

Column 11, line 53, "$N^6$-based" should read --N6-based--.

Column 22, line 66, "virus $^{35}$S-promoter" should read --virus 35S-promoter--.

Column 23, lines 26-27, "7S α' promoter" should read --7Sα promoter--.

Column 44, line 19, "Z7075" should read --Z707S--.

Signed and Sealed this
Eleventh Day of March, 2014

Michelle K. Lee
*Deputy Director of the United States Patent and Trademark Office*

```
                        SEQUENCE LISTING

<160> NUMBER OF SEQ ID NOS: 122

<210> SEQ ID NO 1
<211> LENGTH: 1657
<212> TYPE: DNA
<213> ORGANISM: Arabidopsis thaliana

<400> SEQUENCE: 1
gaagtatagt ttctgtaaca acaatggcca aaaccagagg gtcttgttgt ctcgtcaacg      60
ctctaatcgc tatagctttt ttggcgacag cccatttgtg tgaagctggc ttgtctcaga     120
aagaacagga caaggtctcg aaattgcctg gtcagaattt taatgttagt tttgctcact     180
actctgggtt tgttgctact aatgagcaat tgggaagagc tctcttttac tggttatttg     240
aagccgttga agatgctaag tctaagcctc ttgttctctg gctcaatgga ggaccaggat     300
gttcatctgt tgcatatggt gaagcagaag agataggacc atttcacatt aaggcagatg     360
ggaagactct ttaccttaat caatattctt ggaaccaagc tgcaaatatt ttgttccttg     420
atgcacctgt tggagttggt tattcatact caaacacctc gtctgatttg aagagcaatg     480
gtgataaaag aactgccgaa gattcactga aatttctgct gaaatgggtt gagcggtttc     540
cggaatacaa aggaagggac ttttatatag taggggagag ctatgcagga cattacattc     600
ctcagctgag tgaagccatt gtaaaacata accaaggttc tgacaaaaac agtataaatc     660
tgaagggtta catggtagga aatgggctga tggacgattt ccatgacagg cttggtcttt     720
tccaatatat ttggtcgttg ggttttatat ctgaccaaac atacagctta ctgcaacttc     780
aatgcggttt cgaatcgttt attcactcct ccaaacagtg taacaagatt ctggagatag     840
cggacaaaga aataggtaac atagaccaat acagtgtctt caccccagct tgtgttgcca     900
atgcttccca gtcaaatatg ttgctaaaga aaagacctat gactagccgc gtgagcgaac     960
agtatgatcc ttgtacggag aaacacacta cagtttattt caatcttcca gaggttcaaa    1020
aagccctcca tgtcccacca ggacttgcac catcaaaatg ggatacttgc agtgatgtcg    1080
tgagtgaaca ctggaatgac tctccttcct cggttctaaa catttaccac gagcttatag    1140
ctgctgggct tcgtatctgg gttttcagtg gggacgcaga tgccgttgta ccagtcacat    1200
caacccggta cagtatcgat gcactaaacc ttcgtccttt gagtgcctat ggtccttggt    1260
acttagatgg acaggtggga gggtggagtc agcagtatgc tggtctgaac tttgtgacag    1320
tgagaggtgc aggccatgaa gttcctttgc acagaccgaa gcaagctctt gcgctcttca    1380
aggcttttat atctggaact ccattgtcca cacatgagaa cagcatcagc cgcgacatgt    1440
ctgaactcgt tagtgactca taatgagttc tgatttgatg taatgtgtga tttggattct    1500
```

-continued

```
caatcaaaaa ctttccacat aggccgttga aataagaaga gggaaagaga ataaatcagt    1560
gttttaagtg atacgttcaa tgcttcttct cttctggtt gtttgtttgt ttggataaac    1620
atttgctgct tggaatctaa taaaagaagt ttctacc                            1657
```

<210> SEQ ID NO 2
<211> LENGTH: 479
<212> TYPE: PRT
<213> ORGANISM: Arabidopsis thaliana

<400> SEQUENCE: 2

```
Met Ala Lys Thr Arg Gly Ser Cys Cys Leu Val Asn Ala Leu Ile Ala
1               5                   10                  15

Ile Ala Phe Leu Ala Thr Ala His Leu Cys Glu Ala Gly Leu Ser Gln
            20                  25                  30

Lys Glu Gln Asp Lys Val Ser Lys Leu Pro Gly Gln Asn Phe Asn Val
        35                  40                  45

Ser Phe Ala His Tyr Ser Gly Phe Val Ala Thr Asn Glu Gln Leu Gly
    50                  55                  60

Arg Ala Leu Phe Tyr Trp Leu Phe Glu Ala Val Glu Asp Ala Lys Ser
65                  70                  75                  80

Lys Pro Leu Val Leu Trp Leu Asn Gly Gly Pro Gly Cys Ser Ser Val
                85                  90                  95

Ala Tyr Gly Glu Ala Glu Glu Ile Gly Pro Phe His Ile Lys Ala Asp
            100                 105                 110

Gly Lys Thr Leu Tyr Leu Asn Gln Tyr Ser Trp Asn Gln Ala Ala Asn
        115                 120                 125

Ile Leu Phe Leu Asp Ala Pro Val Gly Val Gly Tyr Ser Tyr Ser Asn
    130                 135                 140

Thr Ser Ser Asp Leu Lys Ser Asn Gly Asp Lys Arg Thr Ala Glu Asp
145                 150                 155                 160

Ser Leu Lys Phe Leu Leu Lys Trp Val Glu Arg Phe Pro Glu Tyr Lys
                165                 170                 175

Gly Arg Asp Phe Tyr Ile Val Gly Glu Ser Tyr Ala Gly His Tyr Ile
            180                 185                 190

Pro Gln Leu Ser Glu Ala Ile Val Lys His Asn Gln Gly Ser Asp Lys
        195                 200                 205

Asn Ser Ile Asn Leu Lys Gly Tyr Met Val Gly Asn Gly Leu Met Asp
    210                 215                 220

Asp Phe His Asp Arg Leu Gly Leu Phe Gln Tyr Ile Trp Ser Leu Gly
225                 230                 235                 240

Phe Ile Ser Asp Gln Thr Tyr Ser Leu Leu Gln Leu Gln Cys Gly Phe
                245                 250                 255

Glu Ser Phe Ile His Ser Ser Lys Gln Cys Asn Lys Ile Leu Glu Ile
            260                 265                 270

Ala Asp Lys Glu Ile Gly Asn Ile Asp Gln Tyr Ser Val Phe Thr Pro
        275                 280                 285

Ala Cys Val Ala Asn Ala Ser Gln Ser Asn Met Leu Leu Lys Lys Arg
    290                 295                 300

Pro Met Thr Ser Arg Val Ser Glu Gln Tyr Asp Pro Cys Thr Glu Lys
305                 310                 315                 320

His Thr Thr Val Tyr Phe Asn Leu Pro Glu Val Gln Lys Ala Leu His
                325                 330                 335

Val Pro Pro Gly Leu Ala Pro Ser Lys Trp Asp Thr Cys Ser Asp Val
            340                 345                 350
```

```
Val Ser Glu His Trp Asn Asp Ser Pro Ser Ser Val Leu Asn Ile Tyr
        355                 360                 365

His Glu Leu Ile Ala Ala Gly Leu Arg Ile Trp Val Phe Ser Gly Asp
370                 375                 380

Ala Asp Ala Val Val Pro Val Thr Ser Thr Arg Tyr Ser Ile Asp Ala
385                 390                 395                 400

Leu Asn Leu Arg Pro Leu Ser Ala Tyr Gly Pro Trp Tyr Leu Asp Gly
                405                 410                 415

Gln Val Gly Gly Trp Ser Gln Gln Tyr Ala Gly Leu Asn Phe Val Thr
            420                 425                 430

Val Arg Gly Ala Gly His Glu Val Pro Leu His Arg Pro Lys Gln Ala
                435                 440                 445

Leu Ala Leu Phe Lys Ala Phe Ile Ser Gly Thr Pro Leu Ser Thr His
    450                 455                 460

Glu Asn Ser Ile Ser Arg Asp Met Ser Glu Leu Val Ser Asp Ser
465                 470                 475
```

<210> SEQ ID NO 3
<211> LENGTH: 669
<212> TYPE: DNA
<213> ORGANISM: Arabidopsis thaliana

<400> SEQUENCE: 3

```
atgaccggtc tagtttcagt cttgttcgcg agcgtcgaga gaaatcgaga ggaaacccta      60
atttggcgag tggaggagca agatgatgag gaacattgga tctgcgtgtg cgaagaaacg     120
ttgatctgtg ttgcgatgga tgaattacag cttggacgcg gagggagatc gtatacggct     180
ggtagatgtg aagattcatc actgatgagg agcaagaaga gtgaaggcac tgcgtcattt     240
gctgttttta ctgtgctaat ggctggcttt gcgggacatt tttggtacag aggaaaagct     300
actctagaac gcttagcccct ctccagagct attgatgaaa agagtaaaaa gattcgtctt     360
cttaaacgag aagtggaggc gatcgaacta aagccctcta actttcttcc cattgataac     420
gacaaggcca tcctcgggga tgttgggatc ccattattgc acagacaaca ggtgacaaca     480
agagcacata gaactcgaat tcgaactaca attagcccgt taatgggcct aagtcatgag     540
ctcgtcagaa gatttgggtc gacaatcgag atcgccatag gcggcttctc aggtcgtgta     600
aagggaaaaac ttccatttaa ggaggatctc atgaagaatg gaagtaatga agatttagac     660
ctaggataa                                                            669
```

<210> SEQ ID NO 4
<211> LENGTH: 222
<212> TYPE: PRT
<213> ORGANISM: Arabidopsis thaliana

<400> SEQUENCE: 4

```
Met Thr Gly Leu Val Ser Val Leu Phe Ala Ser Val Glu Arg Asn Arg
1               5                   10                  15

Glu Glu Thr Leu Ile Trp Arg Val Glu Glu Gln Asp Asp Glu Glu His
            20                  25                  30

Trp Ile Cys Val Cys Glu Glu Thr Leu Ile Cys Val Ala Met Asp Glu
        35                  40                  45

Leu Gln Leu Gly Arg Gly Gly Arg Ser Tyr Thr Ala Gly Arg Cys Glu
    50                  55                  60

Asp Ser Ser Leu Met Arg Ser Lys Lys Ser Glu Gly Thr Ala Ser Phe
65                  70                  75                  80

Ala Val Phe Thr Val Leu Met Ala Gly Phe Ala Gly His Phe Trp Tyr
```

```
                        85                  90                  95
Arg Gly Lys Ala Thr Leu Glu Arg Leu Ala Leu Ser Arg Ala Ile Asp
                100                 105                 110

Glu Lys Ser Lys Lys Ile Arg Leu Leu Lys Arg Glu Val Glu Ala Ile
            115                 120                 125

Glu Leu Lys Pro Ser Asn Phe Leu Pro Ile Asp Asn Asp Lys Ala Ile
        130                 135                 140

Leu Gly Asp Val Gly Ile Pro Leu Leu His Arg Gln Gln Val Thr Thr
145                 150                 155                 160

Arg Ala His Arg Thr Arg Ile Arg Thr Thr Ile Ser Pro Leu Met Gly
                165                 170                 175

Leu Ser His Glu Leu Val Arg Arg Phe Gly Ser Thr Ile Glu Ile Ala
            180                 185                 190

Ile Gly Gly Phe Ser Gly Arg Val Lys Gly Lys Leu Pro Phe Lys Glu
        195                 200                 205

Asp Leu Met Lys Asn Gly Ser Asn Glu Asp Leu Asp Leu Gly
    210                 215                 220

<210> SEQ ID NO 5
<211> LENGTH: 611
<212> TYPE: DNA
<213> ORGANISM: Arabidopsis thaliana

<400> SEQUENCE: 5
atcgatcgaa atattattaa aagagggaag gagcaaaaaa gccctaatttt tcggctggag    60 gagcaagacg atgatgacga tgatgatatg aaggaacctc ggatccgtgt gcgcgaagtt   120
tggccgcgga acgagatcct atagcactaa gaggtctggc caatctaaag atagaacttt   180
ctccaccatg tcctcttcat tggttgaggc agcagcagga ttgccggaaa agggtttgat   240
ggtgtgcaaa tggctaggca caggttcagc aggttatgga ggatacaaag cctctgagta   300
tttttttcct attgacaacg aagagtttag ggaaaacctt gaggattggg aatctacgtt   360
gcaaagttgg gagaaactga aaaattattt ggagggtatg cacaaaggac ctgttggcaa   420
tcaaacaaga actcattgac gaattccaat ctggtggaga gaaactttta atcctttcat   480
gtatctagtt gtgtcatgtt tcatgtcata atcttattat ctatgtttag acacttgtga   540
tcaaattcat accctaatcg ctattctatg atgtcgccaa tgaaagattt gtgttaaatc   600
agttaatgtt g                                                         611

<210> SEQ ID NO 6
<211> LENGTH: 83
<212> TYPE: PRT
<213> ORGANISM: Arabidopsis thaliana

<400> SEQUENCE: 6

Met Ser Ser Ser Leu Val Glu Ala Ala Ala Gly Leu Pro Glu Lys Gly
1               5                   10                  15

Leu Met Val Cys Lys Trp Leu Gly Thr Gly Ser Ala Gly Tyr Gly Gly
            20                  25                  30

Tyr Lys Ala Ser Glu Tyr Phe Phe Pro Ile Asp Asn Glu Glu Phe Arg
        35                  40                  45

Glu Asn Leu Glu Asp Trp Glu Ser Thr Leu Gln Ser Trp Glu Lys Leu
    50                  55                  60

Lys Asn Tyr Leu Glu Gly Met His Lys Gly Pro Val Gly Asn Gln Thr
65                  70                  75                  80

Arg Thr His
```

<210> SEQ ID NO 7
<211> LENGTH: 2223
<212> TYPE: DNA
<213> ORGANISM: Arabidopsis thaliana

<400> SEQUENCE: 7

| | | | | | |
|---|---|---|---|---|---|
| ttccttcttc | ttcttcttct | cacgctcacg | gcctttggag | ttttgtgtta | ccattttcgc | 60 |
| tcgcgtcatt | actggtgtta | gggttttctt | caaaagcttc | ttaatccgtc | gaaattgctc | 120 |
| ttttctctcc | ctcattacag | agataaatgg | cttcaaagat | tattgctggc | aagccggatg | 180 |
| ataccgagta | tgaaatcatt | gaaggtgagt | ctgagagcgc | tttagcagcg | gggacaagcc | 240 |
| cttggatgaa | ttcatcaacg | ttgaagcttc | gacatcgaat | tggaagaggt | cccttcggtg | 300 |
| atgtttggct | ggctactcat | catcagtcaa | ctgaggacta | tgatgagcat | catgaagtgg | 360 |
| ccatcaaaat | gctttatccc | atcaaggaag | atcaaagaag | ggttgtggta | gataagtttg | 420 |
| aagatctctt | ctctaaatgt | caaggactag | agaatgtctg | tctgctcagg | ggagtctcta | 480 |
| gtatcaatgg | aaagatatgt | gtcgtcatga | aattctacga | gggctctctt | ggtgacaaga | 540 |
| tggctcggct | taaaggagga | aagctttcac | tgccagatgt | tttgagatac | ggggttgatc | 600 |
| tggctacagg | gatcctggag | ttgcactcaa | aagggtttct | cattctcaat | ctcaagccct | 660 |
| ctaactttct | tctcagtgat | aacgacaagg | ccatcctcgg | ggatgttggg | atcccttatc | 720 |
| tccttcttag | tatcccttta | ccaagttctg | atatgacaga | gagacttgga | actccaaact | 780 |
| atatggcacc | agaacagtgg | caaccggatg | tcagaggtcc | catgtccttt | gagactgatt | 840 |
| cttggggatt | tggttgcagc | attgttgaaa | tgctgactgg | tgtacaacct | tggtctggga | 900 |
| gatctgccga | tgaaatatat | gatttggtgg | tgagaaagca | agaaaagctt | agtatcccca | 960 |
| gtagcatacc | gcctcctctc | gagaacctac | ttcggggttg | ctttatgtat | gatcttcgaa | 1020 |
| gccgaccttc | gatgactgac | atcttactcg | tcttaaagag | cttgcagaac | tcggaggagg | 1080 |
| aacaggtcag | gagaggcatt | gatagtagag | aaatcaggaa | gagctcggct | actcttggtt | 1140 |
| atacagaatg | gttctcttca | aaggatcatc | tgcaagtgcg | cgacaccgtg | cgttcaagaa | 1200 |
| agcctgccaa | ttcgtgtaag | catgagaaca | tggatgtgcc | agaaggaatg | gtggttggtt | 1260 |
| tagaacgtga | ctcccacagac | ccagatggat | ttgtgctagt | taaagtccat | ggtgtacatg | 1320 |
| atccattaag | ggttcacgta | tctgttcttg | aacgggtaac | taacggctta | gcttctggag | 1380 |
| attgggtgcg | tctgaaggtc | aggaaagaca | agaggcactc | tccggttggt | gttctccatt | 1440 |
| caattgaccg | tgagggaaat | gtagctgttg | gatttattgg | gttgccaact | ctctggaaag | 1500 |
| ggacatcatc | gcagcttcag | atggctaaag | tatacagtgt | gggtcaattt | gtgaaactca | 1560 |
| aagccaatgt | tgtcatcccg | agattcaaat | ggatgcgtaa | aggtagaggt | atttgggcaa | 1620 |
| ctggcaggat | ctctcaggtt | ctaccaaacg | gttgccttga | agtggacttc | cctggaatgt | 1680 |
| tacctttttgg | agaggaacat | ggaagctatc | ttgcagatcc | ggctgaagta | gagattgtga | 1740 |
| atttcaatac | atgtcaagga | gctgtggaaa | aatatcaaca | tctggaggat | tttcattggg | 1800 |
| ctgtgagacc | tttgcttatt | gctatgggtc | tattgacagc | gatgaagtta | gggatctgtg | 1860 |
| tcaggaagaa | aataggaagg | tcaaaggatg | ggaaacaacg | cgatggctcg | actggacaag | 1920 |
| gtgactgtaa | gattccggat | ggtaagggct | ctgacaaatc | taaatggctt | gtgttctttt | 1980 |
| aggtctgcta | tgagacacag | accttgtctg | gtccatatat | tatactgttc | tagtcataat | 2040 |
| aacgtttcat | gtacataatg | acgttttttct | tttttgctct | ttaaaattac | caaaaagctt | 2100 |
| tcacgcacca | agtgttactt | gcaatttgct | tagacaacga | cttcttacaa | agttaagtat | 2160 |

```
ataattacga tagccatgta attggagatc acagatgttt ttatatttat tgattaagag   2220
agc                                                                 2223

<210> SEQ ID NO 8
<211> LENGTH: 611
<212> TYPE: PRT
<213> ORGANISM: Arabidopsis thaliana

<400> SEQUENCE: 8

Met Ala Ser Lys Ile Ile Ala Gly Lys Pro Asp Asp Thr Glu Tyr Glu
1               5                   10                  15

Ile Ile Glu Gly Glu Ser Glu Ser Ala Leu Ala Ala Gly Thr Ser Pro
            20                  25                  30

Trp Met Asn Ser Thr Leu Lys Leu Arg His Arg Ile Gly Arg Gly
        35                  40                  45

Pro Phe Gly Asp Val Trp Leu Ala Thr His His Gln Ser Thr Glu Asp
    50                  55                  60

Tyr Asp Glu His His Glu Val Ala Ile Lys Met Leu Tyr Pro Ile Lys
65                  70                  75                  80

Glu Asp Gln Arg Arg Val Val Asp Lys Phe Glu Asp Leu Phe Ser
                85                  90                  95

Lys Cys Gln Gly Leu Glu Asn Val Cys Leu Leu Arg Gly Val Ser Ser
            100                 105                 110

Ile Asn Gly Lys Ile Cys Val Val Met Lys Phe Tyr Glu Gly Ser Leu
        115                 120                 125

Gly Asp Lys Met Ala Arg Leu Lys Gly Gly Lys Leu Ser Leu Pro Asp
    130                 135                 140

Val Leu Arg Tyr Gly Val Asp Leu Ala Thr Gly Ile Leu Glu Leu His
145                 150                 155                 160

Ser Lys Gly Phe Leu Ile Leu Asn Leu Lys Pro Ser Asn Phe Leu Leu
                165                 170                 175

Ser Asp Asn Asp Lys Ala Ile Leu Gly Asp Val Gly Ile Pro Tyr Leu
            180                 185                 190

Leu Leu Ser Ile Pro Leu Pro Ser Ser Asp Met Thr Glu Arg Leu Gly
        195                 200                 205

Thr Pro Asn Tyr Met Ala Pro Glu Gln Trp Gln Pro Asp Val Arg Gly
    210                 215                 220

Pro Met Ser Phe Glu Thr Asp Ser Trp Gly Phe Gly Cys Ser Ile Val
225                 230                 235                 240

Glu Met Leu Thr Gly Val Gln Pro Trp Ser Gly Arg Ser Ala Asp Glu
                245                 250                 255

Ile Tyr Asp Leu Val Val Arg Lys Gln Glu Lys Leu Ser Ile Pro Ser
            260                 265                 270

Ser Ile Pro Pro Leu Glu Asn Leu Leu Arg Gly Cys Phe Met Tyr
        275                 280                 285

Asp Leu Arg Ser Arg Pro Ser Met Thr Asp Ile Leu Leu Val Leu Lys
    290                 295                 300

Ser Leu Gln Asn Ser Glu Glu Gln Val Arg Arg Gly Ile Asp Ser
305                 310                 315                 320

Arg Glu Ile Arg Lys Ser Ser Ala Thr Leu Gly Tyr Thr Glu Trp Phe
                325                 330                 335

Leu Ser Lys Asp His Leu Gln Val Arg Asp Thr Val Arg Ser Arg Lys
            340                 345                 350

Pro Ala Asn Ser Cys Lys His Glu Asn Met Asp Val Pro Glu Gly Met
```

Val Val Gly Leu Glu Arg Asp Ser Thr Asp Pro Asp Gly Phe Val Leu
            355                 360                 365
Val Lys Val His Gly Val His Asp Pro Leu Arg Val His Val Ser Val
370                 375                 380
Leu Glu Arg Val Thr Asn Gly Leu Ala Ser Asp Trp Val Arg Leu
385                 390                 395                 400
Lys Val Arg Lys Asp Lys Arg His Ser Pro Val Gly Val Leu His Ser
    405                 410                 415
Ile Asp Arg Glu Gly Asn Val Ala Val Gly Phe Ile Gly Leu Pro Thr
420                 425                 430
Leu Trp Lys Gly Thr Ser Ser Gln Leu Gln Met Ala Lys Val Tyr Ser
    435                 440                 445
Val Gly Gln Phe Val Lys Leu Lys Ala Asn Val Val Ile Pro Arg Phe
450                 455                 460
Lys Trp Met Arg Lys Gly Arg Gly Ile Trp Ala Thr Gly Arg Ile Ser
465                 470                 475                 480
Gln Val Leu Pro Asn Gly Cys Leu Glu Val Asp Phe Pro Gly Met Leu
    485                 490                 495
Pro Phe Gly Glu Glu His Gly Ser Tyr Leu Ala Asp Pro Ala Glu Val
500                 505                 510
Glu Ile Val Asn Phe Asn Thr Cys Gln Gly Ala Val Glu Lys Tyr Gln
    515                 520                 525
His Leu Glu Asp Phe His Trp Ala Val Arg Pro Leu Leu Ile Ala Met
530                 535                 540
Gly Leu Leu Thr Ala Met Lys Leu Gly Ile Cys Val Arg Lys Lys Ile
545                 550                 555                 560
Gly Arg Ser Lys Asp Gly Lys Gln Arg Asp Gly Ser Thr Gly Gln Gly
    565                 570                 575
Asp Cys Lys Ile Pro Asp Gly Lys Gly Ser Asp Lys Ser Lys Trp Leu
580                 585                 590
Val Phe Phe
    595                 600                 605
    610

<210> SEQ ID NO 9
<211> LENGTH: 2156
<212> TYPE: DNA
<213> ORGANISM: Arabidopsis thaliana

<400> SEQUENCE: 9
aaatagtttg atttctgttg ttgagtttat gcgatatccc aactggtgaa actgtgttta      60
ttggttcaga cagagataaa tggcttcaaa gattattgct ggcaagccgg atgataccga     120
gtatgaaatc attgaaggtg agtctgagag cgctttagca gcggggacaa gcccttggat     180
gaattcatca acgttgaagc ttcgacatcg aattggaaga ggtcccttcg gtgatgtttg     240
gctggctact catcatcagt caactgagga ctatgatgag catcatgaag tggccatcaa     300
aatgctttat cccatcaagg aagatcaaag aaggggttgtg gtagataagt ttgaagatct     360
cttctctaaa tgtcaaggac tagagaatgt ctgtctgctc aggggagtct ctagtatcaa     420
tggaaagata tgtgtcgtca tgaaattcta cgagggctct cttggtgaca agatggctcg     480
gcttaaagga ggaaagcttt cactgccaga tgttttgaga tacggggttg atctggctac     540
agggatcctg gagttgcact caaaagggtt tctcattctc aatctcaagc cctctaactt     600
tcttctcagt gataacgaca aggccatcct cggggatgtt gggatccctt atctccttct     660

```
tagtatccct ttaccaagtt ctgatatgac agagagactt ggaactccaa actatatggc    720
accagaacag tggcaaccgg atgtcagagg tcccatgtcc tttgagactg attcttgggg    780
atttggttgc agcattgttg aaatgctgac tggtgtacaa ccttggtctg ggagatctgc    840
cgatgaaata tatgatttgg tggtgagaaa gcaagaaaag cttagtatcc ccagtagcat    900
accgcctcct ctcgagaacc tacttcgggg ttgctttatg tatgatcttc gaagccgacc    960
ttcgatgact gacatcttac tcgtcttaaa gagcttgcag aactcggagg aggaacaggt   1020
caggagaggc attgatagta gagaaatcag gaagagctcg gctactcttg gttatacaga   1080
atggtttctt tcaaaggatc atctgcaagt gcgcgacacc gtgcgttcaa gaaagcctgc   1140
caattcgtgt aagcatgaga acatggatgt gccagaagga atggtggttg gtttagaacg   1200
tgactccaca gacccagatg gatttgtgct agttaaagtc catggtgtac atgatccatt   1260
aagggttcac gtatctgttc ttgaacgggt aactaacggc ttagcttctg gagattgggt   1320
gcgtctgaag gtcaggaaag acaagaggca ctctccggtt ggtgttctcc attcaattga   1380
ccgtgaggga aatgtagctg ttggatttat tgggttgcca actctctgga aagggacatc   1440
atcgcagctt cagatggcta agtatacag tgtgggtcaa tttgtgaaac tcaaagccaa   1500
tgttgtcatc ccgagattca atggatgcg taaaggtaga ggtatttggg caactggcag   1560
gatctctcag gttctaccaa acggttgcct tgaagtggac ttccctggaa tgttaccttt   1620
tggagaggaa catggaagct atcttgcaga tccggctgaa gtagagattg tgaatttcaa   1680
tacatgtcaa ggagctgtgg aaaaatatca acatctggag gattttcatt gggctgtgag   1740
acctttgctt attgctatgg gtctattgac agcgatgaag ttagggatct gtgtcaggaa   1800
gaaaatagga aggtcaaagg atgggaaaca acgcgatggc tcgactggac aaggtgactg   1860
taagattccg gatggtaagg gctctgacaa atctaaatgg cttgtgttct tttaggtctg   1920
ctatgagaca cagaccttgt ctggtccata tattatactg ttctagtcat aataacgttt   1980
catgtacata atgacgtttt tctttttgc tcttaaaat taccaaaaag ctttcacgca   2040
ccaagtgtta cttgcaattt gcttagacaa cgacttctta caaagttaag tatataatta   2100
cgatagccat gtaattggag atcacagatg tttttatatt tattgattaa gagagc       2156

<210> SEQ ID NO 10
<211> LENGTH: 611
<212> TYPE: PRT
<213> ORGANISM: Arabidopsis thaliana

<400> SEQUENCE: 10

Met Ala Ser Lys Ile Ile Ala Gly Lys Pro Asp Asp Thr Glu Tyr Glu
1               5                   10                  15

Ile Ile Glu Gly Glu Ser Glu Ser Ala Leu Ala Ala Gly Thr Ser Pro
            20                  25                  30

Trp Met Asn Ser Ser Thr Leu Lys Leu Arg His Arg Ile Gly Arg Gly
        35                  40                  45

Pro Phe Gly Asp Val Trp Leu Ala Thr His Gln Ser Thr Glu Asp
    50                  55                  60

Tyr Asp Glu His His Glu Val Ala Ile Lys Met Leu Tyr Pro Ile Lys
65                  70                  75                  80

Glu Asp Gln Arg Arg Val Val Asp Lys Phe Glu Asp Leu Phe Ser
                85                  90                  95

Lys Cys Gln Gly Leu Glu Asn Val Cys Leu Leu Arg Gly Val Ser Ser
                100                 105                 110

Ile Asn Gly Lys Ile Cys Val Val Met Lys Phe Tyr Glu Gly Ser Leu
```

-continued

```
            115                 120                 125
Gly Asp Lys Met Ala Arg Leu Lys Gly Gly Lys Leu Ser Leu Pro Asp
130                 135                 140

Val Leu Arg Tyr Gly Val Asp Leu Ala Thr Gly Ile Leu Glu Leu His
145                 150                 155                 160

Ser Lys Gly Phe Leu Ile Leu Asn Leu Lys Pro Ser Asn Phe Leu Leu
                    165                 170                 175

Ser Asp Asn Asp Lys Ala Ile Leu Gly Asp Val Gly Ile Pro Tyr Leu
                180                 185                 190

Leu Leu Ser Ile Pro Leu Pro Ser Ser Asp Met Thr Glu Arg Leu Gly
            195                 200                 205

Thr Pro Asn Tyr Met Ala Pro Glu Gln Trp Gln Pro Asp Val Arg Gly
            210                 215                 220

Pro Met Ser Phe Glu Thr Asp Ser Trp Gly Phe Gly Cys Ser Ile Val
225                 230                 235                 240

Glu Met Leu Thr Gly Val Gln Pro Trp Ser Gly Arg Ser Ala Asp Glu
                    245                 250                 255

Ile Tyr Asp Leu Val Val Arg Lys Gln Glu Lys Leu Ser Ile Pro Ser
                260                 265                 270

Ser Ile Pro Pro Pro Leu Glu Asn Leu Leu Arg Gly Cys Phe Met Tyr
            275                 280                 285

Asp Leu Arg Ser Arg Pro Ser Met Thr Asp Ile Leu Leu Val Leu Lys
            290                 295                 300

Ser Leu Gln Asn Ser Glu Glu Glu Gln Val Arg Arg Gly Ile Asp Ser
305                 310                 315                 320

Arg Glu Ile Arg Lys Ser Ser Ala Thr Leu Gly Tyr Thr Glu Trp Phe
                    325                 330                 335

Leu Ser Lys Asp His Leu Gln Val Arg Asp Thr Val Arg Ser Arg Lys
                340                 345                 350

Pro Ala Asn Ser Cys Lys His Glu Asn Met Asp Val Pro Glu Gly Met
            355                 360                 365

Val Val Gly Leu Glu Arg Asp Ser Thr Asp Pro Asp Gly Phe Val Leu
            370                 375                 380

Val Lys Val His Gly Val His Asp Pro Leu Arg Val His Val Ser Val
385                 390                 395                 400

Leu Glu Arg Val Thr Asn Gly Leu Ala Ser Gly Asp Trp Val Arg Leu
                    405                 410                 415

Lys Val Arg Lys Asp Lys Arg His Ser Pro Val Gly Val Leu His Ser
                420                 425                 430

Ile Asp Arg Glu Gly Asn Val Ala Val Gly Phe Ile Gly Leu Pro Thr
            435                 440                 445

Leu Trp Lys Gly Thr Ser Ser Gln Leu Gln Met Ala Lys Val Tyr Ser
            450                 455                 460

Val Gly Gln Phe Val Lys Leu Lys Ala Asn Val Val Ile Pro Arg Phe
465                 470                 475                 480

Lys Trp Met Arg Lys Gly Arg Gly Ile Trp Ala Thr Gly Arg Ile Ser
                    485                 490                 495

Gln Val Leu Pro Asn Gly Cys Leu Glu Val Asp Phe Pro Gly Met Leu
                500                 505                 510

Pro Phe Gly Glu Glu His Gly Ser Tyr Leu Ala Asp Pro Ala Glu Val
            515                 520                 525

Glu Ile Val Asn Phe Asn Thr Cys Gln Gly Ala Val Glu Lys Tyr Gln
            530                 535                 540
```

```
His Leu Glu Asp Phe His Trp Ala Val Arg Pro Leu Leu Ile Ala Met
545                 550                 555                 560

Gly Leu Leu Thr Ala Met Lys Leu Gly Ile Cys Val Arg Lys Lys Ile
                565                 570                 575

Gly Arg Ser Lys Asp Gly Lys Gln Arg Asp Gly Ser Thr Gly Gln Gly
            580                 585                 590

Asp Cys Lys Ile Pro Asp Gly Lys Gly Ser Asp Lys Ser Lys Trp Leu
            595                 600                 605

Val Phe Phe
610

<210> SEQ ID NO 11
<211> LENGTH: 2296
<212> TYPE: DNA
<213> ORGANISM: Arabidopsis thaliana

<400> SEQUENCE: 11
```

| | | | | | |
|---|---|---|---|---|---|
| tttctcttct | ctgtcttttt | cagcttctga | agttacttgt | ttcagttccc | gatgatcaat   60 |
| tcttagtttt | tttggcttgt | tttcttcgtc | tctctttcat | caggcctttg | gagttttgtg  120 |
| ttaccatttt | cgctcgcgtc | attactggtg | ttagggtttt | cttcaaaagc | ttcttaatcc  180 |
| gtcgaaattg | ctcttttctc | tccctcatta | cagagataaa | tggcttcaaa | gattattgct  240 |
| ggcaagccgg | atgataccga | gtatgaaatc | attgaaggtg | agtctgagag | cgctttagca  300 |
| gcggggacaa | gcccttggat | gaattcatca | acgttgaagc | ttcgacatcg | aattggaaga  360 |
| ggtcccttcg | gtgatgtttg | gctggctact | catcatcagt | caactgagga | ctatgatgag  420 |
| catcatgaag | tggccatcaa | aatgctttat | cccatcaagg | aagatcaaag | aagggttgtg  480 |
| gtagataagt | ttgaagatct | cttctctaaa | tgtcaaggac | tagagaatgt | ctgtctgctc  540 |
| aggggagtct | ctagtatcaa | tggaaagata | tgtgtcgtca | tgaaattcta | cgagggctct  600 |
| cttggtgaca | agatggctcg | gcttaaagga | ggaaagcttt | cactgccaga | tgttttgaga  660 |
| tacggggttg | atctggctac | agggatcctg | gagttgcact | caaaagggtt | tctcattctc  720 |
| aatctcaagc | cctctaactt | tcttctcagt | gataacgaca | aggccatcct | cggggatgtt  780 |
| gggatccctt | atctccttct | tagtatccct | ttaccaagtt | ctgatatgac | agagagactt  840 |
| ggaactccaa | actatatggc | accagaacag | tggcaaccgg | atgtcagagg | tcccatgtcc  900 |
| tttgagactg | attcttgggg | atttggttgc | agcattgttg | aaatgctgac | tggtgtacaa  960 |
| ccttggtctg | ggagatctgc | cgatgaaata | tatgatttgg | tggtgagaaa | gcaagaaaag 1020 |
| cttagtatcc | ccagtagcat | accgcctcct | ctcgagaacc | tacttcgggg | ttgctttatg 1080 |
| tatgatcttc | gaagccgacc | ttcgatgact | gacatcttac | tcgtcttaaa | gagcttgcag 1140 |
| aactcggagg | aggaacaggt | caggagaggc | attgatagta | gagaaatcag | gaagagctcg 1200 |
| gctactcttg | gttatacaga | atggtttctt | tcaaaggatc | atctgcaagt | gcgcgacacc 1260 |
| gtgcgttcaa | gaaagcctgc | caattcgtgt | aagcatgaga | catggatgt | gccagaagga 1320 |
| atggtggttg | gtttagaacg | tgactccaca | gacccagatg | gatttgtgct | agttaaagtc 1380 |
| catggtgtac | atgatccatt | aagggttcac | gtatctgttc | ttgaacgggt | aactaacggc 1440 |
| ttagcttctg | gagattgggt | gcgtctgaag | gtcaggaaag | acaagaggca | ctctccggtt 1500 |
| ggtgttctcc | attcaattga | ccgtgaggga | aatgtagctg | ttggatttat | tgggttgcca 1560 |
| actctctgga | aagggacatc | atcgcagctt | cagatggcta | agtatacag | tgtgggtcaa 1620 |
| tttgtgaaac | tcaaagccaa | tgttgtcatc | ccgagattca | aatggatgcg | taaaggtaga 1680 |
| ggtatttggg | caactggcag | gatctctcag | gttctaccaa | acggttgcct | tgaagtggac 1740 |

```
ttccctggaa tgttaccttt tggagaggaa catggaagct atcttgcaga tccggctgaa    1800
gtagagattg tgaatttcaa tacatgtcaa ggagctgtgg aaaaatatca acatctggag    1860
gattttcatt gggctgtgag accttttgctt attgctatgg gtctattgac agcgatgaag   1920
ttagggatct gtgtcaggaa gaaaatagga aggtcaaagg atgggaaaca acgcgatggc    1980
tcgactggac aaggtgactg taagattccg gatggtaagg gctctgacaa atctaaatgg    2040
cttgtgttct tttaggtctg ctatgagaca cagaccttgt ctggtccata tattatactg    2100
ttctagtcat aataacgttt catgtacata atgacgtttt tctttttttgc tctttaaaat   2160 taccaaaaag ctttcacgca ccaagtgtta cttgcaattt gcttagacaa cgacttctta    2220
caaagttaag tatataatta cgatagccat gtaattggag atcacagatg tttttatatt    2280
tattgattaa gagagc                                                    2296
```

<210> SEQ ID NO 12
<211> LENGTH: 611
<212> TYPE: PRT
<213> ORGANISM: Arabidopsis thaliana

<400> SEQUENCE: 12

Met Ala Ser Lys Ile Ile Ala Gly Lys Pro Asp Asp Thr Glu Tyr Glu
1               5                   10                  15

Ile Ile Glu Gly Glu Ser Glu Ser Ala Leu Ala Ala Gly Thr Ser Pro
            20                  25                  30

Trp Met Asn Ser Ser Thr Leu Lys Leu Arg His Arg Ile Gly Arg Gly
        35                  40                  45

Pro Phe Gly Asp Val Trp Leu Ala Thr His His Gln Ser Thr Glu Asp
    50                  55                  60

Tyr Asp Glu His His Glu Val Ala Ile Lys Met Leu Tyr Pro Ile Lys
65                  70                  75                  80

Glu Asp Gln Arg Arg Val Val Val Asp Lys Phe Glu Asp Leu Phe Ser
                85                  90                  95

Lys Cys Gln Gly Leu Glu Asn Val Cys Leu Leu Arg Gly Val Ser Ser
            100                 105                 110

Ile Asn Gly Lys Ile Cys Val Val Met Lys Phe Tyr Glu Gly Ser Leu
        115                 120                 125

Gly Asp Lys Met Ala Arg Leu Lys Gly Gly Lys Leu Ser Leu Pro Asp
    130                 135                 140

Val Leu Arg Tyr Gly Val Asp Leu Ala Thr Gly Ile Leu Glu Leu His
145                 150                 155                 160

Ser Lys Gly Phe Leu Ile Leu Asn Leu Lys Pro Ser Asn Phe Leu Leu
                165                 170                 175

Ser Asp Asn Asp Lys Ala Ile Leu Gly Asp Val Gly Ile Pro Tyr Leu
            180                 185                 190

Leu Leu Ser Ile Pro Leu Pro Ser Ser Asp Met Thr Glu Arg Leu Gly
        195                 200                 205

Thr Pro Asn Tyr Met Ala Pro Glu Gln Trp Gln Pro Asp Val Arg Gly
    210                 215                 220

Pro Met Ser Phe Glu Thr Asp Ser Trp Gly Phe Gly Cys Ser Ile Val
225                 230                 235                 240

Glu Met Leu Thr Gly Val Gln Pro Trp Ser Gly Arg Ser Ala Asp Glu
                245                 250                 255

Ile Tyr Asp Leu Val Val Arg Lys Gln Glu Lys Leu Ser Ile Pro Ser
            260                 265                 270

```
Ser Ile Pro Pro Leu Glu Asn Leu Leu Arg Gly Cys Phe Met Tyr
    275                 280                 285

Asp Leu Arg Ser Arg Pro Ser Met Thr Asp Ile Leu Val Leu Lys
290                 295                 300

Ser Leu Gln Asn Ser Glu Glu Glu Val Arg Arg Gly Ile Asp Ser
305                 310                 315                 320

Arg Glu Ile Arg Lys Ser Ser Ala Thr Leu Gly Tyr Thr Glu Trp Phe
                325                 330                 335

Leu Ser Lys Asp His Leu Gln Val Arg Asp Thr Val Arg Ser Arg Lys
            340                 345                 350

Pro Ala Asn Ser Cys Lys His Glu Asn Met Asp Val Pro Glu Gly Met
                355                 360                 365

Val Val Gly Leu Glu Arg Asp Ser Thr Asp Pro Asp Gly Phe Val Leu
    370                 375                 380

Val Lys Val His Gly Val His Asp Pro Leu Arg Val His Val Ser Val
385                 390                 395                 400

Leu Glu Arg Val Thr Asn Gly Leu Ala Ser Gly Asp Trp Val Arg Leu
                405                 410                 415

Lys Val Arg Lys Asp Lys Arg His Ser Pro Val Gly Val Leu His Ser
            420                 425                 430

Ile Asp Arg Glu Gly Asn Val Ala Val Gly Phe Ile Gly Leu Pro Thr
        435                 440                 445

Leu Trp Lys Gly Thr Ser Ser Gln Leu Gln Met Ala Lys Val Tyr Ser
    450                 455                 460

Val Gly Gln Phe Val Lys Leu Lys Ala Asn Val Val Ile Pro Arg Phe
465                 470                 475                 480

Lys Trp Met Arg Lys Gly Arg Gly Ile Trp Ala Thr Gly Arg Ile Ser
                485                 490                 495

Gln Val Leu Pro Asn Gly Cys Leu Glu Val Asp Phe Pro Gly Met Leu
            500                 505                 510

Pro Phe Gly Glu Glu His Gly Ser Tyr Leu Ala Asp Pro Ala Glu Val
        515                 520                 525

Glu Ile Val Asn Phe Asn Thr Cys Gln Gly Ala Val Glu Lys Tyr Gln
    530                 535                 540

His Leu Glu Asp Phe His Trp Ala Val Arg Pro Leu Leu Ile Ala Met
545                 550                 555                 560

Gly Leu Leu Thr Ala Met Lys Leu Gly Ile Cys Val Arg Lys Lys Ile
                565                 570                 575

Gly Arg Ser Lys Asp Gly Lys Gln Arg Asp Gly Ser Thr Gly Gln Gly
            580                 585                 590

Asp Cys Lys Ile Pro Asp Gly Lys Gly Ser Asp Lys Ser Lys Trp Leu
        595                 600                 605

Val Phe Phe
    610

<210> SEQ ID NO 13
<211> LENGTH: 1033
<212> TYPE: DNA
<213> ORGANISM: Arabidopsis thaliana

<400> SEQUENCE: 13
aatctgacga ccacagcctt tagcttattt gtgtggcgaa gagaagagat aacattccta    60
agcaaatctc ttctctctcc cattcgtctc caaagagatt acagttttga gcatttctca   120
tctctcgaag ctcttctctg tgtgtgtggc gatggctgct aattcgataa tggcttcctc   180
```

```
caaaccccta atctccctgt catccaacca acaaccaaac cgagtccaaa ttcccaaatt      240
cgccaaactt ccccaaattc ccaaatccct cacttcctcc accgatctcc gtagcaaagc      300
actatcactc tcctccgcca ccgccaaatc cttagcttta atcgccgctt cgctcctcc       360
gtcgatggcg gaggcgatgg agaaagcaca gctcttcgat ttcaatctca cgcttccgat      420
catcgttgtt gagtttctct tcttgatgtt cgctctcgac aaggtctatt actctccgct      480
tggtaacttc atggatcaaa gagacgcttc catcaaagag aagctcgcga gtgttaagga      540
cacttcgact gaagtaaagg agctcgatga gcaagccgcc gccgtgatga gagcagctag      600
ggctgagatc gccgccgcgc ttaacaagat gaagaaggag actcaggttg aagtcgagga      660
gaagctagcg gagggaagga agaaggtgga ggaagagcta aagaagcttt ggcgagctt       720
ggagagtcag aaagaagaaa ccattaaagc tttggattct cagattgctg ctcttagtga      780
agacattgtc aagaaggttc ttccttctta aattatattt ttgttaactg tgtaattctc      840
tgtctctcta tctcaaaact tatttacaag aaattactgt aaatctcttc ttcttcttct      900
tctctgtttc ttggattgtt cgtcgttcaa agaagaacaa tttttatttt gtaagtttat      960
aaataattag ctctcttctg tcatttagga tgattaaagt acaagtatgt atatcgagga     1020
attagttgtt acg                                                        1033
```

<210> SEQ ID NO 14
<211> LENGTH: 219
<212> TYPE: PRT
<213> ORGANISM: Arabidopsis thaliana

<400> SEQUENCE: 14

Met Ala Ala Asn Ser Ile Met Ala Ser Ser Lys Pro Leu Ile Ser Leu
1               5                   10                  15

Ser Ser Asn Gln Gln Pro Asn Arg Val Gln Ile Pro Lys Phe Ala Lys
            20                  25                  30

Leu Pro Gln Ile Pro Lys Ser Leu Thr Ser Ser Thr Asp Leu Arg Ser
        35                  40                  45

Lys Ala Leu Ser Leu Ser Ser Ala Thr Ala Lys Ser Leu Ala Leu Ile
    50                  55                  60

Ala Ala Phe Ala Pro Pro Ser Met Ala Glu Ala Met Glu Lys Ala Gln
65                  70                  75                  80

Leu Phe Asp Phe Asn Leu Thr Leu Pro Ile Ile Val Val Glu Phe Leu
                85                  90                  95

Phe Leu Met Phe Ala Leu Asp Lys Val Tyr Tyr Ser Pro Leu Gly Asn
            100                 105                 110

Phe Met Asp Gln Arg Asp Ala Ser Ile Lys Glu Lys Leu Ala Ser Val
        115                 120                 125

Lys Asp Thr Ser Thr Glu Val Lys Glu Leu Asp Glu Gln Ala Ala Ala
    130                 135                 140

Val Met Arg Ala Ala Arg Ala Glu Ile Ala Ala Leu Asn Lys Met
145                 150                 155                 160

Lys Lys Glu Thr Gln Val Glu Val Glu Lys Leu Ala Glu Gly Arg
                165                 170                 175

Lys Lys Val Glu Glu Glu Leu Lys Glu Ala Leu Ala Ser Leu Glu Ser
            180                 185                 190

Gln Lys Glu Glu Thr Ile Lys Ala Leu Asp Ser Gln Ile Ala Ala Leu
        195                 200                 205

Ser Glu Asp Ile Val Lys Lys Val Leu Pro Ser
    210                 215

<210> SEQ ID NO 15
<211> LENGTH: 333
<212> TYPE: DNA
<213> ORGANISM: Arabidopsis thaliana

<400> SEQUENCE: 15

```
atgaagttga aaggagatga gtatctgcca aaagaatgtt ttatcacaaa gcttagaata      60
gagaccaaaa gggtactacg agagctgata tttttaaact ttttggagaa gaaatacagt     120
ccatatcttc atcttttttgt tattttatat cttataataa taagtacaat aaaacatagc    180
gagtggagag ggatcagagt agttaaacaa ttaatgtcca aaacaaagga gcagaagaag     240
cgtaggaaag gcgcagatgt cgtcgataaa attcatctac gagatcttcc caagatttgg     300
aatttgtcca cttgtattgc cactcaatgt taa                                  333
```

<210> SEQ ID NO 16
<211> LENGTH: 110
<212> TYPE: PRT
<213> ORGANISM: Arabidopsis thaliana

<400> SEQUENCE: 16

```
Met Lys Leu Lys Gly Asp Glu Tyr Leu Pro Lys Glu Cys Phe Ile Thr
1               5                   10                  15

Lys Leu Arg Ile Glu Thr Lys Arg Val Leu Arg Glu Leu Ile Phe Leu
            20                  25                  30

Asn Phe Leu Glu Lys Lys Tyr Ser Pro Tyr Leu His Leu Phe Val Ile
        35                  40                  45

Leu Tyr Leu Ile Ile Ile Ser Thr Ile Lys His Ser Glu Trp Arg Gly
    50                  55                  60

Ile Arg Val Val Lys Gln Leu Met Ser Lys Thr Lys Glu Gln Lys Lys
65                  70                  75                  80

Arg Arg Lys Gly Ala Asp Val Val Asp Lys Ile His Leu Arg Asp Leu
                85                  90                  95

Pro Lys Ile Trp Asn Leu Ser Thr Cys Ile Ala Thr Gln Cys
            100                 105                 110
```

<210> SEQ ID NO 17
<211> LENGTH: 258
<212> TYPE: DNA
<213> ORGANISM: Arabidopsis thaliana

<400> SEQUENCE: 17

```
atggcttcca actcaatgag ctctagcgct tcttggacac gtaaggagaa caaattattt      60
gaaagggcgt tggctacata tgaccaggac actcctgacc gttggcataa cgttgcaaga    120
gccgttggcg gcaaatcagc tgaagaaaat atcacaacaa ttatccataa gaaagcattc    180
ataaataata gacatgcact ctccagtttc ttatgcgtgt cttcttgttt caccaggcca    240
gagaaaaaaa aaatctag                                                   258
```

<210> SEQ ID NO 18
<211> LENGTH: 85
<212> TYPE: PRT
<213> ORGANISM: Arabidopsis thaliana

<400> SEQUENCE: 18

```
Met Ala Ser Asn Ser Met Ser Ser Ala Ser Trp Thr Arg Lys Glu
1               5                   10                  15

Asn Lys Leu Phe Glu Arg Ala Leu Ala Thr Tyr Asp Gln Asp Thr Pro
            20                  25                  30
```

```
Asp Arg Trp His Asn Val Ala Arg Ala Val Gly Gly Lys Ser Ala Glu
         35                  40                  45

Glu Asn Ile Thr Thr Ile Ile His Lys Lys Ala Phe Ile Asn Asn Arg
 50                  55                  60

His Ala Leu Ser Ser Phe Leu Cys Val Ser Ser Cys Phe Thr Arg Pro
 65                  70                  75                  80

Glu Lys Lys Lys Ile
             85

<210> SEQ ID NO 19
<211> LENGTH: 1863
<212> TYPE: DNA
<213> ORGANISM: Arabidopsis thaliana

<400> SEQUENCE: 19
```

| | | | | | |
|---|---|---|---|---|---|
| atggctgctt | ctagattgtg | ttccgcggcg | gcgatagctg | ctgcgttcac | ttcaatgtca | 60 |
| atgtctcaga | accgtgctta | cgccgattct | tctcgattcc | ggtttccttt | cttttcttct | 120 |
| tctccttctc | ctcctccgtc | agattctccg | gcgaatcaat | cttcatcgaa | gtctaaagca | 180 |
| gagcctgatg | agcctaaagg | atcgggtttt | gatcctgagg | ctcttgagag | agctgctaaa | 240 |
| gctcttagag | atatcaatag | ctctccccat | tccaagcagg | tgtttgatct | catgaggaag | 300 |
| caggagaaaa | ctcggttagc | tgaattaacg | gcagagactt | ctcattacga | agctattcaa | 360 |
| gcacacaatg | atattggcag | acagcagaaa | ttggctgagg | accagagaaa | tcttttgcag | 420 |
| acacaggcgc | aaaccaaagc | gcaaaatctg | cgatatgagg | atgaattggc | agaaagagaa | 480 |
| cagcagacag | atcatgaagc | tcagaggcat | cataatgtgg | aattggttaa | gatgcaagag | 540 |
| gcgtcttcta | tcaggaaaga | gaaggcaaaa | atcgccacag | aagaacagat | ccaagctcag | 600 |
| catcgccaaa | ctgagaaaga | gagagctgaa | cttgagcgag | agacgattcg | tgtcaaggcc | 660 |
| atggctgaag | ctgaaggtcg | ggctcatgaa | gccaaactta | ctgaagagca | aaacagaaga | 720 |
| ttgcttatgg | aaaggattaa | tggtgaaaga | gagaagtggc | ttgctgcaat | caacacaatg | 780 |
| ttcagtcaca | tcgaaggggg | attcaggacc | ttattaactg | atcgaaataa | gctgattatg | 840 |
| actgttggag | gagctactgc | attagctgca | ggggtttata | caactcggat | gcttggacaa | 900 |
| ccgtcactta | ttcgagaatc | ttccatgcgt | agatttccat | ggacaggctc | agtgtctcaa | 960 |
| tttaagaaca | ggatctcagg | ggctgcagca | gcttctgcag | cagaaggcaa | aaagccgctt | 1020 |
| gataatgtaa | ttctccatac | ttctttgaag | aaacgaatcg | agcgtctcgc | tagagctaca | 1080 |
| gcaaacacca | atcccatca | agcaccattc | cgcaacatga | tgttttatgg | acctcctggt | 1140 |
| accggtaaaa | ctatggtggc | aagggaaata | gctcggaaat | cgggtctgga | ttatgctatg | 1200 |
| atgacaggag | gtgatgttgc | tcccttggga | tcacaagctg | ttactaaaat | ccatcagata | 1260 |
| tttgattggg | ctaagaaatc | gaacaaaggc | ttacttcttt | tcattgatga | agccgatgct | 1320 |
| tttctatgcg | agcgtaacag | cacttacatg | agtgaggctc | aacgtagtgc | tctgaacgct | 1380 |
| ttgctcttcc | gaactggtga | tcaatctcgg | acattgttc | ttgtcttggc | tacaaacaga | 1440 |
| cgtggagatc | tcgatagtgc | ggttacagac | aggattgatg | aagtcattga | gttcccactt | 1500 |
| ccagggggaag | aagaacgttt | caagcttctc | aatctctatc | tcaacaaata | tctaaagatg | 1560 |
| ggtgataaca | acgaagacac | aaaaccgaaa | tggagtcatt | tgtttaagaa | gctgtcacag | 1620 |
| aagattaccg | ttgaagaaga | cttaactgat | aaagtgattt | ctgaggctgc | aaagaagaca | 1680 |
| gaaggattct | ctggccgtga | gattgcaaag | cttgtggctg | gagtacaagc | tggagtgtac | 1740 |
| ggacgagcgg | attgtgtttt | ggattcacag | cttttttaaag | agattgttga | atataaggtt | 1800 |

```
gaagaacatc accgaaggca tatgcttgct tctgaaggtt ttcagccatt actcttctct    1860
tag                                                                 1863
```

<210> SEQ ID NO 20
<211> LENGTH: 620
<212> TYPE: PRT
<213> ORGANISM: Arabidopsis thaliana

<400> SEQUENCE: 20

```
Met Ala Ala Ser Arg Leu Cys Ser Ala Ala Ile Ala Ala Ala Phe
1               5                   10                  15

Thr Ser Met Ser Met Ser Gln Asn Arg Ala Tyr Ala Asp Ser Ser Arg
            20                  25                  30

Phe Arg Phe Pro Phe Phe Ser Ser Pro Ser Pro Pro Ser Asp
        35                  40                  45

Ser Pro Ala Asn Gln Ser Ser Ser Lys Ser Lys Ala Glu Pro Asp Glu
    50                  55                  60

Pro Lys Gly Ser Gly Phe Asp Pro Glu Ala Leu Glu Arg Ala Ala Lys
65                  70                  75                  80

Ala Leu Arg Asp Ile Asn Ser Ser Pro His Ser Lys Gln Val Phe Asp
                85                  90                  95

Leu Met Arg Lys Gln Glu Lys Thr Arg Leu Ala Glu Leu Thr Ala Glu
            100                 105                 110

Thr Ser His Tyr Glu Ala Ile Gln Ala His Asn Asp Ile Gly Arg Gln
        115                 120                 125

Gln Lys Leu Ala Glu Asp Gln Arg Asn Leu Leu Gln Thr Gln Ala Gln
    130                 135                 140

Thr Lys Ala Gln Asn Leu Arg Tyr Glu Asp Glu Leu Ala Arg Lys Arg
145                 150                 155                 160

Gln Gln Thr Asp His Glu Ala Gln Arg His His Asn Val Glu Leu Val
                165                 170                 175

Lys Met Gln Glu Ala Ser Ser Ile Arg Lys Glu Lys Ala Lys Ile Ala
            180                 185                 190

Thr Glu Glu Gln Ile Gln Ala Gln His Arg Gln Thr Glu Lys Glu Arg
        195                 200                 205

Ala Glu Leu Glu Arg Glu Thr Ile Arg Val Lys Ala Met Ala Glu Ala
    210                 215                 220

Glu Gly Arg Ala His Glu Ala Lys Leu Thr Glu Gln Asn Arg Arg
225                 230                 235                 240

Leu Leu Met Glu Arg Ile Asn Gly Glu Arg Glu Lys Trp Leu Ala Ala
                245                 250                 255

Ile Asn Thr Met Phe Ser His Ile Glu Gly Gly Phe Arg Thr Leu Leu
            260                 265                 270

Thr Asp Arg Asn Lys Leu Ile Met Thr Val Gly Gly Ala Thr Ala Leu
        275                 280                 285

Ala Ala Gly Val Tyr Thr Thr Arg Met Leu Gly Gln Pro Ser Leu Ile
    290                 295                 300

Arg Glu Ser Ser Met Arg Arg Phe Pro Trp Thr Gly Ser Val Ser Gln
305                 310                 315                 320

Phe Lys Asn Arg Ile Ser Gly Ala Ala Ala Ser Ala Ala Glu Gly
                325                 330                 335

Lys Lys Pro Leu Asp Asn Val Ile Leu His Thr Ser Leu Lys Lys Arg
            340                 345                 350

Ile Glu Arg Leu Ala Arg Ala Thr Ala Asn Thr Lys Ser His Gln Ala
```

355                 360                 365
Pro Phe Arg Asn Met Met Phe Tyr Gly Pro Gly Thr Gly Lys Thr
                    370                 375                 380

Met Val Ala Arg Glu Ile Ala Arg Lys Ser Gly Leu Asp Tyr Ala Met
385                 390                 395                 400

Met Thr Gly Gly Asp Val Ala Pro Leu Gly Ser Gln Ala Val Thr Lys
                405                 410                 415

Ile His Gln Ile Phe Asp Trp Ala Lys Lys Ser Asn Lys Gly Leu Leu
                420                 425                 430

Leu Phe Ile Asp Glu Ala Asp Ala Phe Leu Cys Glu Arg Asn Ser Thr
            435                 440                 445

Tyr Met Ser Glu Ala Gln Arg Ser Ala Leu Asn Ala Leu Leu Phe Arg
    450                 455                 460

Thr Gly Asp Gln Ser Arg Asp Ile Val Leu Val Leu Ala Thr Asn Arg
465                 470                 475                 480

Arg Gly Asp Leu Asp Ser Ala Val Thr Asp Arg Ile Asp Glu Val Ile
                485                 490                 495

Glu Phe Pro Leu Pro Gly Glu Glu Arg Phe Lys Leu Leu Asn Leu
                500                 505                 510

Tyr Leu Asn Lys Tyr Leu Lys Met Gly Asp Asn Asn Glu Asp Thr Lys
            515                 520                 525

Pro Lys Trp Ser His Leu Phe Lys Lys Leu Ser Gln Lys Ile Thr Val
    530                 535                 540

Glu Glu Asp Leu Thr Asp Lys Val Ile Ser Glu Ala Ala Lys Lys Thr
545                 550                 555                 560

Glu Gly Phe Ser Gly Arg Glu Ile Ala Lys Leu Val Ala Gly Val Gln
                565                 570                 575

Ala Gly Val Tyr Gly Arg Ala Asp Cys Val Leu Asp Ser Gln Leu Phe
            580                 585                 590

Lys Glu Ile Val Glu Tyr Lys Val Glu Glu His His Arg Arg His Met
    595                 600                 605

Leu Ala Ser Glu Gly Phe Gln Pro Leu Leu Phe Ser
610                 615                 620

<210> SEQ ID NO 21
<211> LENGTH: 994
<212> TYPE: DNA
<213> ORGANISM: Arabidopsis thaliana

<400> SEQUENCE: 21
atcaaatttg tcatttgttt attcaaattt ttgagaaaat ggtgagaagt accaaaggtc      60
gtcagaaaat agagatgaaa aaaatggaaa acgaaagcaa ccttcaggtt actttctcaa     120
aaagaagatt cggtcttttc aaaaaagcta gtgaactttg cacattaagt ggtgcagaga     180
ttctgttgat tgtgttctct cctggtggga agtgttttc ttttggccat ccaagtgttc      240
aagaactcat tcatcgcttt tcgaatccta accataattc tgccattgtc catcatcaga     300
acaacaatct ccaacttgtt gaacccgtc cggatagaaa tatccaatat ctcaacaata      360
tactcactga ggtgctggca aaccaggaaa aggagaaaca gaagagaatg gttttggacc     420
tattgaaaga atccagagaa caagtaggaa actggtatga aaagatgtg aaagatctcg      480 acatgaatga aaccaaccag ctgatatctg ctcttcaaga tgtgaaaaag aaactggtaa     540
gagaaatgtc tcaatattct caagtaaatg tttcgcagaa ttactttggt caaagttctg     600
gcgtgattgg tggtggtaat gttggcattg atcttttga tcaaagaaga aatgcattca     660

```
actataatcc aaacatggtg tttcccaatc atacaccacc aatgtttgga tacaacaatg    720
atggagttct cgttccgata tccaacatga actacatgtc aagttacaac ttcaaccaga    780
gctagagtct gaagctagaa gaacatccta atcaatattt gcgttatttt ggctatggtt    840
actgttagga ttgttcttgt attgtgagac ttaagtttgt ttttctttt aatttgtttc     900 agttggttgg ttttcatttt tattcgtcgt ttgttttcct ttgttttgg atattttgt      960 atccagaata aatttattta tcctttaatt ttac                                 994
```

<210> SEQ ID NO 22
<211> LENGTH: 248
<212> TYPE: PRT
<213> ORGANISM: Arabidopsis thaliana

<400> SEQUENCE: 22

```
Met Val Arg Ser Thr Lys Gly Arg Gln Lys Ile Glu Met Lys Lys Met
1               5                   10                  15

Glu Asn Glu Ser Asn Leu Gln Val Thr Phe Ser Lys Arg Arg Phe Gly
            20                  25                  30

Leu Phe Lys Lys Ala Ser Glu Leu Cys Thr Leu Ser Gly Ala Glu Ile
        35                  40                  45

Leu Leu Ile Val Phe Ser Pro Gly Gly Lys Val Phe Ser Phe Gly His
    50                  55                  60

Pro Ser Val Gln Glu Leu Ile His Arg Phe Ser Asn Pro Asn His Asn
65                  70                  75                  80

Ser Ala Ile Val His His Gln Asn Asn Asn Leu Gln Leu Val Glu Thr
                85                  90                  95

Arg Pro Asp Arg Asn Ile Gln Tyr Leu Asn Asn Ile Leu Thr Glu Val
            100                 105                 110

Leu Ala Asn Gln Glu Lys Glu Lys Gln Lys Arg Met Val Leu Asp Leu
        115                 120                 125

Leu Lys Glu Ser Arg Glu Gln Val Gly Asn Trp Tyr Glu Lys Asp Val
    130                 135                 140

Lys Asp Leu Asp Met Asn Glu Thr Asn Gln Leu Ile Ser Ala Leu Gln
145                 150                 155                 160

Asp Val Lys Lys Lys Leu Val Arg Glu Met Ser Gln Tyr Ser Gln Val
                165                 170                 175

Asn Val Ser Gln Asn Tyr Phe Gly Gln Ser Ser Gly Val Ile Gly Gly
            180                 185                 190

Gly Asn Val Gly Ile Asp Leu Phe Asp Gln Arg Arg Asn Ala Phe Asn
        195                 200                 205

Tyr Asn Pro Asn Met Val Phe Pro Asn His Thr Pro Pro Met Phe Gly
    210                 215                 220

Tyr Asn Asn Asp Gly Val Leu Val Pro Ile Ser Asn Met Asn Tyr Met
225                 230                 235                 240

Ser Ser Tyr Asn Phe Asn Gln Ser
                245
```

<210> SEQ ID NO 23
<211> LENGTH: 1259
<212> TYPE: DNA
<213> ORGANISM: Arabidopsis thaliana

<400> SEQUENCE: 23

```
gagagaagaa cgttgatgat gattatgatg cttacgacgg tggtgacgct gacgtggcag     60
aagcaatgct atggatgggg aacggagaca gcagaggata tggttagaaa cgaagcagag    120
```

-continued

| | | |
|---|---|---|
| catgctaaaa acgcagccga gaccgctaag aaaatggcgt ccgatgcggc tcatgacaca | 180 |
| aaggacaaaa ccgcctcttg ggctggttgg ggtttccgac aaaatttcca caggattggg | 240 |
| aggcaagaaa gctgaggcag aagaagcggc tgaatctgcg aagaactacg cttatgacaa | 300 |
| ggctggatcc gcctatgaca atgcgggtta cgccaaggac tttgcatcag acaaagccgg | 360 |
| atctgcttac gatagtgctc ataacgcaaa acattatgct tatgataagg ctggtgatgc | 420 |
| aaaagacatg gcctacgata gaccggtca agccaagtac atggcttacg acaaagcagg | 480 |
| atcagcctac gaaaaggccg gtcaagccaa ggacatggcc tacgacaagg cgggtcaagc | 540 |
| taaagacatg gcctacgaca aggtgggatc agcctacgac aaggcgggtc aagccaagga | 600 |
| catggcctac gacaaagcag gatcagcatc tgagaaggct ggtcaagcca agactttgc | 660 |
| ctatgacaag gcagctcacg caaaagacgc tgcctataac aaagcagagg atgtgattaa | 720 |
| gatggctacg gatacgagtg gtgaagctaa agatagtgcg tatggaacat acgaaagatt | 780 |
| caaagaagga tctaagaatg ctaaagacat tgcatcggat aaagctcacg atgttagaga | 840 |
| aaccgcaggg cgagcggtgg actatgctaa agacaaagca aatgatgcat acgaatcggg | 900 |
| gagcgaagca gccggaagat tcgacgaggc aatgcataag gttggggaga ggtatggtgc | 960 |
| agttaaggat tctatgtcgg agaacacaaa agaagcttat gagagtgcaa aggagaaggc | 1020 |
| ttctgatgct gctggtgagt acggttcata tatgagagac cgtagcgctg agctttagaa | 1080 |
| ctgaaaaaat tataacgtat agccgtatag ggtaagtttg catttagatt tcaaatcttc | 1140 |
| gtttgtacaa taaatttctt atatatatgt gtatatcagc agtatatgta tatgtaagaa | 1200 |
| tggtggagtt gcttgtatta gttgcaaaat cagattctca atgaaaggcg agttgtttc | 1259 |

<210> SEQ ID NO 24
<211> LENGTH: 335
<212> TYPE: PRT
<213> ORGANISM: Arabidopsis thaliana

<400> SEQUENCE: 24

```
Met Asp Gly Glu Arg Arg Gln Gln Arg Ile Trp Leu Glu Thr Lys Gln
1               5                   10                  15

Ser Met Leu Lys Thr Gln Pro Arg Pro Leu Arg Lys Trp Arg Pro Met
            20                  25                  30

Arg Leu Met Thr Gln Arg Thr Lys Pro Pro Leu Gly Leu Val Gly Val
        35                  40                  45

Ser Asp Lys Ile Ser Thr Gly Leu Gly Gly Lys Lys Ala Glu Ala Glu
    50                  55                  60

Glu Ala Ala Glu Ser Ala Lys Asn Tyr Ala Tyr Asp Lys Ala Gly Ser
65                  70                  75                  80

Ala Tyr Asp Asn Ala Gly Tyr Ala Lys Asp Phe Ala Ser Asp Lys Ala
                85                  90                  95

Gly Ser Ala Tyr Asp Ser Ala His Asn Ala Lys His Tyr Ala Tyr Asp
            100                 105                 110

Lys Ala Gly Asp Ala Lys Asp Met Ala Tyr Asp Lys Thr Gly Gln Ala
        115                 120                 125

Lys Tyr Met Ala Tyr Asp Lys Ala Gly Ser Ala Tyr Glu Lys Ala Gly
    130                 135                 140

Gln Ala Lys Asp Met Ala Tyr Asp Lys Ala Gly Gln Ala Lys Asp Met
145                 150                 155                 160

Ala Tyr Asp Lys Val Gly Ser Ala Tyr Asp Lys Ala Gly Gln Ala Lys
                165                 170                 175

Asp Met Ala Tyr Asp Lys Ala Gly Ser Ala Ser Glu Lys Ala Gly Gln
```

|  |  | 180 |  |  | 185 |  |  | 190 |  |  |  |
|---|---|---|---|---|---|---|---|---|---|---|---|

Ala Lys Asp Phe Ala Tyr Asp Lys Ala Ala His Ala Lys Asp Ala Ala
          195                 200                 205

Tyr Asn Lys Ala Glu Asp Val Ile Lys Met Ala Thr Asp Thr Ser Gly
      210                 215                 220

Glu Ala Lys Asp Ser Ala Tyr Gly Thr Tyr Glu Arg Phe Lys Glu Gly
225                 230                 235                 240

Ser Lys Asn Ala Lys Asp Ile Ala Ser Asp Lys Ala His Asp Val Arg
              245                 250                 255

Glu Thr Ala Gly Arg Ala Val Asp Tyr Ala Lys Asp Lys Ala Asn Asp
          260                 265                 270

Ala Tyr Glu Ser Gly Ser Glu Ala Ala Gly Arg Phe Asp Glu Ala Met
      275                 280                 285

His Lys Val Gly Glu Arg Tyr Gly Ala Val Lys Asp Ser Met Ser Glu
      290                 295                 300

Asn Thr Lys Glu Ala Tyr Glu Ser Ala Lys Glu Lys Ala Ser Asp Ala
305                 310                 315                 320

Ala Gly Glu Tyr Gly Ser Tyr Met Arg Asp Arg Ser Ala Glu Leu
              325                 330                 335

<210> SEQ ID NO 25
<211> LENGTH: 2386
<212> TYPE: DNA
<213> ORGANISM: Arabidopsis thaliana

<400> SEQUENCE: 25

```
tagatctctc tcttgctgtg ctcctttct ccctctacac agatctttgg attcagaaga      60
aagaggtttt atgctctgag gatctaaaat gggtgctgct gaaaacaacc ttgaaatgga     120
gggtaccctg gagatcggca tggagtatag aactgttttct ggtgttgcgg gacctctcgt    180
catccttgaa aaagtcaagg ggcctaaata ccaagaaatt gtcaatatcc gtcttgggga    240
tggaactacc cgacgtggtc aagttctcga gttgatgga gagaaagctg ttgttcaggt     300
atttgaggga acatctggaa tcgacaacaa gtacacaact gtgcaattta caggagaggt    360
tttgaaaact cctgtttctt tggatatgct tggtcgcatc ttcaatggtt cagggaagcc    420
cattgacaac ggtccaccta tattgcctga ggcgtacttg atatttctg gaagttctat    480
caatcccagt gagagaacct atcctgaaga gatgattcag acgggtatat ccaccattga    540
tgtcatgaac tctatcgcca gggacagaa gattccctc ttttctgccg caggtcttcc     600
ccacaatgaa attgctgctc agatttgccg tcaggctggt ttggttaagc gtttagagaa    660
gtcagataat cttctcgagc atcaggagga tgataacttc gccattgtgt tcgcagcaat    720
gggtgtgaac atggagactg cacaattttt taaacgtgat ttcgaggaga atggatcgat    780
ggagagagtg actcttttcc ttaacttggc aaacgacccc actattgagc gtatcatcac    840
tcctcgtatc gcacttacaa ctgctgagta cttggcatat gaatgtggca agcatgtcct    900
tgtcattctc acagacatga gttcctacgc cgatgctctt cgtgaggtct ctgctgcccg    960
tgaagaagtg cctggaaggc gtggttaccc aggttacatg tacaccgact ggctaccat    1020
atacgagaga gcagggcgaa ttgaagggag gaaaggttcc atcactcaaa ttcccatttt    1080
aaccatgcca acgatgata tcacgcatcc cacaccagat ctgacaggat acattacaga    1140
ggggcaaatc tatattgacc gacaacttca aatagacag atctacccct cgatcaatgt    1200
cttgccatct ctgtctcgtc tcatgaagag tgccattggt gagggtatga ctcgcaggga    1260
ccactctgat gtttctaatc aattgtatgc caattacgct attggaaagg acgtgcaggc    1320
```

```
catgaaagcc gtggttggag aagaagctct tcttccgag  gatctgctat atcttgagtt  1380
cttggataag ttcgagagga gtttgtggc  tcagggagct tatgataccc gaaacatctt  1440
ccagtcactc gacctggcat ggactctcct cagaatcttc cccgtgagt  tacttcaccg  1500 tatacccgcg aaaacccttg atcagtttta cagtcgcgat accaccaact gaagaacata  1560
gtttctactg ccttggtgtg atgatatgtc caaatgcatc tttatttttt acttctgcgg  1620
ttggatcaca cctctgagtc gtccgtccca ataaatggtg tttgttccca atcgctagac  1680
cctttattat tgtcttcgaa actgagcaag ccaggttgat tattctttt  gtaagagaaa  1740 ttgaaattct tgtataattt atgagatttt gcatctttt  tttggggtac caaattactg  1800
gttcagaaca acatacattt gtttgtctta ttactgtcac gaatgtcaat gcagcttctt  1860 cttcttttt  tataacaatt tgggttttac atttgattct tcgatctaca aatagaattc  1920
aaaagacgtg tatgtttgat aaattggaaa attcggaaaa ccgaagacag cgatcaaacg  1980
aaagttaaaa actagtgtat aatgtttact gtctcaacca gctttagaag ttcttactac  2040
ttttggcagc tcaacagaat caaggtcacc agggtaagga gtccagagcc caaagccgcc  2100
tcggctttcc ttcaaactct ctcccttccc tttgagttcc tgaagactct gacccactc   2160 aatcttcgag gaatgctctc gaatgtgagg gtgcagttcg aagagagagt tatactcaca  2220
gttctggaac atgaacacct tgaaggctcc ttttagtctg tccactacat acccaaagct  2280
tagctggtcc ctcggtgtta acaggtgtac ctcattgaac cacaggcagc tgaacagatt  2340
gttcattgca gtgtgctctc ttattatcac agctccctct ggaaca               2386
```

<210> SEQ ID NO 26
<211> LENGTH: 487
<212> TYPE: PRT
<213> ORGANISM: Arabidopsis thaliana

<400> SEQUENCE: 26

```
Met Gly Ala Ala Glu Asn Asn Leu Glu Met Glu Gly Thr Leu Glu Ile
1               5                   10                  15

Gly Met Glu Tyr Arg Thr Val Ser Gly Val Ala Gly Pro Leu Val Ile
            20                  25                  30

Leu Glu Lys Val Lys Gly Pro Lys Tyr Gln Glu Ile Val Asn Ile Arg
        35                  40                  45

Leu Gly Asp Gly Thr Thr Arg Arg Gly Gln Val Leu Glu Val Asp Gly
    50                  55                  60

Glu Lys Ala Val Val Gln Val Phe Glu Gly Thr Ser Gly Ile Asp Asn
65                  70                  75                  80

Lys Tyr Thr Thr Val Gln Phe Thr Gly Glu Val Leu Lys Thr Pro Val
                85                  90                  95

Ser Leu Asp Met Leu Gly Arg Ile Phe Asn Gly Ser Gly Lys Pro Ile
            100                 105                 110

Asp Asn Gly Pro Pro Ile Leu Pro Glu Ala Tyr Leu Asp Ile Ser Gly
        115                 120                 125

Ser Ser Ile Asn Pro Ser Glu Arg Thr Tyr Pro Glu Glu Met Ile Gln
    130                 135                 140

Thr Gly Ile Ser Thr Ile Asp Val Met Asn Ser Ile Ala Arg Gly Gln
145                 150                 155                 160

Lys Ile Pro Leu Phe Ser Ala Ala Gly Leu Pro His Asn Glu Ile Ala
                165                 170                 175

Ala Gln Ile Cys Arg Gln Ala Gly Leu Val Lys Arg Leu Glu Lys Ser
            180                 185                 190
```

```
Asp Asn Leu Leu Glu His Gln Glu Asp Asn Phe Ala Ile Val Phe
        195                 200                 205

Ala Ala Met Gly Val Asn Met Glu Thr Ala Gln Phe Phe Lys Arg Asp
210                 215                 220

Phe Glu Glu Asn Gly Ser Met Glu Arg Val Thr Leu Phe Leu Asn Leu
225                 230                 235                 240

Ala Asn Asp Pro Thr Ile Glu Arg Ile Ile Thr Pro Arg Ile Ala Leu
            245                 250                 255

Thr Thr Ala Glu Tyr Leu Ala Tyr Glu Cys Gly Lys His Val Leu Val
        260                 265                 270

Ile Leu Thr Asp Met Ser Ser Tyr Ala Asp Ala Leu Arg Glu Val Ser
    275                 280                 285

Ala Ala Arg Glu Glu Val Pro Gly Arg Arg Gly Tyr Pro Gly Tyr Met
290                 295                 300

Tyr Thr Asp Leu Ala Thr Ile Tyr Glu Arg Ala Gly Arg Ile Glu Gly
305                 310                 315                 320

Arg Lys Gly Ser Ile Thr Gln Ile Pro Ile Leu Thr Met Pro Asn Asp
                325                 330                 335

Asp Ile Thr His Pro Thr Pro Asp Leu Thr Gly Tyr Ile Thr Glu Gly
            340                 345                 350

Gln Ile Tyr Ile Asp Arg Gln Leu His Asn Arg Gln Ile Tyr Pro Pro
        355                 360                 365

Ile Asn Val Leu Pro Ser Leu Ser Arg Leu Met Lys Ser Ala Ile Gly
    370                 375                 380

Glu Gly Met Thr Arg Arg Asp His Ser Asp Val Ser Asn Gln Leu Tyr
385                 390                 395                 400

Ala Asn Tyr Ala Ile Gly Lys Asp Val Gln Ala Met Lys Ala Val Val
                405                 410                 415

Gly Glu Glu Ala Leu Ser Ser Glu Asp Leu Leu Tyr Leu Glu Phe Leu
            420                 425                 430

Asp Lys Phe Glu Arg Lys Phe Val Ala Gln Gly Ala Tyr Asp Thr Arg
        435                 440                 445

Asn Ile Phe Gln Ser Leu Asp Leu Ala Trp Thr Leu Leu Arg Ile Phe
    450                 455                 460

Pro Arg Glu Leu Leu His Arg Ile Pro Ala Lys Thr Leu Asp Gln Phe
465                 470                 475                 480

Tyr Ser Arg Asp Thr Thr Asn
                485

<210> SEQ ID NO 27
<211> LENGTH: 2485
<212> TYPE: DNA
<213> ORGANISM: Arabidopsis thaliana

<400> SEQUENCE: 27
attgaattga aatcggtggt atgtatgtat agtccaccaa catagatctc tctcttgctg      60
tggctccttt cttcctctac acagatcttt ggattcagaa gaaagaggtt ttatgctctg     120
agggtaagta atcccgttga tctgatcgag aaattcatat tgatagagct ctaaaattgg     180
atctaaaatg ggtgctgctg aaaacaacct tgaaatggag ggtaccctgg agatcggcat     240
ggagtataga actgtttctg gtgttgcggg acctctcgtc atccttgaaa aagtcaaggg     300
gcctaaatac caagaaattg tcaatatccg tcttggggat ggaactaccc gacgtggtca     360
agttctcgaa gttgatggag agaaagctgt tgttcaggta tttgagggaa catctggaat     420
```

| | | |
|---|---|---|
| cgacaacaag tacacaactg tgcaatttac aggagaggtt ttgaaaactc ctgtttcttt | 480 | |
| ggatatgctt ggtcgcatct tcaatggttc agggaagccc attgacaacg gtccacctat | 540 | |
| attgcctgag gcgtacttgg atatttctgg aagttctatc aatcccagtg agagaaccta | 600 | |
| tcctgaagag atgattcaga cgggtatatc caccattgat gtcatgaact ctatcgccag | 660 | |
| aggacagaag attcccctct tttctgccgc aggtcttccc cacaatgaaa ttgctgctca | 720 | |
| gatttgccgt caggctggtt tggttaagcg tttagagaag tcagataatc ttctcgagca | 780 | |
| tcaggaggat gataacttcg ccattgtgtt cgcagcaatg ggtgtgaaca tggagactgc | 840 | |
| acaatttttt aaacgtgatt tcgaggagaa tggatcgatg gagagagtga ctcttttcct | 900 | |
| taacttggca aacgacccca ctattgagcg tatcatcact cctcgtatcg cacttacaac | 960 | |
| tgctgagtac ttggcatatg aatgtggcaa gcatgtcctt gtcattctca cagacatgag | 1020 | |
| ttcctacgcc gatgctcttc gtgaggtctc tgctgcccgt gaagaagtgc ctggaaggcg | 1080 | |
| tggttaccca ggttacatgt acaccgactt ggctaccata tacgagagag cagggcgaat | 1140 | |
| tgaagggagg aaaggttcca tcactcaaat tcccatttta accatgccaa acgatgatat | 1200 | |
| cacgcatccc acaccagatc tgacaggata cattacagag gggcaaatct atattgaccg | 1260 | |
| acaacttcac aatagacaga tctaccctcc gatcaatgtc ttgccatctc tgtctcgtct | 1320 | |
| catgaagagt gccattggtg agggtatgac tcgcagggac cactctgatg tttctaatca | 1380 | |
| attgtatgcc aattacgcta ttggaaagga cgtgcaggcc atgaaagccg tggttggaga | 1440 | |
| agaagctctt tcttccgagg atctgctata tcttgagttc ttggataagt tcgagaggaa | 1500 | |
| gtttgtggct cagggagctt atgatacccg aaacatcttc cagtcactcg acctggcatg | 1560 | |
| gactctcctc agaatcttcc cccgtgagtt acttcaccgt ataccgcgca aacccttga | 1620 | |
| tcagttttac agtcgcgata ccaccaactg aagaacatag tttctactgc cttggtgtga | 1680 | |
| tgatatgtcc aaatgcatct ttattttta cttctgcggt tggatcacac ctctgagtcg | 1740 | |
| tccgtcccaa taaatggtgt tgttcccaa tcgctagacc cttatatatt gtcttcgaaa | 1800 | |
| ctgagcaagc caggttgatt attcttttg taagagaaat tgaaattctt gtataattta | 1860 | |
| tgagattttg catctttttt ttggggtacc aaaattactgg ttcagaacaa catacatttg | 1920 | |
| tttgtcttat tactgtcacg aatgtcaatg cagcttcttc ttcttttttt ataacaattt | 1980 | |
| gggttttaca tttgattctt cgatctacaa atagaattca aaagacgtgt atgtttgata | 2040 | |
| aattggaaaa ttcggaaaac cgaagacagc gatcaaacga agttaaaaa ctagtgtata | 2100 | |
| atgtttactg tctcaaccag ctttagaagt tcttactact tttggcagct caacagaatc | 2160 | |
| aaggtcacca gggtaaggag tccagagccc aaagccgcct cggctttcct tcaaactctc | 2220 | |
| tcccttccct ttgagttcct gaagactctt gacccactca atcttcgagg aatgctctcg | 2280 | |
| aatgtgaggg tgcagttcga agagagagtt atactcacag ttctggaaca tgaacacctt | 2340 | |
| gaaggctcct tttagtctgt ccactacata cccaaagctt agctggtccc tcggtgttaa | 2400 | |
| caggtgtacc tcattgaacc acaggcagct gaacagattg ttcattgcag tgtgctctct | 2460 | |
| tattatcaca gctccctctg gaaca | 2485 | |

<210> SEQ ID NO 28
<211> LENGTH: 487
<212> TYPE: PRT
<213> ORGANISM: Arabidopsis thaliana

<400> SEQUENCE: 28

Met Gly Ala Ala Glu Asn Asn Leu Glu Met Glu Gly Thr Leu Glu Ile
1               5                   10                  15

-continued

```
Gly Met Glu Tyr Arg Thr Val Ser Gly Val Ala Gly Pro Leu Val Ile
             20                  25                  30
Leu Glu Lys Val Lys Gly Pro Lys Tyr Gln Glu Ile Val Asn Ile Arg
         35                  40                  45
Leu Gly Asp Gly Thr Thr Arg Arg Gly Gln Val Leu Glu Val Asp Gly
     50                  55                  60
Glu Lys Ala Val Val Gln Val Phe Glu Gly Thr Ser Gly Ile Asp Asn
 65                  70                  75                  80
Lys Tyr Thr Thr Val Gln Phe Thr Gly Glu Val Leu Lys Thr Pro Val
                 85                  90                  95
Ser Leu Asp Met Leu Gly Arg Ile Phe Asn Gly Ser Gly Lys Pro Ile
            100                 105                 110
Asp Asn Gly Pro Pro Ile Leu Pro Glu Ala Tyr Leu Asp Ile Ser Gly
        115                 120                 125
Ser Ser Ile Asn Pro Ser Glu Arg Thr Tyr Pro Glu Glu Met Ile Gln
    130                 135                 140
Thr Gly Ile Ser Thr Ile Asp Val Met Asn Ser Ile Ala Arg Gly Gln
145                 150                 155                 160
Lys Ile Pro Leu Phe Ser Ala Ala Gly Leu Pro His Asn Glu Ile Ala
                165                 170                 175
Ala Gln Ile Cys Arg Gln Ala Gly Leu Val Lys Arg Leu Glu Lys Ser
            180                 185                 190
Asp Asn Leu Leu Glu His Gln Glu Asp Asn Phe Ala Ile Val Phe
        195                 200                 205
Ala Ala Met Gly Val Asn Met Glu Thr Ala Gln Phe Phe Lys Arg Asp
    210                 215                 220
Phe Glu Glu Asn Gly Ser Met Glu Arg Val Thr Leu Phe Leu Asn Leu
225                 230                 235                 240
Ala Asn Asp Pro Thr Ile Glu Arg Ile Ile Thr Pro Arg Ile Ala Leu
                245                 250                 255
Thr Thr Ala Glu Tyr Leu Ala Tyr Glu Cys Gly Lys His Val Leu Val
            260                 265                 270
Ile Leu Thr Asp Met Ser Ser Tyr Ala Asp Ala Leu Arg Glu Val Ser
        275                 280                 285
Ala Ala Arg Glu Glu Val Pro Gly Arg Arg Gly Tyr Pro Gly Tyr Met
    290                 295                 300
Tyr Thr Asp Leu Ala Thr Ile Tyr Glu Arg Ala Gly Arg Ile Glu Gly
305                 310                 315                 320
Arg Lys Gly Ser Ile Thr Gln Ile Pro Ile Leu Thr Met Pro Asn Asp
                325                 330                 335
Asp Ile Thr His Pro Thr Pro Asp Leu Thr Gly Tyr Ile Thr Glu Gly
            340                 345                 350
Gln Ile Tyr Ile Asp Arg Gln Leu His Asn Arg Gln Ile Tyr Pro Pro
        355                 360                 365
Ile Asn Val Leu Pro Ser Leu Ser Arg Leu Met Lys Ser Ala Ile Gly
    370                 375                 380
Glu Gly Met Thr Arg Arg Asp His Ser Asp Val Ser Asn Gln Leu Tyr
385                 390                 395                 400
Ala Asn Tyr Ala Ile Gly Lys Asp Val Gln Ala Met Lys Ala Val Val
                405                 410                 415
Gly Glu Glu Ala Leu Ser Ser Glu Asp Leu Leu Tyr Leu Glu Phe Leu
            420                 425                 430
Asp Lys Phe Glu Arg Lys Phe Val Ala Gln Gly Ala Tyr Asp Thr Arg
```

```
                435              440              445
Asn Ile Phe Gln Ser Leu Asp Leu Ala Trp Thr Leu Leu Arg Ile Phe
    450                 455                 460
Pro Arg Glu Leu Leu His Arg Ile Pro Ala Lys Thr Leu Asp Gln Phe
465                 470                 475                 480
Tyr Ser Arg Asp Thr Thr Asn
                485

<210> SEQ ID NO 29
<211> LENGTH: 2377
<212> TYPE: DNA
<213> ORGANISM: Arabidopsis thaliana

<400> SEQUENCE: 29
accaacatag atctctctct tgctgtggct cctttcttcc tctacacaga tctttggatt    60
cagaagaaag agatctaaaa tgggtgctgc tgaaaacaac cttgaaatgg agggtaccct   120
ggagatcggc atggagtata gaactgtttc tggtgttgcg ggacctctcg tcatccttga   180
aaaagtcaag gggcctaaat accaagaaat tgtcaatatc cgtcttgggg atggaactac   240
ccgacgtggt caagttctcg aagttgatgg agagaaagct gttgttcagg tatttgaggg   300
aacatctgga atcgacaaca agtacacaac tgtgcaattt acaggagagg ttttgaaaac   360
tcctgtttct ttggatatgc ttggtcgcat cttcaatggt tcaggaagc ccattgacaa    420
cggtccacct atattgcctg aggcgtactt ggatatttct ggaagttcta tcaatcccag   480
tgagagaacc tatcctgaag atgattca gacgggtata tccaccattg atgtcatgaa    540
ctctatcgcc agaggacaga agattcccct ctttctgcc gcaggtcttc cccacaatga    600
aattgctgct cagatttgcc gtcaggctgg tttggttaag cgtttagaga agtcagataa   660
tcttctcgag catcaggagg atgataactt cgccattgtg ttcgcagcaa tgggtgtgaa   720
catggagact gcacaatttt taaacgtga tttcgaggag aatggatcga tggagagagt   780
gactcttttc cttaacttgg caaacgaccc cactattgag cgtatcatca ctcctcgtat   840
cgcacttaca actgctgagt acttggcata tgaatgtggc aagcatgtcc ttgtcattct   900
cacagacatg agttcctacg ccgatgctct tcgtgaggtc tctgctgccc gtgaagaagt   960
gcctggaagg cgtggttacc caggttacat gtacaccgac ttggctacca tatacgagag  1020
agcagggcga attgaaggga ggaaaggttc catcactcaa attcccattt taaccatgcc  1080
aaacgatgat atcacgcatc ccacaccaga tctgacagga tacattacag aggggcaaat  1140
ctatattgac cgacaacttc acaatagaca gatctaccct ccgatcaatg tcttgccatc  1200
tctgtctcgt ctcatgaaga gtgccattgg tgagggtatg actcgcaggg accactctga  1260
tgtttctaat caattgtatg ccaattacgc tattggaaag gacgtgcagg ccatgaaagc  1320
cgtggttgga gaagaagctc tttcttccga ggatctgcta tatcttgagt cttggataa   1380
gttcgagagg aagtttgtgg ctcagggagc ttatgatacc cgaaacatct tccagtcact  1440
cgacctggca tggactctcc tcagaatctt ccccgtgag ttacttcacc gtataccgc    1500
gaaacccctt gatcagtttt acagtcgcga taccaccaac tgaagaacat agtttctact  1560
gccttggtgt gatgatatgt ccaaatgcat ctttattttt tacttctgcg gttggatcac  1620
acctctgagt cgtccgtccc aataaatggt gtttgttccc aatcgctaga ccctttatta  1680
ttgtcttcga aactgagcaa gccaggttga ttattctttt tgtaagagaa attgaaattc  1740
ttgtataatt tatgagattt tgcatctttt ttttggggta ccaaattact ggttcagaac  1800
aacatacatt tgtttgtctt attactgtca cgaatgtcaa tgcagcttct tcttcttttt  1860
```

```
ttataacaat ttgggtttta catttgattc ttcgatctac aaatagaatt caaaagacgt    1920
gtatgtttga taaattggaa aattcggaaa accgaagaca gcgatcaaac gaaagttaaa    1980
aactagtgta taatgtttac tgtctcaacc agctttagaa gttcttacta cttttggcag    2040
ctcaacagaa tcaaggtcac cagggtaagg agtccagagc ccaaagccgc ctcggctttc    2100
cttcaaactc tctcccttcc ctttgagttc ctgaagactc ttgacccact caatcttcga    2160
ggaatgctct cgaatgtgag ggtgcagttc gaagagagag ttatactcac agttctggaa    2220
catgaacacc ttgaaggctc cttttagtct gtccactaca tacccaaagc ttagctggtc    2280
cctcggtgtt aacaggtgta cctcattgaa ccacaggcag ctgaacagat tgttcattgc    2340
agtgtgctct cttattatca cagctccctc tggaaca                             2377
```

<210> SEQ ID NO 30
<211> LENGTH: 487
<212> TYPE: PRT
<213> ORGANISM: Arabidopsis thaliana

<400> SEQUENCE: 30

```
Met Gly Ala Ala Glu Asn Asn Leu Glu Met Glu Gly Thr Leu Glu Ile
1               5                   10                  15

Gly Met Glu Tyr Arg Thr Val Ser Gly Val Ala Gly Pro Leu Val Ile
                20                  25                  30

Leu Glu Lys Val Lys Gly Pro Lys Tyr Gln Glu Ile Val Asn Ile Arg
            35                  40                  45

Leu Gly Asp Gly Thr Thr Arg Arg Gly Gln Val Leu Glu Val Asp Gly
        50                  55                  60

Glu Lys Ala Val Val Gln Val Phe Glu Gly Thr Ser Gly Ile Asp Asn
65                  70                  75                  80

Lys Tyr Thr Thr Val Gln Phe Thr Gly Glu Val Leu Lys Thr Pro Val
                85                  90                  95

Ser Leu Asp Met Leu Gly Arg Ile Phe Asn Gly Ser Gly Lys Pro Ile
                100                 105                 110

Asp Asn Gly Pro Pro Ile Leu Pro Glu Ala Tyr Leu Asp Ile Ser Gly
            115                 120                 125

Ser Ser Ile Asn Pro Ser Glu Arg Thr Tyr Pro Glu Glu Met Ile Gln
        130                 135                 140

Thr Gly Ile Ser Thr Ile Asp Val Met Asn Ser Ile Ala Arg Gly Gln
145                 150                 155                 160

Lys Ile Pro Leu Phe Ser Ala Ala Gly Leu Pro His Asn Glu Ile Ala
                165                 170                 175

Ala Gln Ile Cys Arg Gln Ala Gly Leu Val Lys Arg Leu Glu Lys Ser
            180                 185                 190

Asp Asn Leu Leu Glu His Gln Glu Asp Asp Asn Phe Ala Ile Val Phe
        195                 200                 205

Ala Ala Met Gly Val Asn Met Glu Thr Ala Gln Phe Phe Lys Arg Asp
    210                 215                 220

Phe Glu Glu Asn Gly Ser Met Gly Arg Val Thr Leu Phe Leu Asn Leu
225                 230                 235                 240

Ala Asn Asp Pro Thr Ile Glu Arg Ile Ile Thr Pro Arg Ile Ala Leu
                245                 250                 255

Thr Thr Ala Glu Tyr Leu Ala Tyr Glu Cys Gly Lys His Val Leu Val
            260                 265                 270

Ile Leu Thr Asp Met Ser Ser Tyr Ala Asp Ala Leu Arg Glu Val Ser
        275                 280                 285
```

```
Ala Ala Arg Glu Glu Val Pro Gly Arg Arg Gly Tyr Pro Gly Tyr Met
    290                 295                 300

Tyr Thr Asp Leu Ala Thr Ile Tyr Glu Arg Ala Gly Arg Ile Glu Gly
305                 310                 315                 320

Arg Lys Gly Ser Ile Thr Gln Ile Pro Ile Leu Thr Met Pro Asn Asp
                325                 330                 335

Asp Ile Thr His Pro Thr Pro Asp Leu Thr Gly Tyr Ile Thr Glu Gly
            340                 345                 350

Gln Ile Tyr Ile Asp Arg Gln Leu His Asn Arg Gln Ile Tyr Pro Pro
        355                 360                 365

Ile Asn Val Leu Pro Ser Leu Ser Arg Leu Met Lys Ser Ala Ile Gly
    370                 375                 380

Glu Gly Met Thr Arg Arg Asp His Ser Asp Val Ser Asn Gln Leu Tyr
385                 390                 395                 400

Ala Asn Tyr Ala Ile Gly Lys Asp Val Gln Ala Met Lys Ala Val Val
                405                 410                 415

Gly Glu Glu Ala Leu Ser Ser Glu Asp Leu Leu Tyr Leu Glu Phe Leu
            420                 425                 430

Asp Lys Phe Glu Arg Lys Phe Val Ala Gln Gly Ala Tyr Asp Thr Arg
        435                 440                 445

Asn Ile Phe Gln Ser Leu Asp Leu Ala Trp Thr Leu Leu Arg Ile Phe
    450                 455                 460

Pro Arg Glu Leu Leu His Arg Ile Pro Ala Lys Thr Leu Asp Gln Phe
465                 470                 475                 480

Tyr Ser Arg Asp Thr Thr Asn
                485

<210> SEQ ID NO 31
<211> LENGTH: 2347
<212> TYPE: DNA
<213> ORGANISM: Arabidopsis thaliana

<400> SEQUENCE: 31
tatcttcgtt ttgaatttgt tgttaggttt tatgctctga ggatctaaaa tgggtgctgc    60
tgaaaacaac cttgaaatgg agggtaccct ggagatcggc atggagtata aactgtttc   120 tggtgttgcg ggacctctcg tcatccttga aaaagtcaag gggcctaaat accaagaat   180 tgtcaatatc cgtcttgggg atggaactac ccgacgtggt caagttctcg aagttgatgg   240
agagaaagct gttgttcagg tatttgaggg aacatctgga atcgacaaca agtacacaac   300
tgtgcaattt acaggagagg ttttgaaaac tcctgttcct ttggatatgc ttggtcgcat   360
cttcaatggt tcagggaagc ccattgacaa cggtccacct atattgcctg aggcgtactt   420
ggatatttct ggaagttcta tcaatcccag tgagagaacc tatcctgaag atgattca   480 gacgggtata tccaccattg atgtcatgaa ctctatcgcc agaggacaga agattcccct   540
cttttctgcc gcaggtcttc cccacaatga aattgctgct cagatttgcc gtcaggctgg   600
tttggttaag cgtttagaga agtcagataa tcttctcgag catcaggagg atgataactt   660
cgccattgtg ttcgcagcaa tgggtgtgaa catggagact gcacaatttt ttaaacgtga   720
tttcgaggag aatggatcga tggagagagt gactcttttc cttaacttgg caaacgaccc   780
cactattgag cgtatcatca ctcctcgtat cgcacttaca actgctgagt acttggcata   840
tgaatgtggc aagcatgtcc ttgtcattct cacagacatg agttcctacg ccgatgctct   900
tcgtgaggtc tctgctgccc gtgaagaagt gcctggaagg cgtggttacc caggttacat   960
```

```
gtacaccgac ttggctacca tatacgagag agcagggcga attgaaggga ggaaaggttc    1020
catcactcaa attcccattt taaccatgcc aaacgatgat atcacgcatc ccacaccaga    1080
tctgacagga tacattacag aggggcaaat ctatattgac cgacaacttc acaatagaca    1140
gatctaccct ccgatcaatg tcttgccatc tctgtctcgt ctcatgaaga gtgccattgg    1200
tgagggtatg actcgcaggg accactctga tgtttctaat caattgtatg ccaattacgc    1260
tattggaaag gacgtgcagg ccatgaaagc cgtggttgga gaagaagctc tttcttccga    1320
ggatctgcta tatcttgagt tcttggataa gttcgagagg aagtttgtgg ctcagggagc    1380
ttatgatacc cgaaacatct tccagtcact cgacctggca tggactctcc tcagaatctt    1440
cccccgtgag ttacttcacc gtatacccgc gaaaacccct gatcagtttt acagtcgcga    1500
taccaccaac tgaagaacat agtttctact gccttggtgt gatgatatgt ccaaatgcat    1560
ctttattttt tacttctgcg gttggatcac acctctgagt cgtccgtccc aataaatggt    1620
gtttgttccc aatcgctaga ccctttatta ttgtcttcga aactgagcaa gccaggttga    1680
ttattctttt tgtaagagaa attgaaattc ttgtataatt tatgagattt tgcatctttt    1740
ttttggggta ccaaattact ggttcagaac aacatacatt tgtttgtctt attactgtca    1800
cgaatgtcaa tgcagcttct tcttcttttt ttataacaat ttgggttttta catttgattc    1860 ttcgatctac aaatagaatt caaaagacgt gtatgtttga taaattggaa aattcggaaa    1920
accgaagaca gcgatcaaac gaaagttaaa aactagtgta taatgtttac tgtctcaacc    1980
agctttagaa gttcttacta cttttggcag ctcaacagaa tcaaggtcac cagggtaagg    2040
agtccagagc ccaaagccgc ctcggctttc cttcaaactc tctcccttcc ctttgagttc    2100
ctgaagactc ttgacccact caatcttcga ggaatgctct cgaatgtgag ggtgcagttc    2160
gaagagagag ttatactcac agttctggaa catgaacacc ttgaaggctc cttttagtct    2220
gtccactaca tacccaaagc ttagctggtc cctcggtgtt aacaggtgta cctcattgaa    2280
ccacaggcag ctgaacagat tgttcattgc agtgtgctct cttattatca cagctccctc    2340
tggaaca                                                              2347
```

<210> SEQ ID NO 32
<211> LENGTH: 487
<212> TYPE: PRT
<213> ORGANISM: Arabidopsis thaliana

<400> SEQUENCE: 32

Met Gly Ala Ala Glu Asn Asn Leu Glu Met Glu Gly Thr Leu Glu Ile
1               5                   10                  15

Gly Met Glu Tyr Arg Thr Val Ser Gly Val Ala Gly Pro Leu Val Ile
            20                  25                  30

Leu Glu Lys Val Lys Gly Pro Lys Tyr Gln Glu Ile Val Asn Ile Arg
        35                  40                  45

Leu Gly Asp Gly Thr Thr Arg Arg Gly Gln Val Leu Glu Val Asp Gly
    50                  55                  60

Glu Lys Ala Val Val Gln Val Phe Glu Gly Thr Ser Gly Ile Asp Asn
65                  70                  75                  80

Lys Tyr Thr Thr Val Gln Phe Thr Gly Glu Val Leu Lys Thr Pro Val
                85                  90                  95

Ser Leu Asp Met Leu Gly Arg Ile Phe Asn Gly Ser Gly Lys Pro Ile
            100                 105                 110

Asp Asn Gly Pro Pro Ile Leu Pro Glu Ala Tyr Leu Asp Ile Ser Gly
        115                 120                 125

Ser Ser Ile Asn Pro Ser Glu Arg Thr Tyr Pro Glu Glu Met Ile Gln
            130                 135                 140

Thr Gly Ile Ser Thr Ile Asp Val Met Asn Ser Ile Ala Arg Gly Gln
145                 150                 155                 160

Lys Ile Pro Leu Phe Ser Ala Ala Gly Leu Pro His Asn Glu Ile Ala
                165                 170                 175

Ala Gln Ile Cys Arg Gln Ala Gly Leu Val Lys Arg Leu Glu Lys Ser
            180                 185                 190

Asp Asn Leu Leu Glu His Gln Glu Asp Asp Asn Phe Ala Ile Val Phe
        195                 200                 205

Ala Ala Met Gly Val Asn Met Glu Thr Ala Gln Phe Phe Lys Arg Asp
    210                 215                 220

Phe Glu Glu Asn Gly Ser Met Glu Arg Val Thr Leu Phe Leu Asn Leu
225                 230                 235                 240

Ala Asn Asp Pro Thr Ile Glu Arg Ile Ile Thr Pro Arg Ile Ala Leu
                245                 250                 255

Thr Thr Ala Glu Tyr Leu Ala Tyr Glu Cys Gly Lys His Val Leu Val
            260                 265                 270

Ile Leu Thr Asp Met Ser Ser Tyr Ala Asp Ala Leu Arg Glu Val Ser
        275                 280                 285

Ala Ala Arg Glu Glu Val Pro Gly Arg Arg Gly Tyr Pro Gly Tyr Met
    290                 295                 300

Tyr Thr Asp Leu Ala Thr Ile Tyr Glu Arg Ala Gly Arg Ile Glu Gly
305                 310                 315                 320

Arg Lys Gly Ser Ile Thr Gln Ile Pro Ile Leu Thr Met Pro Asn Asp
                325                 330                 335

Asp Ile Thr His Pro Thr Pro Asp Leu Thr Gly Tyr Ile Thr Glu Gly
            340                 345                 350

Gln Ile Tyr Ile Asp Arg Gln Leu His Asn Arg Gln Ile Tyr Pro Pro
        355                 360                 365

Ile Asn Val Leu Pro Ser Leu Ser Arg Leu Met Lys Ser Ala Ile Gly
    370                 375                 380

Glu Gly Met Thr Arg Arg Asp His Ser Asp Val Ser Asn Gln Leu Tyr
385                 390                 395                 400

Ala Asn Tyr Ala Ile Gly Lys Asp Val Gln Ala Met Lys Ala Val Val
                405                 410                 415

Gly Glu Glu Ala Leu Ser Ser Glu Asp Leu Leu Tyr Leu Glu Phe Leu
            420                 425                 430

Asp Lys Phe Glu Arg Lys Phe Val Ala Gln Gly Ala Tyr Asp Thr Arg
        435                 440                 445

Asn Ile Phe Gln Ser Leu Asp Leu Ala Trp Thr Leu Leu Arg Ile Phe
    450                 455                 460

Pro Arg Glu Leu Leu His Arg Ile Pro Ala Lys Thr Leu Asp Gln Phe
465                 470                 475                 480

Tyr Ser Arg Asp Thr Thr Asn
            485

<210> SEQ ID NO 33
<211> LENGTH: 2225
<212> TYPE: DNA
<213> ORGANISM: Arabidopsis thaliana

<400> SEQUENCE: 33
cttcattgtt cactgtttcc agacattgaa agaaagatca ttagtttctg aggggataac    60 cattttttt tcttcttaaa aagtttttt ttttgtcaat tggtcttctt cttcctcatc    120

-continued

```
cgctcgctta tatttaattt aataataata aaaatcggtg ttcattttta tataaaagta      180
taaattttgt gtttggttga tccatccgta gtcgtagtag atctacaagc tctgaaattc      240
cacgcccaca tctcctccgt cctcttgaga tccttctctt cattcatttt cttgctcaac      300
ttgagttgct tccaacatct tgcaaggtaa agtttccttt tttttggtag cgaatacgaa      360
ccagttggaa tctgccgcat aaatccttt gttttttttt cttgcttgcc gcatcactaa       420
ttttgctttc ttccgatggt ttccttactt aaagatgtta acttttcaat gttgcatcaa      480
gtttcttaga ttgttcaatc actagactaa tcagtctcac tataatctcc tacagattca     540
tttctattgc cactcataac aattgagttt tctcactttt ttgctcttta gattgtcttt      600
gagttcattc aggtcttgaa gaagagcact cttttaagct gtgtgaaact tgcgccgttc      660
ctgtgaagaa ctacttttgg cattgcagat ttcagagagc tgtgatttgt gctatcttaa      720
aaacggacaa gttctatgtt gtggcggatg agatgaggga tgctatctgg gttgatgaat      780
tttctgaatg cctgtctctg gccacggtca gatcagcagg ctcgttctgc ctcagattct      840
ggtggccgcc aagagggttt gctctggttc agagactccg gccagcacgt ctttggtgac      900
ttctccatgg ccgtcgttca agccaacagc ttgctagagg accagagcca gctcgagtct      960
ggctctctta gctcccacga ctctggtccc tttggcacct tgttggcgt ctacgacggc      1020 cacggtgggc ctgagacatc tcgcttcatc aatgatcata tgttccacca cctcaagagg      1080
tttactgcag agcaacagtg tatgtcatca gaggtgataa aaaaagcgtt ccaagccact      1140
gaagaaggct tcttatccat agttacaaat caatttcaaa ctagacctca gatagccaca      1200
gtgggatcat gctgtcttgt aagtgtcatc tgcgatggga agctatacgt ggccaacgca      1260
ggggactcac gggccgttct gggacaagtc atgagggtaa caggtgaagc tcatgccact      1320
cagctctcag cagagcacaa cgcatctata gagtcagtga cgggaacact caggccctg      1380 catccggatc atccagatat tgtggttctg aaacataacg tctggcgagt aaaaggcatc      1440
attcaggttt caagatccat tggtgatgtg tatttgaaaa ggtcagagtt caacagggaa      1500
ccactgtatg caaaattccg gctgaggtca ccgttcagca agccattact gagtgcagag      1560
ccggcgatca cggtgcatac actggagccg cacgatcagt tcattatatg tgcatcagat      1620
ggactgtggg aacatatgag caaccaagaa gcagtagaca tagtccagaa tcatccgcga      1680
aacgggatag caaagcggct ggtgaaagta gcgctacaag aagcggcaaa gaagagagag      1740
atgagatact cagacctgaa aaagatagac agaggagtga ggagacatt ccacgatgac       1800 ataacagtga ttgttgtctt ctttgataca aacctagtga gcagaggaag tatgttgaga      1860
ggaccagccg tgtcagtgag aggagcgggt gtgaatctac ctcacaacac cctggcgcct      1920
tgcaccacgc ccactcaagc tgctgctgct ggcgcctcct gactattgaa tttttacggt     1980
gtccttaaaa ttcttttccaa gatccttcct gtaactatat ataaatatat atatttgatt   2040
attattatca ttgactggga aaggatatat catcatcaag tgggaaagga tatatcataa     2100
tcaagtggtt agttttgttt gttcccttg ttagctgtgt actggagaaa gaaaggtgac      2160
aagaattctt cttcttcttc attaattttc attgcttgct ttttaaggta ttactgattc     2220
agact                                                                 2225
```

<210> SEQ ID NO 34
<211> LENGTH: 400
<212> TYPE: PRT
<213> ORGANISM: Arabidopsis thaliana

<400> SEQUENCE: 34

```
Met Leu Ser Gly Leu Met Asn Phe Leu Asn Ala Cys Leu Trp Pro Arg
1               5                   10                  15

Ser Asp Gln Gln Ala Arg Ser Ala Ser Asp Ser Gly Gly Arg Gln Glu
            20                  25                  30

Gly Leu Leu Trp Phe Arg Asp Ser Gly Gln His Val Phe Gly Asp Phe
        35                  40                  45

Ser Met Ala Val Val Gln Ala Asn Ser Leu Leu Glu Asp Gln Ser Gln
    50                  55                  60

Leu Glu Ser Gly Ser Leu Ser Ser His Asp Ser Gly Pro Phe Gly Thr
65                  70                  75                  80

Phe Val Gly Val Tyr Asp Gly His Gly Gly Pro Glu Thr Ser Arg Phe
                85                  90                  95

Ile Asn Asp His Met Phe His His Leu Lys Arg Phe Thr Ala Glu Gln
                100                 105                 110

Gln Cys Met Ser Ser Glu Val Ile Lys Lys Ala Phe Gln Ala Thr Glu
            115                 120                 125

Glu Gly Phe Leu Ser Ile Val Thr Asn Gln Phe Gln Thr Arg Pro Gln
    130                 135                 140

Ile Ala Thr Val Gly Ser Cys Cys Leu Val Ser Val Ile Cys Asp Gly
145                 150                 155                 160

Lys Leu Tyr Val Ala Asn Ala Gly Asp Ser Arg Ala Val Leu Gly Gln
                165                 170                 175

Val Met Arg Val Thr Gly Glu Ala His Ala Thr Gln Leu Ser Ala Glu
            180                 185                 190

His Asn Ala Ser Ile Glu Ser Val Arg Arg Glu Leu Gln Ala Leu His
        195                 200                 205

Pro Asp His Pro Asp Ile Val Val Leu Lys His Asn Val Trp Arg Val
    210                 215                 220

Lys Gly Ile Ile Gln Val Ser Arg Ser Ile Gly Asp Val Tyr Leu Lys
225                 230                 235                 240

Arg Ser Glu Phe Asn Arg Glu Pro Leu Tyr Ala Lys Phe Arg Leu Arg
                245                 250                 255

Ser Pro Phe Ser Lys Pro Leu Leu Ser Ala Glu Pro Ala Ile Thr Val
            260                 265                 270

His Thr Leu Glu Pro His Asp Gln Phe Ile Ile Cys Ala Ser Asp Gly
        275                 280                 285

Leu Trp Glu His Met Ser Asn Gln Glu Ala Val Asp Ile Val Gln Asn
    290                 295                 300

His Pro Arg Asn Gly Ile Ala Lys Arg Leu Val Lys Val Ala Leu Gln
305                 310                 315                 320

Glu Ala Ala Lys Lys Arg Glu Met Arg Tyr Ser Asp Leu Lys Lys Ile
                325                 330                 335

Asp Arg Gly Val Arg Arg His Phe His Asp Asp Ile Thr Val Ile Val
            340                 345                 350

Val Phe Phe Asp Thr Asn Leu Val Ser Arg Gly Ser Met Leu Arg Gly
        355                 360                 365

Pro Ala Val Ser Val Arg Gly Ala Gly Val Asn Leu Pro His Asn Thr
    370                 375                 380

Leu Ala Pro Cys Thr Thr Pro Thr Gln Ala Ala Ala Gly Ala Ser
385                 390                 395                 400

<210> SEQ ID NO 35
<211> LENGTH: 1960
<212> TYPE: DNA
```

<213> ORGANISM: Arabidopsis thaliana

<400> SEQUENCE: 35

```
cttcattgtt cactgtttcc agacattgaa agaaagatca ttagtttctg aggggataac      60
cattttttt  tcttcttaaa aagtttttt  ttttgtcaat tggtcttctt cttcctcatc     120
cgctcgctta tatttaattt aataataata aaaatcggtg ttcatttta  tataaaagta     180
taaattttgt gtttggttga tccatccgta gtcgtagtag atctacaagc tctgaaattc     240
cacgcccaca tctcctccgt cctcttgaga tccttctctt cattcatttt cttgctcaac     300
ttgagttgct ccaacatct  tgcaagattg tcttgagtt  cattcaggtc ttgaagaaga     360
gcactctttt aagctgtgtg aaacttgcgc cgttcctgtg aagaactact tttggcattg     420
cagatttcag agagctgtga tttgtgctat cttaaaaacg acaagttct  atgttgtggc     480
ggatgagatg agggatgcta tctgggttga tgaatttct  gaatgcctgt ctctggccac     540
ggtcagatca gcaggctcgt tctgcctcag attctggtgg ccgccaagag ggtttgctct     600
ggttcagaga ctccggccag cacgtctttg gtgacttctc catggccgtc gttcaagcca     660
acagcttgct agaggaccag agccagctcg agtctggctc tcttagctcc cacgactctg     720
gtcccttgg  caccttgtt  ggcgtctacg acggccacgg tgggcctgag acatctcgct     780
tcatcaatga tcatatgttc caccacctca agaggtttac tgcagagcaa cagtgtatgt     840
catcagaggt gataaaaaaa gcgttccaag ccactgaaga aggcttctta tccatagtta     900
caaatcaatt tcaaactaga cctcagatag ccacagtggg atcatgctgt cttgtaagtg     960
tcatctgcga tgggaagcta tacgtggcca acgcagggga ctcacgggcc gttctgggac    1020
aagtcatgag ggtaacaggt gaagctcatg ccactcagct ctcagcagag cacaacgcat    1080
ctatagagtc agtgagacgg gaacttcagg ccctgcatcc ggatcatcca gatattgtgg    1140
ttctgaaaca taacgtctgg cgagtaaaag gcatcattca ggtttcaaga tccattggtg    1200
atgtgtattt gaaaaggtca gagttcaaca gggaaccact gtatgcaaaa ttccggctga    1260
ggtcaccgtt cagcaagcca ttactgagtg cagagccggc gatcacggtg catacactgg    1320
agccgcacga tcagttcatt atatgtgcat cagatggact gtgggaacat atgagcaacc    1380
aagaagcagt agacatagtc cagaatcatc cgcgaaacgg gatagcaaag cggctggtga    1440
agtagcgct  acaagaagcg gcaaagaaga gagagatgag atactcagac ctgaaaaaga    1500
tagacagagg agtgaggaga catttccacg atgacataac agtgattgtt gtcttctttg    1560
atacaaacct agtgagcaga ggaagtatgt tgagaggacc agccgtgtca gtgagaggag    1620
cgggtgtgaa tctacctcac aacaccctgg cgccttgcac cacgcccact caagctgctg    1680
ctgctggcgc ctcctgacta ttgaattttt acggtgtcct taaaattctt tccaagatcc    1740
ttcctgtaac tatatataaa tatatatatt tgattattat tatcattgac tgggaaagga    1800
tatatcatca tcaagtggga aaggatatat cataatcaag tggttagttt tgtttgttcc    1860
ctttgttagc tgtgtactgg agaaagaaag gtgacaagaa ttcttcttct tcttcattaa    1920
ttttcattgc ttgcttttta aggtattact gattcagact                          1960
```

<210> SEQ ID NO 36
<211> LENGTH: 400
<212> TYPE: PRT
<213> ORGANISM: Arabidopsis thaliana

<400> SEQUENCE: 36

```
Met Leu Ser Gly Leu Met Asn Phe Leu Asn Ala Cys Leu Trp Pro Arg
1               5                   10                  15
```

Ser Asp Gln Gln Ala Arg Ser Ala Ser Asp Ser Gly Gly Arg Gln Glu
                20                  25                  30

Gly Leu Leu Trp Phe Arg Asp Ser Gly Gln His Val Phe Gly Asp Phe
         35                  40                  45

Ser Met Ala Val Val Gln Ala Asn Ser Leu Leu Glu Asp Gln Ser Gln
 50                  55                  60

Leu Glu Ser Gly Ser Leu Ser Ser His Asp Ser Gly Pro Phe Gly Thr
 65                  70                  75                  80

Phe Val Gly Val Tyr Asp Gly His Gly Pro Glu Thr Ser Arg Phe
                 85                  90                  95

Ile Asn Asp His Met Phe His His Leu Lys Arg Phe Thr Ala Glu Gln
                100                 105                 110

Gln Cys Met Ser Ser Glu Val Ile Lys Lys Ala Phe Gln Ala Thr Glu
            115                 120                 125

Glu Gly Phe Leu Ser Ile Val Thr Asn Gln Phe Gln Thr Arg Pro Gln
130                 135                 140

Ile Ala Thr Val Gly Ser Cys Cys Leu Val Ser Val Ile Cys Asp Gly
145                 150                 155                 160

Lys Leu Tyr Val Ala Asn Ala Gly Asp Ser Arg Ala Val Leu Gly Gln
                165                 170                 175

Val Met Arg Val Thr Gly Glu Ala His Ala Thr Gln Leu Ser Ala Glu
            180                 185                 190

His Asn Ala Ser Ile Glu Ser Val Arg Arg Glu Leu Gln Ala Leu His
            195                 200                 205

Pro Asp His Pro Asp Ile Val Val Leu Lys His Asn Val Trp Arg Val
210                 215                 220

Lys Gly Ile Ile Gln Val Ser Arg Ser Ile Gly Asp Val Tyr Leu Lys
225                 230                 235                 240

Arg Ser Glu Phe Asn Arg Glu Pro Leu Tyr Ala Lys Phe Arg Leu Arg
                245                 250                 255

Ser Pro Phe Ser Lys Pro Leu Leu Ser Ala Glu Pro Ala Ile Thr Val
            260                 265                 270

His Thr Leu Glu Pro His Asp Gln Phe Ile Ile Cys Ala Ser Asp Gly
        275                 280                 285

Leu Trp Glu His Met Ser Asn Gln Glu Ala Val Asp Ile Val Gln Asn
290                 295                 300

His Pro Arg Asn Gly Ile Ala Lys Arg Leu Val Lys Val Ala Leu Gln
305                 310                 315                 320

Glu Ala Ala Lys Lys Arg Glu Met Arg Tyr Ser Asp Leu Lys Lys Ile
                325                 330                 335

Asp Arg Gly Val Arg Arg His Phe His Asp Ile Thr Val Ile Val
            340                 345                 350

Val Phe Phe Asp Thr Asn Leu Val Ser Arg Gly Ser Met Leu Arg Gly
        355                 360                 365

Pro Ala Val Ser Val Arg Gly Ala Gly Val Asn Leu Pro His Asn Thr
370                 375                 380

Leu Ala Pro Cys Thr Thr Pro Thr Gln Ala Ala Ala Gly Ala Ser
385                 390                 395                 400

<210> SEQ ID NO 37
<211> LENGTH: 1629
<212> TYPE: DNA
<213> ORGANISM: Arabidopsis thaliana

<400> SEQUENCE: 37

```
atcatccctt ccattaagac ctagggtttt ctctctctcc catcattctc ttctcccgat    60
ctcatttcca ttacccaatc ccgctccttt tctctgattt tgaatcgaac ccttaatacc   120
cagaaatctc acggttccga ggagtgggtt tttgggggtt agggttttcg agagatgttg   180
aatgtcaggt tcattgatga atctgttttc tctctgcttc aagccattcg ggcacgtctg   240
tgataattcc gaagctggat cgggtggtgg tggtggcgtt tctggtggaa ccggcggtga   300
aggcaaagac ggattgcttt ggttccgtga tctcggtaaa tattgcggcg gagatttctc   360
catggctgtg attcaagcca atcaggttct tgaagatcag agccaggtcg aatccggtaa   420
ttttgggact tttgttggtg tttacgatgg tcatggtggt cctgaagctg ctcgttatgt   480
ctgtgatcat ctctttaacc attttcgaga aatatcagcg gaaacacaag gagttgtgac   540
gagagagacg atagaaagag cctttcatgc gacagaagaa ggattcgctt ccattgtgtc   600
agagctgtgg caagaaatac caaatttggc aactgttggc acttgttgtt tggttggagt   660
gatatatcaa aatactcttt ttgtggcaag tcttggagat tcacggggttg ttcttggaaa   720
gaaaggcaac tgtggcggac tctctgctat tcagctgtcg actgaacaca atgctaacaa   780
tgaagatatt cgttgggaac tcaaggactt acatcctgat gacccgcaga tcgttgtgtt   840
caggcatgga gtttggagag ttaagggcat cattcaggta tcgaggtcta taggagacat   900
gtacatgaaa cggcccgaat ttaacaagga gccaatcagt caaagttca gaattgcaga    960
gccaatgaaa agacccttga tgtctgcaac accaacaata ctctctcatc ctctgcaccc  1020
taatgattcg tttctcattt ttgcatctga tggtctttgg gagcatttga ctaacgaaaa  1080
agcagttgag attgttcata accatccccg tgctgtaacg caaagagact gataaaggcg  1140
gctcttcacg aggcagcgag gaaacgtgag atgagatatt cagatctaag gaagattgac  1200
aagaaagtga gacgacattt tcatgatgac atcacggtta tagtggtgtt cttgaaccat  1260
gacctcatat cgagaggcca catcaactca acccaagaca caacagtctc tatacggagt  1320
gctcttgaac actgagaatc ccaaacattt tacaacaatg tttcttctta cttgattata  1380
tgacttttgc ctagaatgaa taaaaaaaag gcaacatatg gaaaaaacca aaatgaaaa   1440
aaacaacatc attatcgtac gtaatgagtt ctctcttgta ttaagcggct atgtttgact  1500
tttggtgttt ctcttcaaag ttctgatgag ttccaagtct tttacttctt gccgttcgtc  1560
aaaagtatgt aatgtaacat agccgtgtaa ccatactatt ctcgaatgta acatcaagtc  1620
tctaatcaa                                                          1629
```

<210> SEQ ID NO 38
<211> LENGTH: 316
<212> TYPE: PRT
<213> ORGANISM: Arabidopsis thaliana

<400> SEQUENCE: 38

```
Met Ser Gly Ser Leu Met Asn Leu Phe Ser Leu Cys Phe Lys Pro Phe
1               5                   10                  15

Gly His Val Cys Asp Asn Ser Glu Ala Gly Ser Gly Gly Gly Gly Gly
                20                  25                  30

Val Ser Gly Gly Thr Gly Gly Glu Gly Lys Asp Gly Leu Leu Trp Phe
            35                  40                  45

Arg Asp Leu Gly Lys Tyr Cys Gly Gly Asp Phe Ser Met Ala Val Ile
        50                  55                  60

Gln Ala Asn Gln Val Leu Glu Asp Gln Ser Gln Val Glu Ser Gly Asn
65                  70                  75                  80
```

```
Phe Gly Thr Phe Val Gly Val Tyr Asp Gly His Gly Pro Glu Ala
             85                  90                  95
Ala Arg Tyr Val Cys Asp His Leu Phe Asn His Phe Arg Glu Ile Ser
        100                 105                 110
Ala Glu Thr Gln Gly Val Val Thr Arg Glu Thr Ile Glu Arg Ala Phe
    115                 120                 125
His Ala Thr Glu Glu Gly Phe Ala Ser Ile Val Ser Glu Leu Trp Gln
130                 135                 140
Glu Ile Pro Asn Leu Ala Thr Val Gly Thr Cys Cys Leu Val Gly Val
145                 150                 155                 160
Ile Tyr Gln Asn Thr Leu Phe Val Ala Ser Leu Gly Asp Ser Arg Val
                165                 170                 175
Val Leu Gly Lys Lys Gly Asn Cys Gly Gly Leu Ser Ala Ile Gln Leu
            180                 185                 190
Ser Thr Glu His Asn Ala Asn Asn Glu Asp Ile Arg Trp Glu Leu Lys
        195                 200                 205
Asp Leu His Pro Asp Asp Pro Gln Ile Val Val Phe Arg His Gly Val
    210                 215                 220
Trp Arg Val Lys Gly Ile Ile Gln Val Ser Arg Ser Ile Gly Asp Met
225                 230                 235                 240
Tyr Met Lys Arg Pro Glu Phe Asn Lys Glu Pro Ile Ser Gln Lys Phe
                245                 250                 255
Arg Ile Ala Glu Pro Met Lys Arg Pro Leu Met Ser Ala Thr Pro Thr
            260                 265                 270
Ile Leu Ser His Pro Leu His Pro Asn Asp Ser Phe Leu Ile Phe Ala
        275                 280                 285
Ser Asp Gly Leu Trp Glu His Leu Thr Asn Glu Lys Ala Val Glu Ile
    290                 295                 300
Val His Asn His Pro Arg Ala Val Thr Gln Arg Asp
305                 310                 315

<210> SEQ ID NO 39
<211> LENGTH: 1728
<212> TYPE: DNA
<213> ORGANISM: Arabidopsis thaliana

<400> SEQUENCE: 39
tgatctcaga actaacaagt aagaagaaga agaatgtcgg agagtttcaa agtgtgcttc      60
tgttgcagca gaagctttaa ggagaaaacg aggcagccac cagtgagcat caagagactc     120
ttcgaagctt actcaagaaa cggcaagatg tctttcgatg agcttctaag atttgtgagt     180
gaagtccaag gagaacggca cgcagggttg gactacgtgc aagatatctt ccacagcgtt     240
aaacaccaca cgttttttca tcaccatgga cttgttcatc tcaacgcctt ctatcgctac     300
ctcttcagcg ataccaactc tcctcttccc atgtctggcc aggtgcatca tgacatgaag     360
gcgccgttat cgcattactt tgtgtacacg ggacataact cttacttgac tgggaaccaa     420
gtgaacagca gaagcagcgt agaaccgatc gtgcaggctc tcagaaaagg cgtaaaagtg     480
atcgagctcg acttatggcc taatccttca gggaacgctg ctgaagttcg tcatggcagg     540
acgcttactt cgcatgaaga tttgcagaaa tgtctaaccg ccattaagga taacgcgttt     600
catgtgtctg actatccagt catcatcact ctcgaagatc atttgccacc caagcttcaa     660
gcgcaagttg ctaagatgtt aactaaaaca tacagaggga tgctgtttcg tcgtgtctca     720 gagagttttta gcattttcc atcaccagaa gaacttaagg ggaagatcct gatctctacg     780
aagcctccaa aggagtatct tgagagcaaa actgtacaca ccacaagaac tccaacggtt     840
```

```
aaagagactt cgtggaacag agtagcgaac aagattcttg aagaatataa agatatggag    900
agtgaagctg taggatatag agacttgata gcaatccacg ctgcaaactg caaagatcct    960
tcaaaggatt gcttgagtga tgatccagag aagcctatac gggtcagcat ggacgagcag   1020
tggctagaca ctatggttag gaccagagga acggatcttg tcaggtttac acagaggaat   1080
ctggtgagga tatatccaaa gggcacaaga gtggactcgt caaactacga tcctcatgtt   1140
gggtggacac acggtgctca aatggttgct tttaacatgc aaggacatgg gaagcaacta   1200
tggataatgc aaggaatgtt caggggaat ggtggatgtg ggtacgttaa aaagcctcgc   1260
atcttgctag acgagcacac actcttcgac ccttgcaaaa ggtttcccat taagaccact   1320
cttaaggtta agatttacac tggcgaagga tgggatttgg atttccatca tacacacttt   1380
gatcaatact ctcctccaga tttcttcgtc aagattggaa tagcaggagt accgagagac   1440
acggtctcat acagaacgga aacagctgtc gatcagtggt ttcctatatg gggcaacgac   1500
gagttcctgt ttcagctgtc tgttccagaa ctggcgcttc tgtggttcaa agtccaagac   1560
tacgacaatg acaccagaa tgatttcgca ggacagacat gtcttcctct gccggaactg   1620
aagtccggag ttagagccgt ccggcttcac gatcgaacag gcaaggccta caagaacacg   1680
aggcttctcg tcagcttcgc cttggatcct ccttatacgt ttcgttga                1728
```

```
<210> SEQ ID NO 40
<211> LENGTH: 564
<212> TYPE: PRT
<213> ORGANISM: Arabidopsis thaliana

<400> SEQUENCE: 40
```

```
Met Ser Glu Ser Phe Lys Val Cys Phe Cys Ser Arg Ser Phe Lys
1               5                   10                  15

Glu Lys Thr Arg Gln Pro Pro Val Ser Ile Lys Arg Leu Phe Glu Ala
            20                  25                  30

Tyr Ser Arg Asn Gly Lys Met Ser Phe Asp Glu Leu Leu Arg Phe Val
        35                  40                  45

Ser Glu Val Gln Gly Glu Arg His Ala Gly Leu Asp Tyr Val Gln Asp
    50                  55                  60

Ile Phe His Ser Val Lys His His Asn Val Phe His His Gly Leu
65                  70                  75                  80

Val His Leu Asn Ala Phe Tyr Arg Tyr Leu Phe Ser Asp Thr Asn Ser
                85                  90                  95

Pro Leu Pro Met Ser Gly Gln Val His His Asp Met Lys Ala Pro Leu
            100                 105                 110

Ser His Tyr Phe Val Tyr Thr Gly His Asn Ser Tyr Leu Thr Gly Asn
        115                 120                 125

Gln Val Asn Ser Arg Ser Ser Val Glu Pro Ile Val Gln Ala Leu Arg
    130                 135                 140

Lys Gly Val Lys Val Ile Glu Leu Asp Leu Trp Pro Asn Pro Ser Gly
145                 150                 155                 160

Asn Ala Ala Glu Val Arg His Gly Arg Thr Leu Thr Ser His Glu Asp
                165                 170                 175

Leu Gln Lys Cys Leu Thr Ala Ile Lys Asp Asn Ala Phe His Val Ser
            180                 185                 190

Asp Tyr Pro Val Ile Ile Thr Leu Glu Asp His Leu Pro Pro Lys Leu
        195                 200                 205

Gln Ala Gln Val Ala Lys Met Leu Thr Lys Thr Tyr Arg Gly Met Leu
    210                 215                 220
```

```
Phe Arg Arg Val Ser Glu Ser Phe Lys His Phe Pro Ser Pro Glu Glu
225                 230                 235                 240

Leu Lys Gly Lys Ile Leu Ile Ser Thr Lys Pro Pro Lys Glu Tyr Leu
            245                 250                 255

Glu Ser Lys Thr Val His Thr Thr Arg Thr Pro Thr Val Lys Glu Thr
            260                 265                 270

Ser Trp Asn Arg Val Ala Asn Lys Ile Leu Glu Glu Tyr Lys Asp Met
        275                 280                 285

Glu Ser Glu Ala Val Gly Tyr Arg Asp Leu Ile Ala Ile His Ala Ala
    290                 295                 300

Asn Cys Lys Asp Pro Ser Lys Asp Cys Leu Ser Asp Asp Pro Glu Lys
305                 310                 315                 320

Pro Ile Arg Val Ser Met Asp Glu Gln Trp Leu Asp Thr Met Val Arg
                325                 330                 335

Thr Arg Gly Thr Asp Leu Val Arg Phe Thr Gln Arg Asn Leu Val Arg
            340                 345                 350

Ile Tyr Pro Lys Gly Thr Arg Val Asp Ser Ser Asn Tyr Asp Pro His
        355                 360                 365

Val Gly Trp Thr His Gly Ala Gln Met Val Ala Phe Asn Met Gln Gly
370                 375                 380

His Gly Lys Gln Leu Trp Ile Met Gln Gly Met Phe Arg Gly Asn Gly
385                 390                 395                 400

Gly Cys Gly Tyr Val Lys Lys Pro Arg Ile Leu Leu Asp Glu His Thr
                405                 410                 415

Leu Phe Asp Pro Cys Lys Arg Phe Pro Ile Lys Thr Thr Leu Lys Val
            420                 425                 430

Lys Ile Tyr Thr Gly Glu Gly Trp Asp Leu Asp Phe His His Thr His
        435                 440                 445

Phe Asp Gln Tyr Ser Pro Pro Asp Phe Phe Val Lys Ile Gly Ile Ala
    450                 455                 460

Gly Val Pro Arg Asp Thr Val Ser Tyr Arg Thr Glu Thr Ala Val Asp
465                 470                 475                 480

Gln Trp Phe Pro Ile Trp Gly Asn Asp Glu Phe Leu Phe Gln Leu Ser
                485                 490                 495

Val Pro Glu Leu Ala Leu Leu Trp Phe Lys Val Gln Asp Tyr Asp Asn
            500                 505                 510

Asp Thr Gln Asn Asp Phe Ala Gly Gln Thr Cys Leu Pro Leu Pro Glu
        515                 520                 525

Leu Lys Ser Gly Val Arg Ala Val Arg Leu His Asp Arg Thr Gly Lys
    530                 535                 540

Ala Tyr Lys Asn Thr Arg Leu Leu Val Ser Phe Ala Leu Asp Pro Pro
545                 550                 555                 560

Tyr Thr Phe Arg

<210> SEQ ID NO 41
<211> LENGTH: 1432
<212> TYPE: DNA
<213> ORGANISM: Arabidopsis thaliana

<400> SEQUENCE: 41
aacgcaccat ggaagaagaa ggcagcccag atatcatcat cgttggcgcc ggtatctccg    60
gcctttccac cgctgttgga ctacacaggc ttgggatcag aagcatggtg ctggaatctt   120
cggagacact gagagcgaca ggatttgcat ttaccacttg gttcaatgct tggaaggcca   180
```

-continued

```
tggaagctct cggcgtttct cagcatattc gcagtctcca tgatcgcctt gaaggatggg      240
tggttggaac aatttctgca ggaactcctc ccacagagat gctgtttcca gaatccgaag      300
aatatgagtc tcgatgcgta cagaggaagc tgttgttaga ggctctagca ggtgagttgc      360
ctgaagagac catcaggttt tcgtctaagg ttgttcatat tgaattgtct ggatgctaca      420
agaaggttca tctctccgac gggaccattc tcaaaaccaa ggttttggta gggtgcgatg      480
gagtgtactc agtggttggt aagtggctag gcttcaaaaa tcccgctaca actgcccggt      540
tagcaatccg agggctcaca cattttccgg aaggccatgg atttgggaaa aggttcttcc      600
agttttatgg agacggcgtt cgttccggtt ttatcccatg tgaccacaac actgtctact      660
ggttcctaac ccacacctcc actgatatag atgaggagac aaattcggaa atcctcaaag      720
agtttgtgct gaacaagatc aaagacttgc ctgaaaacat taagaatgtg gtggagacca      780
ctgatcttga tagcatggtg atgtctcaac tgaagtaccg acctccatgg gaactgctat      840
ggtcaaacat cacaaaagac aacgtgtgcg ttgcaggaga tgcacttcac ccaatgactc      900
ctgatatcgg acaaggaggt tgctcagcca tggaggatgg agttatcctt gctcgttgtc      960
taggtgaagc gataaaggca aagagtctga aaggtgaaac agaagaaaat gaagaagagg     1020
gttataagag gattgaagaa ggtttgaaga agtatgcagg agaaaggaaa tggagaagca     1080
ttgatcttat aacaacggca tatacagtag gattcataca gcagagcaga gggaagtgga     1140
tgaacatgtt cagagacagg ttcctgtcgt cttacctttc taggatgctg ctgaaaaagt     1200
cccatttcga ttgcggaagc cttgtcccat gatgattctc aaacataagt caaaagcttg     1260
tgattcttct tgtcatcacc aactgcagaa cagttttcac ctttggtttg cttcaaagac     1320
tatctatctg tttagtgtta tttcatataa caaactcaga attaataaag taagtttgtg     1380
tagtgaacaa gaagctcttt tatttttac ggcaatctaa agctctgata tc             1432
```

<210> SEQ ID NO 42
<211> LENGTH: 407
<212> TYPE: PRT
<213> ORGANISM: Arabidopsis thaliana

<400> SEQUENCE: 42

```
Met Glu Glu Glu Gly Ser Pro Asp Ile Ile Ile Val Gly Ala Gly Ile
1               5                   10                  15

Ser Gly Leu Ser Thr Ala Val Gly Leu His Arg Leu Gly Ile Arg Ser
                20                  25                  30

Met Val Leu Glu Ser Ser Glu Thr Leu Arg Ala Thr Gly Phe Ala Phe
            35                  40                  45

Thr Thr Trp Phe Asn Ala Trp Lys Ala Met Glu Ala Leu Gly Val Ser
        50                  55                  60

Gln His Ile Arg Ser Leu His Asp Arg Leu Glu Gly Trp Val Val Gly
65                  70                  75                  80

Thr Ile Ser Ala Gly Thr Pro Pro Thr Glu Met Leu Phe Pro Glu Ser
                85                  90                  95

Glu Glu Tyr Glu Ser Arg Cys Val Gln Arg Lys Leu Leu Leu Glu Ala
                100                 105                 110

Leu Ala Gly Glu Leu Pro Glu Glu Thr Ile Arg Phe Ser Ser Lys Val
            115                 120                 125

Val His Ile Glu Leu Ser Gly Cys Tyr Lys Lys Val His Leu Ser Asp
        130                 135                 140

Gly Thr Ile Leu Lys Thr Lys Val Leu Val Gly Cys Asp Gly Val Tyr
145                 150                 155                 160
```

```
Ser Val Val Gly Lys Trp Leu Gly Phe Lys Asn Pro Ala Thr Thr Ala
            165                 170                 175

Arg Leu Ala Ile Arg Gly Leu Thr His Phe Pro Glu Gly His Gly Phe
            180                 185                 190

Gly Lys Arg Phe Phe Gln Phe Tyr Gly Asp Gly Val Arg Ser Gly Phe
            195                 200                 205

Ile Pro Cys Asp His Asn Thr Val Tyr Trp Phe Leu Thr His Thr Ser
            210                 215                 220

Thr Asp Ile Asp Glu Glu Thr Asn Ser Glu Ile Leu Lys Glu Phe Val
225                 230                 235                 240

Leu Asn Lys Ile Lys Asp Leu Pro Glu Asn Ile Lys Asn Val Val Glu
            245                 250                 255

Thr Thr Asp Leu Asp Ser Met Val Met Ser Gln Leu Lys Tyr Arg Pro
            260                 265                 270

Pro Trp Glu Leu Leu Trp Ser Asn Ile Thr Lys Asp Asn Val Cys Val
            275                 280                 285

Ala Gly Asp Ala Leu His Pro Met Thr Pro Asp Ile Gly Gln Gly Gly
            290                 295                 300

Cys Ser Ala Met Glu Asp Gly Val Ile Leu Ala Arg Cys Leu Gly Glu
305                 310                 315                 320

Ala Ile Lys Ala Lys Ser Leu Lys Gly Glu Thr Glu Glu Asn Glu Glu
            325                 330                 335

Glu Gly Tyr Lys Arg Ile Glu Glu Leu Lys Lys Tyr Ala Gly Glu
            340                 345                 350

Arg Lys Trp Arg Ser Ile Asp Leu Ile Thr Thr Ala Tyr Thr Val Gly
            355                 360                 365

Phe Ile Gln Gln Ser Arg Gly Lys Trp Met Asn Met Phe Arg Asp Arg
            370                 375                 380

Phe Leu Ser Ser Tyr Leu Ser Arg Met Leu Leu Lys Lys Ser His Phe
385                 390                 395                 400

Asp Cys Gly Ser Leu Val Pro
            405

<210> SEQ ID NO 43
<211> LENGTH: 2227
<212> TYPE: DNA
<213> ORGANISM: Arabidopsis thaliana

<400> SEQUENCE: 43
cgaatcatat ataccagtcg tagtatgacg cgttgaagaa cagaaacgaa acgaaccaaa      60
aagtcttctc cggcaacttt agatcctcca gcagcaagat catttctcaa tcccatcctt     120
tgcctcaacc caatatggac ttcttcactt caagcaaagc taagaaagat agcaaaaaat     180
catcaggact ctttggcaag aaaactgtca gcaagagcac tccgggcagc cctgctcatc     240
cccccggcgc tagatccccg ccccatcgt atctttcaaa caaaagagcc gaaacagagt     300
acgatttccc catgtccaat gaacaaagac catactggaa acagcctgcc tctgaacgcg     360
tccccaactc ccaccctagg cctcccgtgt atggatacgg cacgcccgac catcgtcgag     420
accacggtag agaaagaatg gaggccatga gttatgagcc agagaccaac gctccttcca     480
gcccatatca tccagctgga aaccgcacgc ctgaacgtcc taggaaatca accgagtatc     540
gtcgagaaca ccaggatcga atgtatgaag cagataccccg aagcaatgcg agcccatttc     600
acccattcag aagcccttct ccatctccat tccacacgcc tgatcgccgc agagaccact     660
acgacatgta tgagcctgag gccaacacca tgctgcagaa tagcgctcca gggagcccat     720
```

```
tccatccagc tggaagccgc tctccaccac catacagaac gcctgatcgt cgtagtaact    780
atgataaaga gcaatttgag gacctgtacg agcaagatgg tgatgtcaca ccgcgaaaca    840
gctctccacc gagcccgttt catccagcag catacaaaac gtctgatcaa cgtagtaacc    900
atggtaaaga gcaaattgag gacttttatg agcaagatga cgatgtaaca ccacgaaaca    960
gctctccacc tagcccattg catccagcag caagccattc accaccacca ccacaaccat   1020
acagaacgcc tgaccatcgt agaagccacc aggataacga ggatttcgag gcaatgtatg   1080
agctagatgg cgacttaata caccagaaga gcgctcctcc gagtcccgtt catggaccat   1140
actattcatc cagcgacgac gataatcact ccacctacct ctatccagaa atccgcagcc   1200
cacttcgttc caggatcgta tccgagaaca gcacgcctgt tcaccacaac taccagatag   1260
ttgcggccga gacctatgag caagacaagc agttcgagcc gccggagctg cctgacgagt   1320
cacaaagctt cacaatgcag gagattacca aaatgcgagg actcaagaac tacgaaagcg   1380
gcaaggaaga gagtcaatca atgatatccg aggcttacgt atccgtcgcg aattacagag   1440
tgaggcagag cgtgtcggaa accctgcagg cgatcatcga caagcacggc gacatcgcag   1500
cctcctcgaa gctgcaagca atggcaactc ggtcttatta cctggaatcc ctagccgctg   1560
tggtgatgga gctgaaaaag acggttctga gggatttgac gaaaacgcgc gtggcggaga   1620
tcgcggcggt ggtgaaagac atggagtcgg tgaaaatcaa cgtgtcgtgg ctaaagacag   1680
cggtaacgga actggcggag gcggtggagt atttcgggca gtacgacacg gcgaaggtgg   1740
agaaagaggt gtgcgagaga gatctgacgg cgaaaaaggg ggagatggag gagatgacgg   1800
cggagctggt gaagagggag aaggaaatca agaatgcag agagaaggtg acggtggtcg   1860
cagggaggct agggcagctg gagatgaaag gttcgaaatt gaacaagaat ctcgacctct   1920
tccagtccaa agtccacaaa ttccaaggag aagccgtcct tctccacctt tagctccgtc   1980
tccaatttct tccgttttgg atctcattat tcaattattt tctattgaca tgaaatgttt   2040
ataaatttaa agtttggggc cattagtgta attcttaaaa agatttaaaa agcttttatg   2100
ttgaatgttg agagtcaagg tcagctattg cagaagcgta gattgtttca gagtcaagca   2160
tctcaataca ttgtaataat atgcatgcgt gtgtttcaag ctatatattt atgtatgtgc   2220
attttac                                                              2227
```

```
<210> SEQ ID NO 44
<211> LENGTH: 612
<212> TYPE: PRT
<213> ORGANISM: Arabidopsis thaliana

<400> SEQUENCE: 44

Met Asp Phe Phe Thr Ser Ser Lys Ala Lys Lys Asp Ser Lys Lys Ser
1               5                   10                  15

Ser Gly Leu Phe Gly Lys Lys Thr Val Ser Lys Ser Thr Pro Gly Ser
            20                  25                  30

Pro Ala His Pro Pro Gly Ala Arg Ser Pro Pro Ser Tyr Leu Ser
        35                  40                  45

Asn Lys Arg Ala Glu Thr Glu Tyr Asp Phe Pro Met Ser Asn Glu Gln
    50                  55                  60

Arg Pro Tyr Trp Lys Gln Pro Ala Ser Glu Arg Val Pro Asn Ser His
65                  70                  75                  80

Pro Arg Pro Pro Val Tyr Gly Tyr Gly Thr Pro Asp His Arg Asp
                85                  90                  95

His Gly Arg Glu Arg Met Glu Ala Met Ser Tyr Glu Pro Glu Thr Asn
            100                 105                 110
```

```
Ala Pro Ser Ser Pro Tyr His Pro Ala Gly Asn Arg Thr Pro Glu Arg
            115                 120                 125
Pro Arg Lys Ser Thr Glu Tyr Arg Arg Glu His Gln Asp Arg Met Tyr
        130                 135                 140
Glu Ala Asp Thr Arg Ser Asn Ala Ser Pro Phe His Pro Phe Arg Ser
145                 150                 155                 160
Pro Ser Pro Ser Pro Phe His Thr Pro Asp Arg Arg Arg Asp His Tyr
                165                 170                 175
Asp Met Tyr Glu Pro Glu Ala Asn Thr Met Leu Gln Asn Ser Ala Pro
            180                 185                 190
Gly Ser Pro Phe His Pro Ala Gly Ser Arg Ser Pro Pro Tyr Arg
        195                 200                 205
Thr Pro Asp Arg Arg Ser Asn Tyr Asp Lys Glu Gln Phe Glu Asp Leu
        210                 215                 220
Tyr Glu Gln Asp Gly Asp Val Thr Pro Arg Asn Ser Ser Pro Pro Ser
225                 230                 235                 240
Pro Phe His Pro Ala Ala Tyr Lys Thr Ser Asp Gln Arg Ser Asn His
                245                 250                 255
Gly Lys Glu Gln Ile Glu Asp Phe Tyr Glu Gln Asp Asp Val Thr
            260                 265                 270
Pro Arg Asn Ser Ser Pro Pro Ser Pro Leu His Pro Ala Ala Ser His
        275                 280                 285
Ser Pro Pro Pro Gln Pro Tyr Arg Thr Pro Asp His Arg Arg Ser
        290                 295                 300
His Gln Asp Asn Glu Asp Phe Glu Ala Met Tyr Glu Leu Asp Gly Asp
305                 310                 315                 320
Leu Ile His Gln Lys Ser Ala Pro Pro Ser Pro Val His Gly Pro Tyr
                325                 330                 335
Tyr Ser Ser Ser Asp Asp Asp Asn His Ser Thr Tyr Leu Tyr Pro Glu
            340                 345                 350
Ile Arg Ser Pro Leu Arg Ser Arg Ile Val Ser Glu Asn Ser Thr Pro
        355                 360                 365
Val His His Asn Tyr Gln Ile Val Ala Ala Glu Thr Tyr Glu Gln Asp
        370                 375                 380
Lys Gln Phe Glu Pro Pro Glu Leu Pro Asp Glu Ser Gln Ser Phe Thr
385                 390                 395                 400
Met Gln Glu Ile Thr Lys Met Arg Gly Leu Lys Asn Tyr Glu Ser Gly
                405                 410                 415
Lys Glu Glu Ser Gln Ser Met Ile Ser Glu Ala Tyr Val Ser Val Ala
            420                 425                 430
Asn Tyr Arg Val Arg Gln Ser Val Ser Glu Thr Leu Gln Ala Ile Ile
        435                 440                 445
Asp Lys His Gly Asp Ile Ala Ala Ser Lys Leu Gln Ala Met Ala
        450                 455                 460
Thr Arg Ser Tyr Tyr Leu Glu Ser Leu Ala Ala Val Val Met Glu Leu
465                 470                 475                 480
Lys Lys Thr Val Leu Arg Asp Leu Thr Lys Thr Arg Val Ala Glu Ile
                485                 490                 495
Ala Ala Val Val Lys Asp Met Glu Ser Val Lys Ile Asn Val Ser Trp
            500                 505                 510
Leu Lys Thr Ala Val Thr Glu Leu Ala Glu Ala Val Glu Tyr Phe Gly
        515                 520                 525
Gln Tyr Asp Thr Ala Lys Val Glu Lys Glu Val Cys Glu Arg Asp Leu
```

```
                    530                 535                 540
Thr Ala Lys Lys Gly Glu Met Glu Met Thr Ala Glu Leu Val Lys
545                 550                 555                 560

Arg Glu Lys Glu Ile Lys Glu Cys Arg Glu Lys Val Thr Val Val Ala
                565                 570                 575

Gly Arg Leu Gly Gln Leu Glu Met Lys Gly Ser Lys Leu Asn Lys Asn
                580                 585                 590

Leu Asp Leu Phe Gln Ser Lys Val His Lys Phe Gln Gly Glu Ala Val
            595                 600                 605

Leu Leu His Leu
        610

<210> SEQ ID NO 45
<211> LENGTH: 1566
<212> TYPE: DNA
<213> ORGANISM: Arabidopsis thaliana

<400> SEQUENCE: 45
atgtctggaa tagtacatca tgattgtcct aactcaggaa atccctacca cgagtgccac      60
gatcagtgtt tcaagagaat aagctccgga gatgtcccca agaaggagaa aaaacggttt     120
ggctttggta aaccagcttg tagcaaggaa acgcctctta ccagtccggt tcgtgttatt     180
gcggaaaaca gatcaccact tccgagttat acgaaaaaa gaatggatga gtcagacgag      240
tcccctcct tctcttcctc cgatgactct ttcaatgcaa acttgcccac accacgttcc      300
actttacatg ggaacgaaac tgccccggga atcaattggc tccccatgtc gccttctttc     360
gctgtgtatt gcaagaaaga ttgtttctca tcaaggatcg atcaccgtga aggtgaagct     420
ccaattcttg atgaaatgcc atctaagact cggcttaaga cacctctaag tcctgatact     480
aggccaagga atcagaaaca caggacaaga aaccaaggac cacgctcaaa gactccagaa     540
cctagaggaa gttaccttga accacccagg tctaggatcc acaaactca gccggtacca      600
cacagatccc ttgaaagtgc tggtctcaaa tcacctcaga aaggtgaaac tcggcctcat     660
atccccaaa ctcagccaac atccttcaac atcggtggta actatcatta cgctgctcaa      720
gcatccaaat atcatgctaa taagcggat tcagtgtaca ctaaagacag agacaaatgc      780
gttatacttt atcccgatat tcttttgtcc cctcaagaaa atctgacatc aagatccatt     840
acgatgcttc cccaaaaatc ccgtacacca ctagacaaac aatcgaagga gccattacag     900
ctgcctgtcg aatgccatag ctttactcca tctgagatcg aatgcatgaa agcgttaaag     960
atttacgaaa caggagagga aatgaagtca atgatttcag agtcgtatgt ctctgtagga    1020
agctacaagg tcagagcgag cgtctcgtcc actctgcaga aaatcctgga caagcatgga    1080
gacatagcgt ccggttccaa acttcagtca ctgcgcacaa atcttactc gcttgagact     1140
ctagccgcgg tggttcttga actccaatcg acgcccctga gaaattgaa gcaggcacgc     1200
gtgttggaaa tgctatcggt tgtttatagac gcagagtctg ttaaaatcag agctggttgg    1260
ctcagggaga tcctgaacga gattcttgaa gcggcccacc actatgatgg acacgagaca    1320
acggtggtgg agaaggaagg gcgtgaacgg gatatgctgc ttgaaagaga agaaatgaag    1380
aagatacagg aggaggtgag attgaaggag aaggaggcaa aggactttcg taaggagtc    1440
atggaaatgg cagggcgttt gggagaactg aagatgaagc gagcgcgttt ggagaaacgc    1500
ttggcgtttc tgagctccaa ggtggaaaag tttgaggggg aatctttgtt agagaacgtc    1560
ttttga                                                              1566
```

-continued

```
<210> SEQ ID NO 46
<211> LENGTH: 521
<212> TYPE: PRT
<213> ORGANISM: Arabidopsis thaliana

<400> SEQUENCE: 46
```

| | | | | | | | | | | | | | | |
|---|---|---|---|---|---|---|---|---|---|---|---|---|---|---|
| Met | Ser | Gly | Ile | Val | His | His | Asp | Cys | Pro | Asn | Ser | Gly | Asn | Pro | Tyr |
| 1 | | | | 5 | | | | | 10 | | | | | 15 | |
| His | Glu | Cys | His | Asp | Gln | Cys | Phe | Lys | Arg | Ile | Ser | Ser | Gly | Asp | Val |
| | | | 20 | | | | | 25 | | | | | 30 | | |
| Pro | Lys | Lys | Glu | Lys | Lys | Arg | Phe | Gly | Phe | Gly | Lys | Pro | Ala | Cys | Ser |
| | | | 35 | | | | | 40 | | | | | 45 | | |
| Lys | Glu | Thr | Pro | Leu | Thr | Ser | Pro | Val | Arg | Val | Ile | Ala | Gly | Asn | Arg |
| | 50 | | | | | 55 | | | | | 60 | | | | |
| Ser | Pro | Leu | Pro | Ser | Tyr | Tyr | Gly | Lys | Arg | Met | Asp | Glu | Ser | Asp | Glu |
| 65 | | | | | 70 | | | | | 75 | | | | | 80 |
| Ser | Pro | Ser | Phe | Ser | Ser | Asp | Asp | Ser | Phe | Asn | Ala | Asn | Leu | Pro |
| | | | | 85 | | | | | 90 | | | | | 95 |
| Thr | Pro | Arg | Ser | Thr | Leu | His | Gly | Asn | Glu | Thr | Ala | Pro | Gly | Ile | Asn |
| | | | 100 | | | | | 105 | | | | | 110 | | |
| Trp | Leu | Pro | Met | Ser | Pro | Ser | Phe | Ala | Val | Tyr | Cys | Lys | Lys | Asp | Cys |
| | | | 115 | | | | | 120 | | | | | 125 | | |
| Phe | Ser | Ser | Arg | Ile | Asp | His | Arg | Glu | Gly | Glu | Ala | Pro | Ile | Leu | Asp |
| | 130 | | | | | 135 | | | | | 140 | | | | |
| Glu | Met | Pro | Ser | Lys | Thr | Arg | Leu | Lys | Thr | Pro | Leu | Ser | Pro | Asp | Thr |
| 145 | | | | | 150 | | | | | 155 | | | | | 160 |
| Arg | Pro | Arg | Lys | Ser | Glu | His | Arg | Thr | Arg | Asn | Gln | Gly | Pro | Arg | Ser |
| | | | | 165 | | | | | 170 | | | | | 175 | |
| Lys | Thr | Pro | Glu | Pro | Arg | Gly | Ser | Tyr | Leu | Glu | Pro | Pro | Arg | Ser | Arg |
| | | | 180 | | | | | 185 | | | | | 190 | | |
| Ile | Pro | Gln | Thr | Gln | Pro | Val | Pro | His | Arg | Ser | Leu | Glu | Ser | Ala | Gly |
| | | | 195 | | | | | 200 | | | | | 205 | | |
| Leu | Lys | Ser | Pro | Gln | Lys | Gly | Glu | Thr | Arg | Pro | His | Ile | Pro | Gln | Thr |
| | 210 | | | | | 215 | | | | | 220 | | | | |
| Gln | Pro | Thr | Ser | Phe | Asn | Ile | Gly | Gly | Asn | Tyr | His | Tyr | Ala | Ala | Gln |
| 225 | | | | | 230 | | | | | 235 | | | | | 240 |
| Ala | Ser | Lys | Tyr | His | Ala | Asn | Lys | Ala | Asp | Ser | Val | Tyr | Thr | Lys | Asp |
| | | | | 245 | | | | | 250 | | | | | 255 | |
| Arg | Asp | Lys | Cys | Val | Ile | Leu | Tyr | Pro | Asp | Ile | Leu | Leu | Ser | Pro | Gln |
| | | | 260 | | | | | 265 | | | | | 270 | | |
| Glu | Asn | Leu | Thr | Ser | Arg | Ser | Ile | Thr | Met | Leu | Pro | Gln | Lys | Ser | Arg |
| | | | | 275 | | | | | 280 | | | | | 285 | |
| Thr | Pro | Leu | Asp | Lys | Gln | Ser | Lys | Glu | Pro | Leu | Gln | Leu | Pro | Val | Glu |
| | | | 290 | | | | | 295 | | | | | 300 | | |
| Cys | His | Ser | Phe | Thr | Pro | Ser | Glu | Ile | Glu | Cys | Met | Lys | Ala | Leu | Lys |
| 305 | | | | | 310 | | | | | 315 | | | | | 320 |
| Ile | Tyr | Glu | Thr | Gly | Glu | Glu | Met | Lys | Ser | Met | Ile | Ser | Glu | Ser | Tyr |
| | | | | 325 | | | | | 330 | | | | | 335 | |
| Val | Ser | Val | Gly | Ser | Tyr | Lys | Val | Arg | Ala | Ser | Val | Ser | Ser | Thr | Leu |
| | | | 340 | | | | | 345 | | | | | 350 | | |
| Gln | Lys | Ile | Leu | Asp | Lys | His | Gly | Asp | Ile | Ala | Ser | Gly | Ser | Lys | Leu |
| | | | | 355 | | | | | 360 | | | | | 365 | |
| Gln | Ser | Leu | Arg | Thr | Lys | Ser | Tyr | Ser | Leu | Glu | Thr | Leu | Ala | Ala | Val |
| | | | 370 | | | | | 375 | | | | | 380 | | |
| Val | Leu | Glu | Leu | Gln | Ser | Thr | Pro | Leu | Lys | Lys | Leu | Lys | Gln | Ala | Arg |

| | | | |
|---|---|---|---|
| | 385 | 390 | 395 400 |

Val Leu Glu Met Leu Ser Val Val Ile Asp Ala Glu Ser Val Lys Ile
                  405                  410              415

Arg Ala Gly Trp Leu Arg Glu Ile Leu Asn Glu Ile Leu Glu Ala Ala
            420                  425              430

His His Tyr Asp Gly His Glu Thr Thr Val Val Glu Lys Glu Gly Arg
        435                  440              445

Glu Arg Asp Met Leu Leu Glu Arg Glu Glu Met Lys Lys Ile Gln Glu
            450                  455              460

Glu Val Arg Leu Lys Glu Lys Glu Ala Lys Asp Phe Arg Lys Gly Val
465                  470                  475              480

Met Glu Met Ala Gly Arg Leu Gly Glu Leu Lys Met Lys Arg Ala Arg
                485                  490              495

Leu Glu Lys Arg Leu Ala Phe Leu Ser Ser Lys Val Glu Lys Phe Glu
            500                  505              510

Gly Glu Ser Leu Leu Glu Asn Val Phe
        515                  520

```
<210> SEQ ID NO 47
<211> LENGTH: 1507
<212> TYPE: DNA
<213> ORGANISM: Arabidopsis thaliana

<400> SEQUENCE: 47
```

| | | | | | |
|---|---|---|---|---|---|
| gaaaccgaga | aaagttttac | aaataattta | acaaatgtta | gtactgtatt | tcacaaattg | 60 |
| aatttgagaa | tattaaacga | aaaaacgttt | ttgcttgaga | gagaggcgaa | tctgattctt | 120 |
| gtgagagctt | ccaacaaagt | ctgcaggctc | atcctgcgga | tcccttcgtt | cccaatttct | 180 |
| cttaggcagg | tatcccttca | ttggcgagat | ccttgttttc | ttcgttgggg | aacagattgc | 240 |
| ccaaactgaa | gtctctctct | ctctgttatg | gctaaacaga | gaccggcgac | gttgtcagtc | 300 |
| tacctctaca | ttcccaatat | cgttgggtac | atgagagttc | tcttgaactg | cattgccttc | 360 |
| tctgtgtgct | tctccaacaa | gacactcttc | tccctcttgt | acttttttcag | ttttttgttgt | 420 |
| gatgctgtgg | atggatggtg | cgctcgtaaa | tttaaccaag | tctctacatt | tggagctgtt | 480 |
| ttggatatgg | ttacagatag | agtcagcaca | gcctgtcttc | tcgtgattct | ctcccagata | 540 |
| tacaggccta | gcttggtttt | cctgtcattg | ctggctttag | atatcgctag | tcactggctg | 600 |
| caaatgtaca | gtaccttcct | atcagggaag | accagccata | aggatgtgaa | agatagcacg | 660 |
| agctggctct | ttagactcta | ttatggaaac | cggatgttca | tgggttattg | ctgtgttttcc | 720 |
| tgcgaggttc | tttatataat | ccttcttctc | atagcaacga | accaaaccga | aaacttgatg | 780 |
| aacgtggtag | tgaaatcatt | gatgcagatt | tcaccgctct | cttttactctt | ggctttgagc | 840 |
| atatttggtt | ggtccatcaa | gcagatcatc | aatgtgattc | agatgaaaac | ggctgcagat | 900 |
| gtttgtgtcc | tgtatgacat | agagaaacag | cataagaagc | cttgacgtta | tgtgcccgtg | 960 |
| aatcgtgttt | aactctttttg | tttcatgttg | tgtacgacac | tgtacatacg | gatccatctt | 1020 |
| gtttagtatg | tagataaact | cttgtcttta | aatccattca | ctattttcag | aaatttcatg | 1080 |
| tcttctaagt | tctttagcac | atcatgttttt | gattgcaacc | ataaaacccc | atctctgcta | 1140 |
| gctagaaaaa | ccaaaacaaa | agcataaggt | tgatcaaaag | acgttctcta | acaaagattc | 1200 |
| ccctcaaac | ttttccacct | tggagctcag | aaacgccaag | cgttctcca | aacgcgctcg | 1260 |
| cttcatcttc | agttctccca | aacgccctgc | catttccatg | actcctttac | gaaagtcctt | 1320 |
| tgcctccttc | tccttcaatc | tcacctcctc | ctgtatcttc | ttcatttctt | ctcttttcaag | 1380 |

```
cagcatatcc cgttcacgcc cttccttctc caccaccgtt gtctcgtgtc catcatagtg    1440
gtgggccgct tcaagaatct cgttcaggat ctccctgagc caaccagctc tgattttaac    1500
agactct                                                              1507
```

<210> SEQ ID NO 48
<211> LENGTH: 225
<212> TYPE: PRT
<213> ORGANISM: Arabidopsis thaliana

<400> SEQUENCE: 48

```
Met Ala Lys Gln Arg Pro Ala Thr Leu Ser Val Tyr Leu Tyr Ile Pro
  1               5                  10                  15

Asn Ile Val Gly Tyr Met Arg Val Leu Leu Asn Cys Ile Ala Phe Ser
                 20                  25                  30

Val Cys Phe Ser Asn Lys Thr Leu Phe Ser Leu Leu Tyr Phe Phe Ser
             35                  40                  45

Phe Cys Cys Asp Ala Val Asp Gly Trp Cys Ala Arg Lys Phe Asn Gln
         50                  55                  60

Val Ser Thr Phe Gly Ala Val Leu Asp Met Val Thr Asp Arg Val Ser
 65                  70                  75                  80

Thr Ala Cys Leu Leu Val Ile Leu Ser Gln Ile Tyr Arg Pro Ser Leu
                 85                  90                  95

Val Phe Leu Ser Leu Leu Ala Leu Asp Ile Ala Ser His Trp Leu Gln
            100                 105                 110

Met Tyr Ser Thr Phe Leu Ser Gly Lys Thr Ser His Lys Asp Val Lys
        115                 120                 125

Asp Ser Thr Ser Trp Leu Phe Arg Leu Tyr Tyr Gly Asn Arg Met Phe
    130                 135                 140

Met Gly Tyr Cys Cys Val Ser Cys Glu Val Leu Tyr Ile Ile Leu Leu
145                 150                 155                 160

Leu Ile Ala Thr Asn Gln Thr Glu Asn Leu Met Asn Val Val Lys
                165                 170                 175

Ser Leu Met Gln Ile Ser Pro Leu Ser Leu Leu Ala Leu Ser Ile
            180                 185                 190

Phe Gly Trp Ser Ile Lys Gln Ile Ile Asn Val Ile Gln Met Lys Thr
        195                 200                 205

Ala Ala Asp Val Cys Val Leu Tyr Asp Ile Glu Lys Gln His Lys Lys
    210                 215                 220

Pro
225
```

<210> SEQ ID NO 49
<211> LENGTH: 528
<212> TYPE: DNA
<213> ORGANISM: Arabidopsis thaliana

<400> SEQUENCE: 49

```
atgggtttg ggttcaagat cggatcaaga ttccgattag ccaccgcatt cacatggtgc     60
cttctcatcg catcagcgtg ctttgcatac accgcatcag cagcccggtt cgaggtaaga    120
aacgagatct ccatatacc aggacggaat cgtagcctcg cgattaactg ttggtcgtcg    180
aataacaaat tgggcacgca tgctctcaaa ccaggccaat ccaaaagctg gtcgttcaag    240
ccaatattta ttaagatacc gtttttctac acatactttg agtgcacgtt cttcaccgcg    300
tttggctcgc catttggtca gacagcaacg gttttgccg gggagagatt attcaggtgg     360
caatgtgata atccggatga ggaagagtgc atttgggtgg ttaagagaga cgggctatat    420
```

```
ctaaggagga tcaaaagaga caataaaggc caaaggctct atggagatga attgagaatg      480
gtttggatcg gcggtactaa ttaccaccct gtaaagagg atccataa                    528
```

<210> SEQ ID NO 50
<211> LENGTH: 175
<212> TYPE: PRT
<213> ORGANISM: Arabidopsis thaliana

<400> SEQUENCE: 50

```
Met Gly Phe Gly Phe Lys Ile Gly Ser Arg Phe Arg Leu Ala Thr Ala
1               5                   10                  15

Phe Thr Trp Cys Leu Leu Ile Ala Ser Ala Cys Phe Ala Tyr Thr Ala
            20                  25                  30

Ser Ala Ala Arg Phe Glu Val Arg Asn Glu Ile Ser Ile Tyr Pro Gly
        35                  40                  45

Arg Asn Arg Ser Leu Ala Ile Asn Cys Trp Ser Ser Asn Asn Lys Leu
    50                  55                  60

Gly Thr His Ala Leu Lys Pro Gly Gln Ser Lys Ser Trp Ser Phe Lys
65                  70                  75                  80

Pro Ile Phe Ile Lys Ile Pro Phe Phe Tyr Thr Tyr Phe Glu Cys Thr
                85                  90                  95

Phe Phe Thr Ala Phe Gly Ser Pro Phe Gly Gln Thr Ala Thr Val Phe
            100                 105                 110

Ala Gly Glu Arg Leu Phe Arg Trp Gln Cys Asp Asn Pro Asp Glu Glu
        115                 120                 125

Glu Cys Ile Trp Val Val Lys Arg Asp Gly Leu Tyr Leu Arg Arg Ile
    130                 135                 140

Lys Arg Asp Asn Lys Gly Gln Arg Leu Tyr Gly Asp Glu Leu Arg Met
145                 150                 155                 160

Val Trp Ile Gly Gly Thr Asn Tyr His Pro Val Lys Glu Asp Pro
                165                 170                 175
```

<210> SEQ ID NO 51
<211> LENGTH: 525
<212> TYPE: DNA
<213> ORGANISM: Arabidopsis thaliana

<400> SEQUENCE: 51

```
atggctgaga aaatgaaagc cctagtaata ttttgccttg tttttcaagt aatcattcaa      60
acaggaaact cagctgattc aggagatgtt gatttttcaa tactcatcaa aaacgaaatg     120
tacaatgtcg ataacccgtc ggttttctac aattgtcgat catcgaagaa agacatcgga     180
tggcacaaat cggttccatc ctcagagttt caatgggaat cgaagttcc tcagtttggt      240 aacggcgtga tggtccacaa ttgtcgtttc cggtcgagcg caggaacagc aaacgttgag     300
atcaggacat tgtctactac ggcgatgcta tgcgacggac aaacatgtaa atatgcaatt     360
agacctaatg ggatttattt cattggttac gagttgtatt ctccttatgc tatatttgga     420
aggtatattg aattgtcgag gcccgcggag aagctagttg agccgtggaa accttggtca     480
ccacaacaac tcaaagttat gcatcgtaca caacatggtc catga                     525
```

<210> SEQ ID NO 52
<211> LENGTH: 174
<212> TYPE: PRT
<213> ORGANISM: Arabidopsis thaliana

<400> SEQUENCE: 52

```
Met Ala Glu Lys Met Lys Ala Leu Val Ile Phe Cys Leu Val Phe Gln
1               5                   10                  15

Val Ile Ile Gln Thr Gly Asn Ser Ala Asp Ser Gly Asp Val Asp Phe
            20                  25                  30

Ser Ile Leu Ile Lys Asn Glu Met Tyr Asn Val Asp Asn Pro Ser Val
            35                  40                  45

Phe Tyr Asn Cys Arg Ser Ser Lys Lys Asp Ile Gly Trp His Lys Ser
        50                  55                  60

Val Pro Ser Ser Glu Phe Gln Trp Glu Phe Glu Val Pro Gln Phe Gly
65                  70                  75                  80

Asn Gly Val Met Val His Asn Cys Arg Phe Arg Ser Ser Ala Gly Thr
                85                  90                  95

Ala Asn Val Glu Ile Arg Thr Leu Ser Thr Thr Ala Met Leu Cys Asp
            100                 105                 110

Gly Gln Thr Cys Lys Tyr Ala Ile Arg Pro Asn Gly Ile Tyr Phe Ile
            115                 120                 125

Gly Tyr Glu Leu Tyr Ser Pro Tyr Ala Ile Phe Gly Arg Tyr Ile Glu
        130                 135                 140

Leu Ser Arg Pro Ala Glu Lys Leu Val Glu Pro Trp Lys Pro Trp Ser
145                 150                 155                 160

Pro Gln Gln Leu Lys Val Met His Arg Thr Gln His Gly Pro
                165                 170
```

<210> SEQ ID NO 53
<211> LENGTH: 768
<212> TYPE: DNA
<213> ORGANISM: Arabidopsis thaliana

<400> SEQUENCE: 53

```
atggctgcaa cagtgctcgg ccatttcagt ccaattacat cgtccctaaa accaccgtca      60
cgccaccggc gattcctaca ccacaatttg tcccccaaaa caccccttca atcttctctt     120
atcaaattcg gcgccgaaaa ctccgaacct caacctccac ggccgttgcc ggaaactgat     180
tgtcccgttc cgccggagca gcagccaatc aacgagtatc aatctctctc cacctctttc     240
cctttctcct gggcttcagg agatctaatc gagtactcta ccagacttt t cttaaccggc     300
gcttctttcg catttttcgt cgggttaccc gtttcctggt tcggatccat cggacccgaa     360
tatgaacctg ttaagaggat tctcgccgcc agctctagcg ggatcttcgt tgtcacgctt     420
gctgtcgtaa ggatgtatct tggttgggct tatgtcgatg aagaaactgg ttggtacgat     480
ggtcaggtat gggtgaaaac accagaagtc ttggcacgag accgtcttct tggatctttc     540
tcggtaaagc cagttcttgc gagactgaaa aacacgctag ttattctcgg attatcgctc     600
attcttgtta taaaccttgg tgattctcca attgcaacgt cttatagaac atacagggat     660
cctagggaca gatcctcgct gccaatccca ggagcgtaca atgatgaaac cgcaagaact     720
ttcgaaccag aagctttctg cggtgaacca tcttccgatc ttctttga                  768
```

<210> SEQ ID NO 54
<211> LENGTH: 255
<212> TYPE: PRT
<213> ORGANISM: Arabidopsis thaliana

<400> SEQUENCE: 54

```
Met Ala Ala Thr Val Leu Gly His Phe Ser Pro Ile Thr Ser Ser Leu
1               5                   10                  15

Lys Pro Pro Ser Arg His Arg Arg Phe Leu His His Asn Leu Ser Pro
            20                  25                  30
```

```
Lys Thr Pro Leu Gln Ser Ser Leu Ile Lys Phe Gly Ala Glu Asn Ser
                 35                  40                  45

Glu Pro Gln Pro Pro Arg Pro Leu Pro Glu Thr Asp Cys Pro Val Pro
 50                  55                  60

Pro Glu Gln Gln Pro Ile Asn Glu Tyr Gln Ser Leu Ser Thr Ser Phe
 65                  70                  75                  80

Pro Phe Ser Trp Ala Ser Gly Asp Leu Ile Glu Tyr Ser Thr Arg Leu
                 85                  90                  95

Phe Leu Thr Gly Ala Ser Phe Ala Phe Phe Val Gly Leu Pro Val Ser
                100                 105                 110

Trp Phe Gly Ser Ile Gly Pro Glu Tyr Glu Pro Val Lys Arg Ile Leu
                115                 120                 125

Ala Ala Ser Ser Ser Gly Ile Phe Val Val Thr Leu Ala Val Val Arg
                130                 135                 140

Met Tyr Leu Gly Trp Ala Tyr Val Asp Glu Glu Thr Gly Trp Tyr Asp
145                 150                 155                 160

Gly Gln Val Trp Val Lys Thr Pro Glu Val Leu Ala Arg Asp Arg Leu
                165                 170                 175

Leu Gly Ser Phe Ser Val Lys Pro Val Leu Ala Arg Leu Lys Asn Thr
                180                 185                 190

Leu Val Ile Leu Gly Leu Ser Leu Ile Leu Val Ile Asn Leu Gly Asp
                195                 200                 205

Ser Pro Ile Ala Thr Ser Tyr Arg Thr Tyr Arg Asp Pro Arg Asp Arg
                210                 215                 220

Ser Ser Leu Pro Ile Pro Gly Ala Tyr Asn Asp Glu Thr Ala Arg Thr
225                 230                 235                 240

Phe Glu Pro Glu Ala Phe Cys Gly Glu Pro Ser Ser Asp Leu Leu
                245                 250                 255

<210> SEQ ID NO 55
<211> LENGTH: 2977
<212> TYPE: DNA
<213> ORGANISM: Arabidopsis thaliana

<400> SEQUENCE: 55
agagagagaa agaaatagag agagagatca gttcgtcgtt gacgatcgat gtcgaagatg      60
aagcatcttc tacggaagct ccacatcggc ggaagtagtg gcgtcggcgg cggatttgct     120
gaccatcaca ggttagacga ctcgactaga cctatgatcg atcctagccc tattcttagt     180
actagcccta gccctgcatc gacttcttcc gtctcttcct ctggttttgg taacgcttcc     240
acgacaatgc cgagactgga tacatttgag cctgttggcc gtgatctgac ggctgttgat     300
ggtgttgatt tcaatttgat ggaggaggag taccaagtcc agttagctat ggcgatcagc     360
gtctctgatc ctgatccgag agagaatgca gatacagctc agcttgatgc cgctaagagg     420
attagccttg gggtttctgc tccggtcacc gacgctgatt ccgccgttga ctttctctcg     480
cttcgttatt ggggacataa ggtcattaat tatgaccaga agtcaggga tggattttac     540 gatgtgtatg ggattacatc taattctctt tcacagggga gatgccact tcttgttgat     600 cttcaagcga tctctatttc agataatgtt gattatgagg tcattctagt taacagattg     660
attgatcctg aactacaaga gctagagagg agagtattcg ctttggcttc ggaatgtcca     720
gactttgctc ctggtcaggt gtcaagtgat ttgactcaga aaattgcaaa tatagttgta     780
gagcaaatgg gtggccccgt tgaaaatgct gatgaagcat tgagaaggtg gatgcttcgg     840
agctatgaac taagaaaattc tttgaacact actattcttc cacttggtcg agttaatgtt     900
```

```
ggtcttgcac gacacagggc tttgcttttc aaggtccttg ctgataggat taatctccca    960
tgtatgctgg taaaaggcag ttactacact ggaactgatg atgggctgt gaacttgatt    1020
aaactagatg acaaaagtga atacattatt gatttaatgg gtgctccggg tgctctgatc   1080
ccttctgagg ttccaagcag ttttcttcca gtttcttgca cagatacaag agtatttcct   1140
gagaatttgg actctttgca acattcatcc cccgtacttg agaaagaaat tgaaacgcca   1200
gcattttcag tttcgaagga agcagattct agatctggta tggtagcaaa cttcttcact   1260
ggaaaccagg aagaaaacag tgacagatgt gctgttgaaa acatcaaac agagagattt    1320
gagcatgatt ttgggaagtt aatgcactca cagcagatat ctggtgaaaa tatgccacca   1380
ttttctggga aaccgacttg tgcacagaaa gttaaagtta aaatgtctc aaagtatgtc    1440
ataagtgcag caaagaaccc tgaatttgcg cagaaattac atgctgtgtt gttagaaagt   1500
ggtgcatcac ctcccccaga tttgtttatg gatattaacc cacataactt gaggggaag    1560
aatttgcttc aagagctccg ccaagaaagt agcaattcta tggtttctgg tattccatgc   1620
tacccagaaa aggtagctga acaactgaga gaatctgaaa ggaaccccac agccgagagt   1680
taccaacaat cagtggaggt cgatttgtca atgaagagga actttgattt ggataatact   1740
ggtaaagctt cttcatccga aaatatggag gttggcactg ctgatgggga gtctgctgtt   1800
tgtgatagtc atgaccaagg gattaatcca ttgctcggag aagctgcaaa gtgggaaatt   1860
atgtgggaag atcttcagat tggcgagcgc attggtattg gttcatatgg agaagtttat   1920
cgtgcagagt ggaatggaac tgaagtggct gttaagaagt tctggacca agatttctct   1980
ggtgatgcat tgacacagtt caaatctgaa attgaaataa tgttgaggtt acggcatcca   2040
aacgttgttc ttttcatggg agcagttact cgtcccccaa atttctccat cctgacagag   2100
ttcctaccca ggggaagttt gtatagatta ctccatcggc cgaaccatca gcttgatgag   2160
aagaggagaa tgcggatggc tcttgatgtg caaagggaa tgaactactt acacaccagc    2220
cacccgactg ttgtacatag ggatttaaaa tctccaaacc ttcttgttga taaaaattgg   2280
gttgtgaagg tttgtgattt tggattgtcc cgcatgaaac accacacata tttgtcctcg   2340
aaatcaactg caggaacgcc tgagtggatg gctccagaag tgttgaggaa tgaaccggct   2400
aatgagaaat gtgacgtgta cagctttggt gtcatattgt gggaattagc tacttcacgc   2460
gtcccctgga aaggtttgaa cccgatgcaa gtcgttggag ctgtgggatt ccagaatcga   2520
cgccttgaaa tcccagatga tatcgatcta actgtggcac agataatccg tgaatgttgg   2580
caaacggaac cgcatttacg gccatcgttt acacagctga tgcaaagttt gaagcggctt   2640
cagggtctaa acataagcaa cagagcgaat acgagtgaaa gtttgatgta agatacgtta   2700
gacagaagat gttgccttac ctggtctggt tcaaagagcc aacgggtggg gattgccatt   2760
cttctttgct tttttttgtt cttttgtta ttacggtcag acgagaggag acaaacaaaa    2820
aaagattgat gggttgggga aaagcttgtg gagttcaatc gaagtgggag ctcaacaaga   2880
aaagaaaaag ccctattctt aacccttgt aactattatt attatcatca ttgttgttgc    2940
tacttgtaac gataaaatta ggtgaatgaa caaaaaa                            2977
```

<210> SEQ ID NO 56  
<211> LENGTH: 880  
<212> TYPE: PRT  
<213> ORGANISM: Arabidopsis thaliana

<400> SEQUENCE: 56

Met Ser Lys Met Lys His Leu Leu Arg Lys Leu His Ile Gly Gly Ser

```
              1               5                  10                 15
Ser Gly Val Gly Gly Phe Ala Asp His His Arg Leu Asp Asp Ser
                20                 25                 30

Thr Arg Pro Met Ile Asp Pro Ser Pro Ile Leu Ser Thr Ser Pro Ser
            35                 40                 45

Pro Ala Ser Thr Ser Val Ser Ser Ser Gly Phe Gly Asn Ala Ser
        50                 55                 60

Thr Thr Met Pro Arg Leu Asp Thr Phe Glu Pro Val Gly Arg Asp Leu
65                  70                 75                     80

Thr Ala Val Asp Gly Val Asp Phe Asn Leu Met Glu Glu Tyr Gln
                85                 90                 95

Val Gln Leu Ala Met Ala Ile Ser Val Ser Asp Pro Asp Pro Arg Glu
            100                105                110

Asn Ala Asp Thr Ala Gln Leu Asp Ala Ala Lys Arg Ile Ser Leu Gly
            115                120                125

Val Ser Ala Pro Val Thr Asp Ala Asp Ser Ala Val Asp Phe Leu Ser
        130                135                140

Leu Arg Tyr Trp Gly His Lys Val Ile Asn Tyr Asp Gln Lys Val Arg
145                 150                155                    160

Asp Gly Phe Tyr Asp Val Tyr Gly Ile Thr Ser Asn Ser Leu Ser Gln
                165                170                175

Gly Lys Met Pro Leu Leu Val Asp Leu Gln Ala Ile Ser Ile Ser Asp
            180                185                190

Asn Val Asp Tyr Glu Val Ile Leu Val Asn Arg Leu Ile Asp Pro Glu
        195                200                205

Leu Gln Glu Leu Glu Arg Arg Val Phe Ala Leu Ala Ser Glu Cys Pro
210                215                220

Asp Phe Ala Pro Gly Gln Val Ser Ser Asp Leu Thr Gln Lys Ile Ala
225                 230                235                    240

Asn Ile Val Val Glu Gln Met Gly Gly Pro Val Glu Asn Ala Asp Glu
                245                250                255

Ala Leu Arg Arg Trp Met Leu Arg Ser Tyr Glu Leu Arg Asn Ser Leu
            260                265                270

Asn Thr Thr Ile Leu Pro Leu Gly Arg Val Asn Val Gly Leu Ala Arg
        275                280                285

His Arg Ala Leu Leu Phe Lys Val Leu Ala Asp Arg Ile Asn Leu Pro
            290                295                300

Cys Met Leu Val Lys Gly Ser Tyr Tyr Thr Gly Thr Asp Asp Gly Ala
305                 310                315                    320

Val Asn Leu Ile Lys Leu Asp Asp Lys Ser Glu Tyr Ile Ile Asp Leu
                325                330                335

Met Gly Ala Pro Gly Ala Leu Ile Pro Ser Glu Val Pro Ser Ser Phe
            340                345                350

Leu Pro Val Ser Cys Thr Asp Thr Arg Val Phe Pro Glu Asn Leu Asp
        355                360                365

Ser Leu Gln His Ser Ser Pro Val Leu Glu Lys Glu Ile Glu Thr Pro
    370                375                380

Ala Phe Ser Val Ser Lys Glu Ala Asp Ser Arg Ser Gly Met Val Ala
385                 390                395                    400

Asn Phe Phe Thr Gly Asn Gln Glu Glu Asn Ser Asp Arg Cys Ala Val
                405                410                415

Glu Lys His Gln Thr Glu Arg Phe Glu His Asp Phe Gly Lys Leu Met
            420                425                430
```

-continued

His Ser Gln Gln Ile Ser Gly Glu Asn Met Pro Pro Phe Ser Gly Lys
            435                 440                 445

Pro Thr Cys Ala Gln Lys Val Lys Val Lys Asn Val Ser Lys Tyr Val
450                 455                 460

Ile Ser Ala Ala Lys Asn Pro Glu Phe Ala Gln Lys Leu His Ala Val
465                 470                 475                 480

Leu Leu Glu Ser Gly Ala Ser Pro Pro Asp Leu Phe Met Asp Ile
                485                 490                 495

Asn Pro His Asn Leu Arg Gly Lys Asn Leu Leu Gln Glu Leu Arg Gln
            500                 505                 510

Glu Ser Ser Asn Ser Met Val Ser Gly Ile Pro Cys Tyr Pro Glu Lys
            515                 520                 525

Val Ala Glu Gln Leu Arg Glu Ser Glu Arg Asn Pro Thr Ala Glu Ser
530                 535                 540

Tyr Gln Gln Ser Val Glu Val Asp Leu Ser Met Lys Arg Asn Phe Asp
545                 550                 555                 560

Leu Asp Asn Thr Gly Lys Ala Ser Ser Glu Asn Met Glu Val Gly
                565                 570                 575

Thr Ala Asp Gly Glu Ser Ala Val Cys Asp Ser His Asp Gln Gly Ile
            580                 585                 590

Asn Pro Leu Leu Gly Glu Ala Ala Lys Trp Glu Ile Met Trp Glu Asp
            595                 600                 605

Leu Gln Ile Gly Glu Arg Ile Gly Ile Gly Ser Tyr Gly Glu Val Tyr
610                 615                 620

Arg Ala Glu Trp Asn Gly Thr Glu Val Ala Val Lys Lys Phe Leu Asp
625                 630                 635                 640

Gln Asp Phe Ser Gly Asp Ala Leu Thr Gln Phe Lys Ser Glu Ile Glu
                645                 650                 655

Ile Met Leu Arg Leu Arg His Pro Asn Val Val Leu Phe Met Gly Ala
            660                 665                 670

Val Thr Arg Pro Pro Asn Phe Ser Ile Leu Thr Glu Phe Leu Pro Arg
            675                 680                 685

Gly Ser Leu Tyr Arg Leu Leu His Arg Pro Asn His Gln Leu Asp Glu
690                 695                 700

Lys Arg Arg Met Arg Met Ala Leu Asp Val Ala Lys Gly Met Asn Tyr
705                 710                 715                 720

Leu His Thr Ser His Pro Thr Val Val His Arg Asp Leu Lys Ser Pro
                725                 730                 735

Asn Leu Leu Val Asp Lys Asn Trp Val Lys Val Cys Asp Phe Gly
            740                 745                 750

Leu Ser Arg Met Lys His His Thr Tyr Leu Ser Ser Lys Ser Thr Ala
            755                 760                 765

Gly Thr Pro Glu Trp Met Ala Pro Glu Val Leu Arg Asn Glu Pro Ala
770                 775                 780

Asn Glu Lys Cys Asp Val Tyr Ser Phe Gly Val Ile Leu Trp Glu Leu
785                 790                 795                 800

Ala Thr Ser Arg Val Pro Trp Lys Gly Leu Asn Pro Met Gln Val Val
                805                 810                 815

Gly Ala Val Gly Phe Gln Asn Arg Arg Leu Glu Ile Pro Asp Asp Ile
            820                 825                 830

Asp Leu Thr Val Ala Gln Ile Ile Arg Glu Cys Trp Gln Thr Glu Pro
            835                 840                 845

His Leu Arg Pro Ser Phe Thr Gln Leu Met Gln Ser Leu Lys Arg Leu
850                 855                 860

```
Gln Gly Leu Asn Ile Ser Asn Arg Ala Asn Thr Ser Glu Ser Leu Met
865                 870                 875                 880

<210> SEQ ID NO 57
<211> LENGTH: 1314
<212> TYPE: DNA
<213> ORGANISM: Arabidopsis thaliana

<400> SEQUENCE: 57
tttatttcga agagagagag agaagaagac ggaagctaga agaaatcgtt tttgatcgga      60
gatagtgtat gagctagttg tttgtaattt gacggctctc gggaactgat ctatctccgg     120
tgtctctgct ttgtcggtag ctacaggagt gaagagagtt tctacaaggg ttttaatgga     180
agatgatgac tctccttctt ctcgggattt ggatgcacag aacccttatg atcgattgct     240
tgctctagat acaagtaccg tagatccaaa ttgtaacttg gattcggttt ctgccattta     300
tctagcgatg aagagctcta agctggaatg tgttgacgag cgtggtcaag attcccttat     360
tacttcggta tgcatggagg atgaagagga tgaggagctc gatgagtttg atccttatct     420
gtttatcaag aacttgccga acctgtcttc tgttgtccca actttcaggc cggtcttgct     480
tcctaaacaa acccgaagct gtcctcctat ttctcttgtc ctagaccttg atgaaactct     540
tgtgcactcg actctagagc cgtgtggtga ggtagatttc acattcccag tgaattttaa     600
tgaagaagag catatggtgt atgtgcgatg ccgtcctcac ctcaaagagt ttatggagag     660
agtgtcccga ctttttgaga tcattatatt tacagctagc caaagtattt atgctgagca     720
acttctgaac gtgcttgacc ctaagagaaa gctctttcgc catagagtgt accgtgactc     780
gtgtgttttc tttgatggta actacctcaa ggatttgtca gtcctcgggc gtgatttatc     840
tcgtgttatc attgttgata actccccaca ggcatttggt ttccaagtgg aaaatggagt     900
gccaatagag agctggttta tgacccatc agataaagaa ctccttcact tgctgccatt     960
tcttgaaagc ctaattggag ttgaagatgt aaggccaatg atcgccaaga aattcaatct    1020
aagggagaag attgatgcag ctgtagccgc acctgaatat cctgctgagg cgggagatcc    1080
tttcgaaagg taaagtctat cgccaaaaca cttttaaagg aagaatctgg cacaagagca    1140
gaggttggag aagatatata agtatatcaa tgttgttttc ttattagttt aaattaagaa    1200
cttggtatac agagaaagac aggatatgcc tgtaaaaaca gtttaaggca caataactgt    1260
ataattgttt tctcgtttat ttactagtac acatagatta acatttcaag tttc          1314

<210> SEQ ID NO 58
<211> LENGTH: 305
<212> TYPE: PRT
<213> ORGANISM: Arabidopsis thaliana

<400> SEQUENCE: 58

Met Glu Asp Asp Ser Pro Ser Ser Arg Asp Leu Asp Ala Gln Asn
1               5                   10                  15

Pro Tyr Asp Arg Leu Leu Ala Leu Asp Thr Ser Thr Val Asp Pro Asn
                20                  25                  30

Cys Asn Leu Asp Ser Val Ser Ala Ile Tyr Leu Ala Met Lys Ser Ser
            35                  40                  45

Lys Leu Glu Cys Val Asp Glu Arg Gly Gln Asp Ser Leu Ile Thr Ser
        50                  55                  60

Val Cys Met Glu Asp Glu Glu Asp Glu Glu Leu Asp Glu Phe Asp Pro
65                  70                  75                  80

Tyr Leu Phe Ile Lys Asn Leu Pro Asn Leu Ser Ser Val Val Pro Thr
```

```
                    85                  90                  95
Phe Arg Pro Val Leu Leu Pro Lys Gln Thr Arg Ser Cys Pro Pro Ile
                100                 105                 110

Ser Leu Val Leu Asp Leu Asp Glu Thr Leu Val His Ser Thr Leu Glu
            115                 120                 125

Pro Cys Gly Glu Val Asp Phe Thr Phe Pro Val Asn Phe Asn Glu Glu
        130                 135                 140

Glu His Met Val Tyr Val Arg Cys Arg Pro His Leu Lys Glu Phe Met
145                 150                 155                 160

Glu Arg Val Ser Arg Leu Phe Glu Ile Ile Phe Thr Ala Ser Gln
                165                 170                 175

Ser Ile Tyr Ala Glu Gln Leu Leu Asn Val Leu Asp Pro Lys Arg Lys
            180                 185                 190

Leu Phe Arg His Arg Val Tyr Arg Asp Ser Cys Val Phe Asp Gly
                195                 200                 205

Asn Tyr Leu Lys Asp Leu Ser Val Leu Gly Arg Asp Leu Ser Arg Val
        210                 215                 220

Ile Ile Val Asp Asn Ser Pro Gln Ala Phe Gly Phe Gln Val Glu Asn
225                 230                 235                 240

Gly Val Pro Ile Glu Ser Trp Phe Asn Asp Pro Ser Asp Lys Glu Leu
                245                 250                 255

Leu His Leu Leu Pro Phe Leu Glu Ser Leu Ile Gly Val Glu Asp Val
            260                 265                 270

Arg Pro Met Ile Ala Lys Lys Phe Asn Leu Arg Glu Lys Ile Asp Ala
                275                 280                 285

Ala Val Ala Ala Pro Glu Tyr Pro Ala Glu Ala Gly Asp Pro Phe Glu
            290                 295                 300
Arg
305

<210> SEQ ID NO 59
<211> LENGTH: 1420
<212> TYPE: DNA
<213> ORGANISM: Arabidopsis thaliana

<400> SEQUENCE: 59
gagagaagaa gacggaagct agaagaaatc gttttttgatc ggaggtactt ttttccgacg    60
aatatactct ctctagggtt ttctttttc tctctctccc tctccgtttc ttcttcttag    120
ctcttcaatc tcagctcgaa tttctgggct actgaagttt aatctagata gtgtatgagc    180
tagttgtttg taatttgacg gctctcggga actgatctat ctccggtgtc tctgctttgt    240
cggtagctac aggagtgaag agagtttcta caagggtttt aatggaagat gatgactctc    300
cttcttctcg ggatttggat gcacagaacc cttatgatcg attgcttgct ctagatacaa    360
gtaccgtaga tccaaattgt aacttggatt cggtttctgc catttatcta gcgatgaaga    420
gctctaagct ggaatgtgtt gacgagcgtg gtcaagattc ccttattact cggtatgca    480 tggaggatga agaggatgag gagctcgatg agtttgatcc ttatctgttt atcaagaact    540
tgccgaacct gtcttctgtt gtcccaactt tcaggccggt cttgcttcct aaacaaaccc    600
gaagctgtcc tctatttct cttgtcctag accttgatga aactcttgtg cactcgactc    660
tagagccgtg tggtgaggta gatttcacat tcccagtgaa ttttaatgaa gaagagcata    720
tggtgtatgt gcgatgccgt cctcacctca aagagtttat ggagagagtg tcccgacttt    780
ttgagatcat tatatttaca gctagccaaa gtatttatgc tgagcaactt ctgaacgtgc    840
```

```
ttgaccctaa gagaaagctc tttcgccata gagtgtaccg tgactcgtgt gttttctttg    900
atggtaacta cctcaaggat tgtcagtcc tcgggcgtga tttatctcgt gttatcattg    960
ttgataactc cccacaggca tttggtttcc aagtggaaaa tggagtgcca atagagagct   1020
ggtttaatga cccatcagat aaagaactcc ttcacttgct gccatttctt gaaagcctaa   1080
ttggagttga agatgtaagg ccaatgatcg ccaagaaatt caatctaagg gagaagattg   1140
atgcagctgt agccgcacct gaatatcctg ctgaggcggg agatcctttc gaaaggtaaa   1200
gtctatcgcc aaaacacttt taaggaaga atctggcaca agagcagagg ttggagaaga    1260
tatataagta tatcaatgtt gttttcttat tagtttaaat taagaacttg gtatacagag   1320
aaagacagga tatgcctgta aaaacagttt aaggcacaat aactgtataa ttgttttctc   1380
gtttatttac tagtacacat agattaacat ttcaagtttc                         1420
```

```
<210> SEQ ID NO 60
<211> LENGTH: 305
<212> TYPE: PRT
<213> ORGANISM: Arabidopsis thaliana

<400> SEQUENCE: 60

Met Glu Asp Asp Asp Ser Pro Ser Ser Arg Asp Leu Asp Ala Gln Asn
1               5                   10                  15

Pro Tyr Asp Arg Leu Leu Ala Leu Asp Thr Ser Thr Val Asp Pro Asn
            20                  25                  30

Cys Asn Leu Asp Ser Val Ser Ala Ile Tyr Leu Ala Met Lys Ser Ser
        35                  40                  45

Lys Leu Glu Cys Val Asp Glu Arg Gly Gln Asp Ser Leu Ile Thr Ser
    50                  55                  60

Val Cys Met Glu Asp Glu Glu Asp Glu Leu Asp Glu Phe Asp Pro
65                  70                  75                  80

Tyr Leu Phe Ile Lys Asn Leu Pro Asn Leu Ser Ser Val Val Pro Thr
                85                  90                  95

Phe Arg Pro Val Leu Leu Pro Lys Gln Thr Arg Ser Cys Pro Pro Ile
            100                 105                 110

Ser Leu Val Leu Asp Leu Asp Glu Thr Leu Val His Ser Thr Leu Glu
        115                 120                 125

Pro Cys Gly Glu Val Asp Phe Thr Phe Pro Val Asn Phe Asn Glu Glu
    130                 135                 140

Glu His Met Val Tyr Val Arg Cys Arg Pro His Leu Lys Glu Phe Met
145                 150                 155                 160

Glu Arg Val Ser Arg Leu Phe Glu Ile Ile Ile Phe Thr Ala Ser Gln
                165                 170                 175

Ser Ile Tyr Ala Glu Gln Leu Leu Asn Val Leu Asp Pro Lys Arg Lys
            180                 185                 190

Leu Phe Arg His Arg Val Tyr Arg Asp Ser Cys Val Phe Phe Asp Gly
        195                 200                 205

Asn Tyr Leu Lys Asp Leu Ser Val Leu Gly Arg Asp Leu Ser Arg Val
    210                 215                 220

Ile Ile Val Asp Asn Ser Pro Gln Ala Phe Gly Phe Gln Val Glu Asn
225                 230                 235                 240

Gly Val Pro Ile Glu Ser Trp Phe Asn Asp Pro Ser Asp Lys Glu Leu
                245                 250                 255

Leu His Leu Leu Pro Phe Leu Glu Ser Leu Ile Gly Val Glu Asp Val
            260                 265                 270

Arg Pro Met Ile Ala Lys Lys Phe Asn Leu Arg Glu Lys Ile Asp Ala
```

```
                275                 280                 285
Ala Val Ala Ala Pro Glu Tyr Pro Ala Glu Ala Gly Asp Pro Phe Glu
            290                 295                 300

Arg
305

<210> SEQ ID NO 61
<211> LENGTH: 1429
<212> TYPE: DNA
<213> ORGANISM: Arabidopsis thaliana

<400> SEQUENCE: 61
attgatttct gtcactttcc gcgatgaaaa gttttcgaat tttgcttctt ttggctccaa      60
agtttttatc tttcaaatat tttaaatctg ggtacttttt tgttttggtt ccttctttgt     120
gaattgtatc tagggctttg ctccttttct aatccaagat ctgttttcgt tctcagatag     180
tgtatgagct agttgtttgt aatttgacgg ctctcgggaa ctgatctatc tccggtgtct     240
ctgctttgtc ggtagctaca ggagtgaaga gagtttctac aagggtttta atggaagatg     300
atgactctcc ttcttctcgg gatttggatg cacagaaccc ttatgatcga ttgcttgctc     360
tagatacaag taccgtagat ccaaattgta acttggattc ggtttctgcc atttatctag     420
cgatgaagag ctctaagctg aatgtgttg acgagcgtgg tcaagattcc cttattactt      480
cggtatgcat ggaggatgaa gaggatgagg agctcgatga gtttgatcct tatctgttta     540
tcaagaactt gccgaacctg tcttctgttg tcccaacttt caggccggtc ttgcttccta     600
aacaaacccg aagctgtcct cctatttctc ttgtcctaga ccttgatgaa actcttgtgc     660
actcgactct agagccgtgt ggtgaggtag atttcacatt cccagtgaat tttaatgaag     720
aagagcatat ggtgtatgtg cgatgccgtc ctcacctcaa agagtttatg agagagtgt      780 cccgactttt tgagatcatt atatttacag ctagccaaag tatttatgct gagcaacttc     840
tgaacgtgct tgaccctaag agaaagctct ttcgccatag agtgtaccgt gactcgtgtg     900
ttttctttga tggtaactac ctcaaggatt tgtcagtcct cgggcgtgat ttatctcgtg     960
ttatcattgt tgataactcc ccacaggcat tggtttcca gtggaaaat ggagtgccaa      1020 tagagagctg gtttaatgac ccatcagata agaactcct tcacttgctg ccatttcttg     1080
aaagcctaat tggagttgaa gatgtaaggc aatgatcgc caagaaattc aatctaaggg     1140
agaagattga tgcagctgta gccgcacctg aatatcctgc tgaggcggga gatcctttcg     1200
aaaggtaaag tctatcgcca aaacacttt aaaggaagaa tctggcacaa gagcagaggt     1260
tggagaagat atataagtat atcaatgttg ttttcttatt agtttaaatt aagaacttgg     1320
tatacagaga aagacaggat atgcctgtaa aaacagttta aggcacaata actgtataat     1380 tgtttttctcg tttatttact agtacacata gattaacatt tcaagtttc                1429

<210> SEQ ID NO 62
<211> LENGTH: 305
<212> TYPE: PRT
<213> ORGANISM: Arabidopsis thaliana

<400> SEQUENCE: 62

Met Glu Asp Asp Asp Ser Pro Ser Ser Arg Asp Leu Asp Ala Gln Asn
1               5                   10                  15

Pro Tyr Asp Arg Leu Leu Ala Leu Asp Thr Ser Thr Val Asp Pro Asn
            20                  25                  30

Cys Asn Leu Asp Ser Val Ser Ala Ile Tyr Leu Ala Met Lys Ser Ser
        35                  40                  45
```

```
Lys Leu Glu Cys Val Asp Glu Arg Gly Gln Asp Ser Leu Ile Thr Ser
 50                  55                  60

Val Cys Met Glu Asp Glu Asp Glu Glu Leu Asp Glu Phe Asp Pro
 65                  70                  75                  80

Tyr Leu Phe Ile Lys Asn Leu Pro Asn Leu Ser Ser Val Val Pro Thr
                 85                  90                  95

Phe Arg Pro Val Leu Leu Pro Lys Gln Thr Arg Ser Cys Pro Pro Ile
                100                 105                 110

Ser Leu Val Leu Asp Leu Asp Glu Thr Leu Val His Ser Thr Leu Glu
                115                 120                 125

Pro Cys Gly Glu Val Asp Phe Thr Phe Pro Val Asn Phe Asn Glu Glu
            130                 135                 140

Glu His Met Val Tyr Val Arg Cys Arg Pro His Leu Lys Glu Phe Met
145                 150                 155                 160

Glu Arg Val Ser Arg Leu Phe Glu Ile Ile Phe Thr Ala Ser Gln
                165                 170                 175

Ser Ile Tyr Ala Glu Gln Leu Leu Asn Val Leu Asp Pro Lys Arg Lys
            180                 185                 190

Leu Phe Arg His Arg Val Tyr Arg Asp Ser Cys Val Phe Phe Asp Gly
                195                 200                 205

Asn Tyr Leu Lys Asp Leu Ser Val Leu Gly Arg Asp Leu Ser Arg Val
210                 215                 220

Ile Ile Val Asp Asn Ser Pro Gln Ala Phe Gly Phe Gln Val Glu Asn
225                 230                 235                 240

Gly Val Pro Ile Glu Ser Trp Phe Asn Asp Pro Ser Asp Lys Glu Leu
                245                 250                 255

Leu His Leu Leu Pro Phe Leu Glu Ser Leu Ile Gly Val Glu Asp Val
            260                 265                 270

Arg Pro Met Ile Ala Lys Lys Phe Asn Leu Arg Glu Lys Ile Asp Ala
            275                 280                 285

Ala Val Ala Ala Pro Glu Tyr Pro Ala Glu Ala Gly Asp Pro Phe Glu
            290                 295                 300

Arg
305

<210> SEQ ID NO 63
<211> LENGTH: 907
<212> TYPE: DNA
<213> ORGANISM: Arabidopsis thaliana

<400> SEQUENCE: 63
cctttctttt cttaaactgg aagaagatta atcaatcaga cacaacagag ataactgatt      60
tatccacttc aaacaataca aacctttaaa gtcttcacct ttatagagag aacttttaat     120
ggtgtggttg acgaatcaac agatagggag atggaaaagg aaacgaattt tggttgtggg     180
atcgttcctc tgttggtcaa tcatcatgtt catcactccc aaagttcctc tcgattcatt     240
tcgccatcat atcttcgccg ataaacgcaa tttcatggga gtgcctaata cattgaatgt     300
gatgaccaac tttcccttc ttatcgttgg agttcttggt tttgttcttt gcattggagg     360
aagcttcttc aacataagtt taaatggtga gatctgggga tggacactgt tctacgcagg     420
cattgcaagc ttggcttttg ttctgctttt ttatcatctc aaacctgatg acaacagaat     480
cgtctgggac actttgccta tattgattgc gtattcgtcg cttttctcta gttttttggt     540
tgagagagcg ggggagaaag tgggactag ttgcctcatc ttgcttctat ttatatcatg     600
```

```
tctcagtgtt gcttacgcca gagtgtttaa tgatctccgg ttatgcatga cgttccagtt    660
gataccgtgt ctggtgattc ccgtcatggc ggttttgtta cctcccaaat atacacactc    720
tagattctgg ctctgggcaa cagcggcgta cactattgcc aagattgaag gacttgcaga    780
caacaaaata tacaatgcaa atcgatatat catcagtggg cattcactgg agcatttgtg    840
ttctgccgtg gctacgcttt tacttaccat tatgcttttg tatagaagca ttcggtttaa    900
taggtaa                                                             907
```

<210> SEQ ID NO 64
<211> LENGTH: 262
<212> TYPE: PRT
<213> ORGANISM: Arabidopsis thaliana

<400> SEQUENCE: 64

```
Met Val Trp Leu Thr Asn Gln Gln Ile Gly Arg Trp Lys Arg Lys Arg
1               5                   10                  15

Ile Leu Val Val Gly Ser Phe Leu Cys Trp Ser Ile Ile Met Phe Ile
            20                  25                  30

Thr Pro Lys Val Pro Leu Asp Ser Phe Arg His His Ile Phe Ala Asp
        35                  40                  45

Lys Arg Asn Phe Met Gly Val Pro Asn Thr Leu Asn Val Met Thr Asn
    50                  55                  60

Phe Pro Phe Leu Ile Val Gly Val Leu Gly Phe Val Leu Cys Ile Gly
65                  70                  75                  80

Gly Ser Phe Phe Asn Ile Ser Leu Asn Gly Glu Ile Trp Gly Trp Thr
                85                  90                  95

Leu Phe Tyr Ala Gly Ile Ala Ser Leu Ala Phe Gly Ser Ala Phe Tyr
            100                 105                 110

His Leu Lys Pro Asp Asp Asn Arg Ile Val Trp Asp Thr Leu Pro Ile
        115                 120                 125

Leu Ile Ala Tyr Ser Ser Leu Phe Ser Ser Phe Leu Val Glu Arg Ala
    130                 135                 140

Gly Glu Lys Val Gly Leu Ser Cys Leu Ile Leu Leu Phe Ile Ser
145                 150                 155                 160

Cys Leu Ser Val Ala Tyr Ala Arg Val Phe Asn Asp Leu Arg Leu Cys
                165                 170                 175

Met Thr Phe Gln Leu Ile Pro Cys Leu Val Ile Pro Val Met Ala Val
            180                 185                 190

Leu Leu Pro Pro Lys Tyr Thr His Ser Arg Phe Trp Leu Trp Ala Thr
        195                 200                 205

Ala Ala Tyr Thr Ile Ala Lys Ile Glu Gly Leu Ala Asp Asn Lys Ile
    210                 215                 220

Tyr Asn Ala Asn Arg Tyr Ile Ile Ser Gly His Ser Leu Glu His Leu
225                 230                 235                 240

Cys Ser Ala Val Ala Thr Leu Leu Leu Thr Ile Met Leu Leu Tyr Arg
                245                 250                 255

Ser Ile Arg Phe Asn Arg
            260
```

<210> SEQ ID NO 65
<211> LENGTH: 1698
<212> TYPE: DNA
<213> ORGANISM: Arabidopsis thaliana

<400> SEQUENCE: 65

```
agtgttactg taacagtcgc acacctaaca aaaatcctcc agccatggcg gcagttactc    60
```

```
aatttctctc caaccttca tcaatccgcg gaaccctaaa tcagtaccaa ttgaatcaga    120
cttcactctc aagaatccca tttttgtctc tcaagtcaac attgaagcca cttaaacgcc    180
tctccgtcaa agccgccgtt tcccaaaact ccaccaaaac cctcacgaaa gaatctgctt    240
cctctttcga ccactgtttc aagaaatcat cagatgggtt tctctattgc gaaggaacca    300
aggttcaaga tcatggaa acagtcgaga acgacccttt tacttatat agcaaacctc      360 agatcacgag aaaccttgag gcttataaag aggctttgga aggagtgaga tctgttattg    420
gttacgctat taaagctaat aacaatctca agatttttgga gcatttgagg agtttgggct   480
gtggtgctgt gttggttagt ggaaatgagc tcaggcttgc tcttcttgct ggtttcgatc    540
ccacaaagtg tattttcaat ggaaatggaa agtctttgga agatttagtt ctagctgctc    600
aagaaggtgt tttcgtaaat gttgatagtg agtttgactt gaataacatt gtggaagctt    660
caagaatttc tggtaagcag gtcaatgtgt tgttgcgtat caatcctgat gttgatcctc    720
aggtgcatcc atatgtagct actgggaaca agaactcgaa gtttggtatt aggaacgaga    780
agcttcaatg gtttctggat gaagtgaagg cacatcccaa agagctgaag cttgttggag    840
ctcattgtca tcttggttct accattacaa aggtggatat attcagagat gctgcggttc    900
tcatgattga atacattgat gaaatccggc gtcaaggctt tgaggttagc tacttgaaca    960
ttggtggtgg tttagggata gattattatc atgccggcgc tgtccttcct acacccatgg   1020
atcttatcaa caccgtaaga gagctggttc tttcacgaga cctgaatcta ataatcgagc   1080
cagggagatc actgattgca aacacatgtt gtttcgtcaa ccatgtaact ggtgtgaaga   1140
cgaatggaac taaaaacttc atagtgattg atggaagtat ggctgagctt atccgtccca   1200
gtctttatga tgcctatcag catattgagt tggtctctcc tacaccgcct gaagcagagg   1260
ttaccaaatt cgatgtagtg ggtcctgttt gtgaatctgc tgatttcttg ggcaaagaca   1320
gagagcttcc cactcctcca cagggagctg gtctggtggt tcatgacgct ggtgcatact   1380
gtatgagtat ggcttccact acaatctca agatgcgtcc cccggaatac tgggttgaag   1440
aagatgggtc gatcactaag atcaggcatg ctgagacatt cgatgaccat ttacgtttct   1500
ttgaaggact atgaactccg agatttactc atcattgttg ctatttaga tgaattgtat    1560 gattacgttt ctataatgct attgctgtct tggatttttc cacattctgt gctatgattt   1620
aaagtcctca ataaagtgat catatgaata agaaacaggt cacaagtcaa gaccgaaaat   1680
aaaaggtgta tttgtgag                                                 1698
```

<210> SEQ ID NO 66
<211> LENGTH: 489
<212> TYPE: PRT
<213> ORGANISM: Arabidopsis thaliana

<400> SEQUENCE: 66

```
Met Ala Ala Val Thr Gln Phe Leu Ser Gln Pro Ser Ser Ile Arg Gly
1               5                   10                  15

Thr Leu Asn Gln Tyr Gln Leu Asn Gln Thr Ser Leu Ser Arg Ile Pro
            20                  25                  30

Phe Leu Ser Leu Lys Ser Thr Leu Lys Pro Leu Lys Arg Leu Ser Val
        35                  40                  45

Lys Ala Ala Val Ser Gln Asn Ser Thr Lys Thr Leu Thr Lys Glu Ser
    50                  55                  60

Ala Ser Ser Phe Asp His Cys Phe Lys Lys Ser Ser Asp Gly Phe Leu
65                  70                  75                  80
```

Tyr Cys Glu Gly Thr Lys Val Gln Asp Ile Met Glu Thr Val Glu Lys
                85                  90                  95

Arg Pro Phe Tyr Leu Tyr Ser Lys Pro Gln Ile Thr Arg Asn Leu Glu
            100                 105                 110

Ala Tyr Lys Glu Ala Leu Glu Gly Val Arg Ser Val Ile Gly Tyr Ala
        115                 120                 125

Ile Lys Ala Asn Asn Asn Leu Lys Ile Leu Glu His Leu Arg Ser Leu
    130                 135                 140

Gly Cys Gly Ala Val Leu Val Ser Gly Asn Glu Leu Arg Leu Ala Leu
145                 150                 155                 160

Leu Ala Gly Phe Asp Pro Thr Lys Cys Ile Phe Asn Gly Asn Gly Lys
                165                 170                 175

Ser Leu Glu Asp Leu Val Leu Ala Ala Gln Glu Gly Val Phe Val Asn
            180                 185                 190

Val Asp Ser Glu Phe Asp Leu Asn Asn Ile Val Glu Ala Ser Arg Ile
        195                 200                 205

Ser Gly Lys Gln Val Asn Val Leu Leu Arg Ile Asn Pro Asp Val Asp
    210                 215                 220

Pro Gln Val His Pro Tyr Val Ala Thr Gly Asn Lys Asn Ser Lys Phe
225                 230                 235                 240

Gly Ile Arg Asn Glu Lys Leu Gln Trp Phe Leu Asp Glu Val Lys Ala
                245                 250                 255

His Pro Lys Glu Leu Lys Leu Val Gly Ala His Cys His Leu Gly Ser
            260                 265                 270

Thr Ile Thr Lys Val Asp Ile Phe Arg Asp Ala Ala Val Leu Met Ile
        275                 280                 285

Glu Tyr Ile Asp Glu Ile Arg Arg Gln Gly Phe Glu Val Ser Tyr Leu
    290                 295                 300

Asn Ile Gly Gly Gly Leu Gly Ile Asp Tyr Tyr His Ala Gly Ala Val
305                 310                 315                 320

Leu Pro Thr Pro Met Asp Leu Ile Asn Thr Val Arg Glu Leu Val Leu
                325                 330                 335

Ser Arg Asp Leu Asn Leu Ile Ile Glu Pro Gly Arg Ser Leu Ile Ala
            340                 345                 350

Asn Thr Cys Cys Phe Val Asn His Val Thr Gly Val Lys Thr Asn Gly
        355                 360                 365

Thr Lys Asn Phe Ile Val Ile Asp Gly Ser Met Ala Glu Leu Ile Arg
    370                 375                 380

Pro Ser Leu Tyr Asp Ala Tyr Gln His Ile Glu Leu Val Ser Pro Thr
385                 390                 395                 400

Pro Pro Glu Ala Glu Val Thr Lys Phe Asp Val Val Gly Pro Val Cys
                405                 410                 415

Glu Ser Ala Asp Phe Leu Gly Lys Asp Arg Glu Leu Pro Thr Pro Pro
            420                 425                 430

Gln Gly Ala Gly Leu Val Val His Asp Ala Gly Ala Tyr Cys Met Ser
        435                 440                 445

Met Ala Ser Thr Tyr Asn Leu Lys Met Arg Pro Pro Glu Tyr Trp Val
    450                 455                 460

Glu Glu Asp Gly Ser Ile Thr Lys Ile Arg His Ala Glu Thr Phe Asp
465                 470                 475                 480

Asp His Leu Arg Phe Phe Glu Gly Leu
                485

<210> SEQ ID NO 67

```
<211> LENGTH: 243
<212> TYPE: DNA
<213> ORGANISM: Arabidopsis thaliana

<400> SEQUENCE: 67
atggcggcga tgaaatacaa aggaagcgtt tttatcatat tagtcatcct tcttctttcg      60
tcctcactac ttgctcactc ttcttctaca aaatccttct tttggttagg agaaacacaa     120
gatacgaaag ccatgaaaaa ggagaagaag attgatggag aacagctaa tgaagttgaa      180 gaaagacaag ttccaactgg atccgaccct cttcatcata acacattcc ttttactcca      240 tag                                                                   243

<210> SEQ ID NO 68
<211> LENGTH: 80
<212> TYPE: PRT
<213> ORGANISM: Arabidopsis thaliana

<400> SEQUENCE: 68

Met Ala Ala Met Lys Tyr Lys Gly Ser Val Phe Ile Ile Leu Val Ile
1               5                   10                  15

Leu Leu Leu Ser Ser Ser Leu Leu Ala His Ser Ser Thr Lys Ser
            20                  25                  30

Phe Phe Trp Leu Gly Glu Thr Gln Asp Thr Lys Ala Met Lys Lys Glu
        35                  40                  45

Lys Lys Ile Asp Gly Gly Thr Ala Asn Glu Val Glu Glu Arg Gln Val
    50                  55                  60

Pro Thr Gly Ser Asp Pro Leu His His Lys His Ile Pro Phe Thr Pro
65                  70                  75                  80

<210> SEQ ID NO 69
<211> LENGTH: 6194
<212> TYPE: DNA
<213> ORGANISM: Arabidopsis thaliana

<400> SEQUENCE: 69
ctttgcgtac ttagcagcta agtagcttaa aaagttgtgg ctcctttgct ccgccattgt      60 tagggttct ggatctccgt ttctctggag gctgaggaaa ccttaaaacg atttaaaacc     120
tggaggttat agggtagaca aaatgtctgc tacgagagga ggtcctgatc aagggccgtc     180
tcagcctcag cagcggcgga ttatacgaac tcagactgct ggtaatcttg gagagtcatt     240
cgatagtgaa gttgttccat catctcttgt tgagattgcc cccattcttc gggttgctaa     300
tgaagttgaa tctagtaatc ctagggttgc gtatctctgt cggttttatg catttgagaa     360
agcacataga ttggatccta cctccagtgg aagaggtgtt cggcagttta agactgcact     420
tctacagcgt cttgaaagag aacatgatcc aacactgatg ggcagggtta agaaaagtga     480
tgcccgtgaa atgcaaagct tttatcaaca ctactataag aagtatattc aagctttgca     540
caatgctgct gataaggctg accgtgccca gctgacaaag gcataccaaa ctgccaatgt     600
tttgtttgag gtgttgaagg ctgttaatct gacacagtcc attgaggttg accgggagat     660
tctggaagct caagataagg ttgcagaaaa gacacagttg tatgtcccct ataatatcct     720
acctctcgat cctgatagtg ccaatcaagc gattatgaga tatcctgaga tccaagctgc     780
tgttcttgct ctccgcaata ctagaggtct tccttggcca gaaggtcaca agaaaaagaa     840
agatgaagac atgcttgatt ggcttcaaga aatgtttgga tttcagaaag acaatgtggc     900
taatcaaagg gagcatctga tcttattact tgctaatgtg catataagac aatttcctaa     960
gcctgatcag cagccaaagt ttatcctttc gtttgttctc attgtgccct cacagttaga    1020
```

```
tgatcaagca ttgacagaag tgatgaagaa gcttttcaag aactataaga aatggtgcaa    1080
ataccttggt cgaaagagta gtctttggtt gccaactata cagcaggaaa tgcagcagcg    1140
caaactattg tatatggccc tgtatcttct aatttggggt gaagcagcga acttgagatt    1200
catgccagag tgtctctgct acatttatca tcatatggca tttgaactct atggtatgct    1260
ggctgggaat gttagtccta tgactgggga aaatgtgaag ccagcttatg gaggcgagga    1320
agatgcattc ttgaggaaag ttgtgactcc tatttatgaa gtgattcaga tggaggctca    1380
aagaagcaaa aaagggaagt ctaagcactc tcagtggagg aactacgatg atttgaatga    1440
atacttttgg tcagttgatt gttttcggtt aggttggcca atgcgagctg atgctgattt    1500
cttttgtctg cctgttgctg tacccaatac agaaaaggac ggggataaca gcaagcctat    1560
tgtcgccaga gatagatggg ttggtaaagt taattttgtt gagattcgtt ctttctggca    1620
tgtcttcaga agtttcgatc gaatgtggag cttctatatt ctgtgcctcc aggccatgat    1680
tattatggcc tgggatggcg gacaaccaag ttcagtcttt ggagctgatg tattcaagaa    1740
agttctgagc gtgtttatca cagctgcaat aatgaaactt ggacaagctg ttcttgatgt    1800
gatccttaat ttcaaagctc atcaaagcat gacactacat gttaaactaa gatacattct    1860
gaaagtgttc tctgctgctg cctgggttat tattctgcct gttacttacg cctacagctg    1920
gaaagatcct ccagcatttg ccagaactat caagagttgg tttgggagtg ctatgcactc    1980
accttctcta tttataatag cagtcgtttc ctatttgtca cctaacatgc tcgcggaaac    2040
taacgaaaac cttctgttgt gttgtttaac tgatgtgact ataattaaca ccttgcagcc    2100
cagactctac gttggcagag gaatgcacga gagcgcattt tccctcttca aatataccat    2160
gttctgggtg ttgcttattg caacaaagct ggcattcagt tactacattg agatcaggcc    2220
tttagttgcc ccaacacaag ccattatgaa ggcccgtgtg acaaattttc agtggcatga    2280
gttctttcct cgtgccaaaa acaatattgg tgtcgttatc gccctctggg cccccattat    2340
tctggtatat tttatggata gtcagatttg gtatgctata ttttccacat tatttggagg    2400
tatctacggt gcattccgcc gccttggaga gattcggaca ctgggaatgc tcagatcacg    2460
gtttgaatca ctgcctggag cttttaatga ccgcttaatt ccagatggaa agaaccagca    2520
aaagaagaag ggaataaggg caacgttatc tcataacttt acggaggata aggtacctgt    2580
gaacaaagag aaagaagctg caagatttgc acagttgtgg aacacaataa ttagtagttt    2640
tagagaggaa gatcttataa gtgataggga gatggatctg ttgcttgttc cttattgggc    2700
tgaccgtgat ttggatctca tacagtggcc tcccttctta ttggctagca agattccaat    2760
agcattagat atggcaaaag acagtaatgg aaggacagag agctcaagag agaggattga    2820
gagtgacact tacatgaaat gtgctgtccg tgaatgctat gcttcattca agaatatcat    2880
aaaatttgtg gttcagggaa accgtgaaaa agaggtgata gagatcatat ttgcagaggt    2940
tgacaaacat atagatacag gggatttgat tcaagaatac aagatgagtg ctcttcctag    3000
cctctatgat cactttgtca agttgatcaa atatttggta aatgttcttc ctgtgcttga    3060
caataaggag gaagatagag atcacgttgt aattctcttc caagacatgc tggaagttgt    3120
aacaagagac attatgatgg aggattacaa tatatcgagg ttggcgactt tctaccgcac    3180
cgcaatggct tgtcattcaa gtcatggtgg cacttggcat gggggaatga tccctctcga    3240
acaacaatat cagctgtttg catcctcagg tgccattaga tttcctattg aaccagtaac    3300
agaagcttgg aaagagaaga tcaaacggat atatcttttg ttgactacta agagtctgc    3360 tatggatgtc ccctctaact tggaagcaag aaggcggatc tcattcttct caaattcgtt    3420
```

```
gttcatggac atgcctatgg cacctaaagt tcgcaacatg ctatcatttt ctgttttgac   3480
tccttattac actgaagagg tcctcttctc cttgcgggac ctggaaacac caaatgaaga   3540
tggtgtttca atcctcttct acctacaaaa gattttttcca ggtgatttttt gttcatatgc  3600 tgttaacgta gcctatattc ttgaatcacg tcttgaacct gacctttttat ctccagatga  3660 atggaacaat tttcttgagc gggtgaagtg cttaagtgaa gaggaactta aggagtctga   3720
tgaattagag gaggaacttc gtttatgggc ttcatataga gggcaaactt tgactagaac   3780
tgtaagagga atgatgtact atcgaaaagc cttggagctt caggcattcc ttgacatggc   3840
tatgcatgaa gatttgatgg aaggttacaa ggctgtagaa ctaaattcag agaacaattc   3900
aagaggtgaa agatcactct gggcacagtg ccaagctgtt gctgacatga gtttacata   3960 tgttgtatca tgtcaacaat atggtatcca taaacgatcc ggtgatcctc gtgcgcagga   4020
tatattgagg cttatgacaa gatacccttc actccgtgtt gcatatattg atgaggtcga   4080
agaaccagtg aaagacaagt caaagaaagg gaaccagaaa gtgtattatt ctgtgttggt   4140
aaaggtgcct aagtcaactg atcattctac cctagcacaa aatctggacc aggttatcta   4200
caggattagg cttcctggac ctgctattct tggagaagga aagccagaaa accaaaatca   4260
tgctatcatt ttttcccgtg gagaaggttt acagacaatc gatatgaatc aggataatta   4320
catggaggaa gcgttaaaga tgaggaattt gcttcaagaa tttcttacaa acatgatgg   4380 tgttagacat ccatccattc ttggacttag ggaacatata tttactggat cagtttcatc   4440
ccttgcttgg ttcatgtcaa atcaagagac tagttttgtt accattggtc agagattatt   4500
ggcaaatcca ttgagggtgc gtttccatta tggccatcca gatgttttttg atagactgtt   4560 tcatctaaca agaggtggtg ttagcaaagc atccaaggta atcaacctca gtgaagatat   4620
atttgcagga ttcaattcta cacttcgtga aggaaatgtt acccatcatg aatacataca   4680
agttggtaaa ggaagagatg ttggtctaaa tcagatctct atgtttgagg ccaagattgc   4740
taacggcaat ggagagcaga cattaagtcg ggatatttac aggcttggac accgttttga   4800 cttttttccga atgatgtcat gttacttcac cactgttggc ttttatttca gcaccctgat   4860
tactgttctc actgtctaca tcttccttta tggacgtctc tatcttgttt tgagtgggct   4920
cgaacaaggt ttaagtacgc agaaaggcat ccgagacaat acacctttgc aaatagctct   4980
ggcttcacag tcttttgtcc agattggttt cctgatggct ttacctatgc ttatggaaat   5040
tggattagag aggggttttta ggactgcctt gagtgaattt gtgctgatgc agcttcagtt   5100
ggcgccagtg ttctttacgt tctctcttgg gacaaagact cactactatg ggaggacgtt   5160
acttcatggc ggtgccaagt acaggtccac aggaagagga tttgtcgtct ttcatgccaa   5220
atttgctgat aattacagac tgtattcccg gagccatttt gtgaagggac ttgaaatgat   5280
gctgctactc gttgtgtatc aaatatttgg tagtgcttac agaggcgtcc ttgcatatct   5340
tttgatcacc atatctatgt ggttcatggt cgggacctgg cttttttgctc ccttcctctt   5400 caatccttct ggttttgaat ggcagaagat tgttgatgat tggactgatt ggaataaatg   5460
gataaacaac atcgggggta ttggtgttcc ggcagaaaaa agttgggaat cgtggtggga   5520
ggaagagcaa gaacatctcc ggtattccgg aaaacgtggt ttatggagta tcatggctgg   5580 tgatttttctt gatattgttt gtgatgaaga ctgtttcggt tggaaggcgg agattcagcg   5640
cgagttttca gctgatgttc cggttgataa aggggctgat attcatgacg tttatcgcaa   5700
ttattgtgat attgatcaca ctggctcaca tgacgataca agacataatt gtgtgtatcc   5760
ttgcctttat gcccacaggt tgggggatgc tcttgattgc gcaagcgtgt aagccggtgg   5820
```

-continued

```
ttcatagagc aggattctgg ggatcagtga ggaccctagc tcgtggatac gagatagtaa    5880
tgggactgtt gctgttcacg ccagtggcgt tcttggcatg gtttccattt gtgtcagagt    5940
tccaaacgcg tatgctcttt aatcaagctt tcagtagagg tcttcagatc tctcgtatcc    6000
ttggaggtca tcgtaaggat cgctcttctc gaaacaagga atgattcatc tcttcattgt    6060
aatgacaggg aagggatctt aatttatccc tttttatct tcatggatga ttagggttaa     6120
tgtaatttag ttttcaatat atcgcttagg taaaaacatt gtagtattca tctataaatt    6180
agacgttatc tatc                                                      6194
```

<210> SEQ ID NO 70
<211> LENGTH: 1889
<212> TYPE: PRT
<213> ORGANISM: Arabidopsis thaliana

<400> SEQUENCE: 70

| | | | | | | | | | | | | | | |
|---|---|---|---|---|---|---|---|---|---|---|---|---|---|---|
| Met | Ser | Ala | Thr | Arg | Gly | Gly | Pro | Asp | Gln | Gly | Pro | Ser | Gln | Pro | Gln |
| 1 | | | | 5 | | | | | 10 | | | | | 15 | |
| Gln | Arg | Arg | Ile | Ile | Arg | Thr | Gln | Thr | Ala | Gly | Asn | Leu | Gly | Glu | Ser |
| | | | 20 | | | | | 25 | | | | | 30 | | |
| Phe | Asp | Ser | Glu | Val | Val | Pro | Ser | Ser | Leu | Val | Glu | Ile | Ala | Pro | Ile |
| | | | 35 | | | | | 40 | | | | | 45 | | |
| Leu | Arg | Val | Ala | Asn | Glu | Val | Glu | Ser | Ser | Asn | Pro | Arg | Val | Ala | Tyr |
| | 50 | | | | | 55 | | | | | 60 | | | | |
| Leu | Cys | Arg | Phe | Tyr | Ala | Phe | Glu | Lys | Ala | His | Arg | Leu | Asp | Pro | Thr |
| 65 | | | | | 70 | | | | | 75 | | | | | 80 |
| Ser | Ser | Gly | Arg | Gly | Val | Arg | Gln | Phe | Lys | Thr | Ala | Leu | Leu | Gln | Arg |
| | | | | 85 | | | | | 90 | | | | | 95 | |
| Leu | Glu | Arg | Glu | His | Asp | Pro | Thr | Leu | Met | Gly | Arg | Val | Lys | Lys | Ser |
| | | | 100 | | | | | 105 | | | | | 110 | | |
| Asp | Ala | Arg | Glu | Met | Gln | Ser | Phe | Tyr | Gln | His | Tyr | Tyr | Lys | Lys | Tyr |
| | | | 115 | | | | | 120 | | | | | 125 | | |
| Ile | Gln | Ala | Leu | His | Asn | Ala | Ala | Asp | Lys | Ala | Asp | Arg | Ala | Gln | Leu |
| | 130 | | | | | 135 | | | | | 140 | | | | |
| Thr | Lys | Ala | Tyr | Gln | Thr | Ala | Asn | Val | Leu | Phe | Glu | Val | Leu | Lys | Ala |
| 145 | | | | | 150 | | | | | 155 | | | | | 160 |
| Val | Asn | Leu | Thr | Gln | Ser | Ile | Glu | Val | Asp | Arg | Glu | Ile | Leu | Glu | Ala |
| | | | | 165 | | | | | 170 | | | | | 175 | |
| Gln | Asp | Lys | Val | Ala | Glu | Lys | Thr | Gln | Leu | Tyr | Val | Pro | Tyr | Asn | Ile |
| | | | 180 | | | | | 185 | | | | | 190 | | |
| Leu | Pro | Leu | Asp | Pro | Asp | Ser | Ala | Asn | Gln | Ala | Ile | Met | Arg | Tyr | Pro |
| | | | 195 | | | | | 200 | | | | | 205 | | |
| Glu | Ile | Gln | Ala | Ala | Val | Leu | Ala | Leu | Arg | Asn | Thr | Arg | Gly | Leu | Pro |
| | 210 | | | | | 215 | | | | | 220 | | | | |
| Trp | Pro | Glu | Gly | His | Lys | Lys | Lys | Asp | Glu | Asp | Met | Leu | Asp | Trp |
| 225 | | | | | 230 | | | | | 235 | | | | | 240 |
| Leu | Gln | Glu | Met | Phe | Gly | Phe | Gln | Lys | Asp | Asn | Val | Ala | Asn | Gln | Arg |
| | | | | 245 | | | | | 250 | | | | | 255 | |
| Glu | His | Leu | Ile | Leu | Leu | Ala | Asn | Val | His | Ile | Arg | Gln | Phe | Pro |
| | | | 260 | | | | | 265 | | | | | 270 | | |
| Lys | Pro | Asp | Gln | Gln | Pro | Lys | Phe | Ile | Leu | Ser | Phe | Leu | Ile | Val |
| | | | 275 | | | | | 280 | | | | | 285 | | |
| Pro | Ser | Gln | Leu | Asp | Asp | Gln | Ala | Leu | Thr | Glu | Val | Met | Lys | Lys | Leu |
| | 290 | | | | | 295 | | | | | 300 | | | | |

```
Phe Lys Asn Tyr Lys Lys Trp Cys Lys Tyr Leu Gly Arg Lys Ser Ser
305                 310                 315                 320

Leu Trp Leu Pro Thr Ile Gln Gln Glu Met Gln Gln Arg Lys Leu Leu
            325                 330                 335

Tyr Met Ala Leu Tyr Leu Leu Ile Trp Gly Glu Ala Ala Asn Leu Arg
        340                 345                 350

Phe Met Pro Glu Cys Leu Cys Tyr Ile Tyr His His Met Ala Phe Glu
    355                 360                 365

Leu Tyr Gly Met Leu Ala Gly Asn Val Ser Pro Met Thr Gly Glu Asn
370                 375                 380

Val Lys Pro Ala Tyr Gly Gly Glu Glu Asp Ala Phe Leu Arg Lys Val
385                 390                 395                 400

Val Thr Pro Ile Tyr Glu Val Ile Gln Met Glu Ala Gln Arg Ser Lys
                405                 410                 415

Lys Gly Lys Ser Lys His Ser Gln Trp Arg Asn Tyr Asp Asp Leu Asn
            420                 425                 430

Glu Tyr Phe Trp Ser Val Asp Cys Phe Arg Leu Gly Trp Pro Met Arg
        435                 440                 445

Ala Asp Ala Asp Phe Phe Cys Leu Pro Val Ala Val Pro Asn Thr Glu
450                 455                 460

Lys Asp Gly Asp Asn Ser Lys Pro Ile Val Ala Arg Asp Arg Trp Val
465                 470                 475                 480

Gly Lys Val Asn Phe Val Glu Ile Arg Ser Phe Trp His Val Phe Arg
                485                 490                 495

Ser Phe Asp Arg Met Trp Ser Phe Tyr Ile Leu Cys Leu Gln Ala Met
            500                 505                 510

Ile Ile Met Ala Trp Asp Gly Gly Gln Pro Ser Ser Val Phe Gly Ala
        515                 520                 525

Asp Val Phe Lys Lys Val Leu Ser Val Phe Ile Thr Ala Ala Ile Met
        530                 535                 540

Lys Leu Gly Gln Ala Val Leu Asp Val Ile Leu Asn Phe Lys Ala His
545                 550                 555                 560

Gln Ser Met Thr Leu His Val Lys Leu Arg Tyr Ile Leu Lys Val Phe
                565                 570                 575

Ser Ala Ala Ala Trp Val Ile Ile Leu Pro Val Thr Tyr Ala Tyr Ser
            580                 585                 590

Trp Lys Asp Pro Pro Ala Phe Ala Arg Thr Ile Lys Ser Trp Phe Gly
        595                 600                 605

Ser Ala Met His Ser Pro Ser Leu Phe Ile Ile Ala Val Val Ser Tyr
        610                 615                 620

Leu Ser Pro Asn Met Leu Ala Glu Thr Asn Glu Asn Leu Leu Leu Cys
625                 630                 635                 640

Cys Leu Thr Asp Val Thr Ile Ile Asn Thr Leu Gln Pro Arg Leu Tyr
                645                 650                 655

Val Gly Arg Gly Met His Glu Ser Ala Phe Ser Leu Phe Lys Tyr Thr
            660                 665                 670

Met Phe Trp Val Leu Leu Ile Ala Thr Lys Leu Ala Phe Ser Tyr Tyr
        675                 680                 685

Ile Glu Ile Arg Pro Leu Val Ala Pro Thr Gln Ala Ile Met Lys Ala
        690                 695                 700

Arg Val Thr Asn Phe Gln Trp His Glu Phe Phe Pro Arg Ala Lys Asn
705                 710                 715                 720

Asn Ile Gly Val Val Ile Ala Leu Trp Ala Pro Ile Ile Leu Val Tyr
                725                 730                 735
```

Phe Met Asp Ser Gln Ile Trp Tyr Ala Ile Phe Ser Thr Leu Phe Gly
                740                 745                 750

Gly Ile Tyr Gly Ala Phe Arg Arg Leu Gly Glu Ile Arg Thr Leu Gly
            755                 760                 765

Met Leu Arg Ser Arg Phe Glu Ser Leu Pro Gly Ala Phe Asn Asp Arg
    770                 775                 780

Leu Ile Pro Asp Gly Lys Asn Gln Gln Lys Lys Gly Ile Arg Ala
785                 790                 795                 800

Thr Leu Ser His Asn Phe Thr Glu Asp Lys Val Pro Val Asn Lys Glu
                805                 810                 815

Lys Glu Ala Ala Arg Phe Ala Gln Leu Trp Asn Thr Ile Ile Ser Ser
                820                 825                 830

Phe Arg Glu Glu Asp Leu Ile Ser Asp Arg Glu Met Asp Leu Leu Leu
                835                 840                 845

Val Pro Tyr Trp Ala Asp Arg Asp Leu Asp Leu Ile Gln Trp Pro Pro
            850                 855                 860

Phe Leu Leu Ala Ser Lys Ile Pro Ile Ala Leu Asp Met Ala Lys Asp
865                 870                 875                 880

Ser Asn Gly Lys Asp Arg Glu Leu Lys Lys Arg Ile Glu Ser Asp Thr
                885                 890                 895

Tyr Met Lys Cys Ala Val Arg Glu Cys Tyr Ala Ser Phe Lys Asn Ile
                900                 905                 910

Ile Lys Phe Val Val Gln Gly Asn Arg Glu Lys Glu Val Ile Glu Ile
            915                 920                 925

Ile Phe Ala Glu Val Asp Lys His Ile Asp Thr Gly Asp Leu Ile Gln
            930                 935                 940

Glu Tyr Lys Met Ser Ala Leu Pro Ser Leu Tyr Asp His Phe Val Lys
945                 950                 955                 960

Leu Ile Lys Tyr Leu Val Asn Val Leu Pro Val Leu Asp Asn Lys Glu
                965                 970                 975

Glu Asp Arg Asp His Val Val Ile Leu Phe Gln Asp Met Leu Glu Val
                980                 985                 990

Val Thr Arg Asp Ile Met Met Glu Asp Tyr Asn Ile Ser Arg Leu Ala
            995                 1000                1005

Thr Phe Tyr Arg Thr Ala Met Ala Cys His Ser Ser His Gly Gly
    1010                1015                1020

Thr Trp His Gly Gly Met Ile Pro Leu Glu Gln Gln Tyr Gln Leu
    1025                1030                1035

Phe Ala Ser Ser Gly Ala Ile Arg Phe Pro Ile Glu Pro Val Thr
    1040                1045                1050

Glu Ala Trp Lys Glu Lys Ile Lys Arg Ile Tyr Leu Leu Leu Thr
    1055                1060                1065

Thr Lys Glu Ser Ala Met Asp Val Pro Ser Asn Leu Glu Ala Arg
    1070                1075                1080

Arg Arg Ile Ser Phe Phe Ser Asn Ser Leu Phe Met Asp Met Pro
    1085                1090                1095

Met Ala Pro Lys Val Arg Asn Met Leu Ser Phe Ser Val Leu Thr
    1100                1105                1110

Pro Tyr Tyr Thr Glu Glu Val Leu Phe Ser Leu Arg Asp Leu Glu
    1115                1120                1125

Thr Pro Asn Glu Asp Gly Val Ser Ile Leu Phe Tyr Leu Gln Lys
    1130                1135                1140

Ile Phe Pro Gly Asp Phe Cys Ser Tyr Ala Val Asn Val Ala Tyr

-continued

```
            1145                1150                1155

Ile Leu Glu Ser Arg Leu Glu Pro Asp Leu Leu Ser Pro Asp Glu
1160                1165                1170

Trp Asn Asn Phe Leu Glu Arg Val Lys Cys Leu Ser Glu Glu Glu
    1175                1180                1185

Leu Lys Glu Ser Asp Glu Leu Glu Glu Leu Arg Leu Trp Ala
1190                1195                1200

Ser Tyr Arg Gly Gln Thr Leu Thr Arg Thr Val Arg Gly Met Met
    1205                1210                1215

Tyr Tyr Arg Lys Ala Leu Glu Leu Gln Ala Phe Leu Asp Met Ala
    1220                1225                1230

Met His Glu Asp Leu Met Glu Gly Tyr Lys Ala Val Glu Leu Asn
    1235                1240                1245

Ser Glu Asn Asn Ser Arg Gly Glu Arg Ser Leu Trp Ala Gln Cys
    1250                1255                1260

Gln Ala Val Ala Asp Met Lys Phe Thr Tyr Val Val Ser Cys Gln
    1265                1270                1275

Gln Tyr Gly Ile His Lys Arg Ser Gly Asp Pro Arg Ala Gln Asp
    1280                1285                1290

Ile Leu Arg Leu Met Thr Arg Tyr Pro Ser Leu Arg Val Ala Tyr
    1295                1300                1305

Ile Asp Glu Val Glu Glu Pro Val Lys Asp Lys Ser Lys Lys Gly
    1310                1315                1320

Asn Gln Lys Val Tyr Tyr Ser Val Leu Val Lys Val Pro Lys Ser
    1325                1330                1335

Thr Asp His Ser Thr Leu Ala Gln Asn Leu Asp Gln Val Ile Tyr
    1340                1345                1350

Arg Ile Arg Leu Pro Gly Pro Ala Ile Leu Gly Glu Gly Lys Pro
    1355                1360                1365

Glu Asn Gln Asn His Ala Ile Ile Phe Ser Arg Gly Glu Gly Leu
    1370                1375                1380

Gln Thr Ile Asp Met Asn Gln Asp Asn Tyr Met Glu Glu Ala Leu
    1385                1390                1395

Lys Met Arg Asn Leu Leu Gln Glu Phe Leu Thr Lys His Asp Gly
    1400                1405                1410

Val Arg His Pro Ser Ile Leu Gly Leu Arg Glu His Ile Phe Thr
    1415                1420                1425

Gly Ser Val Ser Ser Leu Ala Trp Phe Met Ser Asn Gln Glu Thr
    1430                1435                1440

Ser Phe Val Thr Ile Gly Gln Arg Leu Leu Ala Asn Pro Leu Arg
    1445                1450                1455

Val Arg Phe His Tyr Gly His Pro Asp Val Phe Asp Arg Leu Phe
    1460                1465                1470

His Leu Thr Arg Gly Gly Val Ser Lys Ala Ser Lys Val Ile Asn
    1475                1480                1485

Leu Ser Glu Asp Ile Phe Ala Gly Phe Asn Ser Thr Leu Arg Glu
    1490                1495                1500

Gly Asn Val Thr His His Glu Tyr Ile Gln Val Gly Lys Gly Arg
    1505                1510                1515

Asp Val Gly Leu Asn Gln Ile Ser Met Phe Glu Ala Lys Ile Ala
    1520                1525                1530

Asn Gly Asn Gly Glu Gln Thr Leu Ser Arg Asp Ile Tyr Arg Leu
    1535                1540                1545
```

| | | | | | | | | | |
|---|---|---|---|---|---|---|---|---|---|
| Gly | His | Arg | Phe | Asp | Phe | Phe | Arg | Met | Met | Ser | Cys | Tyr | Phe | Thr |

Gly His Arg Phe Asp Phe Phe Arg Met Met Ser Cys Tyr Phe Thr
    1550                1555                1560

Thr Val Gly Phe Tyr Phe Ser Thr Leu Ile Thr Val Leu Thr Val
    1565                1570                1575

Tyr Ile Phe Leu Tyr Gly Arg Leu Tyr Leu Val Leu Ser Gly Leu
    1580                1585                1590

Glu Gln Gly Leu Ser Thr Gln Lys Gly Ile Arg Asp Asn Thr Pro
    1595                1600                1605

Leu Gln Ile Ala Leu Ala Ser Gln Ser Phe Val Gln Ile Gly Phe
    1610                1615                1620

Leu Met Ala Leu Pro Met Leu Met Glu Ile Gly Leu Glu Arg Gly
    1625                1630                1635

Phe Arg Thr Ala Leu Ser Glu Phe Val Leu Met Gln Leu Gln Leu
    1640                1645                1650

Ala Pro Val Phe Phe Thr Phe Ser Leu Gly Thr Lys Thr His Tyr
    1655                1660                1665

Tyr Gly Arg Thr Leu Leu His Gly Gly Ala Lys Tyr Arg Ser Thr
    1670                1675                1680

Gly Arg Gly Phe Val Val Phe His Ala Lys Phe Ala Asp Asn Tyr
    1685                1690                1695

Arg Leu Tyr Ser Arg Ser His Phe Val Lys Gly Leu Glu Met Met
    1700                1705                1710

Leu Leu Leu Val Val Tyr Gln Ile Phe Gly Ser Ala Tyr Arg Gly
    1715                1720                1725

Val Leu Ala Tyr Leu Leu Ile Thr Ile Ser Met Trp Phe Met Val
    1730                1735                1740

Gly Thr Trp Leu Phe Ala Pro Phe Leu Phe Asn Pro Ser Gly Phe
    1745                1750                1755

Glu Trp Gln Lys Ile Val Asp Asp Trp Thr Asp Trp Asn Lys Trp
    1760                1765                1770

Ile Asn Asn Ile Gly Gly Ile Gly Val Pro Ala Glu Lys Ser Trp
    1775                1780                1785

Glu Ser Trp Trp Glu Glu Glu Gln Glu His Leu Arg Tyr Ser Gly
    1790                1795                1800

Lys Arg Gly Leu Trp Ser Ile Met Ala Gly Asp Phe Leu Asp Ile
    1805                1810                1815

Val Cys Asp Glu Asp Cys Phe Gly Trp Lys Ala Glu Ile Gln Arg
    1820                1825                1830

Glu Phe Ser Ala Asp Val Pro Val Asp Lys Gly Ala Asp Ile His
    1835                1840                1845

Asp Val Tyr Arg Asn Tyr Cys Asp Ile Asp His Thr Gly Ser His
    1850                1855                1860

Asp Asp Thr Arg His Asn Cys Val Tyr Pro Cys Leu Tyr Ala His
    1865                1870                1875

Arg Leu Gly Asp Ala Leu Asp Cys Ala Ser Val
    1880                1885

<210> SEQ ID NO 71
<211> LENGTH: 4051
<212> TYPE: DNA
<213> ORGANISM: Arabidopsis thaliana

<400> SEQUENCE: 71
tggaatcaat cactcaagag gagttgaagg aaccaaagcc ctaataaact agggaaagta      60
atctatcctc gccggagtcg ttgtctcgcc gataaggaac gaaggacgaa gctgtcttcg     120

```
atttccggga ttgaagattc ggttttgagc tcaaatcgtc gactgagtaa tgggggttga    180
tccattcaaa actacggaaa cgttagaagc cgacaaggaa accaatggtg gtgtccctgt    240
gaaggataaa ttgactttta aagctcctga gagaaagtcc cgtttaggtt tggatgcaag    300
ggcaattgag aaaaaggata atgccaagac tgagggcgag tttaaggttc cgaagaagtc    360
agcaatatct gttacatcat cgttggatga agaagataaa tctgatgtat caggattaga    420
ttttggaaca gaaaacactc gacctgtcca ttccagcagg cgatatagag agaagtcttc    480
aagatctcag tctgcacaag aaagtaccgt gactacagag aatgctggaa cttcagatgt    540
ggtagcaata ggcatcgaga agaacatagg cgtgacagaa gtgaaactcc gcggtcaaga    600
cagagaaaca cttatgatga gatggatcac taccgacgga gggaatctta tcgccaatct    660
gaccgagact atcacggaga aaagcgtagg agatacaata gcgattggag gactccagga    720
cgaatgggaa cgtagtcctc acggagacag aggctctagt tacagcaggc gacctcaacc    780
ttctccatca cccatgttag ctgcagcttc acctgatgct cgtttagcct ccccgtggct    840
ggatacacca cgttcaacta tgtcttctgc ttctccatgg gatatgggtg caccttctcc    900
tattccaatt cgggcttctg gatcatctat cagatcctca agctctaggt atggtggaag    960
atccaatcag cttgcatatt ctagggaagg tgatctgaca aatgaggggc attcagatga   1020
ggatagatcg caaggagctg aagaatttaa acatgagatc acagaaacaa tgcgtgtgga   1080
aatggaatat cagtcagatc gtgcatggta tgatacagac gaagggaact cactgtttga   1140
tgcggacagt gcatcctttt ttcttggaga tgatgcttct ctacagaaga aggaaactga   1200
actggcaaag agactggtta aagagacgg tagcaaaatg tcactcgctc agagtaaaaa   1260
atattctcag ctcaatgcgg ataatgctca atgggaagac cgccagcttc tcagatctgg   1320
agctgttaga ggcacagaag tgcagactga gtttgatagc gaagaagaac ggaaagcaat   1380
tcttcttgta catgatacga agcctccttt ccttgatgga agagtcgttt acacaaagca   1440
agcagagcca gtaatgcctg taaaggatcc cacatcagac atggctataa tttcacgaaa   1500
aggctcaggt cttgtcaaag aaattcggga gaaacaaagt gcgaataagt cacgacagcg   1560
attctgggag cttgcaggtt ctaatcttgg taatatcctt ggtattgaaa aatcagccga   1620
gcagattgat gccgatactg ctgtagttgg tgacgacggt gaagtagatt ttaaaggtga   1680
ggctaaattt gcacaacata tgaagaaggg agaagctgtg agtgaatttg ccatgtcaaa   1740
gaccatggca gagcaacggc agtatcttcc catattttct gttagagatg aactattgca   1800
ggtaataaga gaaaaccagg tgatagtggt ggttggcgaa actggttcgg gaaagaccac   1860
tcaacttaca caggatggtt acactataaa tggtatagtt ggttgcaccc aaccaaggcg   1920
tgtagcagcc atgagtgttg caaagagagt tagtgaagag atggaaacag agttgggcga   1980
taaaattggt tatgcaattc gttttgaaga tgtaactggt ccaaacactg ttatcaagta   2040
catgaccgat ggagtactac tgagagagac cctcaaagat tctgacctgg ataagtatcg   2100
tgtggtggtg atggatgaag cgcatgaaag gtcactcaac acagacgtcc ttttggaat   2160 actgaaaaaa gttgtggctc ggcgtcgtga tttcaagctg atagtcacgt cagcaaccct   2220
taatgctcaa aagttttcca atttctttgg gagtgttcct atcttcaaca ttcctggaag   2280
gactttccct gtcaatattc tctactctaa aactccttgt gaagactatg ttgaagctgc   2340
tgttaaacag gcaatgacga ttcacataac aagcccacct ggggacattc tcatttttat   2400
gaccgggcaa gatgagattg aggcagcgtg cttttcacta aaggagagaa tggaacagct   2460
cgtatcatct tccagtagag aaataacgaa cctactcatt ctcccaatat actctcagtt   2520
```

```
acctgctgac ttgcaagcaa agatattcca gaaaccagaa gatggagccc gtaaatgcat    2580
tgttgccacc aatattgctg aaacatcatt gacagtcgat ggaatatatt atgtgattga    2640
cactgggtat ggaaagatga aggttttcaa tcctagaatg ggtatggatg ctcttcaagt    2700
tttccccata agtcgtgcag cctctgatca gcgtgctgga agagctggaa ggacagggcc    2760
aggaacatgt tacaggttgt atactgagag tgcttatttg aatgagatgt tgccaagtcc    2820
tgtgccagag attcagcgga cgaatctggg taatgttgtg ttgttgttga agtcattgaa    2880
aatagacaac ttgctagatt ttgatttcat ggatccacct ccgcaagaga acatccttaa    2940
ctctatgtac cagctttggg tgttgggtgc tctcaacaat gttggaggat taaccgacct    3000 ggggtgaag atggtggagt tcccattgga tcctcctctt gcaaagatgc ttttaatggg    3060
tgaacggctt gattgcatag atgaggttct gacgatcgtg tcaatgcttt cagtaccttc    3120
agtgttcttc agacctaaag aaagagcaga agagagcgac gctgcaaggg agaagttttt    3180
tgtgccggaa tcggatcatc tgacgctgct gaacgtatat cagcagtgga agagcatga    3240 ctatagagga gactggtgca atgaccatta cctacaagtg aaaggtttga gaaaagctag    3300
agaggtaaga tcccagcttc tggatatcct caagcaactg aaaattgaac tcaggtcgtg    3360
tggaccggat tgggatattg tgagaaaagc catctgttca gcgtatttcc acaactcagc    3420
tagattaaaa ggtgttgggg agtatgtgaa ctgcagaacc gggatgcctt gccatttgca    3480
ccctagcagt gcactgtacg gtctgggata cacaccggac tatgtggtgt accatgaact    3540
gatcttgacc acaaaggagt acatgcagtg tgcgacatcg gttgagccgc attggctggc    3600
tgagttaggg cctatgttct ctcggtcaa ggactcggat acatcgatgt ggagcataa    3660 aaaaaagcag aaggaagaga atcaggaat ggaggaagag atggagaaac tgagaagaga    3720
tcaggtggag tcagagctga aagcaaaga gagagagaga aaaaaaggg caaagcagca    3780 gcaacagatt tcaggcccctg gcttgaaaaa gggcaccact ttcctcaggc ctaagaagct    3840
tggactgtga cattgtaatg taataaaaaa cataccgaaa acgtcaccca acaaaaaaa    3900 acggaaaaaa cacagccaaa atggagcaaa ctgtaatcac catgtatcgt tgttcagata    3960
tttcttgatg tgaacaatat taaattgttc cacgcttgta ttgattcttt ataactaatt    4020
agttagagat cctctacgtc tctagtatag t    4051
```

<210> SEQ ID NO 72
<211> LENGTH: 1226
<212> TYPE: PRT
<213> ORGANISM: Arabidopsis thaliana

<400> SEQUENCE: 72

```
Met Gly Val Asp Pro Phe Lys Thr Thr Glu Thr Leu Glu Ala Asp Lys
1               5                   10                  15

Glu Thr Asn Gly Gly Val Pro Lys Asp Lys Leu Thr Phe Lys Ala
            20                  25                  30

Pro Glu Arg Lys Ser Arg Leu Gly Leu Asp Ala Arg Ala Ile Glu Lys
        35                  40                  45

Lys Asp Asn Ala Lys Thr Glu Gly Glu Phe Lys Val Pro Lys Lys Ser
    50                  55                  60

Ala Ile Ser Val Thr Ser Ser Leu Asp Glu Glu Asp Lys Ser Asp Val
65                  70                  75                  80

Ser Gly Leu Asp Phe Gly Thr Glu Asn Thr Arg Pro Val His Ser Ser
                85                  90                  95

Arg Arg Tyr Arg Glu Lys Ser Ser Arg Ser Gln Ser Ala Gln Glu Ser
```

```
              100                 105                 110
Thr Val Thr Thr Glu Asn Ala Gly Thr Ser Asp Val Ala Ile Gly
            115                 120                 125

Ile Glu Lys Asn Ile Gly Val Thr Glu Val Lys Leu Arg Gly Gln Asp
            130                 135                 140

Arg Glu Thr Leu Met Met Arg Trp Ile Thr Thr Asp Gly Gly Asn Leu
145                 150                 155                 160

Ile Ala Asn Leu Thr Glu Thr Ile Thr Glu Lys Ser Val Gly Asp Thr
                165                 170                 175

Ile Ala Ile Gly Gly Leu Gln Asp Glu Trp Glu Arg Ser Pro His Gly
                180                 185                 190

Asp Arg Gly Ser Ser Tyr Ser Arg Arg Pro Gln Pro Ser Pro Ser Pro
            195                 200                 205

Met Leu Ala Ala Ala Ser Pro Asp Ala Arg Leu Ala Ser Pro Trp Leu
            210                 215                 220

Asp Thr Pro Arg Ser Thr Met Ser Ser Ala Ser Pro Trp Asp Met Gly
225                 230                 235                 240

Ala Pro Ser Pro Ile Pro Ile Arg Ala Ser Gly Ser Ser Ile Arg Ser
                245                 250                 255

Ser Ser Ser Arg Tyr Gly Gly Arg Ser Asn Gln Leu Ala Tyr Ser Arg
                260                 265                 270

Glu Gly Asp Leu Thr Asn Glu Gly His Ser Asp Glu Asp Arg Ser Gln
            275                 280                 285

Gly Ala Glu Glu Phe Lys His Glu Ile Thr Glu Thr Met Arg Val Glu
            290                 295                 300

Met Glu Tyr Gln Ser Asp Arg Ala Trp Tyr Asp Thr Asp Glu Gly Asn
305                 310                 315                 320

Ser Leu Phe Asp Ala Asp Ser Ala Ser Phe Phe Leu Gly Asp Asp Ala
                325                 330                 335

Ser Leu Gln Lys Lys Glu Thr Glu Leu Ala Lys Arg Leu Val Arg Arg
            340                 345                 350

Asp Gly Ser Lys Met Ser Leu Ala Gln Ser Lys Lys Tyr Ser Gln Leu
            355                 360                 365

Asn Ala Asp Asn Ala Gln Trp Glu Asp Arg Gln Leu Leu Arg Ser Gly
            370                 375                 380

Ala Val Arg Gly Thr Glu Val Gln Thr Glu Phe Asp Ser Glu Glu Glu
385                 390                 395                 400

Arg Lys Ala Ile Leu Leu Val His Asp Thr Lys Pro Pro Phe Leu Asp
                405                 410                 415

Gly Arg Val Val Tyr Thr Lys Gln Ala Glu Pro Val Met Pro Val Lys
                420                 425                 430

Asp Pro Thr Ser Asp Met Ala Ile Ile Ser Arg Lys Gly Ser Gly Leu
            435                 440                 445

Val Lys Glu Ile Arg Glu Lys Ser Ala Asn Lys Ser Arg Gln Arg
            450                 455                 460

Phe Trp Glu Leu Ala Gly Ser Asn Leu Gly Asn Ile Leu Gly Ile Glu
465                 470                 475                 480

Lys Ser Ala Glu Gln Ile Asp Ala Asp Thr Ala Val Val Gly Asp Asp
                485                 490                 495

Gly Glu Val Asp Phe Lys Gly Glu Ala Lys Phe Ala Gln His Met Lys
                500                 505                 510

Lys Gly Glu Ala Val Ser Glu Phe Ala Met Ser Lys Thr Met Ala Glu
            515                 520                 525
```

```
Gln Arg Gln Tyr Leu Pro Ile Phe Ser Val Arg Asp Glu Leu Leu Gln
            530                 535                 540

Val Ile Arg Glu Asn Gln Val Ile Val Val Gly Glu Thr Gly Ser
545                 550                 555                 560

Gly Lys Thr Thr Gln Leu Thr Gln Asp Gly Tyr Thr Ile Asn Gly Ile
                565                 570                 575

Val Gly Cys Thr Gln Pro Arg Arg Val Ala Ala Met Ser Val Ala Lys
            580                 585                 590

Arg Val Ser Glu Glu Met Glu Thr Glu Leu Gly Asp Lys Ile Gly Tyr
        595                 600                 605

Ala Ile Arg Phe Glu Asp Val Thr Gly Pro Asn Thr Val Ile Lys Tyr
        610                 615                 620

Met Thr Asp Gly Val Leu Leu Arg Glu Thr Leu Lys Asp Ser Asp Leu
625                 630                 635                 640

Asp Lys Tyr Arg Val Val Met Asp Glu Ala His Glu Arg Ser Leu
                645                 650                 655

Asn Thr Asp Val Leu Phe Gly Ile Leu Lys Lys Val Val Ala Arg Arg
                660                 665                 670

Arg Asp Phe Lys Leu Ile Val Thr Ser Ala Thr Leu Asn Ala Gln Lys
            675                 680                 685

Phe Ser Asn Phe Phe Gly Ser Val Pro Ile Phe Asn Ile Pro Gly Arg
690                 695                 700

Thr Phe Pro Val Asn Ile Leu Tyr Ser Lys Thr Pro Cys Glu Asp Tyr
705                 710                 715                 720

Val Glu Ala Ala Val Lys Gln Ala Met Thr Ile His Ile Thr Ser Pro
                725                 730                 735

Pro Gly Asp Ile Leu Ile Phe Met Thr Gly Gln Asp Glu Ile Glu Ala
            740                 745                 750

Ala Cys Phe Ser Leu Lys Glu Arg Met Glu Gln Leu Val Ser Ser Ser
        755                 760                 765

Ser Arg Glu Ile Thr Asn Leu Leu Ile Leu Pro Ile Tyr Ser Gln Leu
770                 775                 780

Pro Ala Asp Leu Gln Ala Lys Ile Phe Gln Lys Pro Glu Asp Gly Ala
785                 790                 795                 800

Arg Lys Cys Ile Val Ala Thr Asn Ile Ala Glu Thr Ser Leu Thr Val
                805                 810                 815

Asp Gly Ile Tyr Tyr Val Ile Asp Thr Gly Tyr Gly Lys Met Lys Val
            820                 825                 830

Phe Asn Pro Arg Met Gly Met Asp Ala Leu Gln Val Phe Pro Ile Ser
        835                 840                 845

Arg Ala Ala Ser Asp Gln Arg Ala Gly Arg Ala Gly Arg Thr Gly Pro
850                 855                 860

Gly Thr Cys Tyr Arg Leu Tyr Thr Glu Ser Ala Tyr Leu Asn Glu Met
865                 870                 875                 880

Leu Pro Ser Pro Val Pro Glu Ile Gln Arg Thr Asn Leu Gly Asn Val
                885                 890                 895

Val Leu Leu Leu Lys Ser Leu Lys Ile Asp Asn Leu Leu Asp Phe Asp
            900                 905                 910

Phe Met Asp Pro Pro Gln Glu Asn Ile Leu Asn Ser Met Tyr Gln
        915                 920                 925

Leu Trp Val Leu Gly Ala Leu Asn Asn Val Gly Gly Leu Thr Asp Leu
        930                 935                 940

Gly Trp Lys Met Val Glu Phe Pro Leu Asp Pro Pro Leu Ala Lys Met
945                 950                 955                 960
```

Leu Leu Met Gly Glu Arg Leu Asp Cys Ile Asp Glu Val Leu Thr Ile
                965                 970                 975
Val Ser Met Leu Ser Val Pro Ser Val Phe Phe Arg Pro Lys Glu Arg
                980                 985                 990
Ala Glu Glu Ser Asp Ala Ala Arg Glu Lys Phe Phe Val Pro Glu Ser
            995                1000                1005
Asp His Leu Thr Leu Leu Asn Val Tyr Gln Gln Trp Lys Glu His
        1010                1015                1020
Asp Tyr Arg Gly Asp Trp Cys Asn Asp His Tyr Leu Gln Val Lys
        1025                1030                1035
Gly Leu Arg Lys Ala Arg Glu Val Arg Ser Gln Leu Leu Asp Ile
        1040                1045                1050
Leu Lys Gln Leu Lys Ile Glu Leu Arg Ser Cys Gly Pro Asp Trp
        1055                1060                1065
Asp Ile Val Arg Lys Ala Ile Cys Ser Ala Tyr Phe His Asn Ser
        1070                1075                1080
Ala Arg Leu Lys Gly Val Gly Glu Tyr Val Asn Cys Arg Thr Gly
        1085                1090                1095
Met Pro Cys His Leu His Pro Ser Ser Ala Leu Tyr Gly Leu Gly
        1100                1105                1110
Tyr Thr Pro Asp Tyr Val Val Tyr His Glu Leu Ile Leu Thr Thr
        1115                1120                1125
Lys Glu Tyr Met Gln Cys Ala Thr Ser Val Glu Pro His Trp Leu
        1130                1135                1140
Ala Glu Leu Gly Pro Met Phe Phe Ser Val Lys Asp Ser Asp Thr
        1145                1150                1155
Ser Met Leu Glu His Lys Lys Gln Lys Glu Lys Ser Gly
        1160                1165                1170
Met Glu Glu Met Glu Lys Leu Arg Arg Asp Gln Val Glu Ser
        1175                1180                1185
Glu Leu Arg Ser Lys Glu Arg Lys Lys Arg Ala Lys Gln
        1190                1195                1200
Gln Gln Gln Ile Ser Gly Pro Gly Leu Lys Lys Gly Thr Thr Phe
        1205                1210                1215
Leu Arg Pro Lys Lys Leu Gly Leu
        1220            1225

<210> SEQ ID NO 73
<211> LENGTH: 3760
<212> TYPE: DNA
<213> ORGANISM: Arabidopsis thaliana

<400> SEQUENCE: 73
agagacaacc cagaaaaaaa aaacagaggc ttaagaaagc aagggttttt aagcgagggt     60
ttaaggcggc ttcgtcgtgt acgcttcact caccatttgt ttttattttc ttccgtctat    120
gaaactcttc ccaatttgcc attttcttt gctcatgcga tcgaatttat tcaatctcga    180
gttggttatt gttctggttt atcgatttta ctcaatttt aagttcgatt gatgtccagt    240
gctcaaaccc cactgttctt ggcaaatcag actaaggtat tcgatcactt gattccattg    300
cataaaccct ttatttcttc tccaaaccca gtttcccaat ccttcccat gtggagaaac    360
attgctaaac aagcaatttc gaggtcagct gctagattaa acgtcagttc ccaaactcgt    420
ggccttcttg tgtcttctcc ggagtctatt ttctcgaaaa atttgagctt tcggtttccg    480
gtcttgggat caccatgtca cggaaagggt tttcgttgtt aagtgggat cacgaggcga    540

```
gaggagtttt ccaagagcga gaggtgcctt agtgggactt tggctagagg gtacacgagt    600
gtagccgaag aggaggtctt atcaacagat gttgaggaag agcctgaggt agatgaattg    660
ttgaaggaga tgaagaaaga gaagaagaga gaaagtcatc gttcgtggcg gatgaagaag    720
caagaccaat ttggaatggg tcgtaccaag ttccagaatt tatggagaag acaagttaag    780
atcgagactg aagaatggga aagagctgct gcagagtaca tggagctttt gacagatatg    840
tgtgagcaaa agcttgcgcc taatctgcct tatgtgaagt ctttatttct gggttggttc    900
gaaccattaa gagatgcaat tgctaaagac caggagttgt atagattagg gaagagcaaa    960
gcaacttatg cacattacct tgatcagttg cctgccgaca agatatctgt tattacaatg   1020
cacaagttga tggggcattt gatgactggt ggtgataacg gttgtgttaa ggttgttcat   1080
gctgcgtgta cagtaggcga tgccattgaa caagagataa gaatatgcac attcttggat   1140
aagaagaaaa aaggggatga caatgaggag agtgggggag ttgaaaatga aacttctatg   1200
aaggaacaag ataagttaag aaaaaaggtc aatgagttga taaagaaaca gaagttgtca   1260
gcagttagaa agatcttgca gtcacatgac tatacgaaac catggatcgc agatgttagg   1320
gctaaggttg gaagtcgtct aatagagtta ctcgtaagaa cagcttatat acagtctcca   1380
gctgatcagc aggataatga tctgcctgat gtccgacctg catttgtgca taccttcaag   1440
gtagcgaaag gaagcatgaa ttctgggaga aaatatggtg taatcgagtg tgaccctttg   1500
gtccgcaaag gcttggaaaa agtgggagag tatgcagtga tgccatacat gccaatgctg   1560
gttcctcctc tcaaatggtc gggatatgac aaaggtgctt acttgttctt gacgtcttat   1620
ataatgaaaa ctcatggagc caagcaacaa agagaggcac ttaagagcgc acctaaagga   1680
caactacaac cagtctttga ggccctggat acgcttggaa gtactaaatg agagtaaat    1740 aagcgagtct taacggttgt agataggata tggagcagtg gcggatgtgt tgctgatatg   1800
gtggatcgga gtgatgttcc tttaccagaa aagccggata ctgaagatga gggcattctt   1860
aagaaatgga agtgggaagt caaatctgct aaaaaggtga acagcgagag acattctcag   1920
cgatgtgaca cagaactcaa gctttcggta gcacggaaaa tgaaagatga ggaagctttt   1980
tactatcccc acaatatgga cttccggggt cgtgcatatc ccatgccccc acacttaaat   2040
catcttggct ctgatttgtg tcggggtgtt ttggagtttg ctgagggaag gcctatggga   2100
atttcaggct tacgctggct gaagatacac ttagcaaact tgtatgctgg tggtgtagat   2160
aagttatcac ttgatggacg gctagctttc actgaaaatc acttggatga catatttgat   2220
tcggcagaca gaccacttga aggaagcaga tggtggctgc aggctgaaga cccatttcag   2280
tgcttggctg tctgcataag tctgactgaa gctctgagaa gcccatcccc agagacagtt   2340
ctgtcacata ttcctataca tcaggatggt tcctgcaatg gtttacagca ttatgccgct   2400
cttgggagag acacattagg agcagaagct gttaatctag ttgcaggtga aagccggca   2460 gatgtttatt caggaatagc taccagggtt cttgatatta tgcgccgaga tgcagacaga   2520
gatcctgaag ttttttccaga ggcattgcgt gcaagaaaat tacttaacca ggtggatcgt   2580
aagcttgtaa agcagacggt tatgacatca gtctatggtg tcacctacat ggcgctcgg    2640 gatcaaataa agagaaggtt gaaggaacga agtgattttg gtgatgaaaa agaagttttt   2700
ggggctgctt gctatgcagc aaaggtaaca ttagctgcta tagatgagat gtttcaagct   2760
gcacgcgcca tcatgcgttg gtttggtgaa tgtgcgaaga ttattgcttc agaaaatgaa   2820
acagttcgat ggacaacccc attgggtctt cctgttgtac aaccttacca ccaaatggga   2880
acaaaactcg taaagacatc cctccagacc ctatcgcttc agcatgaaac tgatcaggtc   2940
```

-continued

```
attgtgaggc gacaaaggac agcttttcct ccaaatttta ttcactccct ggatgggtct    3000
catatgatga tgactgcggt tgcctgtaaa agagcaggcg tgtgttttgc aggagttcat    3060
gactcttttt ggacgcatgc gtgtgatgtg gataaactaa acataatact acgggaaaag    3120
tttgttgagc tgtattcaca accgatacta gagaatttgc tggagagctt tgagcaatcg    3180
tttcctcatt tagactttcc tcctctgcca gaacgaggag atttggattt aaaagtggtg    3240
ttagattcac cttatttctt caactgataa agaaagtaat gtcttccact aagattctca    3300
gacatctctg aagctctcaa gaaacaatat tctttcagaa catagtatca accccaaggc    3360
ttgagctgta cgtgttagat ggacgagaag aaagacaaac ttcttgcaag ggccagaaca    3420
aaagaaaagc tgctgggttt tgtatacaga gacgcagaca gagagaagga gtagaagaaa    3480
tcctttgaat ttacttgtgc tgacgaagct taatgaaacc tcctgagatg agagttgtag    3540
cttctgatct gagagaaatc ccggtttggg agtaccggaa gttggttaga aactatttga    3600
tgtcatgtgt aaacccgtcg gtacactgta gaatagcaag aactgtacca caagccttga    3660
ctggtgttca ctatacgaaa tggattacta ctattaactg agaaactgaa ttggtggaag    3720 ccatttttc acagaaaata tagattgaaa atatatatgt                           3760
```

<210> SEQ ID NO 74
<211> LENGTH: 1011
<212> TYPE: PRT
<213> ORGANISM: Arabidopsis thaliana

<400> SEQUENCE: 74

```
Met Ser Ser Ala Gln Thr Pro Leu Phe Leu Ala Asn Gln Thr Lys Val
1               5                   10                  15

Phe Asp His Leu Ile Pro Leu His Lys Pro Phe Ile Ser Ser Pro Asn
            20                  25                  30

Pro Val Ser Gln Ser Phe Pro Met Trp Arg Asn Ile Ala Lys Gln Ala
        35                  40                  45

Ile Ser Arg Ser Ala Ala Arg Leu Asn Val Ser Ser Gln Thr Arg Gly
    50                  55                  60

Leu Leu Val Ser Ser Pro Glu Ser Ile Phe Ser Lys Asn Leu Ser Phe
65                  70                  75                  80

Arg Phe Pro Val Leu Gly Ser Pro Cys His Gly Lys Gly Phe Arg Cys
                85                  90                  95

Leu Ser Gly Ile Thr Arg Arg Glu Glu Phe Ser Lys Ser Glu Arg Cys
            100                 105                 110

Leu Ser Gly Thr Leu Ala Arg Gly Tyr Thr Ser Val Ala Glu Glu Glu
        115                 120                 125

Val Leu Ser Thr Asp Val Glu Glu Pro Glu Val Asp Glu Leu Leu
    130                 135                 140

Lys Glu Met Lys Lys Glu Lys Lys Arg Glu Ser His Arg Ser Trp Arg
145                 150                 155                 160

Met Lys Lys Gln Asp Gln Phe Gly Met Gly Arg Thr Lys Phe Gln Asn
                165                 170                 175

Leu Trp Arg Arg Gln Val Lys Ile Glu Thr Glu Trp Glu Arg Ala
            180                 185                 190

Ala Ala Glu Tyr Met Glu Leu Leu Thr Asp Met Cys Glu Gln Lys Leu
        195                 200                 205

Ala Pro Asn Leu Pro Tyr Val Lys Ser Leu Phe Leu Gly Trp Phe Glu
    210                 215                 220

Pro Leu Arg Asp Ala Ile Ala Lys Asp Gln Glu Leu Tyr Arg Leu Gly
```

-continued

```
                225                 230                 235                 240
Lys Ser Lys Ala Thr Tyr Ala His Tyr Leu Asp Gln Leu Pro Ala Asp
                245                 250                 255

Lys Ile Ser Val Ile Thr Met His Lys Leu Met Gly His Leu Met Thr
                260                 265                 270

Gly Gly Asp Asn Gly Cys Val Lys Val Val His Ala Ala Cys Thr Val
                275                 280                 285

Gly Asp Ala Ile Glu Gln Glu Ile Arg Ile Cys Thr Phe Leu Asp Lys
                290                 295                 300

Lys Lys Lys Gly Asp Asp Asn Glu Glu Ser Gly Gly Val Glu Asn Glu
305                 310                 315                 320

Thr Ser Met Lys Glu Gln Asp Lys Leu Arg Lys Lys Val Asn Glu Leu
                325                 330                 335

Ile Lys Lys Gln Lys Leu Ser Ala Val Arg Lys Ile Leu Gln Ser His
                340                 345                 350

Asp Tyr Thr Lys Pro Trp Ile Ala Asp Val Arg Ala Lys Val Gly Ser
                355                 360                 365

Arg Leu Ile Glu Leu Leu Val Arg Thr Ala Tyr Ile Gln Ser Pro Ala
                370                 375                 380

Asp Gln Gln Asp Asn Asp Leu Pro Asp Val Arg Pro Ala Phe Val His
385                 390                 395                 400

Thr Phe Lys Val Ala Lys Gly Ser Met Asn Ser Gly Arg Lys Tyr Gly
                405                 410                 415

Val Ile Glu Cys Asp Pro Leu Val Arg Lys Gly Leu Glu Lys Ser Gly
                420                 425                 430

Arg Tyr Ala Val Met Pro Tyr Met Pro Met Leu Val Pro Pro Leu Lys
                435                 440                 445

Trp Ser Gly Tyr Asp Lys Gly Ala Tyr Leu Phe Leu Thr Ser Tyr Ile
                450                 455                 460

Met Lys Thr His Gly Ala Lys Gln Gln Arg Glu Ala Leu Lys Ser Ala
465                 470                 475                 480

Pro Lys Gly Gln Leu Gln Pro Val Phe Glu Ala Leu Asp Thr Leu Gly
                485                 490                 495

Ser Thr Lys Trp Arg Val Asn Lys Arg Val Leu Thr Val Val Asp Arg
                500                 505                 510

Ile Trp Ser Ser Gly Gly Cys Val Ala Asp Met Val Asp Arg Ser Asp
                515                 520                 525

Val Pro Leu Pro Glu Lys Pro Asp Thr Glu Asp Glu Gly Ile Leu Lys
                530                 535                 540

Lys Trp Lys Trp Glu Val Lys Ser Ala Lys Lys Val Asn Ser Glu Arg
545                 550                 555                 560

His Ser Gln Arg Cys Asp Thr Glu Leu Lys Leu Ser Val Ala Arg Lys
                565                 570                 575

Met Lys Asp Glu Glu Ala Phe Tyr Tyr Pro His Asn Met Asp Phe Arg
                580                 585                 590

Gly Arg Ala Tyr Pro Met Pro Pro His Leu Asn His Leu Gly Ser Asp
                595                 600                 605

Leu Cys Arg Gly Val Leu Glu Phe Ala Glu Gly Arg Pro Met Gly Ile
                610                 615                 620

Ser Gly Leu Arg Trp Leu Lys Ile His Leu Ala Asn Leu Tyr Ala Gly
625                 630                 635                 640

Gly Val Asp Lys Leu Ser Leu Asp Gly Arg Leu Ala Phe Thr Glu Asn
                645                 650                 655
```

His Leu Asp Asp Ile Phe Asp Ser Ala Asp Arg Pro Leu Glu Gly Ser
            660                 665                 670

Arg Trp Trp Leu Gln Ala Glu Asp Pro Phe Gln Cys Leu Ala Val Cys
        675                 680                 685

Ile Ser Leu Thr Glu Ala Leu Arg Ser Pro Ser Pro Glu Thr Val Leu
    690                 695                 700

Ser His Ile Pro Ile His Gln Asp Gly Ser Cys Asn Gly Leu Gln His
705                 710                 715                 720

Tyr Ala Ala Leu Gly Arg Asp Thr Leu Gly Ala Glu Ala Val Asn Leu
                725                 730                 735

Val Ala Gly Glu Lys Pro Ala Asp Val Tyr Ser Gly Ile Ala Thr Arg
            740                 745                 750

Val Leu Asp Ile Met Arg Arg Asp Ala Asp Arg Asp Pro Glu Val Phe
        755                 760                 765

Pro Glu Ala Leu Arg Ala Arg Lys Leu Leu Asn Gln Val Asp Arg Lys
    770                 775                 780

Leu Val Lys Gln Thr Val Met Thr Ser Val Tyr Gly Val Thr Tyr Ile
785                 790                 795                 800

Gly Ala Arg Asp Gln Ile Lys Arg Arg Leu Lys Glu Arg Ser Asp Phe
                805                 810                 815

Gly Asp Glu Lys Glu Val Phe Gly Ala Ala Cys Tyr Ala Ala Lys Val
            820                 825                 830

Thr Leu Ala Ala Ile Asp Glu Met Phe Gln Ala Ala Arg Ala Ile Met
        835                 840                 845

Arg Trp Phe Gly Glu Cys Ala Lys Ile Ile Ala Ser Glu Asn Glu Thr
    850                 855                 860

Val Arg Trp Thr Thr Pro Leu Gly Leu Pro Val Val Gln Pro Tyr His
865                 870                 875                 880

Gln Met Gly Thr Lys Leu Val Lys Thr Ser Leu Gln Thr Leu Ser Leu
                885                 890                 895

Gln His Glu Thr Asp Gln Val Ile Val Arg Arg Gln Arg Thr Ala Phe
            900                 905                 910

Pro Pro Asn Phe Ile His Ser Leu Asp Gly Ser His Met Met Met Thr
        915                 920                 925

Ala Val Ala Cys Lys Arg Ala Gly Val Cys Phe Ala Gly Val His Asp
    930                 935                 940

Ser Phe Trp Thr His Ala Cys Asp Val Asp Lys Leu Asn Ile Ile Leu
945                 950                 955                 960

Arg Glu Lys Phe Val Glu Leu Tyr Ser Gln Pro Ile Leu Glu Asn Leu
                965                 970                 975

Leu Glu Ser Phe Glu Gln Ser Phe Pro His Leu Asp Phe Pro Pro Leu
            980                 985                 990

Pro Glu Arg Gly Asp Leu Asp Leu  Lys Val Val Leu Asp  Ser Pro Tyr
        995                 1000                1005

Phe Phe  Asn
     1010

<210> SEQ ID NO 75
<211> LENGTH: 1880
<212> TYPE: DNA
<213> ORGANISM: Arabidopsis thaliana

<400> SEQUENCE: 75
atctctctct tcttcgtgtt actaaaaagg acgaagcttg ttgcataata tgttgaggta      60
aattactaat tactgatcca aagttcgaat ctttgctcca actccaggct agctgattgc     120

```
gtagcttccg attgatttct acctgagttt tgagttcctt tgtggccact tcgttgttct    180
tctgctgggt tttttgctcg aggatctgat acttctgttt ggtcgatgat cgagtgatct    240
tcgttgggtt ttggggatct aagtcgtcta tatagctaat ggtttggatt tgagtttgaa    300
tggagcgttt aggattttgg ggattgctaa tgggtagtgt ggaaaagtca ttggattctg    360
gaaattcgtt ggcttgctct gcatctgcta agaatggaga cgaagagagt agtacttcat    420
cgaagcaagt ttcaccattg aagggttctg ggtcgagaaa tactagtcct ttaggtcgag    480
ttgggtcgag aaacacgagt ccttctaggc agaaagtggt gaagacgaag cctcgtggtc    540
tagaggaaga aacagttgct tcatttggta acaagttgt tgctgatgtg cagatggaag     600
atggtatatg ggcaatgctt ccagaggatt tgctcaatga gatttagct agggttccac     660
cgtttatgat atttcgaatc cggtctgttt gtaaaaaatg gaacttgatt cttcaggata    720
atagtttct caagtttcac tcaaatgtgt catctcatgg gccttgtctt ctcactttct     780
ggaagaactc gccgcagatt ccgcaatgct cagttttag tttgccattg aagacatggt      840
acaaaattcc attcacgttt ttgcctccat gggcttttg gttggttggt tcttcaggtg     900
gtctcgtttg ttttcgggt cttgatggtc taactttcag aactttagta tgcaatcctc      960
tgatgcagag ttggaggact ctaccgagta tgcactataa ccaacaaagg caattgatta    1020
tggtcgtgga tcgctcagac aaatcgttca aagtcatagc cacaagtgat atatacgggg    1080
ataagtcact tcctactgaa gttatgatt ccaaaactga caaatggtcc ttacatcaga     1140
taatgcctgc ggtgaactta tgctcctcga aatggcttta tgtgattcc cggttatatc     1200
tagaaactct ttcgcctctt ggtttgatga tgtatcggct tgattcaggg caatgggaac    1260
acattccagc taaaattccg agatctttgt tggatggtta cttagttgct ggaactcaga    1320
agagattgtt tctcgtggga aggattggcc tctacagtac tctccaaagc atgagaatat    1380
gggagcttga tcacacaaag gtctcttggg tagagataag tagaatgcca ccaaagtact    1440
tccgagcact tctgagactt tcggctgaga ggttcgagtg ttttggacaa gataatttga    1500
tctgctttac gtcttggaat caaggaaaag gtcttctata caatgtggat aagaaaattt    1560
ggtcttggat ttccggttgt gctcttcagt catgcaacag ccaagtgtgc ttttatgagc    1620
caagatttga tgcatctgtc ctctgaacaa taagttatcg tctgtctcac atcattcttg    1680
aaaacttaca agttcgccag caaaacatgt cagaaatatg aaatcaaaga gggtttgatg    1740
tgtaccttca gtgttaatga agacctggtc agcaatgata tgcttcacca atggttaaca    1800
atatcgagga gaaaaactgt aagataaact tgtttctagc tttctgtaaa ttagcattca    1860
ctcgatatga aaactttctc                                                1880

<210> SEQ ID NO 76
<211> LENGTH: 448
<212> TYPE: PRT
<213> ORGANISM: Arabidopsis thaliana

<400> SEQUENCE: 76

Met Glu Arg Leu Gly Phe Trp Gly Leu Leu Met Gly Ser Val Glu Lys
1               5                   10                  15

Ser Leu Asp Ser Gly Asn Ser Leu Ala Cys Ser Ala Ser Ala Lys Asn
            20                  25                  30

Gly Asp Glu Glu Ser Ser Thr Ser Ser Lys Gln Val Ser Pro Leu Lys
        35                  40                  45

Gly Ser Gly Ser Arg Asn Thr Ser Pro Leu Gly Arg Val Gly Ser Arg
    50                  55                  60
```

Asn Thr Ser Pro Ser Arg Gln Lys Val Val Lys Thr Lys Pro Arg Gly
 65                  70                  75                  80

Leu Glu Glu Glu Thr Val Ala Ser Phe Gly Lys Gln Val Val Ala Asp
                 85                  90                  95

Val Gln Met Glu Asp Gly Ile Trp Ala Met Leu Pro Glu Asp Leu Leu
            100                 105                 110

Asn Glu Ile Leu Ala Arg Val Pro Pro Phe Met Ile Phe Arg Ile Arg
        115                 120                 125

Ser Val Cys Lys Lys Trp Asn Leu Ile Leu Gln Asp Asn Ser Phe Leu
    130                 135                 140

Lys Phe His Ser Asn Val Ser Ser His Gly Pro Cys Leu Leu Thr Phe
145                 150                 155                 160

Trp Lys Asn Ser Pro Gln Ile Pro Gln Cys Ser Val Phe Ser Leu Pro
                165                 170                 175

Leu Lys Thr Trp Tyr Lys Ile Pro Phe Thr Phe Leu Pro Pro Trp Ala
            180                 185                 190

Phe Trp Leu Val Gly Ser Ser Gly Leu Val Cys Phe Ser Gly Leu
        195                 200                 205

Asp Gly Leu Thr Phe Arg Thr Leu Val Cys Asn Pro Leu Met Gln Ser
    210                 215                 220

Trp Arg Thr Leu Pro Ser Met His Tyr Asn Gln Gln Arg Gln Leu Ile
225                 230                 235                 240

Met Val Val Asp Arg Ser Asp Lys Ser Phe Lys Val Ile Ala Thr Ser
                245                 250                 255

Asp Ile Tyr Gly Asp Lys Ser Leu Pro Thr Glu Val Tyr Asp Ser Lys
            260                 265                 270

Thr Asp Lys Trp Ser Leu His Gln Ile Met Pro Ala Val Asn Leu Cys
        275                 280                 285

Ser Ser Lys Met Ala Tyr Cys Asp Ser Arg Leu Tyr Leu Glu Thr Leu
    290                 295                 300

Ser Pro Leu Gly Leu Met Met Tyr Arg Leu Asp Ser Gly Gln Trp Glu
305                 310                 315                 320

His Ile Pro Ala Lys Phe Pro Arg Ser Leu Leu Asp Gly Tyr Leu Val
                325                 330                 335

Ala Gly Thr Gln Lys Arg Leu Phe Leu Val Gly Arg Ile Gly Leu Tyr
            340                 345                 350

Ser Thr Leu Gln Ser Met Arg Ile Trp Glu Leu Asp His Thr Lys Val
        355                 360                 365

Ser Trp Val Glu Ile Ser Arg Met Pro Pro Lys Tyr Phe Arg Ala Leu
    370                 375                 380

Leu Arg Leu Ser Ala Glu Arg Phe Glu Cys Phe Gly Gln Asp Asn Leu
385                 390                 395                 400

Ile Cys Phe Thr Ser Trp Asn Gln Gly Lys Gly Leu Leu Tyr Asn Val
                405                 410                 415

Asp Lys Lys Ile Trp Ser Trp Ile Ser Gly Cys Ala Leu Gln Ser Cys
            420                 425                 430

Asn Ser Gln Val Cys Phe Tyr Glu Pro Arg Phe Asp Ala Ser Val Leu
        435                 440                 445

<210> SEQ ID NO 77
<211> LENGTH: 1280
<212> TYPE: DNA
<213> ORGANISM: Arabidopsis thaliana

<400> SEQUENCE: 77

| | | |
|---|---|---|
| gaaagagata aagatagtaa ccaagcatga aaagtttgtt gatttgtctt gtgttgttag | 60 |
| agcttgtctg gttaggcaat ggccaatcta gagatcatca acctcttgct ccagctttct | 120 |
| ttgtctttgg agattcttta gttgatagtg gaaacaacaa ttacattcca actcttgcac | 180 |
| gagctaatta tttcccttat ggaattgatt ttggcttccc cactggtcgt ttctgcaatg | 240 |
| gccgtaccgt tgttgattat ggagcaacgt acctcggctt gccattggtg ccaccatact | 300 |
| tatctccttt atccattggg caaaatgcct tacgaggggt taactacgca tctgcagcag | 360 |
| ctgggatttt agatgaaacc ggtcgacatt atggagcaag aactacattt aatggacaga | 420 |
| tatcgcagtt tgagattacg atcgagttac gcctccggcg tttctttcaa accctgcag | 480 |
| atctgagaaa gtatcttgca aaatcgataa ttgggatcaa tataggaagc aatgactata | 540 |
| tcaacaacta ccttatgcct gagagatact ccaccagcca aacctacagt ggagaagatt | 600 |
| atgcagatct cttgatcaag actctctcag ctcaaatatc cagactatac aacttaggtg | 660 |
| caagaaaaat ggtgttagct gggtcaggac cattaggttg catacctagt cagctatcta | 720 |
| tggtaactgg caacaacacc agcgggtgtg tgacaaaaat caacaatatg gtttcaatgt | 780 |
| tcaatagccg tctgaaagat ctagcaaata ctctcaacac aactctgcca ggatctttct | 840 |
| ttgtctatca aaacgtcttt gatctatttc atgatatggt tgtgaatcct tctagatatg | 900 |
| gtcttgtagt atcaaacgaa gcgtgctgcg gtaacgggag atatggagga gccttaacat | 960 |
| gccttccatt gcagcaacct tgcttggata ggaatcaata tgtcttttgg gatgcatttc | 1020 |
| atccaacaga aactgccaac aaaataatag ctcacaatac cttcagcaag ctgcaaaact | 1080 |
| actcctaccc tatcagtgtc tatgaattag ctaaattgta gagaaatgta tctcaaagct | 1140 |
| agattacctc cccatttcaa gagtctcctc ggttttctag tttctagtta gaagacatta | 1200 |
| agtatgggat ttgtatgtac caattgccca aatgtttaag atcacatcta tattccaatg | 1260 |
| ttataactta aaactttctc | 1280 |

<210> SEQ ID NO 78
<211> LENGTH: 364
<212> TYPE: PRT
<213> ORGANISM: Arabidopsis thaliana

<400> SEQUENCE: 78

```
Met Lys Ser Leu Leu Ile Cys Leu Val Leu Glu Leu Val Trp Leu
1               5                   10                  15

Gly Asn Gly Gln Ser Arg Asp His Gln Pro Leu Ala Pro Ala Phe Phe
            20                  25                  30

Val Phe Gly Asp Ser Leu Val Asp Ser Gly Asn Asn Asn Tyr Ile Pro
        35                  40                  45

Thr Leu Ala Arg Ala Asn Tyr Phe Pro Tyr Gly Ile Asp Phe Gly Phe
    50                  55                  60

Pro Thr Gly Arg Phe Cys Asn Gly Arg Thr Val Val Asp Tyr Gly Ala
65                  70                  75                  80

Thr Tyr Leu Gly Leu Pro Leu Val Pro Pro Tyr Leu Ser Pro Leu Ser
                85                  90                  95

Ile Gly Gln Asn Ala Leu Arg Gly Val Asn Tyr Ala Ser Ala Ala Ala
            100                 105                 110

Gly Ile Leu Asp Glu Thr Gly Arg His Tyr Gly Ala Arg Thr Thr Phe
        115                 120                 125

Asn Gly Gln Ile Ser Gln Phe Glu Ile Thr Ile Glu Leu Arg Leu Arg
    130                 135                 140
```

```
Arg Phe Phe Gln Asn Pro Ala Asp Leu Arg Lys Tyr Leu Ala Lys Ser
145                 150                 155                 160

Ile Ile Gly Ile Asn Ile Gly Ser Asn Asp Tyr Ile Asn Asn Tyr Leu
            165                 170                 175

Met Pro Glu Arg Tyr Ser Thr Ser Gln Thr Tyr Ser Gly Glu Asp Tyr
        180                 185                 190

Ala Asp Leu Leu Ile Lys Thr Leu Ser Ala Gln Ile Ser Arg Leu Tyr
        195                 200                 205

Asn Leu Gly Ala Arg Lys Met Val Leu Ala Gly Ser Gly Pro Leu Gly
210                 215                 220

Cys Ile Pro Ser Gln Leu Ser Met Val Thr Gly Asn Asn Thr Ser Gly
225                 230                 235                 240

Cys Val Thr Lys Ile Asn Asn Met Val Ser Met Phe Asn Ser Arg Leu
                245                 250                 255

Lys Asp Leu Ala Asn Thr Leu Asn Thr Thr Leu Pro Gly Ser Phe Phe
                260                 265                 270

Val Tyr Gln Asn Val Phe Asp Leu Phe His Asp Met Val Asn Pro
        275                 280                 285

Ser Arg Tyr Gly Leu Val Val Ser Asn Glu Ala Cys Cys Gly Asn Gly
290                 295                 300

Arg Tyr Gly Gly Ala Leu Thr Cys Leu Pro Leu Gln Gln Pro Cys Leu
305                 310                 315                 320

Asp Arg Asn Gln Tyr Val Phe Trp Asp Ala Phe His Pro Thr Glu Thr
                325                 330                 335

Ala Asn Lys Ile Ile Ala His Asn Thr Phe Ser Lys Ser Ala Asn Tyr
            340                 345                 350

Ser Tyr Pro Ile Ser Val Tyr Glu Leu Ala Lys Leu
            355                 360

<210> SEQ ID NO 79
<211> LENGTH: 485
<212> TYPE: DNA
<213> ORGANISM: Arabidopsis thaliana

<400> SEQUENCE: 79
aaggtcaagt attgaagaac tgataaatac tttacaaaag caacgcaact acttttcagt      60
acaaacgacc aaggatataa tatgaagaag acgagtttga agttaatgac cctcgtttta     120
gggttttgct tcgtcattta tcttcttcaa gggcctcgag gcggttcgag aaatggagat     180
ctcttgatag cacgaaagtt gatatctctg gaaccgattg aaacaaaaaa tgcagcgaga     240
tcgttgaaag attcaatatc aacagattta gaggaagagg ttgatcgtct gatggagcac     300
gaatatcctt caccagtaaa gccgaggaaa agaactccgg ttcacaatgg cgtgcgtaat     360
cgtcactaat tgacccttgt tctattgttc tttcaattag tagtttaata agtttggtaa     420
aatcataaaa tggacgtatc ctgtaatgct gaatattagt atattactta tacaaagact     480
ttatc                                                                485

<210> SEQ ID NO 80
<211> LENGTH: 95
<212> TYPE: PRT
<213> ORGANISM: Arabidopsis thaliana

<400> SEQUENCE: 80

Met Lys Lys Thr Ser Leu Lys Leu Met Thr Leu Val Leu Gly Phe Cys
1               5                   10                  15

Phe Val Ile Tyr Leu Leu Gln Gly Pro Arg Gly Gly Ser Arg Asn Gly
```

```
                    20                  25                  30

Asp Leu Leu Ile Ala Arg Lys Leu Ile Ser Leu Glu Pro Ile Glu Thr
            35                  40                  45

Lys Asn Ala Ala Arg Ser Leu Lys Asp Ser Ile Ser Thr Asp Leu Glu
 50                  55                  60

Glu Glu Val Asp Arg Leu Met Glu His Glu Tyr Pro Ser Pro Val Lys
 65                  70                  75                  80

Pro Arg Lys Arg Thr Pro Val His Asn Gly Val Arg Asn Arg His
                85                  90                  95

<210> SEQ ID NO 81
<211> LENGTH: 1615
<212> TYPE: DNA
<213> ORGANISM: Arabidopsis thaliana

<400> SEQUENCE: 81
atgtagattt gactttgttt caaagcggag gaagaaggag aaggcaacac taaaagatca        60
aaaccttaga tctttgctta cgctttcgcc tggttaggaa cggttttttca gaaacaaaag      120 attccatttt tagattcaat tcccttctgg tttgaaaaat gatatcaaaa tggtgaatag      180
aagtgatttg gtggtgattg gcatctcggt tgggcttgca cttggtctct tgctcgctct      240
gcttttgttc ttcgccataa aatggtacta tggccgctct cacctcaggc gatgcgctaa      300
tgaacagaat tccccgactc tacctgttca cactgctaaa agaggtgtag taatccctga      360
tgatagagca aacacagaat cgtcacagcc acctgagaat ggagcaccaa ctcaacatca      420
gccatggtgg aacaaccaca ccaaagatct cactgtatct gcatccggca tacctagata      480
taactacaag gatattcaga aagcaacaca aaatttcaca accgttctag acaaggatc       540 ttttggtcct gtctacaaag cggttatgcc caatggagaa ttagctgcag cgaaagttca      600
tggctctaat tcaagtcaag gagacagaga gtttcaaacc gaggtatctt tacttgggag      660
actgcatcac cggaatcttg tgaacttgac aggatactgt gtcgataaaa gtcaccggat      720
gttgatctat gagttcatga gtaatggaag tttggagaat cttttgtatg gcggaatgca      780
agtcttgaat tgggaagagc ggcttcaaat cgctcttgac atctcccacg cattgaata       840 ccttcacgaa ggggccgtac cgccagttat tcaccgtgat cttaagtcag caaacatttt      900
gttagatcat tccatgagag ctaaggtcgc ggatttcggg ttgtcgaaag atggttttt      960 agatagaatg acttccggat tgaagggtac tcacggctac atggatccaa catacatttc     1020
gactaacaaa tacacgatga agagcgacat ttacagtttc ggtgtcatca ttcttgagct     1080
cattactgca atccatcccc aacagaatct gatggaatac atcaacctgg cttcgatgag     1140
tccagatggt atcgacgaaa tactcgatca gaaactagtg ggaaacgcaa gcattgaaga     1200
agtgaggtta ctggcgaaga ttgcaaacag gtgtgtgcat aagacaccaa gaaaaagacc     1260
atctattgga gaagtaacac agttcatact aaagatcaaa caaagtcggt ctcgaggaag     1320
aagacaggac acgatgtctt catcgtttgg tgttggttat gaggaagatc tgtcaagggt     1380
tatgagcagg attaaggatc agcatgttga gttaggggtta ttggctggtg ttaaggaaga     1440
gaatcatcaa gagaggaaca ttgcaacaac atagtaactc tttactttag gagtaagtct     1500
ttttgtacat attaccacat gagtctcaaa agtaagattt ctccctcttc tgcaaaaga      1560 aaagagtttt tgcttgctga caacaacaac aaaaatttga ggttatgtta taaag          1615

<210> SEQ ID NO 82
<211> LENGTH: 434
<212> TYPE: PRT
```

<213> ORGANISM: Arabidopsis thaliana

<400> SEQUENCE: 82

```
Met Val Asn Arg Ser Asp Leu Val Val Ile Gly Ile Ser Val Gly Leu
1               5                   10                  15

Ala Leu Gly Leu Leu Ala Leu Leu Leu Phe Phe Ala Ile Lys Trp
            20                  25                  30

Tyr Tyr Gly Arg Ser His Leu Arg Arg Cys Ala Asn Glu Gln Asn Ser
            35                  40                  45

Pro Thr Leu Pro Val His Thr Ala Lys Arg Gly Val Val Ile Pro Asp
    50                  55                  60

Asp Arg Ala Asn Thr Glu Ser Ser Gln Pro Pro Glu Asn Gly Ala Pro
65                  70                  75                  80

Thr Gln His Gln Pro Trp Trp Asn Asn His Thr Lys Asp Leu Thr Val
                85                  90                  95

Ser Ala Ser Gly Ile Pro Arg Tyr Asn Tyr Lys Asp Ile Gln Lys Ala
            100                 105                 110

Thr Gln Asn Phe Thr Thr Val Leu Gly Gln Gly Ser Phe Gly Pro Val
        115                 120                 125

Tyr Lys Ala Val Met Pro Asn Gly Glu Leu Ala Ala Lys Val His
    130                 135                 140

Gly Ser Asn Ser Ser Gln Gly Asp Arg Glu Phe Gln Thr Glu Val Ser
145                 150                 155                 160

Leu Leu Gly Arg Leu His His Arg Asn Leu Val Asn Leu Thr Gly Tyr
                165                 170                 175

Cys Val Asp Lys Ser His Arg Met Leu Ile Tyr Glu Phe Met Ser Asn
            180                 185                 190

Gly Ser Leu Glu Asn Leu Leu Tyr Gly Gly Met Gln Val Leu Asn Trp
        195                 200                 205

Glu Glu Arg Leu Gln Ile Ala Leu Asp Ile Ser His Gly Ile Glu Tyr
    210                 215                 220

Leu His Glu Gly Ala Val Pro Pro Val Ile His Arg Asp Leu Lys Ser
225                 230                 235                 240

Ala Asn Ile Leu Leu Asp His Ser Met Arg Ala Lys Val Ala Asp Phe
                245                 250                 255

Gly Leu Ser Lys Glu Met Val Leu Asp Arg Met Thr Ser Gly Leu Lys
            260                 265                 270

Gly Thr His Gly Tyr Met Asp Pro Thr Tyr Ile Ser Thr Asn Lys Tyr
        275                 280                 285

Thr Met Lys Ser Asp Ile Tyr Ser Phe Gly Val Ile Ile Leu Glu Leu
    290                 295                 300

Ile Thr Ala Ile His Pro Gln Gln Asn Leu Met Glu Tyr Ile Asn Leu
305                 310                 315                 320

Ala Ser Met Ser Pro Asp Gly Ile Asp Glu Ile Leu Asp Gln Lys Leu
                325                 330                 335

Val Gly Asn Ala Ser Ile Glu Glu Val Arg Leu Leu Ala Lys Ile Ala
            340                 345                 350

Asn Arg Cys Val His Lys Thr Pro Arg Lys Arg Pro Ser Ile Gly Glu
        355                 360                 365

Val Thr Gln Phe Ile Leu Lys Ile Lys Gln Ser Arg Ser Arg Gly Arg
    370                 375                 380

Arg Gln Asp Thr Met Ser Ser Ser Phe Gly Val Gly Tyr Glu Glu Asp
385                 390                 395                 400

Leu Ser Arg Val Met Ser Arg Ile Lys Asp Gln His Val Glu Leu Gly
```

```
                            405                 410                 415
Leu Leu Ala Gly Val Lys Glu Glu Asn His Gln Glu Arg Asn Ile Ala
                420                 425                 430

Thr Thr

<210> SEQ ID NO 83
<211> LENGTH: 1290
<212> TYPE: DNA
<213> ORGANISM: Arabidopsis thaliana

<400> SEQUENCE: 83
atgctaaaat gtgtttctgt ccaaattcaa accagttttg tcttgtcttg tcttcttctt       60
cttcagagca ttgcaatgaa agttccagat tcttcttcac cgaccggagt tctcgaagaa      120
ttcttcagaa ccgaagaatt caatagctcc tccgagacgg tcaagaaccc ttcctcttct      180
cgtttccgca agatggttca gcttctcaga agcaaatcca aaaagtctct tgagaatgtc      240
aagattccgt ttcacaacaa tggtgttatt aagagttctt ttagaagatg cagtagcatg      300
agagaaaatc tcagatttag ctccaatgat tctcactttc ttctacattc tcctagaaga      360
atcttcacct tctctgacct caagtctgct acaaacaatt tctctttaga aaatctaatt      420
gggaaaggag ttatgctgaa gtttacaaa gggatgttac caaatggaca atggtagcg       480 ataaaacggt tgatgcgggg aaatagtgaa agatcattg tagactttct tcggagatg       540 ggtataatgg cacatgttaa ccatcccaac atagctaagc ttttaggcta tggagttgaa      600
ggaggaatgc atcttgttct tgagttatca cctcatggca gcttagcttc tatgctctat      660
agctccaagg agaagatgaa atggagcatt aggtacaaga tagcattagg agttgcggag      720
ggtctagtgt atcttcatag aggatgtcat aggagaatta tacatagaga tatcaaagcc      780
gcaaacattc ttctcacaca tgatttttct cctcagatat gtgactttgg gcttgcgaag      840
tggttacctg aaaattggac acaccacatt gtttccaaat ttgagggcac attcgggtat      900
cttgctccag agtacttaac acatgggata gtagatgaaa agaccgatgt attcgccttg      960
ggtgtacttt tactggaact tgttaccgga cgacgagctc tcgattactc caagcaaagt     1020
cttgttctat gggctaaacc attgatgaag aagaacaaaa ttagagagct aatcgatcca     1080
tctctggcgg tgagtacga atggaggcag ataaaacttg tgcttttggc tgctgcgtta     1140
tcaatccaac aatcatcgat agagaggcct gaaatgagtc aggttgttga gatcctcaaa     1200
ggcaacttga agatctcaa gtgcatcatg aaatgcagag ttcccttta taggaaagct      1260 ttcagggatg aagttggcaa aaaagattag                                       1290

<210> SEQ ID NO 84
<211> LENGTH: 429
<212> TYPE: PRT
<213> ORGANISM: Arabidopsis thaliana

<400> SEQUENCE: 84

Met Leu Lys Cys Val Ser Val Gln Ile Gln Thr Ser Phe Val Leu Ser
1               5                   10                  15

Cys Leu Leu Leu Gln Ser Ile Ala Met Lys Val Pro Asp Ser Ser
                20                  25                  30

Ser Pro Thr Gly Val Leu Glu Glu Phe Phe Arg Thr Glu Glu Phe Asn
            35                  40                  45

Ser Ser Ser Glu Thr Val Lys Asn Pro Ser Ser Arg Phe Arg Lys
        50                  55                  60

Met Val Gln Leu Leu Arg Ser Lys Ser Lys Lys Ser Leu Glu Asn Val
```

```
                65                  70                  75                  80
Lys Ile Pro Phe His Asn Asn Gly Val Ile Lys Ser Ser Phe Arg Arg
                85                  90                  95

Cys Ser Ser Met Arg Glu Asn Leu Arg Phe Ser Ser Asn Asp Ser His
                100                 105                 110

Phe Leu Leu His Ser Pro Arg Arg Ile Phe Thr Phe Ser Asp Leu Lys
                115                 120                 125

Ser Ala Thr Asn Asn Phe Ser Leu Glu Asn Leu Ile Gly Lys Gly Gly
                130                 135                 140

Tyr Ala Glu Val Tyr Lys Gly Met Leu Pro Asn Gly Gln Met Val Ala
145                 150                 155                 160

Ile Lys Arg Leu Met Arg Gly Asn Ser Glu Glu Ile Ile Val Asp Phe
                165                 170                 175

Leu Ser Glu Met Gly Ile Met Ala His Val Asn His Pro Asn Ile Ala
                180                 185                 190

Lys Leu Leu Gly Tyr Gly Val Glu Gly Gly Met His Leu Val Leu Glu
                195                 200                 205

Leu Ser Pro His Gly Ser Leu Ala Ser Met Leu Tyr Ser Ser Lys Glu
                210                 215                 220

Lys Met Lys Trp Ser Ile Arg Tyr Lys Ile Ala Leu Gly Val Ala Glu
225                 230                 235                 240

Gly Leu Val Tyr Leu His Arg Gly Cys His Arg Ile Ile His Arg
                245                 250                 255

Asp Ile Lys Ala Ala Asn Ile Leu Leu Thr His Asp Phe Ser Pro Gln
                260                 265                 270

Ile Cys Asp Phe Gly Leu Ala Lys Trp Leu Pro Glu Asn Trp Thr His
                275                 280                 285

His Ile Val Ser Lys Phe Glu Gly Thr Phe Gly Tyr Leu Ala Pro Glu
                290                 295                 300

Tyr Leu Thr His Gly Ile Val Asp Glu Lys Thr Asp Val Phe Ala Leu
305                 310                 315                 320

Gly Val Leu Leu Leu Glu Leu Val Thr Gly Arg Arg Ala Leu Asp Tyr
                325                 330                 335

Ser Lys Gln Ser Leu Val Leu Trp Ala Lys Pro Leu Met Lys Lys Asn
                340                 345                 350

Lys Ile Arg Glu Leu Ile Asp Pro Ser Leu Ala Gly Glu Tyr Glu Trp
                355                 360                 365

Arg Gln Ile Lys Leu Val Leu Leu Ala Ala Ala Leu Ser Ile Gln Gln
                370                 375                 380

Ser Ser Ile Glu Arg Pro Glu Met Ser Gln Val Val Glu Ile Leu Lys
385                 390                 395                 400

Gly Asn Leu Lys Asp Leu Lys Cys Ile Met Lys Cys Arg Val Pro Phe
                405                 410                 415

Tyr Arg Lys Ala Phe Arg Asp Glu Val Gly Lys Lys Asp
                420                 425

<210> SEQ ID NO 85
<211> LENGTH: 3314
<212> TYPE: DNA
<213> ORGANISM: Arabidopsis thaliana

<400> SEQUENCE: 85
tttcaccaaa aaatgaaaca aaataaaaa tatttctgag aacctcaagt ttaattttgc     60
ggcttagatt taaattcgtc tctcaaactc aaatatctga aaaaaccttt ctccaatata    120
```

```
taaataagtt acacgagact ttcaatttct ctgtatattt tccttttgat tcccagaaaa    180
tgtcactaga ttccactttc tagcttgcgt tttctcggga atctgaagtt tccttttgtg    240
ttgaatcgct gggaaaaatc tgatggaagc agcttcaagt tttttgtgta aagtattcg     300
gattccgtcg actactacgg cgacggcggc gttcacgttc actcgaccgc cgttaaacta    360
cgtttgtgtt gtcggagttc gtgttttccc gacgcggaag gtcttttgca gcggcgttaa    420
tggcggctcc agtgttacta agaagaagcc acgaaggaaa agtaacgttt ccgataaact    480
taggtttaag aaaattgaga gaggaacga taatactgaa tctgagagtt aagtgttgt     540
tgaggaaccg aagaacgata aagaattgag tcttcgagct ttgaatcaaa atggtgatcc    600
attagggcgg agagatttag ggaggaacgt agtgaagtgg attagtcagg cgatgaaagc    660
gatggcttcg gattttgcaa ctgcggaggt tcaggggga ttttcggagt tgaggcagaa     720
cgtcggatct ggtttgacgt tgtgattca agctcaaccg tatctcaatg ctattcccat     780
gccattaggt tctgaagtca tttgtttgaa ggcttgtact cattatccta ccttgttcga    840
tcatttccag agagagttgc gtgatgttct tcaagacctg gagcggaaga atataatgga    900
gagttggaag gagtctgagt cttggaagct gctcaaggag attgcaaatt cagctcagca    960
tcgggaggtt gctcgcaaag ctgctcaagc taagcctgtt caaggagttt tggggatgga   1020
ctcagagaag gtgaaggcta tacaggaaag gattgatgag ttcaccagcc agatgtcgca   1080
gttacttcaa gtggaacgag atacagaact ggaagttaca caggaagaac tagatgttgt   1140
tcctactcca gatgagagct ctgattcctc aaaaccgatt gagttcttgg ttaggcatgg   1200
tgatgctcca caggaacttt gtgatacaat ttgcaattt tatgcagtta gtacctccac    1260
agggctcgga ggtatgcact ggtgttgtt taaggttggg ggaaaccacc gtcttcctcc    1320
tactacactt tccctggtg acatggtttg cataagagtt tgtgacagta ggggtgctgg    1380
ggcaactgcc tgtacgcagg gctttgttca caaccttgga gaagatgggt gtagcattgg   1440
tgtggctcta gaatctcgtc atggagatcc tactttttcc aagctctttg aaagagtgt   1500
gagaattgat cgtattcatg gttggccga tgcccttact tacgagcgta actgcgaagc    1560
cctaatgctt ctgcagaaga atggtctgca gaagaaaaat ccatcaatat ctgttgtggc   1620
gactttatt ggggatggtg aagatataac atggctggag caaatgatt atgtagactg     1680
gagtgaagcg gagttgagtg atgagccagt gagtaagtta tttgattctt cccaaaggag   1740
agccatagct cttggagtaa acaaaaaag acctgttatg atagtccaag gacctcctgg    1800
cacgggaaag actggaatgc ttaaggaggt cattaccctg gctgttcaac agggggaaag   1860
agtacttgta acagcgccta ctaatgcagc tgttgataac atggtcgaga agctcttgca   1920
tcttggacta acattgtcc gagtaggaaa tcccgctaga atatcatctg ctgttgcttc     1980
aaagtctttg ggaaattg tgaactctaa gcttgcaagc ttccgagcag aattggaaag     2040
gaagaagtca gatttaagaa aagatcttcg gcaatgcctg agggatgatg ttcttgcagc   2100
tggcattcgg cagctcttga aacagcttgg aaagacgttg aagaagaagg aaaaagagac   2160
tgtgaaggaa atactatcaa atgcacaggt tgtttttgcc actaacattg gagcagctga   2220
tcctttgatt aggaggttag aaacatttga tttggttgtt atagatgaag ctggtcagtc   2280
tatcgagcct tcatgctgga tcccaatatt gcagggaaa cgttgtattc tttccggtga    2340
tccatgccaa ttagcaccag ttgttctatc acgtaaagct ttagaaggtg gacttggtgt   2400
atccttactg gaaagagctg catctttaca tgatggagtt cttgcgacaa aattaacaac   2460
tcagtatcgt atgaacgatg taatcgctgg ttgggcatca aaggagatgt atggtggatg   2520
```

```
gttgaaatct gctccaagtg tggcctctca tctgcttatc gattctcctt ttgtgaaggc    2580
tacttggata acgcaatgcc cactggttct gcttgacaca agaatgccat atgggagttt    2640
atccgtgggc tgcgaggagc gtttggatcc agctggcaca ggctcattat acaatgaagg    2700
agaagcagat attgtggtta atcacgtcat ttctttgata tacgcaggtg ttagtccaat    2760
ggctattgct gttcaatccc catatgttgc tcaggttcaa cttctcagag aaaggctgga    2820
tgatttccca gtggctgatg gagttgaggt cgcaaccatt gacagctttc aagggcggga    2880
ggctgatgca gtgatcatct caatggtacg gtcaaacaac ctaggtgcag tgggattcct    2940
aggggatagc agacggatga atgtagccat tacaagagcc cggaagcacg tggcagtggt    3000
atgtgacagc tccacaatct gccacaacac gttcctagca agactgttgc gccacatacg    3060
ctatttcggg agagttaagc atgcagaccc tggtagcttg ggagggtcag gactaggctt    3120
ggacccaatg ttgccctacc ttggttaaaa ccgttgtaag tactacaaaa accagaacct    3180
tctgcttact ctctccctct ctctctatct ctcccgctga aagaaacagt ttccatagca    3240
aattgtcgtt gtacagaaca attgttacca cagaaaatag tctctgtata tgatgacaat    3300
atataattca tgta                                                      3314
```

<210> SEQ ID NO 86
<211> LENGTH: 961
<212> TYPE: PRT
<213> ORGANISM: Arabidopsis thaliana

<400> SEQUENCE: 86

```
Met Glu Ala Ala Ser Ser Phe Leu Cys Arg Ser Ile Arg Ile Pro Ser
1               5                   10                  15

Thr Thr Thr Ala Thr Ala Ala Phe Thr Phe Thr Arg Pro Pro Leu Asn
            20                  25                  30

Tyr Val Cys Val Val Gly Val Arg Val Phe Pro Thr Arg Lys Val Phe
        35                  40                  45

Cys Ser Gly Val Asn Gly Gly Ser Ser Val Thr Lys Lys Pro Arg
    50                  55                  60

Arg Lys Ser Asn Val Ser Asp Lys Leu Arg Phe Lys Lys Ile Glu Lys
65                  70                  75                  80

Arg Asn Asp Asn Thr Glu Ser Glu Ser Leu Ser Val Val Glu Pro
                85                  90                  95

Lys Asn Asp Lys Glu Leu Ser Leu Arg Ala Leu Asn Gln Asn Gly Asp
            100                 105                 110

Pro Leu Gly Arg Arg Asp Leu Gly Arg Asn Val Val Lys Trp Ile Ser
        115                 120                 125

Gln Ala Met Lys Ala Met Ala Ser Asp Phe Ala Thr Ala Glu Val Gln
    130                 135                 140

Gly Glu Phe Ser Glu Leu Arg Gln Asn Val Gly Ser Gly Leu Thr Phe
145                 150                 155                 160

Val Ile Gln Ala Gln Pro Tyr Leu Asn Ala Ile Pro Met Pro Leu Gly
                165                 170                 175

Ser Glu Val Ile Cys Leu Lys Ala Cys Thr His Tyr Pro Thr Leu Phe
            180                 185                 190

Asp His Phe Gln Arg Glu Leu Arg Asp Val Leu Gln Asp Leu Glu Arg
        195                 200                 205

Lys Asn Ile Met Glu Ser Trp Lys Glu Ser Glu Ser Trp Lys Leu Leu
    210                 215                 220

Lys Glu Ile Ala Asn Ser Ala Gln His Arg Glu Val Ala Arg Lys Ala
225                 230                 235                 240
```

```
Ala Gln Ala Lys Pro Val Gln Gly Val Leu Gly Met Asp Ser Glu Lys
                245                 250                 255

Val Lys Ala Ile Gln Glu Arg Ile Asp Glu Phe Thr Ser Gln Met Ser
            260                 265                 270

Gln Leu Leu Gln Val Glu Arg Asp Thr Glu Leu Glu Val Thr Gln Glu
        275                 280                 285

Glu Leu Asp Val Val Pro Thr Pro Asp Glu Ser Ser Asp Ser Ser Lys
    290                 295                 300

Pro Ile Glu Phe Leu Val Arg His Gly Asp Ala Pro Gln Glu Leu Cys
305                 310                 315                 320

Asp Thr Ile Cys Asn Leu Tyr Ala Val Ser Thr Ser Thr Gly Leu Gly
                325                 330                 335

Gly Met His Leu Val Leu Phe Lys Val Gly Gly Asn His Arg Leu Pro
            340                 345                 350

Pro Thr Thr Leu Ser Pro Gly Asp Met Val Cys Ile Arg Val Cys Asp
        355                 360                 365

Ser Arg Gly Ala Gly Ala Thr Ala Cys Thr Gln Gly Phe Val His Asn
    370                 375                 380

Leu Gly Glu Asp Gly Cys Ser Ile Gly Val Ala Leu Glu Ser Arg His
385                 390                 395                 400

Gly Asp Pro Thr Phe Ser Lys Leu Phe Gly Lys Ser Val Arg Ile Asp
                405                 410                 415

Arg Ile His Gly Leu Ala Asp Ala Leu Thr Tyr Glu Arg Asn Cys Glu
            420                 425                 430

Ala Leu Met Leu Leu Gln Lys Asn Gly Leu Gln Lys Lys Asn Pro Ser
        435                 440                 445

Ile Ser Val Val Ala Thr Leu Phe Gly Asp Gly Glu Asp Ile Thr Trp
    450                 455                 460

Leu Glu Gln Asn Asp Tyr Val Asp Trp Ser Glu Ala Glu Leu Ser Asp
465                 470                 475                 480

Glu Pro Val Ser Lys Leu Phe Asp Ser Ser Gln Arg Arg Ala Ile Ala
                485                 490                 495

Leu Gly Val Asn Lys Lys Arg Pro Val Met Ile Val Gln Gly Pro Pro
            500                 505                 510

Gly Thr Gly Lys Thr Gly Met Leu Lys Glu Val Ile Thr Leu Ala Val
        515                 520                 525

Gln Gln Gly Glu Arg Val Leu Val Thr Ala Pro Thr Asn Ala Ala Val
    530                 535                 540

Asp Asn Met Val Glu Lys Leu Leu His Leu Gly Leu Asn Ile Val Arg
545                 550                 555                 560

Val Gly Asn Pro Ala Arg Ile Ser Ser Ala Val Ala Ser Lys Ser Leu
                565                 570                 575

Gly Glu Ile Val Asn Ser Lys Leu Ala Ser Phe Arg Ala Glu Leu Glu
            580                 585                 590

Arg Lys Lys Ser Asp Leu Arg Lys Asp Leu Arg Gln Cys Leu Arg Asp
        595                 600                 605

Asp Val Leu Ala Ala Gly Ile Arg Gln Leu Leu Lys Gln Leu Gly Lys
    610                 615                 620

Thr Leu Lys Lys Lys Glu Lys Glu Thr Val Lys Glu Ile Leu Ser Asn
625                 630                 635                 640

Ala Gln Val Val Phe Ala Thr Asn Ile Gly Ala Ala Asp Pro Leu Ile
                645                 650                 655

Arg Arg Leu Glu Thr Phe Asp Leu Val Val Ile Asp Glu Ala Gly Gln
```

```
                   660              665               670
Ser Ile Glu Pro Ser Cys Trp Ile Pro Ile Leu Gln Gly Lys Arg Cys
            675                  680                 685
Ile Leu Ser Gly Asp Pro Cys Gln Leu Ala Pro Val Val Leu Ser Arg
        690                  695                 700
Lys Ala Leu Glu Gly Gly Leu Gly Val Ser Leu Leu Glu Arg Ala Ala
705                 710                 715                 720
Ser Leu His Asp Gly Val Leu Ala Thr Lys Leu Thr Thr Gln Tyr Arg
                725                 730                 735
Met Asn Asp Val Ile Ala Gly Trp Ala Ser Lys Glu Met Tyr Gly Gly
            740                 745                 750
Trp Leu Lys Ser Ala Pro Ser Val Ala Ser His Leu Leu Ile Asp Ser
        755                 760                 765
Pro Phe Val Lys Ala Thr Trp Ile Thr Gln Cys Pro Leu Val Leu Leu
    770                 775                 780
Asp Thr Arg Met Pro Tyr Gly Ser Leu Ser Val Gly Cys Glu Arg
785                 790                 795                 800
Leu Asp Pro Ala Gly Thr Gly Ser Leu Tyr Asn Glu Gly Glu Ala Asp
                805                 810                 815
Ile Val Val Asn His Val Ile Ser Leu Ile Tyr Ala Gly Val Ser Pro
            820                 825                 830
Met Ala Ile Ala Val Gln Ser Pro Tyr Val Ala Gln Val Gln Leu Leu
        835                 840                 845
Arg Glu Arg Leu Asp Asp Phe Pro Val Ala Asp Gly Val Glu Val Ala
    850                 855                 860
Thr Ile Asp Ser Phe Gln Gly Arg Glu Ala Asp Ala Val Ile Ile Ser
865                 870                 875                 880
Met Val Arg Ser Asn Asn Leu Gly Ala Val Gly Phe Leu Gly Asp Ser
                885                 890                 895
Arg Arg Met Asn Val Ala Ile Thr Arg Ala Arg Lys His Val Ala Val
            900                 905                 910
Val Cys Asp Ser Ser Thr Ile Cys His Asn Thr Phe Leu Ala Arg Leu
        915                 920                 925
Leu Arg His Ile Arg Tyr Phe Gly Arg Val Lys His Ala Asp Pro Gly
    930                 935                 940
Ser Leu Gly Gly Ser Gly Leu Gly Leu Asp Pro Met Leu Pro Tyr Leu
945                 950                 955                 960
Gly

<210> SEQ ID NO 87
<211> LENGTH: 3778
<212> TYPE: DNA
<213> ORGANISM: Arabidopsis thaliana

<400> SEQUENCE: 87
ggggaagcag aagaagaaag aacaaaaatc aggagttggc attttgaaga cgaaactcat      60
catcatcttc ttcctcagac aacaaaaaaa gcttttcact ttctctccac ccttctctct     120
ctccttctga aagtctctct ctttgccgtc gttagcctct tcctacactt ggggctgcga     180
ttcttccaat cctccgattt caatttcatc ctctcaatca tagttgaaa tcatcgagct      240 tttacggtgc tgttggtgtt tgacgccgta aaattcgatc cttttttata catttgatgt     300
tgattttatc gatagttttg tgagatcgat ttttagggt ttcgagtttg gcgctgactt     360
gagggtttga ttggatgaga ataagggggtt atgggacttg agtcaattgg gtttgtctcc     420
```

```
ctaatcatcg caaattcctg atttctcagc tctttggaag gaattaggat tcgttgattt     480
cgagttttgt gttgtgttgg ttgatgagag agttgggttt ggtcaattga ggggtttagg     540
tgttgtttta ctgttttgat tctgatcatg gatgacattg attcaagcga tggtgctgcg     600
gctgcacgag ctggtgagat tggctctatt ggggtatcca caccgtggaa gccaattcag     660
ctggttttta agcgttattt gccacaaaat gggtctgcta gcaaagttca tgttgccgtg     720
aagaagccgg tggtggtgag actaactagg acttggttg  agacgtacaa aatatgtgac     780
ccacagttca aatatagagg agagttgaat cccaagcggt acttgactac tccatcagtt     840
ggtgtgaaca atgatggctt tgataatgtc aactacgatc taattctggc tgtaaatgat     900 gattttgca gttcagattc acggcagaga tacattgtca aagatcttct tggccatggg     960
acttttggtc aggttgctaa atgctgggtt cctgagacaa acagctttgt tgctgtaaaa    1020
gtaataaaaa accagcttgc atactatcag caggcattgg ttgaagtatc tattttgaca    1080
acgctaaaca agaagtatga tcctgaggat aagaaccata tcgttcgcat atacgactac    1140
ttcttacatc aaagtcattt gtgcatatgc tttgaacttc tagacatgaa tctgtatgag    1200
ctcataaaga taaatcaatt cagaggccta tcattaagca tagtcaagct cttctctaag    1260
cagatcttac ttggtttggc tcttttgaaa gatgctggca taatccattg tgatctgaag    1320
ccagagaata ttcttctgtg cgccagtgtg aagccaactg aaattaagat aattgacttt    1380
ggatcagcgt gcatggaaga taaaactgtt tattcatata ttcagagtcg ttactacaga    1440
tcgccggaag tcttacttgg ttaccaatac actacagcta ttgacatgtg gtcttttggc    1500
tgcattgttg ccgagctgtt tcttggattg ccactatttc caggaggttc agaatttgat    1560
atcttgaggc gtatgattga aatactaggc aaacaaccac ctgattatgt gctcaaggaa    1620
gcaaaaaata cgaataagtt ctttaaatgt gttgggagtg tccacaattt agggaatggt    1680
ggaacttatg gtggcctcaa aagtgcttat atggctttga ctggagaaga gtttgaagct    1740
agagaaaaga aaaagccaga aattgggaaa gagtacttca accataagaa ccttgaagaa    1800
attgttaaaa gctatccgta caagataaat ctacctgagg acgatgtagt caaagaaact    1860
caaatccggt tagctcttat tgattttctg aaaggactta tggaatttga tccagcaaaa    1920
cgttggtcac cttttcaggc agcaaagcac cctttcatta ctggagaacc ttttacgtgc    1980
ccatacaacc ctccgccaga aacacctcgt gtgcatgtta cccaaaacat caagttgac    2040 catcatccag gtgaagggca ctggtttgcc gctggtctct ctcctcatgt atcagggaga    2100
accagaatcc cgatgcacaa tagtccccat tttcagatga tgccttattc acatgcaaat    2160
agttatggga gcattggaag ctatggtagc tacaatgatg gtactataca ggacaatagc    2220
tatgggagct atggagggac tggcaatatg tttgcatact attctcctgt gaatcatcca    2280
ggcctataca tgcaaaacca aggtgggtc tcaatgcttg gaactagtcc tgatgccaga    2340
cgtcgggtta tgcagtaccc acatggaaat gggccaaatg gccttggtac aagtccatct    2400
gctggaaatt ttgcaccact acccttggc actagtccgt cacaatttac tccaaataca    2460
aacaatcaat tttagctgg gtctcctgga caccatggcc cgacatctcc agtaagaaac    2520
agctgccatg ggtctccttt gggaaagatg gctgcattta gtcaaattaa tagaagaatg    2580
agcgctggat attctggagg ttctcagtcg caagattctt ccttgtcaca gcccaaggg    2640 catgggatgg ataacttta tcaaaatgag gggtattctg acaattctc tggttcacct    2700 tcacgccggc aactggattc tggtgtcaaa aatcgtaaac agacacaagg aggcactaca    2760
ttaagtactg ggtactctac tcataacaat gccaactcat cacttcggtc caatatgtat    2820
```

```
aacccttcca gtactgcaca ccatcttgaa aatccggata ctgccttatc agtacctgat    2880
ccaggagact gggacccaaa ttacagtgat gacttgcttc tagaagaaga tagtgcagat    2940
gagagttctc ttgctaatgc attcagcaga ggtatgcaac ttggttcaac agatgcctcc    3000
agttattcca gaaggttcaa cagtaatgcc tcgacctcat cctcaaatcc gactacccaa    3060
aggagatatg ctcccaatca agccttttca caagtagaga ctggcagccc tccaagtaat    3120
gatcctcatg ccagatttgg ccaacatata ccaggatcac aatatattcc tcatgtctcc    3180
cagaactctc caagtcgctt agggcagcaa cctcctcaac ggtataatca tgggagacca    3240
aatgctggaa gaactatgga tcggaatcac atgaacgctc agcttcctcc ttccaataca    3300
aattctgggg gtcaacaacg ttcacccaga agtagctcat atacaaatgg tgtcccttgg    3360
ggtcgtagga ctaacaatca tgtcccgaat gttccatcga cgtcccatgg aagggtagac    3420
tacggaagta ttgcttaatt ctgcagtctt tcttctcatt tattttgttc tttcccttgg    3480
tgtgcaatct tcttgttaga agtgtgggaa caaagttgta ctgagacaag aaacaaactt    3540
agttcatggc ttgtgggctt ctgatcagaa cgtgcttatt cattgtgctt tttgcacaaa    3600
taaacaaaaa aaaaaagtat gttataattg atattgttat ctttctggca tctatctctc    3660
tgaatttctt tttggtattc tctgatgaat gtatcttttg ggaaagttgt tcaagtgttt    3720
aagcctagcc ttgaaaaaag atccttaatt tccgtaaatt tcagtttatt agcagact      3778

<210> SEQ ID NO 88
<211> LENGTH: 956
<212> TYPE: PRT
<213> ORGANISM: Arabidopsis thaliana

<400> SEQUENCE: 88

Met Asp Asp Ile Asp Ser Ser Asp Gly Ala Ala Ala Arg Ala Gly
  1               5                  10                  15

Glu Ile Gly Ser Ile Gly Val Ser Thr Pro Trp Lys Pro Ile Gln Leu
             20                  25                  30

Val Phe Lys Arg Tyr Leu Pro Gln Asn Gly Ser Ala Ser Lys Val His
         35                  40                  45

Val Ala Val Lys Lys Pro Val Val Arg Leu Thr Arg Asp Leu Val
     50                  55                  60

Glu Thr Tyr Lys Ile Cys Asp Pro Gln Phe Lys Tyr Arg Gly Glu Leu
 65                  70                  75                  80

Asn Pro Lys Arg Tyr Leu Thr Thr Pro Ser Val Gly Val Asn Asn Asp
                 85                  90                  95

Gly Phe Asp Asn Val Asn Tyr Asp Leu Ile Leu Ala Val Asn Asp Asp
            100                 105                 110

Phe Cys Ser Ser Asp Ser Arg Gln Arg Tyr Ile Val Lys Asp Leu Leu
        115                 120                 125

Gly His Gly Thr Phe Gly Gln Val Ala Lys Cys Trp Val Pro Glu Thr
    130                 135                 140

Asn Ser Phe Val Ala Val Lys Val Ile Lys Asn Gln Leu Ala Tyr Tyr
145                 150                 155                 160

Gln Gln Ala Leu Val Glu Val Ser Ile Leu Thr Thr Leu Asn Lys Lys
                165                 170                 175

Tyr Asp Pro Glu Asp Lys Asn His Ile Val Arg Ile Tyr Asp Tyr Phe
            180                 185                 190

Leu His Gln Ser His Leu Cys Ile Cys Phe Glu Leu Leu Asp Met Asn
        195                 200                 205

Leu Tyr Glu Leu Ile Lys Ile Asn Gln Phe Arg Gly Leu Ser Leu Ser
```

```
                210                 215                 220
Ile Val Lys Leu Phe Ser Lys Gln Ile Leu Leu Gly Leu Ala Leu Leu
225                 230                 235                 240

Lys Asp Ala Gly Ile Ile His Cys Asp Leu Lys Pro Glu Asn Ile Leu
                245                 250                 255

Leu Cys Ala Ser Val Lys Pro Thr Glu Ile Lys Ile Ile Asp Phe Gly
                260                 265                 270

Ser Ala Cys Met Glu Asp Lys Thr Val Tyr Ser Tyr Ile Gln Ser Arg
                275                 280                 285

Tyr Tyr Arg Ser Pro Glu Val Leu Leu Gly Tyr Gln Tyr Thr Thr Ala
                290                 295                 300

Ile Asp Met Trp Ser Phe Gly Cys Ile Val Ala Glu Leu Phe Leu Gly
305                 310                 315                 320

Leu Pro Leu Phe Pro Gly Gly Ser Glu Phe Asp Ile Leu Arg Arg Met
                325                 330                 335

Ile Glu Ile Leu Gly Lys Gln Pro Pro Asp Tyr Val Leu Lys Glu Ala
                340                 345                 350

Lys Asn Thr Asn Lys Phe Phe Lys Cys Val Gly Ser Val His Asn Leu
                355                 360                 365

Gly Asn Gly Gly Thr Tyr Gly Gly Leu Lys Ser Ala Tyr Met Ala Leu
370                 375                 380

Thr Gly Glu Glu Phe Glu Ala Arg Glu Lys Lys Pro Glu Ile Gly
385                 390                 395                 400

Lys Glu Tyr Phe Asn His Lys Asn Leu Glu Glu Ile Val Lys Ser Tyr
                405                 410                 415

Pro Tyr Lys Ile Asn Leu Pro Glu Asp Asp Val Val Lys Glu Thr Gln
                420                 425                 430

Ile Arg Leu Ala Leu Ile Asp Phe Leu Lys Gly Leu Met Glu Phe Asp
                435                 440                 445

Pro Ala Lys Arg Trp Ser Pro Phe Gln Ala Ala Lys His Pro Phe Ile
                450                 455                 460

Thr Gly Glu Pro Phe Thr Cys Pro Tyr Asn Pro Pro Glu Thr Pro
465                 470                 475                 480

Arg Val His Val Thr Gln Asn Ile Lys Val Asp His His Pro Gly Glu
                485                 490                 495

Gly His Trp Phe Ala Ala Gly Leu Ser Pro His Val Ser Gly Arg Thr
                500                 505                 510

Arg Ile Pro Met His Asn Ser Pro His Phe Gln Met Met Pro Tyr Ser
                515                 520                 525

His Ala Asn Ser Tyr Gly Ser Ile Gly Ser Tyr Gly Ser Tyr Asn Asp
                530                 535                 540

Gly Thr Ile Gln Asp Asn Ser Tyr Gly Ser Tyr Gly Thr Gly Asn
545                 550                 555                 560

Met Phe Ala Tyr Tyr Ser Pro Val Asn His Pro Gly Leu Tyr Met Gln
                565                 570                 575

Asn Gln Gly Gly Val Ser Met Leu Gly Thr Ser Pro Asp Ala Arg Arg
                580                 585                 590

Arg Val Met Gln Tyr Pro His Gly Asn Gly Pro Asn Gly Leu Gly Thr
                595                 600                 605

Ser Pro Ser Ala Gly Asn Phe Ala Pro Leu Pro Leu Gly Thr Ser Pro
                610                 615                 620

Ser Gln Phe Thr Pro Asn Thr Asn Asn Gln Phe Leu Ala Gly Ser Pro
625                 630                 635                 640
```

-continued

```
Gly His His Gly Pro Thr Ser Pro Val Arg Asn Ser Cys His Gly Ser
            645                 650                 655

Pro Leu Gly Lys Met Ala Ala Phe Ser Gln Ile Asn Arg Arg Met Ser
        660                 665                 670

Ala Gly Tyr Ser Gly Gly Ser Gln Ser Gln Asp Ser Ser Leu Ser Gln
    675                 680                 685

Ala Gln Gly His Gly Met Asp Asn Phe Tyr Gln Asn Glu Gly Tyr Ser
690                 695                 700

Gly Gln Phe Ser Gly Ser Pro Ser Arg Arg Gln Leu Asp Ser Gly Val
705                 710                 715                 720

Lys Asn Arg Lys Gln Thr Gln Gly Gly Thr Thr Leu Ser Thr Gly Tyr
                725                 730                 735

Ser Thr His Asn Asn Ala Asn Ser Ser Leu Arg Ser Asn Met Tyr Asn
            740                 745                 750

Pro Ser Ser Thr Ala His His Leu Glu Asn Pro Asp Thr Ala Leu Ser
        755                 760                 765

Val Pro Asp Pro Gly Asp Trp Asp Pro Asn Tyr Ser Asp Leu Leu
    770                 775                 780

Leu Glu Glu Asp Ser Ala Asp Glu Ser Ser Leu Ala Asn Ala Phe Ser
785                 790                 795                 800

Arg Gly Met Gln Leu Gly Ser Thr Asp Ala Ser Ser Tyr Ser Arg Arg
                805                 810                 815

Phe Asn Ser Asn Ala Ser Thr Ser Ser Ser Asn Pro Thr Thr Gln Arg
            820                 825                 830

Arg Tyr Ala Pro Asn Gln Ala Phe Ser Gln Val Glu Thr Gly Ser Pro
        835                 840                 845

Pro Ser Asn Asp Pro His Ala Arg Phe Gly Gln His Ile Pro Gly Ser
    850                 855                 860

Gln Tyr Ile Pro His Val Ser Gln Asn Ser Pro Ser Arg Leu Gly Gln
865                 870                 875                 880

Gln Pro Pro Gln Arg Tyr Asn His Gly Arg Pro Asn Ala Gly Arg Thr
                885                 890                 895

Met Asp Arg Asn His Met Asn Ala Gln Leu Pro Pro Ser Asn Thr Asn
            900                 905                 910

Ser Gly Gly Gln Gln Arg Ser Pro Arg Ser Ser Ser Tyr Thr Asn Gly
        915                 920                 925

Val Pro Trp Gly Arg Arg Thr Asn Asn His Val Pro Asn Val Pro Ser
    930                 935                 940

Thr Ser His Gly Arg Val Asp Tyr Gly Ser Ile Ala
945                 950                 955
```

<210> SEQ ID NO 89
<211> LENGTH: 3029
<212> TYPE: DNA
<213> ORGANISM: Arabidopsis thaliana

<400> SEQUENCE: 89

| | | | | | |
|---|---|---|---|---|---|
| ggggaagcag | aagaagaaag | aacaaaaatc | aggagttggc | attttgaaga | cgaaactcat | 60 |
| catcatcttc | ttcctcagac | aacaaaaaaa | gcttttcact | ttctctccac | ccttctctct | 120 |
| ctccttctga | aagtctctct | ctttgccgtc | gttagcctct | tcctacactt | ggggctgcga | 180 |
| ttcttccaat | cctccgattt | caatttcatc | ctctcaatca | tagtttgaaa | tcatcgagct | 240 |
| tttacggtgc | tgttggtgtt | tgacgccgta | aaattcgatc | cttttttata | catttgatgt | 300 |
| tgatttatc | gatagttttg | tgagatcgat | ttttagggt | ttcgagtttg | cgcctgactt | 360 |

```
gagggtttga ttggatgaga ataaggggtt atgggacttg agtcaattgg gtttgtctcc    420
ctaatcatcg caaattcctg atttctcagc tcttttggaag gaattaggat tcgttgattt    480
cgagttttgt gttgtgttgg ttgatgagag agttgggttt ggtcaattga ggggtttagg    540
tgttgtttta ctgttttgat tctgatcatg gatgacattg attcaagcga tggtgctgcg    600
gctgcacgag ctggtgagat tggctctatt ggggtatcca caccgtggaa gccaattcag    660
ctggttttta agcgttattt gccacaaaat gggtctgcta gcaaagttca tgttgccgtg    720
aagaagccgg tggtggtgag actaactagg gacttggttg agacgtacaa aatatgtgac    780
ccacagttca aatatagagg agagttgaat cccaagcgt acttgactac tccatcagtt    840
ggtgtgaaca atgatggctt tgataatgtc aactacgatc taattctggc tgtaaatgat    900 gattttgca gttcagattc acggcagaga tacattgtca aagatcttct tggccatggg    960
acttttggtc aggttgctaa atgctgggtt cctgagacaa acagctttgt tgctgtaaaa   1020
gtaataaaaa accagcttgc atactatcag caggcattgg ttgaagtatc tattttgaca   1080
acgctaaaca agaagtatga tcctgaggat aagaaccata tcgttcgcat atacgactac   1140
ttcttacatc aaagtcattt gtgcatatgc tttgaacttc tagacatgaa tctgtatgag   1200
ctcataaaga taaatcaatt cagaggccta tcattaagca tagtcaagct cttctctaag   1260
cagatcttac ttggtttggc tcttttgaaa gatgctggca taatccattg tgatctgaag   1320
ccagagaata ttcttctgtg cgccagtgtg aagccaactg aaattaagat aattgacttt   1380
ggatcagcgt gcatggaaga taaaactgtt tattcatata ttcagagtcg ttactacaga   1440
tcgccggaag tcttacttgg ttaccaatac actacagcta ttgacatgtg gtcttttggc   1500
tgcattgttg ccgagctgtt tcttggattg ccactatttc caggaggttc agaatttgat   1560
atcttgaggc gtatgattga aatactaggc aaacaaccac ctgattatgt gctcaaggaa   1620
gcaaaaaata cgaataagtt ctttaaatgt gttgggagtg tccacaattt agggaatggt   1680
ggaacttatg gtggcctcaa aagtgcttat atggctttga ctggagaaga gtttgaagct   1740
agagaaaaga aaaagccaga aattgggaaa gagtacttca accataagaa ccttgaagaa   1800
attgttaaaa gctatccgta caagataaat ctacctgagg acgatgtagt caaagaaact   1860
caaatccggt tagctcttat tgattttctg aaaggactta tggaatttga tccagcaaaa   1920
cgttggtcac ctttcaggc agcaaagcac ccttttcatta ctggagaacc ttttacgtgc   1980
ccatacaacc ctccgccaga aacacctcgt gtgcatgtta cccaaaacat caaagttgac   2040
catcatccag gtgaagggca ctggtttgcc gctggtctct ctcctcatgt atcagggaga   2100
accagaatcc cgatgcacaa tagtccccat tttcagatga tgccttattc acatgcaaat   2160
agttatggga gcattggaag ctatggtagc tacaatgatg gtactataca ggacaatagc   2220
tatgggagct atggagggac tggcaatatg tttgcatact attctcctgt gaatcatcca   2280
ggcctataca tgcaaaacca aggtggggtc tcaatgcttg gaactagtcc tgatgccaga   2340
cgtcgggtta tgcagtaccc acatggaaat gggccaaatg gccttggtac aagtccatct   2400
gctggaaatt ttgcaccact accccttggc actagtccgt cacaatttac tccaaataca   2460
aacaatcaat ttttagctgg gtctcctgga caccatggcc cgacatctcc agtaagaaac   2520
agctgccatg ggtctccttt gggaaagatg gctgcattta gtcaaattaa tagaagaatg   2580
agcgctggat attctggagg ttctcagtcg caagattctt ccttgtcaca agcccaaggg   2640
catgggatgg ataactttta tcaaaatgag gggtattctg gacaattctc tggttcacct   2700
tcacgccggc aactggattc tggtgtcaaa atcgtaaac agacacaagg aggcactaca   2760
```

-continued

```
ttaagtactg ggtactctac tcataacaat gccaactcat cacttcggtc caatatgtat   2820
aacccttcca gtactgcaca ccatcttgaa aatccggata ctgccttatc agtacctgat   2880
ccaggagact gggacccaaa ttacaggcaa gtaaacaaga tatctctcta atttaccagt   2940
taatgaatgt caaggttctt tgtctgtatg ttagtgtgta tatgatgtgt acttgaacaa   3000
atctggctgg tttagctaga attcgtgat                                      3029
```

<210> SEQ ID NO 90
<211> LENGTH: 787
<212> TYPE: PRT
<213> ORGANISM: Arabidopsis thaliana

<400> SEQUENCE: 90

```
Met Asp Asp Ile Asp Ser Ser Asp Gly Ala Ala Ala Arg Ala Gly
1               5                   10                  15

Glu Ile Gly Ser Ile Gly Val Ser Thr Pro Trp Lys Pro Ile Gln Leu
                20                  25                  30

Val Phe Lys Arg Tyr Leu Pro Gln Asn Gly Ser Ala Ser Lys Val His
            35                  40                  45

Val Ala Val Lys Lys Pro Val Val Arg Leu Thr Arg Asp Leu Val
50                  55                  60

Glu Thr Tyr Lys Ile Cys Asp Pro Gln Phe Lys Tyr Arg Gly Glu Leu
65                  70                  75                  80

Asn Pro Lys Arg Tyr Leu Thr Thr Pro Ser Val Gly Val Asn Asn Asp
                85                  90                  95

Gly Phe Asp Asn Val Asn Tyr Asp Leu Ile Leu Ala Val Asn Asp Asp
            100                 105                 110

Phe Cys Ser Ser Asp Ser Arg Gln Arg Tyr Ile Val Lys Asp Leu Leu
        115                 120                 125

Gly His Gly Thr Phe Gly Gln Val Ala Lys Cys Trp Val Pro Glu Thr
    130                 135                 140

Asn Ser Phe Val Ala Val Lys Val Ile Lys Asn Gln Leu Ala Tyr Tyr
145                 150                 155                 160

Gln Gln Ala Leu Val Glu Val Ser Ile Leu Thr Thr Leu Asn Lys Lys
                165                 170                 175

Tyr Asp Pro Glu Asp Lys Asn His Ile Val Arg Ile Tyr Asp Tyr Phe
            180                 185                 190

Leu His Gln Ser His Leu Cys Ile Cys Phe Glu Leu Leu Asp Met Asn
        195                 200                 205

Leu Tyr Glu Leu Ile Lys Ile Asn Gln Phe Arg Gly Leu Ser Leu Ser
    210                 215                 220

Ile Val Lys Leu Phe Ser Lys Gln Ile Leu Leu Gly Leu Ala Leu Leu
225                 230                 235                 240

Lys Asp Ala Gly Ile Ile His Cys Asp Leu Lys Pro Glu Asn Ile Leu
                245                 250                 255

Leu Cys Ala Ser Val Lys Pro Thr Glu Ile Lys Ile Asp Phe Gly
            260                 265                 270

Ser Ala Cys Met Glu Asp Lys Thr Val Tyr Ser Tyr Ile Gln Ser Arg
        275                 280                 285

Tyr Tyr Arg Ser Pro Glu Val Leu Leu Gly Tyr Gln Tyr Thr Thr Ala
    290                 295                 300

Ile Asp Met Trp Ser Phe Gly Cys Ile Val Ala Glu Leu Phe Leu Gly
305                 310                 315                 320

Leu Pro Leu Phe Pro Gly Gly Ser Glu Phe Asp Ile Leu Arg Arg Met
                325                 330                 335
```

```
Ile Glu Ile Leu Gly Lys Gln Pro Pro Asp Tyr Val Leu Lys Glu Ala
            340                 345                 350
Lys Asn Thr Asn Lys Phe Phe Lys Cys Val Gly Ser Val His Asn Leu
        355                 360                 365
Gly Asn Gly Gly Thr Tyr Gly Gly Leu Lys Ser Ala Tyr Met Ala Leu
    370                 375                 380
Thr Gly Glu Glu Phe Glu Ala Arg Glu Lys Lys Lys Pro Glu Ile Gly
385                 390                 395                 400
Lys Glu Tyr Phe Asn His Lys Asn Leu Glu Glu Ile Val Lys Ser Tyr
                405                 410                 415
Pro Tyr Lys Ile Asn Leu Pro Glu Asp Asp Val Val Lys Glu Thr Gln
            420                 425                 430
Ile Arg Leu Ala Leu Ile Asp Phe Leu Lys Gly Leu Met Glu Phe Asp
        435                 440                 445
Pro Ala Lys Arg Trp Ser Pro Phe Gln Ala Ala Lys His Pro Phe Ile
    450                 455                 460
Thr Gly Glu Pro Phe Thr Cys Pro Tyr Asn Pro Pro Glu Thr Pro
465                 470                 475                 480
Arg Val His Val Thr Gln Asn Ile Lys Val Asp His His Pro Gly Glu
                485                 490                 495
Gly His Trp Phe Ala Ala Gly Leu Ser Pro His Val Ser Gly Arg Thr
            500                 505                 510
Arg Ile Pro Met His Asn Ser Pro His Phe Gln Met Met Pro Tyr Ser
        515                 520                 525
His Ala Asn Ser Tyr Gly Ser Ile Gly Ser Tyr Gly Ser Tyr Asn Asp
    530                 535                 540
Gly Thr Ile Gln Asp Asn Ser Tyr Gly Ser Tyr Gly Thr Gly Asn
545                 550                 555                 560
Met Phe Ala Tyr Tyr Ser Pro Val Asn His Pro Gly Leu Tyr Met Gln
                565                 570                 575
Asn Gln Gly Gly Val Ser Met Leu Gly Thr Ser Pro Asp Ala Arg Arg
            580                 585                 590
Arg Val Met Gln Tyr Pro His Gly Asn Gly Pro Asn Gly Leu Gly Thr
        595                 600                 605
Ser Pro Ser Ala Gly Asn Phe Ala Pro Leu Pro Leu Gly Thr Ser Pro
    610                 615                 620
Ser Gln Phe Thr Pro Asn Thr Asn Gln Phe Leu Ala Gly Ser Pro
625                 630                 635                 640
Gly His His Gly Pro Thr Ser Pro Val Arg Asn Ser Cys His Gly Ser
                645                 650                 655
Pro Leu Gly Lys Met Ala Ala Phe Ser Gln Ile Asn Arg Arg Met Ser
            660                 665                 670
Ala Gly Tyr Ser Gly Gly Ser Gln Ser Gln Asp Ser Ser Leu Ser Gln
        675                 680                 685
Ala Gln Gly His Gly Met Asp Asn Phe Tyr Gln Asn Glu Gly Tyr Ser
    690                 695                 700
Gly Gln Phe Ser Gly Ser Pro Ser Arg Arg Gln Leu Asp Ser Gly Val
705                 710                 715                 720
Lys Asn Arg Lys Gln Thr Gln Gly Gly Thr Thr Leu Ser Thr Gly Tyr
                725                 730                 735
Ser Thr His Asn Asn Ala Asn Ser Ser Leu Arg Ser Asn Met Tyr Asn
            740                 745                 750
Pro Ser Ser Thr Ala His His Leu Glu Asn Pro Asp Thr Ala Leu Ser
```

```
                    755                 760                 765
Val Pro Asp Pro Gly Asp Trp Asp Pro Asn Tyr Arg Gln Val Asn Lys
            770                 775                 780

Ile Ser Leu
785

<210> SEQ ID NO 91
<211> LENGTH: 1755
<212> TYPE: DNA
<213> ORGANISM: Arabidopsis thaliana

<400> SEQUENCE: 91
agtcaatatc ccaaaatccc taattcatat ctttgaaact gataaagata caaagaaat      60 ggcctctcaa ttgcttttac ctccaaacca attcactaaa tcagtctcac ctcaagtttt    120
cattactggt gattgtcaag gatttagtga cttaactctg aaagaaaat caaaccaagc     180 tacaagagtt tcaaatggat ctagcttaag agtaaaagca gctttgagat ctactcacaa    240
caaatcagtg gttgagattc aaaacaatg gtataatctt gttgctgatc tttcagtcaa     300
gcctcctcca ccgttgcatc caaagacttt cgaaccgata aaacccgaag atttggctca    360
tcttttcccc aatgagttga ttaaacaaga agctacacaa gagaggttta ttgatatccc    420
tgaggaagtt cttgaaatct ataagctttg gcgtccaact cctctaatca gagcaaagag    480
attagagaag cttcttcaaa caccggcaag gatttacttc aagtatgaag gtggtagccc    540
agctggttca cacaaaccaa acacagcggt tccacaagct tattacaatg cgaaagaagg    600
cgtcaagaac gttgtgacgg aaaccggtgc tggtcaatgg ggaagttctt tagcctttgc    660
ttctagtcta tttggtctcg actgcgaagt atggcaagta gccaactctt accatacaaa    720
gccatatcgc cggttaatga tgcaaacttg gggtgcaaag gttcatccgt cgccatcgga    780
tctcactgag gcgggtagaa gaatcctcga atccgatcca tcaagtccgg gaagtttagg    840
cattgcgata tcagaagcgg ttgaagttgc agcgagaaac gaggatacaa aatactgcct    900
agggagtgta ttgaaccatg tgttgttaca ccaaacaatt attggagaag aatgcattca    960
acaaatggag aattttggtg aaacacctga cctgatcata gggtgtactg gtggaggatc   1020
aaattttgct ggtttgagtt ttccttttat ccgggagaaa ctcaaaggca aaatcaaccc   1080
tgttataaga gcggttgagc catctgcttg tccttccttg accaaggggg tttatgctta   1140
tgattttggc gatacggctg gattgactcc tttgatgaag atgcatactt gggacatga    1200 cttcattcct gatcctatcc atgccggtgg attaaggtac catgggatgg caccattgat   1260
ctcacatgtt tatgaacaag gattcatgga agcaatttca attcctcaaa ttgagtgttt   1320
ccaaggtgct attcagtttg caagaacaga agggatcata cccgcaccag aaccgaccca   1380
cgccattgct gcaaccataa gagaggctct ccgatgtaaa gagacgggag aagcaaaagt   1440
gatactaatg gcgatgtgtg acatggcca tttcgacctt acttcttacg acaagtattt   1500
aaaaggcgag ttggtggatt tatcattcag cgaagagaag atacgagagt ctttgtccaa   1560
ggttcctcat gttgtttaag ctcgaatggc cccataacca cgggaaacca atgtcccatg   1620
ttccaaacta gacgtgagac agaagttagg tttaatcttg gcttttgaaa tgaagagtga   1680
gagagaggac aacttcaaaa catgaacaaa attatctctt gaaataagaa taaaaaggc    1740 atttacagaa acacc                                                    1755

<210> SEQ ID NO 92
<211> LENGTH: 506
<212> TYPE: PRT
```

<213> ORGANISM: Arabidopsis thaliana

<400> SEQUENCE: 92

| Met<br>1 | Ala | Ser | Gln | Leu<br>5 | Leu | Pro | Pro | Asn | Gln<br>10 | Phe | Thr | Lys | Ser | Val<br>15 |
| Ser | Pro | Gln | Val<br>20 | Phe | Ile | Thr | Gly | Asp<br>25 | Cys | Gln | Gly | Phe | Ser<br>30 | Asp | Leu |
| Thr | Leu | Lys<br>35 | Arg | Lys | Ser | Asn | Gln<br>40 | Ala | Thr | Arg | Val | Ser<br>45 | Asn | Gly | Ser |
| Ser | Leu<br>50 | Arg | Val | Lys | Ala | Ala<br>55 | Leu | Arg | Ser | Thr | His<br>60 | Asn | Lys | Ser | Val |
| Val<br>65 | Glu | Ile | Pro | Lys | Gln<br>70 | Trp | Tyr | Asn | Leu | Val<br>75 | Ala | Asp | Leu | Ser | Val<br>80 |
| Lys | Pro | Pro | Pro | Leu<br>85 | His | Pro | Lys | Thr | Phe<br>90 | Glu | Pro | Ile | Lys | Pro<br>95 |
| Glu | Asp | Leu | Ala<br>100 | His | Leu | Phe | Pro | Asn<br>105 | Glu | Leu | Ile | Lys | Gln<br>110 | Glu | Ala |
| Thr | Gln | Glu<br>115 | Arg | Phe | Ile | Asp | Ile<br>120 | Pro | Glu | Glu | Val | Leu<br>125 | Glu | Ile | Tyr |
| Lys | Leu<br>130 | Trp | Arg | Pro | Thr | Pro<br>135 | Leu | Ile | Arg | Ala | Lys<br>140 | Arg | Leu | Glu | Lys |
| Leu<br>145 | Leu | Gln | Thr | Pro | Ala<br>150 | Arg | Ile | Tyr | Phe | Lys<br>155 | Tyr | Glu | Gly | Gly | Ser<br>160 |
| Pro | Ala | Gly | Ser | His<br>165 | Lys | Pro | Asn | Thr | Ala<br>170 | Val | Pro | Gln | Ala | Tyr<br>175 | Tyr |
| Asn | Ala | Lys | Glu<br>180 | Gly | Val | Lys | Asn | Val<br>185 | Val | Thr | Glu | Thr | Gly<br>190 | Ala | Gly |
| Gln | Trp | Gly<br>195 | Ser | Ser | Leu | Ala | Phe<br>200 | Ala | Ser | Ser | Leu | Phe<br>205 | Gly | Leu | Asp |
| Cys | Glu<br>210 | Val | Trp | Gln | Val | Ala<br>215 | Asn | Ser | Tyr | His | Thr<br>220 | Lys | Pro | Tyr | Arg |
| Arg<br>225 | Leu | Met | Met | Gln | Thr<br>230 | Trp | Gly | Ala | Lys | Val<br>235 | His | Pro | Ser | Pro | Ser<br>240 |
| Asp | Leu | Thr | Glu | Ala<br>245 | Gly | Arg | Arg | Ile | Leu<br>250 | Glu | Ser | Asp | Pro | Ser<br>255 | Ser |
| Pro | Gly | Ser | Leu | Gly<br>260 | Ile | Ala | Ile | Ser | Glu<br>265 | Ala | Val | Glu | Val | Ala<br>270 | Ala |
| Arg | Asn | Glu | Asp<br>275 | Thr | Lys | Tyr | Cys | Leu<br>280 | Gly | Ser | Val | Leu | Asn<br>285 | His | Val |
| Leu | Leu<br>290 | His | Gln | Thr | Ile | Ile<br>295 | Gly | Glu | Glu | Cys | Ile<br>300 | Gln | Gln | Met | Glu |
| Asn<br>305 | Phe | Gly | Glu | Thr | Pro<br>310 | Asp | Leu | Ile | Ile | Gly<br>315 | Cys | Thr | Gly | Gly | Gly<br>320 |
| Ser | Asn | Phe | Ala | Gly<br>325 | Leu | Ser | Phe | Pro | Phe<br>330 | Ile | Arg | Glu | Lys | Leu<br>335 | Lys |
| Gly | Lys | Ile | Asn<br>340 | Pro | Val | Ile | Arg | Ala<br>345 | Val | Glu | Pro | Ser | Ala<br>350 | Cys | Pro |
| Ser | Leu | Thr<br>355 | Lys | Gly | Val | Tyr | Ala<br>360 | Tyr | Asp | Phe | Gly | Asp<br>365 | Thr | Ala | Gly |
| Leu | Thr<br>370 | Pro | Leu | Met | Lys | Met<br>375 | His | Thr | Leu | Gly | His<br>380 | Asp | Phe | Ile | Pro |
| Asp<br>385 | Pro | Ile | His | Ala | Gly<br>390 | Gly | Leu | Arg | Tyr | His<br>395 | Gly | Met | Ala | Pro | Leu<br>400 |
| Ile | Ser | His | Val | Tyr | Glu | Gln | Gly | Phe | Met | Glu | Ala | Ile | Ser | Ile | Pro |

```
                    405                 410                 415
Gln Ile Glu Cys Phe Gln Gly Ala Ile Gln Phe Ala Arg Thr Glu Gly
            420                 425                 430

Ile Ile Pro Ala Pro Glu Pro Thr His Ala Ile Ala Ala Thr Ile Arg
        435                 440                 445

Glu Ala Leu Arg Cys Lys Glu Thr Gly Glu Ala Lys Val Ile Leu Met
    450                 455                 460

Ala Met Cys Gly His Gly His Phe Asp Leu Thr Ser Tyr Asp Lys Tyr
465                 470                 475                 480

Leu Lys Gly Glu Leu Val Asp Leu Ser Phe Ser Glu Glu Lys Ile Arg
                485                 490                 495

Glu Ser Leu Ser Lys Val Pro His Val Val
            500                 505

<210> SEQ ID NO 93
<211> LENGTH: 1488
<212> TYPE: DNA
<213> ORGANISM: Arabidopsis thaliana

<400> SEQUENCE: 93
atgttgatat ataatgctga ctctgtggta ttttattct cactattttt gcagtttgag      60
ataaaccatc tacaagatga acatcttgaa tctgttgacg cttactacaa caaaaagtct    120
tatggtttgc aagcaattca attcaaaacc aatttcagga cctctgaact gatggggtat    180
agttatgagt gtaccatgtt tacgctagcc gtcaaaggaa agaagatcat ggggtttcat    240
ggatctgata atgtacatat atactctctt ggagcttact tcacttccat tactcctacg    300
agattggaag tgaaaggtgg tatgggaggc aagaagtggg aggatggatt cgaccatgac    360
aatgtatcaa agatccaagt gctaggtggt tttgaaggca tactgtacat caaagttgac    420
tatatcaaga tgaaaaact agaaactgga ttaatccatg gtgactctgg tggtgatggt    480
tttttacaga agatggagat taaccagtca agaacgaat atctagtata tgttgaaggt    540
tactacgatg atgcttctga aaccattcaa gggcttcatt tccaaactaa cctcaacaat    600
cctgttatga tggggtataa aaagggcagg aagttttta ttgcatccaa tggaaataag    660
atcattgggt tcatggata tgccgacaaa agtctaaact ctcttggagc atatttcagt    720
agggccactc ctaacaaatt ggaatgccaa ggtgattgta gaggaatgtc ttgggatgat    780
ggttgtaatt atgacggagt tagaaaggtg ttcgtcgatg gtataggtaa cgaaatatat    840
actgtcaggt ttgagtacga taatggcgga aaagtggaaa agacaccgta tcgacgtgat    900
gttaaaaatg agaaggagtt tgtgcttgat tatccaaatg aatttatcac gtctgtggag    960
gggaccttag cagctccgaa aagtgttaac atcacgtgga ttcgtcatt gacattcaaa   1020 acatcaaaaa agagaagctc tccaacattt ggatcagcta gtagtagaaa atttgtgctg   1080
gagaagaatg gtagtcctct tgttgggttc catggatata atagtgttgg gaatactctt   1140
aattctcttg gagcatatta tcgcccgatt cctcctactc ctgatgtgga gaaactaaaa   1200
gcacaaggtg gtgtggagga gcttcttggg atgatggtgt tcgagttgga tcctcttgaa   1260
cgtatcacat cagtggaggg tacttatgat gataaaatcg gaggtataac catgcttagg   1320
ttcaagacca caaaaaaaga ctctccgtac tttggattcg gtacattacc aagcttcgtg   1380
cttcacaagg ataatcacca gatcgttggg ttccatggaa aatccagtaa catgcttcat   1440
caacttgggg tccatgttct acccaatggt tttaaatttg tttcttaa            1488

<210> SEQ ID NO 94
```

```
<211> LENGTH: 495
<212> TYPE: PRT
<213> ORGANISM: Arabidopsis thaliana

<400> SEQUENCE: 94

Met Leu Ile Tyr Asn Ala Asp Ser Val Val Phe Leu Phe Ser Leu Phe
1               5                   10                  15

Leu Gln Phe Glu Ile Asn His Leu Gln Asp Glu His Leu Glu Ser Val
            20                  25                  30

Asp Ala Tyr Tyr Asn Lys Lys Ser Tyr Gly Leu Gln Ala Ile Gln Phe
        35                  40                  45

Lys Thr Asn Phe Arg Thr Ser Glu Leu Met Gly Tyr Ser Tyr Glu Cys
50                  55                  60

Thr Met Phe Thr Leu Ala Val Lys Gly Lys Ile Ile Gly Phe His
65                  70                  75                  80

Gly Ser Asp Asn Val His Ile Tyr Ser Leu Gly Ala Tyr Phe Thr Ser
                85                  90                  95

Ile Thr Pro Thr Arg Leu Glu Val Lys Gly Gly Met Gly Gly Lys Lys
            100                 105                 110

Trp Glu Asp Gly Phe Asp His Asp Asn Val Ser Lys Ile Gln Val Leu
        115                 120                 125

Gly Gly Phe Glu Gly Ile Leu Tyr Ile Lys Val Asp Tyr Ile Lys Asn
130                 135                 140

Gly Lys Leu Glu Thr Gly Leu Ile His Gly Asp Ser Gly Asp Gly
145                 150                 155                 160

Phe Leu Gln Lys Met Glu Ile Asn Gln Ser Lys Asn Glu Tyr Leu Val
                165                 170                 175

Tyr Val Glu Gly Tyr Tyr Asp Asp Ala Ser Glu Thr Ile Gln Gly Leu
            180                 185                 190

His Phe Gln Thr Asn Leu Asn Asn Pro Val Met Met Gly Tyr Lys Lys
        195                 200                 205

Gly Arg Lys Phe Leu Leu Ala Ser Asn Gly Asn Lys Ile Ile Gly Phe
210                 215                 220

His Gly Tyr Ala Asp Lys Ser Leu Asn Ser Leu Gly Ala Tyr Phe Ser
225                 230                 235                 240

Arg Ala Thr Pro Asn Lys Leu Glu Cys Gln Gly Asp Cys Arg Gly Met
                245                 250                 255

Ser Trp Asp Asp Gly Cys Asn Tyr Asp Gly Val Arg Lys Val Phe Val
            260                 265                 270

Asp Gly Ile Gly Asn Glu Ile Tyr Thr Val Arg Phe Glu Tyr Asp Asn
        275                 280                 285

Gly Gly Lys Val Glu Lys Thr Pro Tyr Arg Arg Asp Val Lys Asn Glu
290                 295                 300

Lys Glu Phe Val Leu Asp Tyr Pro Asn Glu Phe Ile Thr Ser Val Glu
305                 310                 315                 320

Gly Thr Leu Ala Ala Pro Lys Ser Val Asn Ile Thr Trp Ile Thr Ser
                325                 330                 335

Leu Thr Phe Lys Thr Ser Lys Lys Arg Ser Ser Pro Thr Phe Gly Ser
            340                 345                 350

Ala Ser Ser Arg Lys Phe Val Leu Glu Lys Asn Gly Ser Pro Leu Val
        355                 360                 365

Gly Phe His Gly Tyr Asn Ser Val Gly Asn Thr Leu Asn Ser Leu Gly
370                 375                 380

Ala Tyr Tyr Arg Pro Ile Pro Thr Pro Asp Val Glu Lys Leu Lys
385                 390                 395                 400
```

```
Ala Gln Gly Gly Val Glu Glu Leu Leu Gly Met Met Val Phe Glu Leu
                405                 410                 415

Asp Pro Leu Glu Arg Ile Thr Ser Val Glu Gly Thr Tyr Asp Asp Lys
            420                 425                 430

Ile Gly Gly Ile Thr Met Leu Arg Phe Lys Thr Asn Lys Lys Asp Ser
        435                 440                 445

Pro Tyr Phe Gly Phe Gly Thr Leu Pro Ser Val Leu His Lys Asp
    450                 455                 460

Asn His Gln Ile Val Gly Phe His Gly Lys Ser Ser Asn Met Leu His
465                 470                 475                 480

Gln Leu Gly Val His Val Leu Pro Asn Gly Phe Lys Phe Val Ser
                485                 490                 495
```

<210> SEQ ID NO 95
<211> LENGTH: 1969
<212> TYPE: DNA
<213> ORGANISM: Arabidopsis thaliana

<400> SEQUENCE: 95

| | | | | | |
|---|---|---|---|---|---|
| actgatcagc | atagcagtct | gttcatcttc | agagattatt | gtactaggaa | acacaagaac | 60 |
| cacttcatat | ccagctgaat | attgataaca | tcagttcaag | atgatccaaa | agttgggagc | 120 |
| gaaaggaatc | aagtcagatg | aacgtaatca | gcgggagtgg | gatgatggat | ctaacatga | 180 |
| tgatgtaaca | aagatatacg | tacgaggtgg | tcgtgaagga | ataagatcca | tttatttcaa | 240 |
| ctatgtgaag | aatggaaaac | ccaaagatgg | atcaatccat | ggttactttg | actctggttt | 300 |
| cacacaaacg | tttgagatta | accatctacg | aggtgaatat | cttgaatctg | ttgacgctta | 360 |
| ctacgacaaa | aagtcctacg | gtatgcaagc | aattcaattc | aaaactaact | tcaggacttc | 420 |
| tgaactgatg | gggtatagtt | atgagtgtac | tatgtttacg | ctagccgtcc | aaggaaagaa | 480 |
| gatcattgga | tttcatggat | ctaattatgt | acatatatta | tctcttggag | cttacttcat | 540 |
| ttccattgct | cctacgagat | tggaagtgaa | aggtagtaag | ggaagcaaga | agtgggacga | 600 |
| tggatttgac | catgaaaatg | tatcaaagat | cgaggtacta | ggtggttttg | aaggcatact | 660 |
| gtacatcaaa | gttgactata | tcaagaatgg | aaaactagaa | actggattag | tccatggtca | 720 |
| ctctggtggt | gatggttttt | tacagaagat | ggagattaac | cagtcaaaga | acgaatatct | 780 |
| agtatatgtt | gaaggttact | acgatgatgc | ttctgaaacc | attcaagggc | ttcatttcca | 840 |
| aactaacctc | aacaatcctg | ttatgatggg | gtataaaaag | ggcaggaagt | ttttacttgc | 900 |
| atccaatgga | aataagatca | ttgggtttca | tggatatgcc | gacaaaagcc | taaactctct | 960 |
| tggagcatat | ttcagtacga | ccactcctaa | taaactggaa | tgccaaggtg | atcgtaaagg | 1020 |
| actgccttgg | gatgatggtt | gtaattatga | cggcgtaaaa | aaggtgtatg | tcgatagtat | 1080 |
| aagtgatata | gatagtgtca | ggtttgagta | cgataatggc | ggaaaagtgg | aaaagactcc | 1140 |
| gtaccggcgt | gatgttacaa | atgagaagga | gtttgtgctt | gactatccaa | atgagtttat | 1200 |
| cacgtctgtg | gagggaccct | tagcaactcc | gactaatttt | gacattacgt | ggattctctc | 1260 |
| actgacattc | aaaacatcaa | aagggagaac | ctctccaaca | tttggatcat | cgtctcctgg | 1320 |
| tagaaaattt | gtgctggaga | agaatggtag | cgctcttgtt | gggttccatg | atatattgg | 1380 |
| tcctggttat | aatattaaag | ctcttggagc | atattatcgc | ccgattcctc | ctactcctga | 1440 |
| tgtgaaaaga | ctagaagcac | aaggtggtga | tggaggagct | tcttgggatg | atggtggtac | 1500 |
| tttcaacagt | gttagaaaga | tctacattgg | actaggcaaa | aacgttgtag | ctttgtcaa | 1560 |
| gttttttgtac | tacaaaaacg | ctcgtgttgt | catcggagat | gatcatggca | acaagaccct | 1620 |

```
ttcatctgat ctcctagagt tcttgttgga tccgtttgaa catatcatat cagtggaggg    1680
tacttatgat gatacatctg gaggtataac catgcttagg ttcgagacca acttacaaaa    1740
atctccatac tttggatttg gtacaacatc aaacttcttg cttcacaagg ataatcacca    1800
gatcgttgga ttccatggaa atccagtaa  catgcttcat caacttgggg tccacgttat    1860
acccaacggt tttaaattta tttaataacg ttctcttact tttttctttta ataagtcatg    1920 ttttaatgac atcacatctt caactatcac aatataattt tcttctcct               1969
```

<210> SEQ ID NO 96
<211> LENGTH: 594
<212> TYPE: PRT
<213> ORGANISM: Arabidopsis thaliana

<400> SEQUENCE: 96

```
Met Ile Gln Lys Leu Gly Ala Lys Gly Ile Lys Ser Asp Glu Arg Asn
1               5                   10                  15

Gln Arg Glu Trp Asp Asp Gly Ser Glu His Asp Val Thr Lys Ile
            20                  25                  30

Tyr Val Arg Gly Gly Arg Glu Gly Ile Arg Ser Ile Tyr Phe Asn Tyr
            35                  40                  45

Val Lys Asn Gly Lys Pro Lys Asp Gly Ser Ile His Gly Tyr Phe Asp
        50                  55                  60

Ser Gly Phe Thr Gln Thr Phe Glu Ile Asn His Leu Arg Gly Glu Tyr
65                  70                  75                  80

Leu Glu Ser Val Asp Ala Tyr Tyr Asp Lys Lys Ser Tyr Gly Met Gln
                85                  90                  95

Ala Ile Gln Phe Lys Thr Asn Phe Arg Thr Ser Glu Leu Met Gly Tyr
            100                 105                 110

Ser Tyr Glu Cys Thr Met Phe Thr Leu Ala Val Gln Gly Lys Lys Ile
        115                 120                 125

Ile Gly Phe His Gly Ser Asn Tyr Val His Ile Leu Ser Leu Gly Ala
    130                 135                 140

Tyr Phe Ile Ser Ile Ala Pro Thr Arg Leu Glu Val Lys Gly Ser Lys
145                 150                 155                 160

Gly Ser Lys Lys Trp Asp Asp Gly Phe Asp His Glu Asn Val Ser Lys
                165                 170                 175

Ile Glu Val Leu Gly Gly Phe Glu Gly Ile Leu Tyr Ile Lys Val Asp
            180                 185                 190

Tyr Ile Lys Asn Gly Lys Leu Glu Thr Gly Leu Val His Gly His Ser
        195                 200                 205

Gly Gly Asp Gly Phe Leu Gln Lys Met Glu Ile Asn Gln Ser Lys Asn
    210                 215                 220

Glu Tyr Leu Val Tyr Val Glu Gly Tyr Tyr Asp Asp Ala Ser Glu Thr
225                 230                 235                 240

Ile Gln Gly Leu His Phe Gln Thr Asn Leu Asn Asn Pro Val Met Met
                245                 250                 255

Gly Tyr Lys Lys Gly Arg Lys Phe Leu Leu Ala Ser Asn Gly Asn Lys
            260                 265                 270

Ile Ile Gly Phe His Gly Tyr Ala Asp Lys Ser Leu Asn Ser Leu Gly
        275                 280                 285

Ala Tyr Phe Ser Thr Thr Thr Pro Asn Lys Leu Glu Cys Gln Gly Asp
    290                 295                 300

Arg Lys Gly Leu Pro Trp Asp Asp Gly Cys Asn Tyr Asp Gly Val Lys
305                 310                 315                 320
```

```
Lys Val Tyr Val Asp Ser Ile Ser Asp Ile Asp Ser Val Arg Phe Glu
            325                 330                 335
Tyr Asp Asn Gly Gly Lys Val Glu Lys Thr Pro Tyr Arg Arg Asp Val
            340                 345                 350
Thr Asn Glu Lys Glu Phe Val Leu Asp Tyr Pro Asn Glu Phe Ile Thr
            355                 360                 365
Ser Val Glu Gly Thr Leu Ala Thr Pro Thr Asn Phe Asp Ile Thr Trp
    370                 375                 380
Ile Leu Ser Leu Thr Phe Lys Thr Ser Lys Gly Arg Thr Ser Pro Thr
385                 390                 395                 400
Phe Gly Ser Ser Ser Pro Gly Arg Lys Phe Val Leu Glu Lys Asn Gly
                405                 410                 415
Ser Ala Leu Val Gly Phe His Gly Tyr Ile Gly Pro Gly Tyr Asn Ile
            420                 425                 430
Lys Ala Leu Gly Ala Tyr Tyr Arg Pro Ile Pro Pro Thr Pro Asp Val
            435                 440                 445
Lys Arg Leu Glu Ala Gln Gly Gly Asp Gly Gly Ala Ser Trp Asp Asp
    450                 455                 460
Gly Gly Thr Phe Asn Ser Val Arg Lys Ile Tyr Ile Gly Leu Gly Lys
465                 470                 475                 480
Asn Val Val Gly Phe Val Lys Phe Leu Tyr Tyr Lys Asn Ala Arg Val
                485                 490                 495
Val Ile Gly Asp Asp His Gly Asn Lys Thr Leu Ser Ser Asp Leu Leu
            500                 505                 510
Glu Phe Leu Leu Asp Pro Phe Glu His Ile Ile Ser Val Glu Gly Thr
    515                 520                 525
Tyr Asp Asp Thr Ser Gly Gly Ile Thr Met Leu Arg Phe Glu Thr Asn
    530                 535                 540
Leu Gln Lys Ser Pro Tyr Phe Gly Phe Gly Thr Thr Ser Asn Phe Leu
545                 550                 555                 560
Leu His Lys Asp Asn His Gln Ile Val Gly Phe His Gly Lys Ser Ser
                565                 570                 575
Asn Met Leu His Gln Leu Gly Val His Val Ile Pro Asn Gly Phe Lys
            580                 585                 590
Phe Ile
```

<210> SEQ ID NO 97
<211> LENGTH: 2798
<212> TYPE: DNA
<213> ORGANISM: Arabidopsis thaliana

<400> SEQUENCE: 97

```
aaaacgaaac tcaagtcaat gaataaaaag acgaaacaat gctatgataa gaaaagaaac      60
aacactcgaa aaagttcttc tttttcttcc gcacatgtct gactctctca taagcgtaaa     120
tcgctctgtc aaatatctct gaccagagag acagagttgc ctccacgttt cttcagacaa     180
gactcacgct cttcccttc accacattcc cttctccatt tctcaatctc acttaccttc     240
tcgattcttg ctccaatttc gaatcttccg agtgaaaaaa gcttcaaagt ttggaacttt     300
ctagtgttta ttaatctggg tctgctctga gtttcgtgtg tagctgcata tgagcttaaa     360
gctcgagttt ttccatctgg gtttggaatt ctagggctag tgattggaga ttttgggaat     420
ttaggttgat tttagtaggt ttgacttcag gttgcgtaat ttaggttgat tttgatccga     480
tttgtggaat tagggtttgt ttgttcacaa agcttcaatt tttggagttt aaatggatcg     540
```

| | |
|---|---|
| ataacgactg tgttagaaga aagtttgctg cttcagattc gtattcgata tagaaatgag | 600 |
| tttggttcct cctttaccga ttttatcacc accgtcgtca aattcttcaa caactgcacc | 660 |
| tcctccgtta cagactcagc ccaccactcc atctgctcca cctccggtta caccacctcc | 720 |
| ttctccgccg caatctccgc cgccggttgt atcatcatca ccaccaccac cggttgtttc | 780 |
| gtcacctcca ccgtcttctt ctccaccacc gtcacctcct gtcatcactt cacctcctcc | 840 |
| caccgttgct tcttcccctc cacctcctgt ggtgattgct tccctcctc cctcaactcc | 900 |
| ggcgacaaca ccaccagctc ctccgcaaac tgtctcacct ccaccgcctc ctgatgcttc | 960 |
| tccatcacct cccgcaccaa caacaacaaa tcctcctcct aaaccttctc cttcaccgcc | 1020 |
| gggagaaaca ccttcaccac cgggagaaac accttcaccg cctaaacctt ctccgtcaac | 1080 |
| tccaactcca acaacaacca catctcctcc tcctcctcca gctacctctg cttctcctcc | 1140 |
| gtcttcaaat cctactgatc cttctacgtt agctcctcct ccaactccat acctgttgt | 1200 |
| tcccagagag aaaccaattg ctaaaccaac tggaccagct tcaaacaatg gaaacaacac | 1260 |
| tttgccgtct agttcaccag gtaaaagcga agttggtact ggaggtattg tagctatcgg | 1320 |
| agtgattgtg ggattggttt tcttagcct ttttgtgatg ggtgtgtggt tcactcggaa | 1380 |
| acgaaagcga aaggaccctg gaacctttgt tggatacaca atgcctcctt ccgcttattc | 1440 |
| atctcctcaa ggctcagatg tagtgctctt caactcgcgt tcttcagctc ctcctaaaat | 1500 |
| gagaagccat tctggtagcg attacatgta tgcgtcatct gattcaggca tggttagcaa | 1560 |
| ccaaagatca tggttttcat atgatgagtt atctcaagtt accagtgggt tctccgagaa | 1620 |
| gaatcttctc ggtgaaggag ggtttggctg tgtatacaaa ggcgttcttt ctgacggaag | 1680 |
| ggaagtggca gttaaacagt taagattgg tggaagccaa ggggagagag agttcaaagc | 1740 |
| agaagttgaa atcatttctc gggttcatca ccgccatttg gttacactag ttggttattg | 1800 |
| catctcagag caacataggt tgcttgtata tgattatgta cctaacaaca ctctccatta | 1860 |
| tcatctccat gctccaggaa gaccagttat gacttgggaa actcgggtaa gggtcgctgc | 1920 |
| tggtgcagct cgtggaatcg cctacttaca tgaagactgt catccccgca ttattcaccg | 1980 |
| tgacataaaa tcttccaaca tacttcttga taacagcttt gaagcttggg ttgcggattt | 2040 |
| tggacttgca aaaattgcac aagaactgga tttaaacaca cacgtctcaa cgcgcgtaat | 2100 |
| gggaaccttt gggtacatgg ctcctgaata tgcaacaagt ggaaagctgt ctgaaaaagc | 2160 |
| agatgtttat tcgtatgggg taatactgtt ggagcttata actggccgta aacccgtaga | 2220 |
| tacgtctcaa ccactggtg atgagagcct tgttgaatgg caagaccct tgctgggtca | 2280 |
| agcaatcgag aacgaagaat tcgacgagct agtagatccg aggctaggga aaaacttcat | 2340 |
| cccaggagag atgttcagaa tggtagaagc tgcggctgca tgtgtccgcc actcagctgc | 2400 |
| aaaaagacca aagatgagtc aagtggtgag agctttggac acacttgaag aagcaacgga | 2460 |
| cataaccaac ggaatgagac caggacagag ccaagtgttt gactcgagac aacaatctgc | 2520 |
| tcagataagg atgtttcaaa gaatggcttt tgggagtcaa gattatagtt ctgacttctt | 2580 |
| tgatcgctca cagtcacata gtagctgggg cagtcgtgac cagtccagat ttgtaccttc | 2640 |
| gtagttttta ttgcctttgc ttctttcttc tttcccttta aacatgtcct cgatcttgta | 2700 |
| tattcttttg catgatataa tgtattttg aaatatacat acatacacac ataaatttg | 2760 |
| gtagtctttt gaagaaaaag aataacagat gtatttga | 2798 |

<210> SEQ ID NO 98
<211> LENGTH: 681
<212> TYPE: PRT

<213> ORGANISM: Arabidopsis thaliana

<400> SEQUENCE: 98

```
Met Ser Leu Val Pro Leu Pro Ile Leu Ser Pro Ser Ser Asn
1               5                   10                  15

Ser Ser Thr Thr Ala Pro Pro Leu Gln Thr Gln Pro Thr Thr Pro
                20                  25                  30

Ser Ala Pro Pro Pro Val Thr Pro Pro Ser Pro Pro Gln Ser Pro
            35                  40                  45

Pro Pro Val Val Ser Ser Pro Pro Pro Val Val Ser Ser Pro
    50                  55                  60

Pro Pro Ser Ser Ser Pro Pro Ser Pro Pro Val Ile Thr Ser Pro
65                  70                  75                  80

Pro Pro Thr Val Ala Ser Ser Pro Pro Pro Val Val Ile Ala Ser
                85                  90                  95

Pro Pro Pro Ser Thr Pro Ala Thr Thr Pro Pro Ala Pro Pro Gln Thr
                100                 105                 110

Val Ser Pro Pro Pro Pro Asp Ala Ser Pro Ser Pro Pro Ala Pro
            115                 120                 125

Thr Thr Thr Asn Pro Pro Pro Lys Pro Ser Pro Ser Pro Pro Gly Glu
                130                 135                 140

Thr Pro Ser Pro Pro Gly Glu Thr Pro Ser Pro Pro Lys Pro Ser Pro
145                 150                 155                 160

Ser Thr Pro Thr Pro Thr Thr Thr Thr Ser Pro Pro Pro Pro Ala
                165                 170                 175

Thr Ser Ala Ser Pro Pro Ser Ser Asn Pro Thr Asp Pro Ser Thr Leu
                180                 185                 190

Ala Pro Pro Pro Thr Pro Leu Pro Val Val Pro Arg Glu Lys Pro Ile
                195                 200                 205

Ala Lys Pro Thr Gly Pro Ala Ser Asn Asn Gly Asn Asn Thr Leu Pro
                210                 215                 220

Ser Ser Ser Pro Gly Lys Ser Glu Val Gly Thr Gly Gly Ile Val Ala
225                 230                 235                 240

Ile Gly Val Ile Val Gly Leu Val Phe Leu Ser Leu Phe Val Met Gly
                245                 250                 255

Val Trp Phe Thr Arg Lys Arg Lys Arg Lys Asp Pro Gly Thr Phe Val
                260                 265                 270

Gly Tyr Thr Met Pro Pro Ser Ala Tyr Ser Ser Pro Gln Gly Ser Asp
                275                 280                 285

Val Val Leu Phe Asn Ser Arg Ser Ser Ala Pro Pro Lys Met Arg Ser
                290                 295                 300

His Ser Gly Ser Asp Tyr Met Tyr Ala Ser Ser Asp Ser Gly Met Val
305                 310                 315                 320

Ser Asn Gln Arg Ser Trp Phe Ser Tyr Asp Glu Leu Ser Gln Val Thr
                325                 330                 335

Ser Gly Phe Ser Glu Lys Asn Leu Leu Gly Glu Gly Phe Gly Cys
                340                 345                 350

Val Tyr Lys Gly Val Leu Ser Asp Gly Arg Glu Val Ala Val Lys Gln
                355                 360                 365

Leu Lys Ile Gly Gly Ser Gln Gly Glu Arg Glu Phe Lys Ala Glu Val
                370                 375                 380

Glu Ile Ile Ser Arg Val His His Arg His Leu Val Thr Leu Val Gly
385                 390                 395                 400

Tyr Cys Ile Ser Glu Gln His Arg Leu Leu Val Tyr Asp Tyr Val Pro
```

|     |     |     |     | 405 |     |     |     | 410 |     |     |     | 415 |     |
| --- | --- | --- | --- | --- | --- | --- | --- | --- | --- | --- | --- | --- | --- |
| Asn | Asn | Thr | Leu | His | Tyr | His | Leu | His | Ala | Pro | Gly | Arg | Pro | Val | Met |
|     |     |     | 420 |     |     |     |     | 425 |     |     |     | 430 |     |

Thr Trp Glu Thr Arg Val Arg Val Ala Ala Gly Ala Ala Arg Gly Ile
            435                 440                 445

Ala Tyr Leu His Glu Asp Cys His Pro Arg Ile Ile His Arg Asp Ile
        450                 455                 460

Lys Ser Ser Asn Ile Leu Leu Asp Asn Ser Phe Glu Ala Leu Val Ala
465                 470                 475                 480

Asp Phe Gly Leu Ala Lys Ile Ala Gln Glu Leu Asp Leu Asn Thr His
                485                 490                 495

Val Ser Thr Arg Val Met Gly Thr Phe Gly Tyr Met Ala Pro Glu Tyr
            500                 505                 510

Ala Thr Ser Gly Lys Leu Ser Glu Lys Ala Asp Val Tyr Ser Tyr Gly
        515                 520                 525

Val Ile Leu Leu Glu Leu Ile Thr Gly Arg Lys Pro Val Asp Thr Ser
530                 535                 540

Gln Pro Leu Gly Asp Glu Ser Leu Val Glu Trp Ala Arg Pro Leu Leu
545                 550                 555                 560

Gly Gln Ala Ile Glu Asn Glu Phe Asp Glu Leu Val Asp Pro Arg
                565                 570                 575

Leu Gly Lys Asn Phe Ile Pro Gly Glu Met Phe Arg Met Val Glu Ala
                580                 585                 590

Ala Ala Ala Cys Val Arg His Ser Ala Ala Lys Arg Pro Lys Met Ser
        595                 600                 605

Gln Val Val Arg Ala Leu Asp Thr Leu Glu Glu Ala Thr Asp Ile Thr
610                 615                 620

Asn Gly Met Arg Pro Gly Gln Ser Gln Val Phe Asp Ser Arg Gln Gln
625                 630                 635                 640

Ser Ala Gln Ile Arg Met Phe Gln Arg Met Ala Phe Gly Ser Gln Asp
                645                 650                 655

Tyr Ser Ser Asp Phe Phe Asp Arg Ser Gln Ser His Ser Ser Trp Gly
                660                 665                 670

Ser Arg Asp Gln Ser Arg Phe Val Pro
            675                 680

<210> SEQ ID NO 99
<211> LENGTH: 990
<212> TYPE: DNA
<213> ORGANISM: Arabidopsis thaliana

<400> SEQUENCE: 99

| atggaagaat tagaaaaaac ccagaaattt cagaagaaga agaagcaaca acaagagaaa | 60 |
| caagaccagt cttcaccaat caacttcgag atgtcttcaa gatcatcact tcattcatta | 120 |
| ccacaaacaa cgattgaatc acctcctgat tcaccaaccc tctcttcaat ccccgatagc | 180 |
| catggatctt ctcctcacac gattattcca actccttctg tggccaagac ggagactcct | 240 |
| tttagggtta ctaacggaga ggaggagaag aaagtcagcg agagtaggag acaattgaga | 300 |
| ccgagctttt cttcttcttc ttctactccg cgtgaatcga aatgggcaag tttgattagg | 360 |
| aaagctctac ttgatttag ggttattgcg ctttgtttcgt gtcttgtttc gttctctgta | 420 |
| atggtttctg atagagataa aggatgggct catgattctt tctacaacta caagaattc | 480 |
| aggttctgtt tggctgcgaa tgtgattggt tttgtctact ctggttttat gatatgtgat | 540 |
| cttgtatacc tgttatctac tagcatccga agatcacgac ataacctgcg acatttcttg | 600 |

```
gaatttggtc ttgatcaaat gctagcttat cttcttgcat cagcttcaac ttcagcttcg    660
atccgcgtag atgattggca atcaaactgg ggagcagaca agttcccaga cttagctaga    720
gcatctgtcg cactgtctta cgtctccttt gtcgcattcg ccttctgctc attggcttcc    780
ggttatgctc tatgtgcact ccggtccatc taaactaaac aagcgcaagc tcgagacaaa    840
aagtctcatt ttgtctactc tcagaagttg tatccttgac cctaaacggg tccagtttct    900 gattttaga agaaactttt attttatata gtggagaata ttccatcttg ttaaaagatg    960
gtgcgaatgc tcgtttatac atcactttat                                     990
```

<210> SEQ ID NO 100
<211> LENGTH: 270
<212> TYPE: PRT
<213> ORGANISM: Arabidopsis thaliana

<400> SEQUENCE: 100

```
Met Glu Glu Leu Glu Lys Thr Gln Lys Phe Gln Lys Lys Lys Lys Gln
1               5                   10                  15

Gln Gln Glu Lys Gln Asp Gln Ser Ser Pro Ile Asn Phe Glu Met Ser
            20                  25                  30

Ser Arg Ser Ser Leu His Ser Leu Pro Gln Thr Thr Ile Glu Ser Pro
        35                  40                  45

Pro Asp Ser Pro Thr Leu Ser Ser Ile Pro Asp Ser His Gly Ser Ser
    50                  55                  60

Pro His Thr Ile Ile Pro Thr Pro Ser Val Ala Lys Thr Glu Thr Pro
65                  70                  75                  80

Phe Arg Val Thr Asn Gly Glu Glu Lys Lys Val Ser Glu Ser Arg
                85                  90                  95

Arg Gln Leu Arg Pro Ser Phe Ser Ser Ser Ser Thr Pro Arg Glu
            100                 105                 110

Ser Lys Trp Ala Ser Leu Ile Arg Lys Ala Leu Leu Gly Phe Arg Val
        115                 120                 125

Ile Ala Phe Val Ser Cys Leu Val Ser Phe Ser Val Met Val Ser Asp
130                 135                 140

Arg Asp Lys Gly Trp Ala His Asp Ser Phe Tyr Asn Tyr Lys Glu Phe
145                 150                 155                 160

Arg Phe Cys Leu Ala Ala Asn Val Ile Gly Phe Val Tyr Ser Gly Phe
                165                 170                 175

Met Ile Cys Asp Leu Val Tyr Leu Leu Ser Thr Ser Ile Arg Arg Ser
            180                 185                 190

Arg His Asn Leu Arg His Phe Leu Glu Phe Gly Leu Asp Gln Met Leu
        195                 200                 205

Ala Tyr Leu Leu Ala Ser Ala Ser Thr Ser Ala Ser Ile Arg Val Asp
    210                 215                 220

Asp Trp Gln Ser Asn Trp Gly Ala Asp Lys Phe Pro Asp Leu Ala Arg
225                 230                 235                 240

Ala Ser Val Ala Leu Ser Tyr Val Ser Phe Val Ala Phe Ala Phe Cys
                245                 250                 255

Ser Leu Ala Ser Gly Tyr Ala Leu Cys Ala Leu Arg Ser Ile
            260                 265                 270
```

<210> SEQ ID NO 101
<211> LENGTH: 1047
<212> TYPE: DNA
<213> ORGANISM: Arabidopsis thaliana

```
<400> SEQUENCE: 101
atggatacat gcaggaacaa gtgtggaggg tgttataggc aattcaacaa gaaggagcac      60
ttggtggaac acatgaggat ctcttatcat tcggttcatg aacctacttg tggtatttgc     120
aacaaacatt gccgatcttt tgactccctc cgtgaacatc tcattgggcc attgccgaaa     180
caagaatgta agaacatttt cagcattcgc ggctgcagat tctgtcttac gatcctcgaa     240
agccccaacg ctcgtagaat ccatcaagag agatgccagc tctcaaacgt cacttctgga     300
ttaatgattc gtatggcggc cttaggccta agaaacaact caacaattga ctacacttct     360
tcgaggtcac ctcgagtggt ggcactctca tgcaagatgg ttggaggagg cagtgacgga     420
tcgcttgacc tatgcgcaag agtttgcatt acggatgaga gcgaaaatgt tgtgttccac     480
acgtatgtga agccaacgat acccgtaacg aattataggt atgagatgac agggattcga     540
cctgaaaatc taagggacgc aatgcgatta agcacgcac  agagaaaggt tcaagagttt     600
ctttgtaatg agaaccaat gtggaagatt cgtccaagaa atgggaaagc aaggattctc      660
gttggacatg gacttgataa ccatcttgac tctcttcaac ttgaatattc ttcctctatg     720
ataagagata ctgcggaata ccctccattg atgaaatcaa gcaagctaag caactctctc     780
aagtacttaa cccaagccta tctcggttat gatattcatg tgggaataca agatccttac     840
gaggactgtg tcgcgacaat gaggctatac acgagaatgc gatatcagaa acacagggcc     900
gaggcctatc cgctggcctc ggacacgcag aaccacaata actttgcggc gtggaggcag     960
aatgaactag agaggatgtc tccagaggag ttgctcgacc tttcacgttc agactattac    1020
tgctggtgct tggactcggt tgcttga                                        1047

<210> SEQ ID NO 102
<211> LENGTH: 348
<212> TYPE: PRT
<213> ORGANISM: Arabidopsis thaliana

<400> SEQUENCE: 102

Met Asp Thr Cys Arg Asn Lys Cys Gly Gly Cys Tyr Arg Gln Phe Asn
1               5                   10                  15

Lys Lys Glu His Leu Val Glu His Met Arg Ile Ser Tyr His Ser Val
                20                  25                  30

His Glu Pro Thr Cys Gly Ile Cys Asn Lys His Cys Arg Ser Phe Asp
            35                  40                  45

Ser Leu Arg Glu His Leu Ile Gly Pro Leu Pro Lys Gln Glu Cys Lys
        50                  55                  60

Asn Ile Phe Ser Ile Arg Gly Cys Arg Phe Cys Leu Thr Ile Leu Glu
65                  70                  75                  80

Ser Pro Asn Ala Arg Arg Ile His Gln Glu Arg Cys Gln Leu Ser Asn
                85                  90                  95

Val Thr Ser Gly Leu Met Ile Arg Met Ala Ala Leu Gly Leu Arg Asn
            100                 105                 110

Asn Ser Thr Ile Asp Tyr Thr Ser Arg Ser Pro Arg Val Val Ala
        115                 120                 125

Leu Ser Cys Lys Met Val Gly Gly Ser Asp Gly Ser Leu Asp Leu
    130                 135                 140

Cys Ala Arg Val Cys Ile Thr Asp Glu Ser Glu Asn Val Val Phe His
145                 150                 155                 160

Thr Tyr Val Lys Pro Thr Ile Pro Val Thr Asn Tyr Arg Tyr Glu Met
                165                 170                 175

Thr Gly Ile Arg Pro Glu Asn Leu Arg Asp Ala Met Arg Leu Lys His
```

```
                    180             185              190
Ala Gln Arg Lys Val Gln Glu Phe Leu Cys Asn Gly Glu Pro Met Trp
                195                 200             205
Lys Ile Arg Pro Arg Asn Gly Lys Ala Arg Ile Leu Val Gly His Gly
210                 215                 220
Leu Asp Asn His Leu Asp Ser Leu Gln Leu Glu Tyr Ser Ser Ser Met
225                 230                 235                 240
Ile Arg Asp Thr Ala Glu Tyr Pro Pro Leu Met Lys Ser Ser Lys Leu
                245                 250                 255
Ser Asn Ser Leu Lys Tyr Leu Thr Gln Ala Tyr Leu Gly Tyr Asp Ile
                260                 265                 270
His Val Gly Ile Gln Asp Pro Tyr Glu Asp Cys Val Ala Thr Met Arg
                275                 280                 285
Leu Tyr Thr Arg Met Arg Tyr Gln Lys His Arg Ala Glu Ala Tyr Pro
                290                 295                 300
Leu Ala Ser Asp Thr Gln Asn His Asn Asn Phe Ala Ala Trp Arg Gln
305                 310                 315                 320
Asn Glu Leu Glu Arg Met Ser Pro Glu Glu Leu Leu Asp Leu Ser Arg
                325                 330                 335
Ser Asp Tyr Tyr Cys Trp Cys Leu Asp Ser Val Ala
                340                 345

<210> SEQ ID NO 103
<211> LENGTH: 1785
<212> TYPE: DNA
<213> ORGANISM: Arabidopsis thaliana

<400> SEQUENCE: 103
atggtcctag ttgaggagct ctctgacgta tcatcaccta caaatgaagc aaatcaagca      60
tattcctatg atgatgatga tgatgatgat ggatcattaa ccccatccat ggtgtttgac     120
cagatcatgg gaacttctct gatgcttcca tttcacgaac atcctgtata caaccactat     180
agcagcactg tcaatgcgca cggatgcccc gaacttcgag aaaacggtct ccatggctat     240
aactgcaata cttgcgggct caccgtccac aaagaatgtg ctgaatcatc accagagatt     300
aaccatcctt ctcaccagag acaccctctc atgctcctaa cacatggctt accacaagaa     360
gctgaagatg acaaatgtcg tctatgtgga gaaaaggttg gaaaattagt ttatcattgt     420
tcaatatgtg acttcagttt ggatcttttt tgtgctcgaa acccgctttc actagttgtt     480
tacttccgga aaggtcatga acatacactc actctcatgc aaggctcat acgcttcact     540
tgtaatgcat gtggtcttga atccgatcga tctccttaca tttgtgctca atgtgatttt     600
atgatccatg aagattgtat ctacttacca cgcgtcatta gcatcatacg ccatgaacat     660
cgaatttctc gaacttattt tcttggttct ggagattgga aatgcggagt tgtagaaga      720
agaatggatg ggagatatgg agcatattct tgctcgattt gtccggatta tgcagttcat     780
tctagatgtg ccacgaggag ggatgtgtgg gatggattag aacttgagga cgagccagaa     840
gatatcgaag aatgtgaaga accgtttaga gttgtgagtg atggagtaat caatcacttt     900
agtcatcgag aacatgatct aaggcttgaa gatggtctta ctaatcgcca tgatgaaaat     960
attcgatgca gagcatgcgt ccgtcctgtc tacgctaaca cattctacag ttgtatgcaa    1020
tgtgatgatt tcattctcca cgagacatgt gctaatcttc ctcgaaagaa gcgacatgta    1080
ctacacaatc atcagcttac tctataccc gatgacaaca tagtcatgga ctttccgatg    1140
cttcgtggag tatttttatg cactgcttgt cgccgactct gtagtggttt caggtatgaa    1200
```

```
tgttgcaata tcaaattaga cgtacgatgc ggttccatat ccgaaccatt tttctacgag    1260
tgtcacccgc atcctctgtt ccagacttca ctagatagca aggtatgtga gacttgcaag    1320
gaagagtcag attatgttct aacttgtatg gattgtgatt atgttttgga tttcgagtgt    1380
gctactttac cacctacggt aaggtacaaa tatgatagac atcctcttaa actatgctac    1440
gatggagaca aggacatggc cggtagttat tggtgcgaga tatgtgagaa agaaatggat    1500
caaaatataa tattctacac ttgtgaaagt tctggtccga ctattcatat cgagtgtgta    1560
cttggagatt tcaggtatgt gaagcctcga ctacattttg agttcaataa aaagaaatgg    1620
gaagtggctt tgaatggtat aaaccgacca ggatgctaca aatgtggctt tcgttgcaag    1680
ggaccttttg ttgcagtaag tgtagactat gatattagtt atgtttgttc tcttttatgt    1740
ttatggaaag gagaaactct cgtgtacggt agtataagag attga                    1785
```

<210> SEQ ID NO 104
<211> LENGTH: 594
<212> TYPE: PRT
<213> ORGANISM: Arabidopsis thaliana

<400> SEQUENCE: 104

```
Met Val Leu Val Glu Glu Leu Ser Asp Val Ser Ser Pro Thr Asn Glu
1               5                   10                  15

Ala Asn Gln Ala Tyr Ser Tyr Asp Asp Asp Asp Asp Asp Gly Ser
            20                  25                  30

Leu Thr Pro Ser Met Val Phe Asp Gln Ile Met Gly Thr Ser Leu Met
        35                  40                  45

Leu Pro Phe His Glu His Pro Val Tyr Asn His Tyr Ser Ser Thr Gly
    50                  55                  60

Gln Cys Asp Gly Cys Pro Glu Leu Arg Glu Asn Gly Leu His Gly Tyr
65                  70                  75                  80

Asn Cys Asn Thr Cys Gly Leu Thr Val His Lys Glu Cys Ala Glu Ser
                85                  90                  95

Ser Pro Glu Ile Asn His Pro Ser His Gln Arg His Pro Leu Met Leu
            100                 105                 110

Leu Thr His Gly Leu Pro Gln Glu Ala Glu Asp Asp Lys Cys Arg Leu
        115                 120                 125

Cys Gly Glu Lys Val Gly Lys Leu Val Tyr His Cys Ser Ile Cys Asp
    130                 135                 140

Phe Ser Leu Asp Leu Phe Cys Ala Arg Asn Pro Leu Ser Leu Val Val
145                 150                 155                 160

Tyr Phe Arg Lys Gly His Glu His Thr Leu Thr Leu Met Pro Arg Leu
                165                 170                 175

Ile Arg Phe Thr Cys Asn Ala Cys Gly Leu Glu Ser Asp Arg Ser Pro
            180                 185                 190

Tyr Ile Cys Ala Gln Cys Asp Phe Met Ile His Glu Asp Cys Ile Tyr
        195                 200                 205

Leu Pro Arg Val Ile Ser Ile Arg His Glu His Arg Ile Ser Arg
    210                 215                 220

Thr Tyr Phe Leu Gly Ser Gly Asp Trp Lys Cys Gly Val Cys Arg Arg
225                 230                 235                 240

Arg Met Asp Gly Arg Tyr Gly Ala Tyr Ser Cys Ser Ile Cys Pro Asp
                245                 250                 255

Tyr Ala Val His Ser Arg Cys Ala Thr Arg Arg Asp Val Trp Asp Gly
            260                 265                 270

Leu Glu Leu Glu Asp Glu Pro Glu Asp Ile Glu Glu Cys Glu Glu Pro
```

```
                275                 280                 285
Phe Arg Val Val Ser Asp Gly Val Ile Asn His Phe Ser His Arg Glu
290                 295                 300
His Asp Leu Arg Leu Glu Asp Gly Leu Thr Asn Arg His Asp Glu Asn
305                 310                 315                 320
Ile Arg Cys Arg Ala Cys Val Arg Pro Val Tyr Ala Asn Thr Phe Tyr
            325                 330                 335
Ser Cys Met Gln Cys Asp Phe Ile Leu His Glu Thr Cys Ala Asn
            340                 345                 350
Leu Pro Arg Lys Lys Arg His Val Leu His Asn His Gln Leu Thr Leu
            355                 360                 365
Tyr Pro Asp Asp Asn Ile Val Met Asp Phe Pro Met Leu Arg Gly Val
370                 375                 380
Phe Leu Cys Thr Ala Cys Arg Arg Leu Cys Ser Gly Phe Arg Tyr Glu
385                 390                 395                 400
Cys Cys Asn Ile Lys Leu Asp Val Arg Cys Gly Ser Ile Ser Glu Pro
                405                 410                 415
Phe Phe Tyr Glu Cys His Pro His Pro Leu Phe Gln Thr Ser Leu Asp
            420                 425                 430
Ser Lys Val Cys Glu Thr Cys Lys Glu Glu Ser Asp Tyr Val Leu Thr
            435                 440                 445
Cys Met Asp Cys Asp Tyr Val Leu Asp Phe Glu Cys Ala Thr Leu Pro
450                 455                 460
Pro Thr Val Arg Tyr Lys Tyr Asp Arg His Pro Leu Lys Leu Cys Tyr
465                 470                 475                 480
Asp Gly Asp Lys Asp Met Ala Gly Ser Tyr Trp Cys Glu Ile Cys Glu
                485                 490                 495
Lys Glu Met Asp Gln Asn Ile Ile Phe Tyr Thr Cys Glu Ser Ser Gly
                500                 505                 510
Pro Thr Ile His Ile Glu Cys Val Leu Gly Asp Phe Arg Tyr Val Lys
            515                 520                 525
Pro Arg Leu His Phe Glu Phe Asn Lys Lys Lys Trp Glu Val Ala Leu
530                 535                 540
Asn Gly Ile Asn Arg Pro Gly Cys Tyr Lys Cys Gly Phe Arg Cys Lys
545                 550                 555                 560
Gly Pro Phe Val Ala Val Ser Val Asp Tyr Asp Ile Ser Tyr Val Cys
                565                 570                 575
Ser Leu Leu Cys Leu Trp Lys Gly Glu Thr Leu Val Tyr Gly Ser Ile
            580                 585                 590
Arg Asp

<210> SEQ ID NO 105
<211> LENGTH: 5224
<212> TYPE: DNA
<213> ORGANISM: Arabidopsis thaliana

<400> SEQUENCE: 105
atggaaggtg ggtctgaaaa acaacacct gaaggttgtg gtggtgagag taagtctaaa      60
cggaaaatga aaactgctgc tcaacttgaa gttcttgaaa acacttattc agctgagcct    120
tatccttcgg aagctataag agcggatctc tcagtgaaac tgaatctttc cgatagacag    180
ttacagatgt ggttttgtca ccggcggctt aaagaacgga atctactac gccgagcaaa    240 cgtcagcgta aggagttagt aactccaacg gctatggaat cctgggaacc acccgtcaat    300
gccggtgatt tagtggcggg aaatgagctt gattctagaa gagctgctcg aggcagtggc    360
```

```
ggtagtggtg tgacggttgt gaggcggttt aatgaaccgt cttctgctga ggttagagct    420
attggttatg ttgaagctca attgggagag cggttgagag ataacggacc ggttcttgga    480
atggagtttg atcctttacc tcctggtgca tttggcatgc ctattgagat gccaagccat    540
cgcaaggcga ctaggcaagc tttcgagacc aacatatatg tccgatccga tgtcaagcct    600
atcaaagatc atgtgaggcc tattcgtgaa tatcagttca ttcctgagct gccatcttcg    660
aggactgatc attcggaacg agtttctccg tcacatcatt ttggagttcc acttgatggt    720
tcggttatga gggtttcagc tgtgtctgct ggacatcggg atgactataa aatttcacct    780
cagataccaa atttgaatct tgcaactcat caagggaagc cggggcatgt ctattcgcct    840
aacttggtcg aatatgactc accgtatcag aaaagctaca tggatactgc tgcacaagtt    900
catgatgatc cttttgtgaa atcagagaga gaagttggta atgaggatga ggatgatgat    960
gccctgcaat tagagagaca ccgcaagaat gaagaagcaa gaatagctcg ggaagtcgag   1020
gctcatgaga agaggatccg aagggaacta gagaaacaag atatgctgag gcgaaagaga   1080
gaagagcaaa taaggaaaga aatggagagg caagatcgtg aaagacggaa agaggaagaa   1140
cgtctttac gtgaaaaaca gagagaggaa gagaggtacc ttaaagagca gatgcgagag   1200
ttgcagcgaa gagagaagtt cttgaagaaa gaaacaatca gggctgagaa aatgcgacaa   1260
aaagaagaga tgcgtaaaga aaaagaggtt gccaggctta agctgctaa tgagagggcc   1320
attgctcgta agatcgcaaa ggaatctatg gaacttattg aagatgaacg cttagagctc   1380
atggaggttc tgcgttaac aaaaggcttg ccttcaatgc tcgcccttga ctttgaaact   1440
ctacagaacc tcgatgaata tagagacaag caggcaatat ttcccccaac atctgtaaaa   1500
ttgaaaaagc cctttgcagt caagccgtgg aatggttctg atgagaatgt tgcaaatctt   1560
cttatggtgt ggagattctt aatcactttc gcagacgttc ttggtctttg gccatttacc   1620
ctggacgagt ttgctcaggc attccatgac tatgacccac ggctaatggg agagatacac   1680
attgttctat tgaagactat aatcaaagat atcgagggtg tggtaagaac gctgtcgacc   1740
ggtgttggag caaaccagaa tgttgctgct aatcccggag ggggtcatcc tcacgttgtg   1800
gagggtgcat acgcgtgggg ttttgatata cgcagctgga gaaaaaactt gaatgttttt   1860
acatggcctg aaatcttgag gcaactcgct ctctctgccg ggttgggacc gcaactgaag   1920
aaaatgaaca ttaggactgt gtctgttcat gatgacaatg aggccaacaa ctctgagaat   1980
gtgattttca acctaaggaa aggagtagca gctgagaatg cttttgccaa gatgcaagag   2040
aggggacttt ctaatccacg acgttcacgg catcgtttga ctccaggcac tgttaagttt   2100
gctgcatttc atgttctatc tcttgaaggt gaaaaaggtt tgaacattct tgaggttgca   2160
gagaagattc agaaatcagg attgagggat ctaacgacga gtaggacacc tgaagcctcg   2220
gttgctgctg cgttgtctcg agatacaaaa ctctttgaga gggtagctcc ttctacgtat   2280
tgtgtacgtg cttcctatag aaaagatgca ggtgatgctg agactatatt tgctgaagcg   2340
agagagagaa tacgtgcatt caagagcggc atcactgatg tagaagatgt tgatgacgct   2400
gagagagatg aagactctga aagcgatgtc ggagaagacc cagaggttga tgtgaacctt   2460
aaaaaggaag atcccaatcc tctgaaggta gaaaacttaa ttggagtcga accattgttg   2520
gaaaatggga aactggatac cgtgcccatg aaaactgaac tgggactgcc tcttactccc   2580
tctctccccg aggaaatgaa agatgagaaa agagatgaca ctttagcgga ccaatctcta   2640
gaggatgcgg tagcaaacgg tgaagatagt gcttgttttg acgagagcaa acttgggaa   2700
cagtgggttc aaggacttgt agaaggagat tactcgaatc ttagcagcga ggaacgttta   2760
```

```
aacgcacttg ttgctctgat tggtattgcc accgaaggaa acacaatccg aatcgccctt   2820
gaggaacggt tggaggtagc aagtgcatta agaaacaga tgtggggtga agtgcaactc    2880
gacaaacgct ggaaagaaga gtctttgatt cgagcaaatt acctctcata cccaacagca   2940
aagccggggc ttaatatcgc aacccctgca tctggaaatc aagaaagttc atcagcggat   3000
gtgactccaa tctcctcaca ggacccggtg agtcttccac agatcgatgt gaataacgtg   3060
attgctggac caagcttgca attgcaagaa aatgtacctg gagtggagaa tttgcagtat   3120
cagcagcaac aggggtacac agcggaccgg gaaaggctgc gtgcacagtt aaaagcgtat   3180
gttgggtata aagctgaaga gctatatgta tataggtcgc ttccgctagg tcaagatcga   3240
agacgcaatc gctattggcg gttttcagca tccgcctctc gaaatgatcc tggttgtggt   3300
agaatattcg tggaacttca ggacggacgc tggaggctca ttgattccga agaggctttt   3360
gactatttgg tgaagtcact agatgttcgc ggtgtaagag aatcacattt acactttatg   3420
ttgctgaaga tcgaagcatc cttcaaggaa gcattaagga ggaatgtggc agcaaatccc   3480
ggggtgtgtt ccatatcttc tagcttggat tccgatactg cggaaatctc cacgacgttt   3540
aagatcgagc taggggatag taacgccgtt gagagatgca gcgtattgca acgcttccat   3600
agtttcgaga agtggatgtg ggataaatatg ctgcatccta gtgctttatc tgcatttaag   3660
tatggtgcta agcaaagcag tccgcttttt cgcatatgca gaatctgtgc ggaactacac   3720
tttgtcggag atatttgctg tcctagttgc ggtcagatgc atgctggtcc agatgttggt   3780
gagttgtgtt ttgctgagca gtggctcaa ctcggggata atttgagaag aggagatact   3840
ggctttatct tgcgtagctc aatcttgtct cctcttagaa taagactact caaggttcag   3900
ttagcacttg tcgaagcttc tcttccacct gaaggacttg aagcttttg gacagagaat    3960 cttaggaaat cttggggtat gaagctgttg tcatcaagtt cccatgaaga tctttatcag   4020
gttctcacaa cgttagaggc agcactaaag agggatttct tgtcttcaaa ctttgaaaca   4080
acttctgaac tcttgggttt acaagaagga gctctcgcca gcgatcttac ttgtggggtt   4140
aatgtactac cgtggatacc aaagacagca ggaggtgtag cttttgagact cttttgatttc   4200 gacagctcga ttgtttacac acccgatcaa aacaacgatc ctctaaaaga caaagaatct   4260
gaagatttcg tgggtttgga gacaaatatt ctgagaaact acatgagaa ggacgtaatg    4320 gaaactccgg tgcaagttgc tgcttataag caagaagaga actggacgga tcctggttta   4380
ggtggtgtgt ctagctctgg gagaggaggt cgaccaccac gaggacgtgg ccggcctcgt   4440
gcccgtggca atggcaagaa accggcagtt tctgttaaac caccacgagg tgcagcaaac   4500
tcaaatggtg aaaccatgtt gagaccgaga gcacaaccac gtgggggtag aaagaatggg   4560
cggcgtagtg gcaccaaagg ccgaaagaga ccaacgcaag gaacactcgg tatatgtaat   4620
gaagtaggag gaggacgtcg ggttaaggaa gttgctgtaa ccgccaaaac cagtcttcct   4680
gataacgatg acgattggat cgaaacccct gaactgcaag acgatgacgg agaagctagc   4740
agctcgggga atcgtttca gtatgaggac tatgatgatg atgatgtcat ggctccgatt   4800
gatgattttg atggcggcgg cgaatcaagt aaattagtag gtaggggga atttagctta   4860 catagtgatg atgaatacga agaagaagag gaagaagaag aagacatgaa catgaaaatg   4920
gatgtgaatg ttgttgatga tgaggatgaa gattacataa acgaagactc gtatggtaga   4980
aagcagcatg ggattagcat tagcaacgat gcagcgactc ggaaaaggtt taataagttt   5040
gaagatcctg atctaacatc ttcatcgtct tctgattttc aatgactgat tttagacaag   5100
aacctacgaa gcttgttttt gtattcttca aaatgaattc ttttagtgta acaacctttt   5160
```

```
tgtaaggtaa cgtcaatgta atccttttgt ctcttatgag cttgcttata cggttattat    5220
tatt                                                                 5224
```

<210> SEQ ID NO 106
<211> LENGTH: 1694
<212> TYPE: PRT
<213> ORGANISM: Arabidopsis thaliana

<400> SEQUENCE: 106

```
Met Glu Gly Gly Ser Glu Lys Thr Thr Pro Glu Gly Cys Gly Gly Glu
1               5                   10                  15

Ser Lys Ser Lys Arg Lys Met Lys Thr Ala Ala Gln Leu Glu Val Leu
            20                  25                  30

Glu Asn Thr Tyr Ser Ala Glu Pro Tyr Pro Ser Glu Ala Ile Arg Ala
        35                  40                  45

Asp Leu Ser Val Lys Leu Asn Leu Ser Asp Arg Gln Leu Gln Met Trp
    50                  55                  60

Phe Cys His Arg Arg Leu Lys Glu Arg Lys Ser Thr Thr Pro Ser Lys
65                  70                  75                  80

Arg Gln Arg Lys Glu Leu Val Thr Pro Thr Ala Met Glu Ser Trp Glu
                85                  90                  95

Pro Pro Val Asn Ala Gly Asp Leu Val Ala Gly Asn Glu Leu Asp Ser
            100                 105                 110

Arg Arg Ala Ala Arg Gly Ser Gly Gly Ser Gly Val Thr Val Val Arg
        115                 120                 125

Arg Phe Asn Glu Pro Ser Ser Ala Glu Val Arg Ala Ile Gly Tyr Val
    130                 135                 140

Glu Ala Gln Leu Gly Glu Arg Leu Arg Asp Asn Gly Pro Val Leu Gly
145                 150                 155                 160

Met Glu Phe Asp Pro Leu Pro Pro Gly Ala Phe Gly Met Pro Ile Glu
                165                 170                 175

Met Pro Ser His Arg Lys Ala Thr Arg Gln Ala Phe Glu Thr Asn Ile
            180                 185                 190

Tyr Val Arg Ser Asp Val Lys Pro Ile Lys Asp His Val Arg Pro Ile
        195                 200                 205

Arg Glu Tyr Gln Phe Ile Pro Glu Leu Pro Ser Ser Arg Thr Asp His
    210                 215                 220

Ser Glu Arg Val Ser Pro Ser His His Phe Gly Val Pro Leu Asp Gly
225                 230                 235                 240

Ser Val Met Arg Val Ser Ala Val Ser Ala Gly His Arg Asp Asp Tyr
                245                 250                 255

Lys Ile Ser Pro Gln Ile Pro Asn Leu Asn Leu Ala Thr His Gln Gly
            260                 265                 270

Lys Pro Gly His Val Tyr Ser Pro Asn Leu Val Glu Tyr Asp Ser Pro
        275                 280                 285

Tyr Gln Lys Ser Tyr Met Asp Thr Ala Ala Gln Val His Asp Asp Pro
    290                 295                 300

Phe Val Lys Ser Glu Arg Glu Val Gly Asn Glu Asp Glu Asp Asp
305                 310                 315                 320

Ala Leu Gln Leu Glu Arg His Arg Lys Asn Glu Ala Arg Ile Ala
                325                 330                 335

Arg Glu Val Glu Ala His Glu Lys Arg Ile Arg Arg Glu Leu Glu Lys
            340                 345                 350

Gln Asp Met Leu Arg Arg Lys Arg Glu Glu Gln Ile Arg Lys Glu Met
```

```
            355                 360                 365
Glu Arg Gln Asp Arg Glu Arg Lys Glu Glu Arg Leu Leu Arg
    370                 375                 380
Glu Lys Gln Arg Glu Glu Arg Tyr Leu Lys Glu Gln Met Arg Glu
385                 390                 395                 400
Leu Gln Arg Arg Glu Lys Phe Leu Lys Lys Glu Thr Ile Arg Ala Glu
                405                 410                 415
Lys Met Arg Gln Lys Glu Glu Met Arg Lys Glu Lys Glu Val Ala Arg
            420                 425                 430
Leu Lys Ala Ala Asn Glu Arg Ala Ile Ala Arg Lys Ile Ala Lys Glu
            435                 440                 445
Ser Met Glu Leu Ile Glu Asp Glu Arg Leu Glu Leu Met Glu Val Ala
    450                 455                 460
Ala Leu Thr Lys Gly Leu Pro Ser Met Leu Ala Leu Asp Phe Glu Thr
465                 470                 475                 480
Leu Gln Asn Leu Asp Glu Tyr Arg Asp Lys Gln Ala Ile Phe Pro Pro
                485                 490                 495
Thr Ser Val Lys Leu Lys Lys Pro Phe Ala Val Lys Pro Trp Asn Gly
            500                 505                 510
Ser Asp Glu Asn Val Ala Asn Leu Leu Met Val Trp Arg Phe Leu Ile
            515                 520                 525
Thr Phe Ala Asp Val Leu Gly Leu Trp Pro Phe Thr Leu Asp Glu Phe
    530                 535                 540
Ala Gln Ala Phe His Asp Tyr Asp Pro Arg Leu Met Gly Glu Ile His
545                 550                 555                 560
Ile Val Leu Leu Lys Thr Ile Ile Lys Asp Ile Glu Gly Val Val Arg
                565                 570                 575
Thr Leu Ser Thr Gly Val Gly Ala Asn Gln Asn Val Ala Ala Asn Pro
            580                 585                 590
Gly Gly Gly His Pro His Val Val Glu Gly Ala Tyr Ala Trp Gly Phe
            595                 600                 605
Asp Ile Arg Ser Trp Arg Lys Asn Leu Asn Val Phe Thr Trp Pro Glu
    610                 615                 620
Ile Leu Arg Gln Leu Ala Leu Ser Ala Gly Leu Gly Pro Gln Leu Lys
625                 630                 635                 640
Lys Met Asn Ile Arg Thr Val Ser Val His Asp Asn Glu Ala Asn
                645                 650                 655
Asn Ser Glu Asn Val Ile Phe Asn Leu Arg Lys Gly Val Ala Ala Glu
            660                 665                 670
Asn Ala Phe Ala Lys Met Gln Glu Arg Gly Leu Ser Asn Pro Arg Arg
            675                 680                 685
Ser Arg His Arg Leu Thr Pro Gly Thr Val Lys Phe Ala Ala Phe His
    690                 695                 700
Val Leu Ser Leu Glu Gly Glu Lys Gly Leu Asn Ile Leu Glu Val Ala
705                 710                 715                 720
Glu Lys Ile Gln Lys Ser Gly Leu Arg Asp Leu Thr Thr Ser Arg Thr
                725                 730                 735
Pro Glu Ala Ser Val Ala Ala Ala Leu Ser Arg Asp Thr Lys Leu Phe
            740                 745                 750
Glu Arg Val Ala Pro Ser Thr Tyr Cys Val Arg Ala Ser Tyr Arg Lys
            755                 760                 765
Asp Ala Gly Asp Ala Glu Thr Ile Phe Ala Glu Ala Arg Glu Arg Ile
    770                 775                 780
```

```
Arg Ala Phe Lys Ser Gly Ile Thr Asp Val Glu Asp Val Asp Ala
785                 790                 795                 800

Glu Arg Asp Glu Asp Ser Glu Ser Asp Val Gly Asp Pro Glu Val
            805                 810                 815

Asp Val Asn Leu Lys Lys Glu Asp Pro Asn Pro Leu Lys Val Glu Asn
            820                 825                 830

Leu Ile Gly Val Glu Pro Leu Leu Glu Asn Gly Lys Leu Asp Thr Val
            835                 840                 845

Pro Met Lys Thr Glu Leu Gly Leu Pro Leu Thr Pro Ser Leu Pro Glu
850                 855                 860

Glu Met Lys Asp Glu Lys Arg Asp Asp Thr Leu Ala Asp Gln Ser Leu
865                 870                 875                 880

Glu Asp Ala Val Ala Asn Gly Glu Asp Ser Ala Cys Phe Asp Glu Ser
                885                 890                 895

Lys Leu Gly Glu Gln Trp Val Gln Gly Leu Val Glu Gly Asp Tyr Ser
            900                 905                 910

Asn Leu Ser Ser Glu Glu Arg Leu Asn Ala Leu Val Ala Leu Ile Gly
            915                 920                 925

Ile Ala Thr Glu Gly Asn Thr Ile Arg Ile Ala Leu Glu Glu Arg Leu
930                 935                 940

Glu Val Ala Ser Ala Leu Lys Lys Gln Met Trp Gly Glu Val Gln Leu
945                 950                 955                 960

Asp Lys Arg Trp Lys Glu Ser Leu Ile Arg Ala Asn Tyr Leu Ser
            965                 970                 975

Tyr Pro Thr Ala Lys Pro Gly Leu Asn Ile Ala Thr Pro Ala Ser Gly
            980                 985                 990

Asn Gln Glu Ser Ser Ser Ala Asp  Val Thr Pro Ile Ser  Ser Gln Asp
        995                 1000                1005

Pro Val  Ser Leu Pro Gln Ile  Asp Val Asn Asn Val  Ile Ala Gly
    1010                1015                1020

Pro Ser  Leu Gln Leu Gln Glu  Asn Val Pro Gly Val  Glu Asn Leu
    1025                1030                1035

Gln Tyr  Gln Gln Gln Gln Gly  Tyr Thr Ala Asp Arg  Glu Arg Leu
    1040                1045                1050

Arg Ala  Gln Leu Lys Ala Tyr  Val Gly Tyr Lys Ala  Glu Glu Leu
    1055                1060                1065

Tyr Val  Tyr Arg Ser Leu Pro  Leu Gly Gln Asp Arg  Arg Arg Asn
    1070                1075                1080

Arg Tyr  Trp Arg Phe Ser Ala  Ser Ala Ser Arg Asn  Asp Pro Gly
    1085                1090                1095

Cys Gly  Arg Ile Phe Val Glu  Leu Gln Asp Gly Arg  Trp Arg Leu
    1100                1105                1110

Ile Asp  Ser Glu Glu Ala Phe  Asp Tyr Leu Val Lys  Ser Leu Asp
    1115                1120                1125

Val Arg  Gly Val Arg Glu Ser  His Leu His Phe Met  Leu Leu Lys
    1130                1135                1140

Ile Glu  Ala Ser Phe Lys Glu  Ala Leu Arg Arg Asn  Val Ala Ala
    1145                1150                1155

Asn Pro  Gly Val Cys Ser Ile  Ser Ser Ser Leu Asp  Ser Asp Thr
    1160                1165                1170

Ala Glu  Ile Ser Thr Thr Phe  Lys Ile Glu Leu Gly  Asp Ser Asn
    1175                1180                1185

Ala Val  Glu Arg Cys Ser Val  Leu Gln Arg Phe His  Ser Phe Glu
    1190                1195                1200
```

```
Lys Trp Met Trp Asp Asn Met  Leu His Pro Ser Ala  Leu Ser Ala
    1205             1210                1215

Phe Lys Tyr Gly Ala Lys Gln  Ser Ser Pro Leu Phe  Arg Ile Cys
    1220             1225                1230

Arg Ile Cys Ala Glu Leu His  Phe Val Gly Asp Ile  Cys Cys Pro
    1235             1240                1245

Ser Cys Gly Gln Met His Ala  Gly Pro Asp Val Gly  Glu Leu Cys
    1250             1255                1260

Phe Ala Glu Gln Val Ala Gln  Leu Gly Asp Asn Leu  Arg Arg Gly
    1265             1270                1275

Asp Thr Gly Phe Ile Leu Arg  Ser Ser Ile Leu Ser  Pro Leu Arg
    1280             1285                1290

Ile Arg Leu Leu Lys Val Gln  Leu Ala Leu Val Glu  Ala Ser Leu
    1295             1300                1305

Pro Pro Glu Gly Leu Glu Ala  Phe Trp Thr Glu Asn  Leu Arg Lys
    1310             1315                1320

Ser Trp Gly Met Lys Leu Leu  Ser Ser Ser Ser His  Glu Asp Leu
    1325             1330                1335

Tyr Gln Val Leu Thr Thr Leu  Glu Ala Ala Leu Lys  Arg Asp Phe
    1340             1345                1350

Leu Ser Ser Asn Phe Glu Thr  Thr Ser Glu Leu Leu  Gly Leu Gln
    1355             1360                1365

Glu Gly Ala Leu Ala Ser Asp  Leu Thr Cys Gly Val  Asn Val Leu
    1370             1375                1380

Pro Trp Ile Pro Lys Thr Ala  Gly Gly Val Ala Leu  Arg Leu Phe
    1385             1390                1395

Asp Phe Asp Ser Ser Ile Val  Tyr Thr Pro Asp Gln  Asn Asn Asp
    1400             1405                1410

Pro Leu Lys Asp Lys Glu Ser  Glu Asp Phe Val Gly  Leu Glu Thr
    1415             1420                1425

Asn Ile Leu Arg Asn Leu His  Glu Lys Asp Val Met  Glu Thr Pro
    1430             1435                1440

Val Gln Val Ala Ala Tyr Lys  Gln Glu Glu Asn Trp  Thr Asp Pro
    1445             1450                1455

Gly Leu Gly Gly Val Ser Ser  Ser Gly Arg Gly Gly  Arg Pro Pro
    1460             1465                1470

Arg Gly Arg Gly Arg Pro Arg  Ala Arg Gly Asn Gly  Lys Lys Pro
    1475             1480                1485

Ala Val Ser Val Lys Pro Pro  Arg Gly Ala Ala Asn  Ser Asn Gly
    1490             1495                1500

Glu Thr Met Leu Arg Pro Arg  Ala Gln Pro Arg Gly  Gly Arg Lys
    1505             1510                1515

Asn Gly Arg Arg Ser Gly Thr  Lys Gly Arg Lys Arg  Pro Thr Gln
    1520             1525                1530

Gly Thr Leu Gly Ile Cys Asn  Glu Val Gly Gly Gly  Arg Arg Val
    1535             1540                1545

Lys Glu Val Ala Val Thr Ala  Lys Thr Ser Leu Pro  Asp Asn Asp
    1550             1555                1560

Asp Asp Trp Ile Glu Thr Pro  Glu Leu Gln Asp Asp  Asp Gly Glu
    1565             1570                1575

Ala Ser Ser Ser Gly Arg Ser  Phe Gln Tyr Glu Asp  Tyr Asp Asp
    1580             1585                1590

Asp Asp Val Met Ala Pro Ile  Asp Asp Phe Asp Gly  Gly Gly Glu
```

```
                1595                1600                1605
Ser Ser Lys Leu Val Gly Arg Gly Glu Phe Ser Leu His Ser Asp
        1610                1615                1620
Asp Glu Tyr Glu Glu Glu Glu Glu Glu Asp Met Asn Met
        1625                1630                1635
Lys Met Asp Val Asn Val Val Asp Glu Asp Glu Asp Tyr Ile
        1640                1645                1650
Asn Glu Asp Ser Tyr Gly Arg Lys Gln His Gly Ile Ser Ile Ser
        1655                1660                1665
Asn Asp Ala Ala Thr Arg Lys Arg Phe Asn Lys Phe Glu Asp Pro
        1670                1675                1680
Asp Leu Thr Ser Ser Ser Ser Asp Phe Gln
        1685                1690

<210> SEQ ID NO 107
<211> LENGTH: 3097
<212> TYPE: DNA
<213> ORGANISM: Arabidopsis thaliana

<400> SEQUENCE: 107
ggcgccaaaa aaaacctttt tgacaaaga gggaaaaaaa aagtttttat ttttattgtt      60
tttgttgggc gaaatcgatt tgacaaaatc ccgaatttca gttgggcaaa ttcttctatt     120
tctcaatctg ggtctttctc tctggtcgtg atttggtgac cgtacgagcg aataacgcgt     180
aaagattcat agctatggag catcagaacg cggtcaaaga agccctaaac gcactgtatc     240
atcacccgga tgatacagtg cgtgtgcacg ctgatcgctg gcttcagaac ttccaaggaa     300
ctctcgatgc ttggcaggtt gcggataatt tacttcatga ttcttctagc aatttggaaa     360 cttttgatatt ctgttctcag acccttcgaa gcaaggttca cgagattttt gaagaactac     420
cacctggggc ttttcagaag ctacggcaat cattaacgac attgttaaaa agttccaca     480 agggccctcc aaaagttagg acccagatta gcattgctgt tgctgccttg gcggtgcatg     540
ttcctgcggc agactgggga gatggtggta taattagctg gcttagggat gagatgcata     600
tgcatcctga atatgtgcct ggtttcttgg aactcttgac agttttgccc gaggaaacat     660
ttaactacaa aatagctgct cgtccggatc gacgacgtca attcgaaaaa gagcttactt     720
ctcaaatgga agctgcactt agtatcttat cagcatgttt gaaaatatcc gaacttaagg     780
aacaggttct cgaggcattt gcttcttggc tccgtcttag gcatgggatt cctggaacag     840
tgcttgcctg tcatccattg gtgcatgcag ctctctcaag tttgaactgt gatccactat     900
cagaggcatc tgttaatgtt atctctgaat gatacatca cacagcatca ccaagttctg     960
gtggtatttc tgcacaaaca cccttgattc aagttattgt gcctcagatt ttaagtcttc    1020
aggcccatct aagagattct tcaaaggatg aagaagatgt caaagctatt ggtcgattat    1080
tcgctgacgt aggcgattca tatgttgaac taatagctac tggttcagat gaaccaatgg    1140
ttattgtgca tgccctgctg gaagttactg cacacccaga atttgatata gcctcgatga    1200
ccttcaactt ttggcacagt cttcaactta tgttgacaaa gagggaatct tatagttcat    1260
tgggtagtga agcatccatt gaagttgaga gaaaccgaag actgcatatc tttcagccag    1320
cttatcagag cctttgtatct ttggttggct tcagagttca gtatcctgaa gattatcaag    1380
gcctctcata tgaggacctt aaggaattca agcagactag atatgctgtt gcagatgtat    1440
taatagatgc agcgttaatc ctgggagggg atactactct taagattctc tatatgaagc    1500
ttcttgaggc caatgcccag acaggaaaca attttcaaga ttggcgtcca gcagaagcta    1560
```

-continued

```
tttttgttctg tatatgggca atatcaaatt atgtttcggt tgttgaagct gaagtgatgc    1620
cccaggtgat ggcgttgctt caaaatcttc ctcagcaagc gcaactactt cagacagcat    1680
gcttacttgt tggggcatat tcaaaatggc ttaatgctgc accagccagt gtttcaatat    1740
taccatcaat cattagaatt cttatgagtg gaatgggcac atctgaagat tgcgcagcag    1800
ctgcagcttt ggcttttaga catacttgtg acgattgccg aaaaaatctt tgtgggtatt    1860
ttgaagattt gtttaatatc tattgtatgg cgatcaatgg cggtggtggt tataaagtct    1920
ctgctgagga ttcactaaat ctcgttgaag ctttaggtat ggttgttacc gaactgcctt    1980
tagatcaggc caagggcgct cttgaaaaat tatgcttttc agccgcctct cctctagagg    2040
aagcggcgaa agaagatttg gagaagaagc atgcacgtga attaactgtt catattgacc    2100
gatttgcctt cctcttcagg tatgtgaacc accctgaagc ggtggctgct gagattaata    2160
agcattgggc aattttccga gttattttg atgctcgtcc ttgggacatg aggactatgg    2220
aatctctatg cagggcatgc aaatatgctg tacgtacttc tggaagatac ataattgata    2280
caattggaga aatgctggaa aagattcaat tccattatca gcagcatcat cagccatgct    2340
ttctatactt atccagtgaa gttataaaga ttttggttc tgatccatcg tgtgctgtct    2400
acttgaagaa cctgattgaa accctctttg cacatacaac atgtcttatg acaagtatca    2460
aggaagtcac tgcgagacca gatatagccg atgactgctt tttgttggcg tctagatgtc    2520
ttcgctactg tccacattta ttcattccgt ctcctatatt tccagctctt gtaaactgcg    2580
caatgattgg aatcacagtg cagcacagag aagcctgcca ctcgatattg acctttctaa    2640
ccgacatttt tgacctcgag aagtctgtga atgaagaaca gttcgtacgg atcagggaca    2700
atatcattat tcctcgggga gctacaatca ccagaatatt gatagcctca ttagctgggg    2760
cacttcccag ttctcggcta gatacggtaa catattcgct gctagctctg acaagaacat    2820
acaggttaca agcagtgagt tgggctaagg aaagtgtaag cctgatacct cgaacagcct    2880
tgacagagac cgaatctacc aagttcttac aagcattgtc cgatattgct tatggagcag    2940
atgtgaattc tctgatagga caggttgagg agctctcaga tgtttgtcga cgtaaccgta    3000
ctgttcaaga gcttgttcag gcagctttga agcctcttga gttgaatctg gttactgctc    3060
ctgtatcata aagatgatga aaaacaaaga aagaaag                             3097
```

<210> SEQ ID NO 108
<211> LENGTH: 958
<212> TYPE: PRT
<213> ORGANISM: Arabidopsis thaliana

<400> SEQUENCE: 108

```
Met Glu His Gln Asn Ala Val Lys Glu Ala Leu Asn Ala Leu Tyr His
1               5                   10                  15

His Pro Asp Asp Thr Val Arg Val His Ala Asp Arg Trp Leu Gln Asn
            20                  25                  30

Phe Gln Gly Thr Leu Asp Ala Trp Gln Val Ala Asp Asn Leu Leu His
        35                  40                  45

Asp Ser Ser Asn Leu Glu Thr Leu Ile Phe Cys Ser Gln Thr Leu
    50                  55                  60

Arg Ser Lys Val Gln Arg Asp Phe Glu Glu Leu Pro Pro Gly Ala Phe
65                  70                  75                  80

Gln Lys Leu Arg Gln Ser Leu Thr Thr Leu Leu Lys Lys Phe His Lys
                85                  90                  95

Gly Pro Pro Lys Val Arg Thr Gln Ile Ser Ile Ala Val Ala Ala Leu
            100                 105                 110
```

```
Ala Val His Val Pro Ala Ala Asp Trp Gly Asp Gly Ile Ile Ser
        115                 120                 125

Trp Leu Arg Asp Glu Met His Met His Pro Glu Tyr Val Pro Gly Phe
    130                 135                 140

Leu Glu Leu Leu Thr Val Leu Pro Glu Glu Thr Phe Asn Tyr Lys Ile
145                 150                 155                 160

Ala Ala Arg Pro Asp Arg Arg Gln Phe Glu Lys Glu Leu Thr Ser
                165                 170                 175

Gln Met Glu Ala Ala Leu Ser Ile Leu Ser Ala Cys Leu Lys Ile Ser
            180                 185                 190

Glu Leu Lys Glu Gln Val Leu Glu Ala Phe Ala Ser Trp Leu Arg Leu
        195                 200                 205

Arg His Gly Ile Pro Gly Thr Val Leu Ala Cys His Pro Leu Val His
    210                 215                 220

Ala Ala Leu Ser Ser Leu Asn Cys Asp Pro Leu Ser Glu Ala Ser Val
225                 230                 235                 240

Asn Val Ile Ser Glu Leu Ile His His Thr Ala Ser Pro Ser Ser Gly
                245                 250                 255

Gly Ile Ser Ala Gln Thr Pro Leu Ile Gln Val Ile Val Pro Gln Ile
            260                 265                 270

Leu Ser Leu Gln Ala His Leu Arg Asp Ser Ser Lys Asp Glu Glu Asp
        275                 280                 285

Val Lys Ala Ile Gly Arg Leu Phe Ala Asp Val Gly Asp Ser Tyr Val
    290                 295                 300

Glu Leu Ile Ala Thr Gly Ser Asp Glu Pro Met Val Ile Val His Ala
305                 310                 315                 320

Leu Leu Glu Val Thr Ala His Pro Glu Phe Asp Ile Ala Ser Met Thr
                325                 330                 335

Phe Asn Phe Trp His Ser Leu Gln Leu Met Leu Thr Lys Arg Glu Ser
            340                 345                 350

Tyr Ser Ser Leu Gly Ser Glu Ala Ser Ile Glu Val Glu Arg Asn Arg
        355                 360                 365

Arg Leu His Ile Phe Gln Pro Ala Tyr Gln Ser Leu Val Ser Leu Val
    370                 375                 380

Gly Phe Arg Val Gln Tyr Pro Asp Tyr Gln Gly Leu Ser Tyr Glu
385                 390                 395                 400

Asp Leu Lys Glu Phe Lys Gln Thr Arg Tyr Ala Val Ala Asp Val Leu
                405                 410                 415

Ile Asp Ala Ala Leu Ile Leu Gly Gly Asp Thr Thr Leu Lys Ile Leu
            420                 425                 430

Tyr Met Lys Leu Leu Glu Ala Asn Ala Gln Thr Gly Asn Asn Phe Gln
        435                 440                 445

Asp Trp Arg Pro Ala Glu Ala Ile Leu Phe Cys Ile Trp Ala Ile Ser
    450                 455                 460

Asn Tyr Val Ser Val Val Glu Ala Glu Val Met Pro Gln Val Met Ala
465                 470                 475                 480

Leu Leu Gln Asn Leu Pro Gln Gln Ala Gln Leu Gln Thr Ala Cys
                485                 490                 495

Leu Leu Val Gly Ala Tyr Ser Lys Trp Leu Asn Ala Ala Pro Ala Ser
            500                 505                 510

Val Ser Ile Leu Pro Ser Ile Ile Arg Ile Leu Met Ser Gly Met Gly
        515                 520                 525

Thr Ser Glu Asp Cys Ala Ala Ala Ala Ala Leu Ala Phe Arg His Thr
```

-continued

```
            530                 535                 540
Cys Asp Asp Cys Arg Lys Asn Leu Cys Gly Tyr Phe Glu Asp Leu Phe
545                 550                 555                 560

Asn Ile Tyr Cys Met Ala Ile Asn Gly Gly Gly Tyr Lys Val Ser
                565                 570                 575

Ala Glu Asp Ser Leu Asn Leu Val Glu Ala Leu Gly Met Val Val Thr
                580                 585                 590

Glu Leu Pro Leu Asp Gln Ala Lys Gly Ala Leu Glu Lys Leu Cys Phe
            595                 600                 605

Ser Ala Ala Ser Pro Leu Glu Glu Ala Ala Lys Glu Asp Leu Glu Lys
610                 615                 620

Lys His Ala Arg Glu Leu Thr Val His Ile Asp Arg Phe Ala Phe Leu
625                 630                 635                 640

Phe Arg Tyr Val Asn His Pro Glu Ala Val Ala Glu Ile Asn Lys
                645                 650                 655

His Trp Ala Ile Phe Arg Val Ile Phe Asp Ala Arg Pro Trp Asp Met
                660                 665                 670

Arg Thr Met Glu Ser Leu Cys Arg Ala Cys Lys Tyr Ala Val Arg Thr
                675                 680                 685

Ser Gly Arg Tyr Ile Ile Asp Thr Ile Gly Glu Met Leu Glu Lys Ile
690                 695                 700

Gln Phe His Tyr Gln His His Gln Pro Cys Phe Leu Tyr Leu Ser
705                 710                 715                 720

Ser Glu Val Ile Lys Ile Phe Gly Ser Asp Pro Ser Cys Ala Val Tyr
                725                 730                 735

Leu Lys Asn Leu Ile Glu Thr Leu Phe Ala His Thr Thr Cys Leu Met
                740                 745                 750

Thr Ser Ile Lys Glu Val Thr Ala Arg Pro Asp Ile Ala Asp Asp Cys
            755                 760                 765

Phe Leu Leu Ala Ser Arg Cys Leu Arg Tyr Cys Pro His Leu Phe Ile
770                 775                 780

Pro Ser Pro Ile Phe Pro Ala Leu Val Asn Cys Ala Met Ile Gly Ile
785                 790                 795                 800

Thr Val Gln His Arg Glu Ala Cys His Ser Ile Leu Thr Phe Leu Thr
                805                 810                 815

Asp Ile Phe Asp Leu Glu Lys Ser Val Asn Glu Gln Phe Val Arg
            820                 825                 830

Ile Arg Asp Asn Ile Ile Pro Arg Gly Ala Thr Ile Thr Arg Ile
            835                 840                 845

Leu Ile Ala Ser Leu Ala Gly Ala Leu Pro Ser Ser Arg Leu Asp Thr
850                 855                 860

Val Thr Tyr Ser Leu Leu Ala Leu Thr Arg Thr Tyr Arg Leu Gln Ala
865                 870                 875                 880

Val Ser Trp Ala Lys Glu Ser Val Ser Leu Ile Pro Arg Thr Ala Leu
                885                 890                 895

Thr Glu Thr Glu Ser Thr Lys Phe Leu Gln Ala Leu Ser Asp Ile Ala
                900                 905                 910

Tyr Gly Ala Asp Val Asn Ser Leu Ile Gly Gln Val Glu Glu Leu Ser
            915                 920                 925

Asp Val Cys Arg Arg Asn Arg Thr Val Gln Glu Leu Val Gln Ala Ala
            930                 935                 940

Leu Lys Pro Leu Glu Leu Asn Leu Val Thr Ala Pro Val Ser
945                 950                 955
```

<210> SEQ ID NO 109
<211> LENGTH: 1252
<212> TYPE: DNA
<213> ORGANISM: Arabidopsis thaliana

<400> SEQUENCE: 109

```
attatcacta cccacatctg tcttaccttc tccgatctct ctctctattt gtccacctca      60
cacacaaccc tataaacaag acaagacctc gcaaagctca aacctttttcc ttcttttttt     120
ctatcaagtt cctcacttct cggatccggg tcctaaatct gggtcaaccc ttttttacgat    180
catcggaaat ggaccctcca ctagtgaacg attcctcctt ctctgcagct aatccttctt     240
cttacactct ctccgagatt tggccttttcc ctgtaaacga cgccgttcgc tctggtctcc   300
gtttagctgt taactccggt cgagtctttta ctcgctctga acattccggc aataaagacg    360
tctccgcggc tgaggaatct acagtcaccg atctaactgc tggctgggga agtagaaaga    420
ctagagattt gaactctgag gatgattctt caaagatggt ttcttccagc agcagtggta    480
atgaattgaa agaatcaggg gataagaaaa gaaaactgtg tggatctgaa agtggaaatg    540
gagatggttc gatgagacct gaaggcgaaa caagttcggg tggtggtgga agcaaagcaa    600
cggaacagaa gaacaaacct gagccaccaa aggattatat tcatgtgaga gcaagaagag    660
gacaagctac tgaccggcat agtttagcag agcgagctag aagagaaaag atcagtgaga    720
agatgacagc tcttcaagat ataattccag gatgtaataa gataatcgga aaagcccttg    780
tgctcgatga gattatcaat tatattcagt cattgcagcg gcaagttgag tttctatcaa    840
tgaagctaga agttgttaac tcgggtgcaa gtactggtcc gacaatagga gttttttcctt   900
ccggtgatct cgggacttta ccgattgacg ttcatcgaac aatatacgag caacaagaag    960
ctaatgaaac ccgagtatct caaccggagt ggctccatat gcaggttgat gggaacttta   1020
accgaaccac ataaaaaaga gtctttctct gattgatgga tgtgttttgt aggcagtaaa   1080
aatgaatgca acccttttatt ttttatccta tgcgtgtgta tcattttgct gttatatcat   1140
aagatagaat atgagagtga ccagagagat taacacttta taaaacattg ttgtattgtc   1200
ctattatata acttgtaaca attgattcag taacatatgt tggtcttaaa tc            1252
```

<210> SEQ ID NO 110
<211> LENGTH: 281
<212> TYPE: PRT
<213> ORGANISM: Arabidopsis thaliana

<400> SEQUENCE: 110

```
Met Asp Pro Pro Leu Val Asn Asp Ser Ser Phe Ser Ala Ala Asn Pro
1               5                   10                  15

Ser Ser Tyr Thr Leu Ser Glu Ile Trp Pro Phe Pro Val Asn Asp Ala
            20                  25                  30

Val Arg Ser Gly Leu Arg Leu Ala Val Asn Ser Gly Arg Val Phe Thr
        35                  40                  45

Arg Ser Glu His Ser Gly Asn Lys Asp Val Ser Ala Ala Glu Glu Ser
    50                  55                  60

Thr Val Thr Asp Leu Thr Ala Gly Trp Gly Ser Arg Lys Thr Arg Asp
65                  70                  75                  80

Leu Asn Ser Glu Asp Asp Ser Ser Lys Met Val Ser Ser Ser Ser Ser
                85                  90                  95

Gly Asn Glu Leu Lys Glu Ser Gly Asp Lys Lys Arg Lys Leu Cys Gly
            100                 105                 110

Ser Glu Ser Gly Asn Gly Asp Gly Ser Met Arg Pro Glu Gly Glu Thr
```

```
                115                 120                 125
Ser Ser Gly Gly Gly Ser Lys Ala Thr Glu Gln Lys Asn Lys Pro
    130                 135                 140
Glu Pro Pro Lys Asp Tyr Ile His Val Arg Ala Arg Arg Gly Gln Ala
145                 150                 155                 160
Thr Asp Arg His Ser Leu Ala Glu Arg Ala Arg Glu Lys Ile Ser
                165                 170                 175
Glu Lys Met Thr Ala Leu Gln Asp Ile Ile Pro Gly Cys Asn Lys Ile
            180                 185                 190
Ile Gly Lys Ala Leu Val Leu Asp Glu Ile Ile Asn Tyr Ile Gln Ser
            195                 200                 205
Leu Gln Arg Gln Val Glu Phe Leu Ser Met Lys Leu Glu Val Val Asn
    210                 215                 220
Ser Gly Ala Ser Thr Gly Pro Thr Ile Gly Val Phe Pro Ser Gly Asp
225                 230                 235                 240
Leu Gly Thr Leu Pro Ile Asp Val His Arg Thr Ile Tyr Glu Gln Gln
                245                 250                 255
Glu Ala Asn Glu Thr Arg Val Ser Gln Pro Glu Trp Leu His Met Gln
            260                 265                 270
Val Asp Gly Asn Phe Asn Arg Thr Thr
            275                 280

<210> SEQ ID NO 111
<211> LENGTH: 1799
<212> TYPE: DNA
<213> ORGANISM: Arabidopsis thaliana

<400> SEQUENCE: 111
tatggatatt cttcttcctt atgctagcct ctctggtctt cttcttcttc gttcgtttca        60
gcgaatcaca tttgatctat gacacatcta tacaaggaat tagctttcat catcaagtct       120
ctctctcgaa aactctcctt tggtttcgtt tgatctgaga aaagaagaaa ttcaaatatt       180
gataactgtg gatgggtgca ccaaagcaga agtggacacc ggaagaagaa gcagctctta       240
aagctggagt tcttaagcat gggactggga agtggcgtac atactctcg gatactgagt        300
ttagtttaat ccttaagtct cgctctaatg ttgatcttaa ggacaaatgg agaaatataa       360
gcgtgacagc tttatggggt tcaaggaaga aggctaaact tgcgcttaag aggactccac       420
caggtactaa acaggatgat aacaacacag ctcttaccat tgtggctttg actaatgatg       480
atgaacgtgc aaaaccaact tcccccggag gttctggtgg tggatcacca cgcacttgtg       540
cttctaagag atcaattaca agtttggata agatcatctt tgaggcaatt accaacttga       600
gggaactacg cggttctgac agaacatcaa tcttctgta tatagaggag aatttcaaga        660
ctccaccgaa tatgaaaagg catgtcgcag tacgattaaa gcatttatca tcgaatggaa       720
cattagttaa gataaagcac aagtacaggt tttcttctaa ttttattccc gcaggtgcaa       780
gacagaaggc tcctcaactc tttctggaag gaaacaacaa gaaagaccca acaaaacccg       840
aggagaacgg tgccaacagt ctcactaaat tccgagtaga cggtgaatta tatatgataa       900
aaggcatgac agctcaagaa gctgcagagg ctgcagcaag agcagttgca gaggcagaat       960
tgctatcac agaggctgaa caagcagcaa agaggcagaa agagcagaa gcagaagctg      1020
aagctgctca gatatttgca aaggcagcca tgaaagcttt gaagttcagg atccgtaatc      1080
atccttggtg aaacagaaag aaatagccat catggggaag ttctgtaaca aagcaagcca      1140
taaaatatat atacttagtg ggtttactgg tttcttaaga gtgccgatct tgaatcaggc      1200
```

```
gatatctcat cacctgcaga gttttttaag tttccaaacc tatctgctct cttttttgg    1260 ttagtaacag tgtaaatccg cagtttgatc atatgtatgt tcttctccg aatctgagat    1320 tctgtataac tgatctttta ttgtatgtgg atgatctgtt tagtaacctt gaaactattt   1380
tgaagtgaga tgagtaagca aaaaaattga gattttgttc tactaaagat tttgaggaaa   1440
tttacaagca ttttcattct ttcttactac tctcttccca ttctttcaga atgtcataaa   1500
ctgaaagtga atcagagtcg ctagattctt catcatcatc aatctcgagt tcttctagac   1560
ccaacgtttc gagttcagtc tctgtaaatt cccaagcttc accattagca ctattatcat   1620
cttccattgt tgtatcttgc agaagcaaat cttcctccgg tttttcgccc tgactttgag   1680
ttgttacatc tacggctaac aatggttgtg ctgaagaaga agaagaccca catcgagatt   1740
tcaatgactt tgagaggttt gagaccgttg gttcacttac ataatcacac tcaatgaga    1799
```

<210> SEQ ID NO 112
<211> LENGTH: 299
<212> TYPE: PRT
<213> ORGANISM: Arabidopsis thaliana

<400> SEQUENCE: 112

```
Met Gly Ala Pro Lys Gln Lys Trp Thr Pro Glu Glu Ala Ala Leu
1               5                   10                  15

Lys Ala Gly Val Leu Lys His Gly Thr Gly Lys Trp Arg Thr Ile Leu
            20                  25                  30

Ser Asp Thr Glu Phe Ser Leu Ile Leu Lys Ser Arg Ser Asn Val Asp
        35                  40                  45

Leu Lys Asp Lys Trp Arg Asn Ile Ser Val Thr Ala Leu Trp Gly Ser
    50                  55                  60

Arg Lys Lys Ala Lys Leu Ala Leu Lys Arg Thr Pro Pro Gly Thr Lys
65                  70                  75                  80

Gln Asp Asp Asn Asn Thr Ala Leu Thr Ile Val Ala Leu Thr Asn Asp
                85                  90                  95

Asp Glu Arg Ala Lys Pro Thr Ser Pro Gly Ser Gly Gly Gly Ser
            100                 105                 110

Pro Arg Thr Cys Ala Ser Lys Arg Ser Ile Thr Ser Leu Asp Lys Ile
        115                 120                 125

Ile Phe Glu Ala Ile Thr Asn Leu Arg Glu Leu Arg Gly Ser Asp Arg
    130                 135                 140

Thr Ser Ile Phe Leu Tyr Ile Glu Glu Asn Phe Lys Thr Pro Pro Asn
145                 150                 155                 160

Met Lys Arg His Val Ala Val Arg Leu Lys His Leu Ser Ser Asn Gly
                165                 170                 175

Thr Leu Val Lys Ile Lys His Lys Tyr Arg Phe Ser Ser Asn Phe Ile
            180                 185                 190

Pro Ala Gly Ala Arg Gln Lys Ala Pro Gln Leu Phe Leu Glu Gly Asn
        195                 200                 205

Asn Lys Lys Asp Pro Thr Lys Pro Glu Glu Asn Gly Ala Asn Ser Leu
    210                 215                 220

Thr Lys Phe Arg Val Asp Gly Glu Leu Tyr Met Ile Lys Gly Met Thr
225                 230                 235                 240

Ala Gln Glu Ala Ala Glu Ala Ala Ala Arg Ala Val Ala Glu Ala Glu
                245                 250                 255

Phe Ala Ile Thr Glu Ala Glu Gln Ala Ala Lys Glu Ala Glu Arg Ala
            260                 265                 270

Glu Ala Glu Ala Glu Ala Ala Gln Ile Phe Ala Lys Ala Ala Met Lys
```

```
                275                 280                 285
Ala Leu Lys Phe Arg Ile Arg Asn His Pro Trp
    290                 295
```

<210> SEQ ID NO 113
<211> LENGTH: 1720
<212> TYPE: DNA
<213> ORGANISM: Arabidopsis thaliana

<400> SEQUENCE: 113

```
ttcttcttct tcgttcgttt cagcgaatca catttgatct atgacacatc tatacaagga    60
attagctttc atcatcaaag aaaagaagaa attcaaatat tgataactgt ggatgggtgc   120
accaaagcag aagtggacac cggaagaaga agcagctctt aaagctggag ttcttaagca   180
tgggactggg aagtggcgta ccatactctc ggatactgag tttagtttaa tccttaagtc   240
tcgctctaat gttgatctta aggacaaatg agaaatatata agcgtgacag ctttatgggg   300
ttcaaggaag aaggctaaac ttgcgcttaa gggactcca ccaggtacta aacaggatga   360
taacaacaca gctcttacca ttgtggcttt gactaatgat gatgaacgtg caaaaccaac   420
ttccccggga ggtctggtg gtggatcacc acgcacttgt gcttctaaga atcaattac   480
aagtttggat aagatcatct ttgaggcaat taccaacttg agggaactac gcggttctga   540
cagaacatca atctttctgt atatagagga gaattcaag actccaccga atatgaaaag   600
gcatgtcgca gtacgattaa agcatttatc atcgaatgga acattagtta agataaagca   660
caagtacagg ttttcttcta attttattcc cgcaggtgca agacagaagg ctcctcaact   720
cttctggaa ggaaacaaca agaaagaccc aacaaaaccc gaggagaacg gtgccaacag   780
tctcactaaa ttccgagtag acggtgaatt atatatgata aaaggcatga cagctcaaga   840
agctgcagag gctgcagcaa gagcagttgc agaggcagaa tttgctatca cagaggctga   900
acaagcagca aaagaggcag aaagagcaga agcagaagct gaagctgctc agatatttgc   960
aaaggcagcc atgaaagctt tgaagttcag gatccgtaat catccttggt gaaacagaaa  1020
gaaatagcca tcatgggga gttctgtaac aaagcaagcc ataaaatata tacttagt   1080
gggttactg gtttcttaag agtgccgatc ttgaatcagg cgatatctca tcacctgcag  1140
agttttttaa gttccaaac ctatctgctc tcttttttg gttagtaaca gtgtaaatcc  1200
gcagtttgat catatgtatg ttcttttctcc gaatctgaga ttctgtataa ctgatctttt  1260
attgtatgtg gatgatctgt ttagtaacct tgaaactatt ttgaagtgag atgagtaagc  1320
aaaaaaattg agattttgtt ctactaaaga ttttgaggaa atttacaagc attttcattc  1380
tttcttacta ctctcttccc attctttcag aatgtcataa actgaaagtg aatcagagtc  1440
gctagattct tcatcatcat caatctcgag ttcttctaga cccaacgttt cgagttcagt  1500
ctctgtaaat tcccaagctt caccattagc actattatca tcttccattg ttgtatcttg  1560
cagaagcaaa tcttcctccg gttttttcgcc ctgactttga gttgttacat ctacggctaa  1620
caatggttgt gctgaagaag aagaagaccc acatcgagat ttcaatgact ttgagaggtt  1680
tgagaccgtt ggttcactta cataatcaca ctcaatgaga                        1720
```

<210> SEQ ID NO 114
<211> LENGTH: 299
<212> TYPE: PRT
<213> ORGANISM: Arabidopsis thaliana

<400> SEQUENCE: 114

Met Gly Ala Pro Lys Gln Lys Trp Thr Pro Glu Glu Glu Ala Ala Leu

|  | 1 |  |  |  | 5 |  |  |  |  | 10 |  |  |  |  | 15 |
|---|---|---|---|---|---|---|---|---|---|---|---|---|---|---|---|
| Lys | Ala | Gly | Val | Leu | Lys | His | Gly | Thr | Gly | Lys | Trp | Arg | Thr | Ile | Leu |
|  |  |  | 20 |  |  |  |  | 25 |  |  |  |  | 30 |  |  |
| Ser | Asp | Thr | Glu | Phe | Ser | Leu | Ile | Leu | Lys | Ser | Arg | Ser | Asn | Val | Asp |
|  |  | 35 |  |  |  |  | 40 |  |  |  |  | 45 |  |  |  |
| Leu | Lys | Asp | Lys | Trp | Arg | Asn | Ile | Ser | Val | Thr | Ala | Leu | Trp | Gly | Ser |
|  | 50 |  |  |  |  | 55 |  |  |  |  | 60 |  |  |  |  |
| Arg | Lys | Lys | Ala | Lys | Leu | Ala | Leu | Lys | Arg | Thr | Pro | Pro | Gly | Thr | Lys |
| 65 |  |  |  |  | 70 |  |  |  |  | 75 |  |  |  |  | 80 |
| Gln | Asp | Asp | Asn | Asn | Thr | Ala | Leu | Thr | Ile | Val | Ala | Leu | Thr | Asn | Asp |
|  |  |  |  | 85 |  |  |  |  | 90 |  |  |  |  | 95 |  |
| Asp | Glu | Arg | Ala | Lys | Pro | Thr | Ser | Pro | Gly | Gly | Ser | Gly | Gly | Gly | Ser |
|  |  |  | 100 |  |  |  |  | 105 |  |  |  |  | 110 |  |  |
| Pro | Arg | Thr | Cys | Ala | Ser | Lys | Arg | Ser | Ile | Thr | Ser | Leu | Asp | Lys | Ile |
|  |  | 115 |  |  |  |  | 120 |  |  |  |  | 125 |  |  |  |
| Ile | Phe | Glu | Ala | Ile | Thr | Asn | Leu | Arg | Glu | Leu | Arg | Gly | Ser | Asp | Arg |
|  | 130 |  |  |  |  | 135 |  |  |  |  | 140 |  |  |  |  |
| Thr | Ser | Ile | Phe | Leu | Tyr | Ile | Glu | Glu | Asn | Phe | Lys | Thr | Pro | Pro | Asn |
| 145 |  |  |  |  | 150 |  |  |  |  | 155 |  |  |  |  | 160 |
| Met | Lys | Arg | His | Val | Ala | Val | Arg | Leu | Lys | His | Leu | Ser | Ser | Asn | Gly |
|  |  |  |  | 165 |  |  |  |  | 170 |  |  |  |  | 175 |  |
| Thr | Leu | Val | Lys | Ile | Lys | His | Lys | Tyr | Arg | Phe | Ser | Ser | Asn | Phe | Ile |
|  |  |  | 180 |  |  |  |  | 185 |  |  |  |  | 190 |  |  |
| Pro | Ala | Gly | Ala | Arg | Gln | Lys | Ala | Pro | Gln | Leu | Phe | Leu | Glu | Gly | Asn |
|  |  | 195 |  |  |  |  | 200 |  |  |  |  | 205 |  |  |  |
| Asn | Lys | Lys | Asp | Pro | Thr | Lys | Pro | Glu | Glu | Asn | Gly | Ala | Asn | Ser | Leu |
|  | 210 |  |  |  |  | 215 |  |  |  |  | 220 |  |  |  |  |
| Thr | Lys | Phe | Arg | Val | Asp | Gly | Glu | Leu | Tyr | Met | Ile | Lys | Gly | Met | Thr |
| 225 |  |  |  |  | 230 |  |  |  |  | 235 |  |  |  |  | 240 |
| Ala | Gln | Glu | Ala | Ala | Glu | Ala | Ala | Arg | Ala | Val | Ala | Glu | Ala | Glu |  |
|  |  |  |  | 245 |  |  |  |  | 250 |  |  |  |  | 255 |  |
| Phe | Ala | Ile | Thr | Glu | Ala | Glu | Gln | Ala | Ala | Lys | Glu | Ala | Glu | Arg | Ala |
|  |  |  | 260 |  |  |  |  | 265 |  |  |  |  | 270 |  |  |
| Glu | Ala | Glu | Ala | Glu | Ala | Ala | Gln | Ile | Phe | Ala | Lys | Ala | Ala | Met | Lys |
|  |  | 275 |  |  |  |  | 280 |  |  |  |  | 285 |  |  |  |
| Ala | Leu | Lys | Phe | Arg | Ile | Arg | Asn | His | Pro | Trp |  |  |  |  |  |
|  | 290 |  |  |  |  | 295 |  |  |  |  |  |  |  |  |  |

<210> SEQ ID NO 115
<211> LENGTH: 731
<212> TYPE: DNA
<213> ORGANISM: Arabidopsis thaliana

<400> SEQUENCE: 115

```
acagaagtag aagaaaccaa agcgaaatca aaaagctcag caattttcca gatttctcta      60
attgacgatg gcgctttgtg ctactactca aaggactatc cgtatagcgg cgacgctccg     120
gcgtgttgct cgacctttcg ctactgacgc ggtggttgag tcggattaca agcgtggtga     180
gatcggtaag gtctccggaa tcccagagga gcatctttct cgcaaggtga taatatactc     240
acctgctaga acagctaccc agtcaggatc tggaaaactc ggaaaatgga agattaactt     300
cgtctccacc ttaaagtggg agaatccgtt gatgggatgg acttctacag gtgaccccta     360
tgctaatgtt ggtgactctg ctcttgcttt tgattctgaa gaagctgcta agtcttttgc     420
tgagcgtcat ggttgggatt ataaggtcaa gaagcccaac acaccattat tgaaggtcaa     480
```

```
gtcttactcg acaacttca agtggaaagg caatcctcaa ccagaaaact gatgttacac      540
cttcttccaa ttcttctcga gcaaaagaag aaacctcatt tgatattaat tctcatgttt      600
ctttgttatt ttagcatctg tgagctttt ggttgaaaag aaccattatc catggctatg      660
tttacttatt acaataatat gatgatgatg atgaaacaca ctcctttgat atttcatcaa      720
gatttctgat c                                                          731
```

<210> SEQ ID NO 116
<211> LENGTH: 154
<212> TYPE: PRT
<213> ORGANISM: Arabidopsis thaliana

<400> SEQUENCE: 116

```
Met Ala Leu Cys Ala Thr Thr Gln Arg Thr Ile Arg Ile Ala Ala Thr
1               5                   10                  15

Leu Arg Arg Val Ala Arg Pro Phe Ala Thr Asp Ala Val Val Glu Ser
                20                  25                  30

Asp Tyr Lys Arg Gly Glu Ile Gly Lys Val Ser Gly Ile Pro Glu Glu
            35                  40                  45

His Leu Ser Arg Lys Val Ile Ile Tyr Ser Pro Ala Arg Thr Ala Thr
        50                  55                  60

Gln Ser Gly Ser Gly Lys Leu Gly Lys Trp Lys Ile Asn Phe Val Ser
65                  70                  75                  80

Thr Leu Lys Trp Glu Asn Pro Leu Met Gly Trp Thr Ser Thr Gly Asp
                85                  90                  95

Pro Tyr Ala Asn Val Gly Asp Ser Ala Leu Ala Phe Asp Ser Glu Glu
            100                 105                 110

Ala Ala Lys Ser Phe Ala Glu Arg His Gly Trp Asp Tyr Lys Val Lys
        115                 120                 125

Lys Pro Asn Thr Pro Leu Leu Lys Val Lys Ser Tyr Ser Asp Asn Phe
    130                 135                 140

Lys Trp Lys Gly Asn Pro Gln Pro Glu Asn
145                 150
```

<210> SEQ ID NO 117
<211> LENGTH: 515
<212> TYPE: DNA
<213> ORGANISM: Arabidopsis thaliana

<400> SEQUENCE: 117

```
gttataaagg aaaggaacag agtttgcttt taaacaaaga gagaagaaa aaaaagctca       60 aagaactcag aagaagaaga aagatgtatc atcaagaaca acatcctgtc ggtgctcctc      120
ctccccaagg gtatccacct aaggacggtt atcctccggc cggttatcct ccagccggtt      180
atccaccgcc aggatatgct cagggatacc ctgcacaagg ttatcctccg ccgcagtact      240
ctcaagctcc gcagcagaag caaaacgccg gtatgcttga aggatgtttg gctgcgctct      300
gttgttgctg tctcttggat gcatgtttct gatcggagga taattatata cgttgcctca      360
gtcaactttt atttcctcat atatgttatg taatgttcaa caatctttct tctgttgtta      420
tcttctttca attcgaattt tggtatctta tgttttattg actccgacca taattatctc      480
tctctttcat aatccaatca cacgaattcg aaata                                 515
```

<210> SEQ ID NO 118
<211> LENGTH: 82
<212> TYPE: PRT
<213> ORGANISM: Arabidopsis thaliana

<400> SEQUENCE: 118

| Met | Tyr | His | Gln | Glu | Gln | His | Pro | Val | Gly | Ala | Pro | Pro | Gln | Gly |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Tyr | Pro | Pro | Lys | Asp | Gly | Tyr | Pro | Ala | Gly | Tyr | Pro | Ala | Gly |
|-----|-----|-----|-----|-----|-----|-----|-----|-----|-----|-----|-----|-----|-----|
|     |     |     | 20  |     |     |     | 25  |     |     |     | 30  |     |     |

Tyr Pro Pro Gly Tyr Ala Gln Gly Tyr Pro Ala Gln Gly Tyr Pro
            35              40              45

Pro Pro Gln Tyr Ser Gln Ala Pro Gln Gln Lys Gln Asn Ala Gly Met
    50                  55                  60

Leu Glu Gly Cys Leu Ala Ala Leu Cys Cys Cys Cys Leu Leu Asp Ala
65              70                  75                  80

Cys Phe

<210> SEQ ID NO 119
<211> LENGTH: 1814
<212> TYPE: DNA
<213> ORGANISM: Arabidopsis thaliana

<400> SEQUENCE: 119

```
ctgaaaccca caaggaagaa atcgatgggt gattatcgtc ttctacgaaa ctccggcgtc    60
gttatcggaa taatcttgct acatctcttt actttcgcct ctcttgtttc atccgatgaa   120
cttcagtttg gtgttgtggt taatttcttg tggccttatg ggacagttgt gggagaaagc   180
ggagagcttc aagtgactcc tagtttagag gtaaaaggtt ctcctggatt gaagccagat   240
agaacctctc tttgtgagag gattcatatc catggacttg aaggtttaa acatctagac    300
aagtatgcac attcgctcaa gttgatagtt aacgcgtcaa tctctgggaa acaaataac    360
attgacgttt gctttcaccg gaatttgtcg cgtggaattg aatgtgccc tcatagtcga    420
tgggagaaag cctctaaagg ttcatgggtt cagacaatgt caccttcga ccataaaatc    480
cttgatgtta gagtacctag ctctaacaag gtctcattgg aagtgtctgc tgtagaagaa   540
ttatttatgc atcgcatagt attcttactc cttggtgctg tattactggc ttcggcttct   600
acactgagcc aatctttagc gttttactac agtagtgcaa tggctgttgg tattatcctt   660
gtcgtgctgc ttgttctctt tcagggaatg aagcttctac ctactggacg gagttcgttt   720
gcattgttca tatactcaac cctgcttggt ttgggtggtt tcttcttcg ctacttaccc    780
ggattgtttg aaagtctgct aacagagatg ggaatcgacg aagaaatgta cacacctgcg   840
gcgatttttg tgggggcgtt tctgtctttg ggtggagcat tttttggatt ttggactgtg   900
aggaaactta ttctgacgga agatggctcc attgatgtta gcacatcact atttgtttct   960
tggtccatcc gaattatggc tgctgttttg atccttcaga gctctgtaga tcctttactt  1020
gctggaggag ccctgatatc tgtaattctt atgtcatcga ctttaaagaa gatcaccaga  1080
ttgaagttcc ttctacgctt attcgagatt ccattgaatt tactgctagg aatctgggag  1140
gcaattcgtg atactgatat accatccgtc ccgggatatc tccatgactt tatgcaaaag  1200
agtcctgatg cttctggatt tcgcaaccgt gtaacttctg cttctccatc aggaggaatc  1260
aacaacggga tgcgagaatc tccaccgtct gaatcagata catttccttc ctcttttccat 1320
aaaactcctg aaaggagcca actaacaaaa gaagaatgga aaaagctcac taaggatagc  1380
acgacaaagg ctgttcaaga attggtttct tcacccgatt ttggcaaatg ggcagcagtt  1440
aatgcggata ggatcaatgt aacaccaaga aaaggatctt ctagcaaaaa ccagccacgg  1500
aaatggatgc gttggttctg atttctgaac caagccggtt taagtttcat aacgtttaga  1560
gagaaaagga actctttgt agaaagagag agagcctttg taggtaaagt tgctttcttc   1620
```

-continued

```
tttatgact tgttcagtgt tttagctttt tttttgtgg atgagaccac gatttgttgt    1680
aacgatccta attgggtttt taggttgcgt catgtttgtg tgtagacaat gcaatgagca   1740 ttcttttcc ttttatgatc ttgaatgggt tcaacttttc atggtgatgt gaatctttta   1800
gtatggatat taat                                                    1814
```

<210> SEQ ID NO 120
<211> LENGTH: 498
<212> TYPE: PRT
<213> ORGANISM: Arabidopsis thaliana

<400> SEQUENCE: 120

```
Met Gly Asp Tyr Arg Leu Leu Arg Asn Ser Gly Val Val Ile Gly Ile
1               5                   10                  15

Ile Leu Leu His Leu Phe Thr Phe Ala Ser Leu Val Ser Ser Asp Glu
            20                  25                  30

Leu Gln Phe Gly Val Val Asn Phe Leu Trp Pro Tyr Gly Thr Val
        35                  40                  45

Val Gly Glu Ser Gly Glu Leu Gln Val Thr Pro Ser Leu Glu Val Lys
    50                  55                  60

Gly Ser Pro Gly Leu Lys Pro Asp Arg Thr Ser Leu Cys Glu Arg Ile
65                  70                  75                  80

His Ile His Gly Leu Gly Arg Phe Lys His Leu Asp Lys Tyr Ala His
                85                  90                  95

Ser Leu Lys Leu Ile Val Asn Ala Ser Ile Ser Gly Lys Thr Asn Asn
            100                 105                 110

Ile Asp Val Cys Phe His Arg Asn Leu Ser Arg Gly Ile Gly Met Cys
        115                 120                 125

Pro His Ser Arg Trp Glu Lys Ala Ser Lys Gly Ser Trp Val Gln Thr
    130                 135                 140

Met Ser Pro Phe Asp His Lys Ile Leu Asp Val Arg Val Pro Ser Ser
145                 150                 155                 160

Asn Lys Val Ser Leu Glu Val Ser Ala Val Glu Glu Leu Phe Met His
                165                 170                 175

Arg Ile Val Phe Leu Leu Leu Gly Ala Val Leu Leu Ala Ser Ala Ser
            180                 185                 190

Thr Leu Ser Gln Ser Leu Ala Phe Tyr Tyr Ser Ser Ala Met Ala Val
        195                 200                 205

Gly Ile Ile Leu Val Val Leu Leu Val Leu Phe Gln Gly Met Lys Leu
    210                 215                 220

Leu Pro Thr Gly Arg Ser Ser Phe Ala Leu Phe Ile Tyr Ser Thr Leu
225                 230                 235                 240

Leu Gly Leu Gly Gly Phe Leu Leu Arg Tyr Leu Pro Gly Leu Phe Glu
                245                 250                 255

Ser Leu Leu Thr Glu Met Gly Ile Asp Glu Met Tyr Thr Pro Ala
            260                 265                 270

Ala Ile Phe Val Gly Ala Phe Leu Ser Leu Gly Gly Ala Phe Phe Gly
        275                 280                 285

Phe Trp Thr Val Arg Lys Leu Ile Leu Thr Glu Asp Gly Ser Ile Asp
    290                 295                 300

Val Ser Thr Ser Leu Phe Val Ser Trp Ser Ile Arg Ile Met Ala Ala
305                 310                 315                 320

Val Leu Ile Leu Gln Ser Ser Val Asp Pro Leu Leu Ala Gly Gly Ala
                325                 330                 335
```

Leu Ile Ser Val Ile Leu Met Ser Ser Thr Leu Lys Lys Ile Thr Arg
            340                 345                 350

Leu Lys Phe Leu Leu Arg Leu Phe Glu Ile Pro Leu Asn Leu Leu Leu
        355                 360                 365

Gly Ile Trp Glu Ala Ile Arg Asp Thr Asp Ile Pro Ser Val Pro Gly
    370                 375                 380

Tyr Leu His Asp Phe Met Gln Lys Ser Pro Asp Ala Ser Gly Phe Arg
385                 390                 395                 400

Asn Arg Val Thr Ser Ala Ser Pro Ser Gly Gly Ile Asn Asn Gly Met
                405                 410                 415

Arg Glu Ser Pro Pro Ser Glu Ser Asp Thr Phe Pro Ser Ser Phe His
            420                 425                 430

Lys Thr Pro Glu Arg Ser Gln Leu Thr Lys Glu Glu Trp Lys Lys Leu
        435                 440                 445

Thr Lys Asp Ser Thr Thr Lys Ala Val Gln Glu Leu Val Ser Ser Pro
    450                 455                 460

Asp Phe Gly Lys Trp Ala Ala Val Asn Ala Asp Arg Ile Asn Val Thr
465                 470                 475                 480

Pro Arg Lys Gly Ser Ser Ser Lys Asn Gln Pro Arg Lys Trp Met Arg
                485                 490                 495

Trp Phe

<210> SEQ ID NO 121
<211> LENGTH: 1717
<212> TYPE: DNA
<213> ORGANISM: Arabidopsis thaliana

<400> SEQUENCE: 121
ctgaaaccca caaggaagaa atcgatgggt gattatcgtc ttctacgaaa ctccggcgtc      60
gttatcggaa taatcttgct acatctcttt actttcgcct ctcttgtttc atccgatgaa     120
cttcagtttg ttgtgggaga aagcggagag cttcaagtga ctcctagttt agaggtaaaa     180
ggttctcctg gattgaagcc agatagaacc tctctttgtg agaggattca tatccatgga     240
cttggaaggt ttaaacatct agacaagtat gcacattcgc tcaagttgat agttaacgcg     300
tcaatctctg ggaaaacaaa taacattgac gtttgctttc accggaattt gtcgcgtgga     360
attggaatgt gccctcatag tcgatgggag aaagcctcta aaggttcatg ggttcagaca     420
atgtcaccct cgaccataaa atccttgatg ttagagtac ctagctctaa caaggtctca     480
ttggaagtgt ctgctgtaga agaattattt atgcatcgca tagtattctt actccttggt     540
gctgtattac tggcttcggc ttctacactg agccaatctt tagcgtttta ctacagtagt     600
gcaatggctg ttggtattat ccttgtcgtg ctgcttgttc tctttcaggg aatgaagctt     660
ctacctactg gacggagttc gtttgcattg ttcatatact caaccctgct tggtttgggt     720
ggttttcttc ttcgctactt acccggattg tttgaaagtc tgctaacaga gatgggaatc     780
gacgaagaaa tgtacacacc tgcggcgatt tttgtggggg cgtttctgtc tttgggtgga     840 gcatttttg gattttggac tgtgaggaaa cttattctga cggaagatgg ctccattgat     900
gttagcacat cactatttgt tccttggtcc atccgaatta tggctgctgt tttgatcctt     960
cagagctctg tagatccttt acttgctgga ggagccctga tatctgtaat tcttatgtca     1020
tcgactttaa agaagatcac cagattgaag ttccttctac gcttattcga gattccattg     1080
aatttactgc taggaatctg ggaggcaatt cgtgatactg atataccatc cgtcccggga     1140
tatctccatg actttatgca aaagagtcct gatgcttctg gatttcgcaa ccgtgtaact     1200

```
tctgcttctc catcaggagg aatcaacaac gggatgcgag aatctccacc gtctgaatca    1260 gatacattc cttcctcttt ccataaaact cctgaaagga gccaactaac aaaagaagaa     1320
tggaaaaagc tcactaagga tagcacgaca aaggctgttc aagaattggt ttcttcaccc    1380
gattttggca aatgggcagc agttaatgcg gataggatca atgtaacacc aagaaaagga    1440
tcttctagca aaaccagcc acggaaatgg atgcgttggt tctgatttct gaaccaagcc     1500
ggtttaagtt tcataacgtt tagagagaaa aggaactctt ttgtagaaag agagagagcc    1560
tttgtaggta aagttgcttt cttctttat gacttgttca gtgttttagc tttttttttt     1620
gtggatgaga ccacgatttg ttgtaacgat cctaattggg tttttaggtt gcgtcatgtt    1680
tgtgtgtaga caatgcaatg agcattcttt ttccttt                             1717
```

<210> SEQ ID NO 122
<211> LENGTH: 486
<212> TYPE: PRT
<213> ORGANISM: Arabidopsis thaliana

<400> SEQUENCE: 122

```
Met Gly Asp Tyr Arg Leu Leu Arg Asn Ser Gly Val Val Ile Gly Ile
1               5                   10                  15

Ile Leu Leu His Leu Phe Thr Phe Ala Ser Leu Val Ser Ser Asp Glu
            20                  25                  30

Leu Gln Phe Val Val Gly Glu Ser Gly Glu Leu Gln Val Thr Pro Ser
        35                  40                  45

Leu Glu Val Lys Gly Ser Pro Gly Leu Lys Pro Asp Arg Thr Ser Leu
    50                  55                  60

Cys Glu Arg Ile His Ile His Gly Leu Gly Arg Phe Lys His Leu Asp
65                  70                  75                  80

Lys Tyr Ala His Ser Leu Lys Leu Ile Val Asn Ala Ser Ile Ser Gly
                85                  90                  95

Lys Thr Asn Asn Ile Asp Val Cys Phe His Arg Asn Leu Ser Arg Gly
            100                 105                 110

Ile Gly Met Cys Pro His Ser Arg Trp Glu Lys Ala Ser Lys Gly Ser
        115                 120                 125

Trp Val Gln Thr Met Ser Pro Phe Asp His Lys Ile Leu Asp Val Arg
    130                 135                 140

Val Pro Ser Ser Asn Lys Val Ser Leu Glu Val Ser Ala Val Glu Glu
145                 150                 155                 160

Leu Phe Met His Arg Ile Val Phe Leu Leu Gly Ala Val Leu Leu
                165                 170                 175

Ala Ser Ala Ser Thr Leu Ser Gln Ser Leu Ala Phe Tyr Tyr Ser Ser
            180                 185                 190

Ala Met Ala Val Gly Ile Ile Leu Val Val Leu Leu Val Leu Phe Gln
        195                 200                 205

Gly Met Lys Leu Leu Pro Thr Gly Arg Ser Ser Phe Ala Leu Phe Ile
    210                 215                 220

Tyr Ser Thr Leu Leu Gly Leu Gly Gly Phe Leu Leu Arg Tyr Leu Pro
225                 230                 235                 240

Gly Leu Phe Glu Ser Leu Leu Thr Glu Met Gly Ile Asp Glu Glu Met
                245                 250                 255

Tyr Thr Pro Ala Ala Ile Phe Val Gly Ala Phe Leu Ser Leu Gly Gly
            260                 265                 270

Ala Phe Phe Gly Phe Trp Thr Val Arg Lys Leu Ile Leu Thr Glu Asp
        275                 280                 285
```

-continued

```
Gly Ser Ile Asp Val Ser Thr Ser Leu Phe Val Ser Trp Ser Ile Arg
    290                 295                 300
Ile Met Ala Ala Val Leu Ile Leu Gln Ser Ser Val Asp Pro Leu Leu
305                 310                 315                 320
Ala Gly Gly Ala Leu Ile Ser Val Ile Leu Met Ser Ser Thr Leu Lys
            325                 330                 335
Lys Ile Thr Arg Leu Lys Phe Leu Leu Arg Leu Phe Glu Ile Pro Leu
            340                 345                 350
Asn Leu Leu Leu Gly Ile Trp Glu Ala Ile Arg Asp Thr Asp Ile Pro
        355                 360                 365
Ser Val Pro Gly Tyr Leu His Asp Phe Met Gln Lys Ser Pro Asp Ala
    370                 375                 380
Ser Gly Phe Arg Asn Arg Val Thr Ser Ala Ser Pro Ser Gly Gly Ile
385                 390                 395                 400
Asn Asn Gly Met Arg Glu Ser Pro Pro Ser Glu Ser Asp Thr Phe Pro
                405                 410                 415
Ser Ser Phe His Lys Thr Pro Glu Arg Ser Gln Leu Thr Lys Glu Glu
            420                 425                 430
Trp Lys Lys Leu Thr Lys Asp Ser Thr Thr Lys Ala Val Gln Glu Leu
            435                 440                 445
Val Ser Ser Pro Asp Phe Gly Lys Trp Ala Ala Val Asn Ala Asp Arg
    450                 455                 460
Ile Asn Val Thr Pro Arg Lys Gly Ser Ser Ser Lys Asn Gln Pro Arg
465                 470                 475                 480
Lys Trp Met Arg Trp Phe
            485
```